US008242095B2

(12) United States Patent
Sehgal et al.

(10) Patent No.: US 8,242,095 B2
(45) Date of Patent: Aug. 14, 2012

(54) IN VIVO AND EX VIVO GENE TRANSFER INTO RENAL TISSUE USING GUTLESS ADENOVIRUS VECTORS

(75) Inventors: Lakshman R. Sehgal, Monarch Beach, CA (US); Jonathan Wong, Palo Alto, CA (US)

(73) Assignee: BIOVEC, LLC, Chicago, IL (US)

( * ) Notice: Subject to any disclaimer, the term of this patent is extended or adjusted under 35 U.S.C. 154(b) by 184 days.

(21) Appl. No.: 12/778,340

(22) Filed: May 12, 2010

(65) Prior Publication Data
US 2010/0247487 A1 Sep. 30, 2010

Related U.S. Application Data

(63) Continuation of application No. 12/320,434, filed on Jan. 26, 2009, which is a continuation-in-part of application No. 11/650,478, filed on Jan. 8, 2007, now Pat. No. 7,501,114, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
*A61K 48/00* (2006.01)
*C07H 21/04* (2006.01)

(52) U.S. Cl. .............. 514/44 R; 424/93.2; 536/23.2; 536/23.5; 536/24.1

(58) Field of Classification Search .............. None
See application file for complete search history.

(56) References Cited

U.S. PATENT DOCUMENTS

| | | | |
|---|---|---|---|
| 4,826,811 A | 5/1989 | Sehgal et al. |
| 4,868,116 A | 9/1989 | Morgan et al. |
| 5,061,688 A | 10/1991 | Beissinger et al. |
| 5,339,346 A | 8/1994 | White |
| 5,438,041 A | 8/1995 | Zheng et al. |
| 5,449,614 A | 9/1995 | Danos et al. |
| 5,466,668 A | 11/1995 | Glaser et al. |
| 5,639,625 A | 6/1997 | Carson et al. |
| 5,661,033 A | 8/1997 | Ho et al. |
| 5,827,824 A | 10/1998 | Light et al. |
| 5,863,760 A | 1/1999 | Light et al. |
| 5,916,874 A | 6/1999 | Fujiwara et al. |
| 5,919,619 A | 7/1999 | Tullis |
| 5,981,225 A | 11/1999 | Kochanek et al. |
| 5,985,846 A | 11/1999 | Kochanek et al. |
| 5,994,132 A | 11/1999 | Chamberlain et al. |
| 6,083,750 A | 7/2000 | Chamberlain et al. |
| 6,207,455 B1 | 3/2001 | Chang |
| 6,290,949 B1 | 9/2001 | French et al. |
| 6,328,958 B1 | 12/2001 | Amalfitano et al. |
| 6,334,194 B1 | 12/2001 | Hihara |
| 6,335,011 B1 | 1/2002 | Podsakoff et al. |
| 6,342,214 B1 | 1/2002 | Tryggvason et al. |
| 7,132,277 B1 | 11/2006 | Bett et al. |
| 7,179,459 B2 | 2/2007 | Sehgal et al. |
| 7,481,998 B2 | 1/2009 | Sehgal et al. |
| 7,501,114 B2 | 3/2009 | Sehgal et al. |
| 2002/0068713 A1 | 6/2002 | Rade et al. |
| 2002/0193336 A1 | 12/2002 | Elkins et al. |
| 2004/0198683 A1 | 10/2004 | Sehgal et al. |
| 2006/0147429 A1* | 7/2006 | Diamond .............. 424/93.7 |
| 2007/0212334 A1* | 9/2007 | Sehgal et al. ............ 424/93.2 |

FOREIGN PATENT DOCUMENTS

| | | |
|---|---|---|
| WO | 96/06933 A1 | 3/1996 |
| WO | 99/14346 A1 | 3/1999 |
| WO | 00/46360 A1 | 8/2000 |
| WO | 01/29058 A1 | 4/2001 |
| WO | 2004/050844 A2 | 6/2004 |

OTHER PUBLICATIONS

Haspot et al (Am. J. Trans. 5: 2339-2348, 2005).*
Brandacher et al (Kidney Internat. 71: 60-67, 2007).*
Mohib et al (Am. J. Physiol. Renal Physiol. 295:F226-F234, 2008).*
Yang et al (J Am Soc Nephrol 14: 214-225, 2003).*
Kolls et al (Proc. Natl. Acad. Sci. USA vol. 91, pp. 215-219, Jan. 1994).*
Ritter et al (Exp. Eye Res. (1999) 69, 563-568).*
Zheng et al (Methods Mol Biol. 2008 ; 434: 205-219).*
Supplementary European Search Report mailed Aug. 25, 2011 (Application No. EP 07772782.4, based on PCT Application No. PCT/US2007/006371, filed Mar. 14, 2007).
Parks, et al., "Effects of stuffer DNA on transgene expression from helper-dependent adenovirus vectors", J. Viral. 70 (10): 8027-8034, Oct. 1999.
GenBank Acc. No. M26434, "Human hypoxanthine phosphoribosyltransferase (HPRT) gene, complete cds", US Natl. Library of Med., Bethesda, MD, USA, Nov. 26, 2001.
Orkin, et al., "Report and Recommendations of the Panel to Assess the NIH Investment in Research on Gene Therapy", US National Institutes of Health, Bethesda, MD, USA, Dec. 7, 1995.
Verma, et al, "Gene therapy—promises, problems and prospects", Nature 389: 239-242,1997.
Rosenberg, et al., Gene therapist, heal thyself, Science 287: 1751,2000.
Zuckerbraun, B.S., "Vascular gene therapy: a reality of the 21st century", Arch. Surg. 137: 854-861, Jul. 2002.
Esmon, C.T., "Protein C in sepsis", Ann. Med. 34: 598-605, 2002.
Waugh, et al., "Local Overexpression of Thrombomodulin for in Vivo Prevention of Arterial Thrombosis in a Rabbit Model", Circulation Research, vol. 84, No. 1, pp. 84-92, 1999.
Waugh, et al., "Thrombomodulin Overexpression to Limit Neointima Formation", Circulation, vol. 102, No. 3, pp. 332-337, 2000.

(Continued)

*Primary Examiner* — Richard Schnizer
(74) *Attorney, Agent, or Firm* — Ping Wang; Andrews Kurth, LLP

(57) ABSTRACT

A method for treating a renal disease in a subject is disclosed. The method includes administering into a kidney of the subject with an effective amount of a gutless adenoviral vector containing a polynucleotide encoding a therapeutic agent. The gutless adenoviral vector contains the nucleotide sequence of SEQ ID NO:13 or SEQ ID NO:15 and expresses the therapeutic agent in a kidney tissue of the subject.

8 Claims, 16 Drawing Sheets
(5 of 16 Drawing Sheet(s) Filed in Color)

OTHER PUBLICATIONS

Vassalli, et al., "Gene therapy for arterial thrombosis", Cardiovascular Research, vol. 19, No. 6, pp. 459-459, 1997.
Umana, et al., "Efficient FLPe recombinase enables scalable production of helper-dependent adenoviral vectors with negligible helper-virus contamination", Nature Biotechnology, vol. 19, No. 6, pp. 582-585, 2001.
Wen, et al., "Human Thrombomodulin: Complete eDNA Sequence and Chromosome Localization of the Gene", Biochemistry, vol. 26, pp. 4350-4357, 1987.
Borroni, et al., "Peripheral Blood Abnormalities in Alzheimer Disease: Evidence for Early Endothelial Dysfunction", Alzheimer Disease and Associated Disorders, vol. 16, No. 3, pp. 150-155,2002.
McKay, et al., "Gene Transfer Therapy in Vascular Disease", Cardiovascular Drug Reviews, vol. 19, No. 3, pp. 245-262, 2001.
Ausbel, et al., (eds) Greene Publishing Associates, "Current Protocols in Molecular Biology", Sections 9.10-9.14,1989.
Ng, et al., "Development of a FLP/fre System for Generating Helper-Dependent Adenoviral Vectors", Molecular Therapy, vol. 3, No. 5, pp. 809-815, 2001.
Bledsoe, et al., "Cytokine production in motor neurons by poliovirus replicon vector gene delivery", Nature Biotechnol., vol. 18, pp. 964-969, 2000.
Chen, et al., "Low-Dose Vaccinia Virus-Mediated Cytokine Gene Therapy of Glioma", Journal of Immunotherapy, vol. D 24, pp. 46-57, 2001.
Chen, et al., "Gene therapy for brain tumors: Regression of experimental gliomas by adenovirus-mediated gene transfer in vivo", Proc. Natl. Acad. Sci. USA, vol. 91, pp. 3054-3057, 1994.
Cui, et al., "Plasmid DNA-Entrapped Nanoparticles Engineered from Microemulsion Precursers: In Vitro and In Vivo Evaluation", Bioconjugate Chern., vol. 13, pp. 1319-1327, 2002.
Curiel, "Strategies to Adapt Adenoviral Vectors for Targeted Delivery", Annals New York Academy of Sciences, vol. 886, pp. 158-171, 1991.
Gossen, et al., "Transcriptional Activation by Tetracyclines in Mammalian Cells", Science, vol. 268, pp. 1766-1769, 1995.
Gossen, et al., "Tight control of gene expression in mammalian cells by tetracycline-responsive promoters", Proc. Natl. Acad. Sci. USA, vol. 89, pp. 5547-5551, 1992.
Fink, et al., "Gene Transfer to Neurons Using Herpes Simplex Virus-Based Vectors", Annual Rev. Neurosci., vol. 19, pp. 265-287, 1996.
Flotte, et al., "Gene Expression from Adeno-associated Virus Vectors in Airway Epithelial Cells", Am. J. Respir. Cell. Mol. Biol., vol. 7, pp. 349-356, 1992.
Green, et al., "A New Scalable Method for the Purification of Recombinant Adenovirus Vectors", Human Gene Therapy, vol. 13, pp. 1921-1934,2002.
Haj-Ahmand, et al., "Development of a Helper-Independent Human Adenovirus Vector and Its Use in the Transfer of the Herpes Simplex Virus Thymidine Kinase Gene", J. Virol., vol. 57., pp. 267-273, 1986.
Howell, et al., "High-Level Dystrophin Expression After Adenovirus-Mediated Dystrophin Minigene Transfer to Skeletal Muscle of Dystrophic Dogs: Prolongation of Expression with Immunosuppression", Human Gene Therapy, vol. 9, pp. 629-634, 1998.
Kay, et al., "Evidence for gene transfer and expression of factor IX in haemophilia B patients treated with an AAV vector", Nature Genetics, vol. 24, pp. 257-261, 2000.
Kessler, et al., "Gene delivery to skeletal muscle results in sustained expression and systemic delivery of a therapeutic protein", Proc. Natl. Acad. Sci. USA, vol. 96, pp. 14082-14087, 1996.
Kistner, et al., "Doxycycline-mediated quantitative and tissue-specific control of gene expression in transgenic mice", Proc. Natl. Acad. Sci. USA, vol. 93, pp. 10933-10938, 1996.
Magari, et al., "Pharmacologic Control of a Humanized Gene Therapy System Implanted into Nude Mice", J. Clin. Invest., vol. 100, pp. 173-206, 1997.
Miller, "Progress Toward Human Gene Therapy", Blood, vol. 76, pp. 271-278,1990.
Muzyczka, et al., "Use of Adeno-Associated Virus as a General Transduction Vector for Mammalian Cells", Curro Topics in Micro. and Immunology, vol. 158, pp. 97-129, 1990.

Naldni, et al., "In Vivo Gene Delivery and Stable Transduction of Nondividing Cells by a Lentiviral Vector", Science, vol. 272, pp. 263-267, 1996.
No, et al., "Ecdysone-inducible gene expression in mammalian cells and transgenic mice", Proc. Natl. Acad. Sci., USA, vol. 93, pp. 3346-3351, 1996.
Pruchnic, et al., "The Use of Adeno-Associated Virus to Circumvent the Maturation-Dependent Viral Transduction of Muscle Fibers", Human Gene Therapy, vol. 11, pp. 521-536, 2000.
Ragot, et al., "Efficient adenovirus-mediated transfer of a human minidystrophin gene to skeletal muscle of mdx mice", Nature, vol. 361, pp. 647-650,1993.
Romano, et al., "Latest Developments in Gene Transfer: Achievements, Perspectives, and Controversies Over Therapeutic Applications", Stem Cells, vol. 18, pp. 19-39, 2000.
Ropert, "Liposomes as a gene delivery system", Brazilian Journal of Medical and Biological Research, vol. 32, pp. 163-169, 1999.
Sakhuja, et al., "Optimization of the Generation and Propagation of Gutless Adenoviral Vectors", Human Gene Therapy, vol. 14, pp. 243-254, 2003.
Samulski, at al., "Helper-Free Stocks of Recombinant Adeno-Associated Viruses: Normal Integration Does Not Require Viral Gene Expression", Journal of Virology, vol. 63, No. 9, pp. 3822-3828,1989.
Schwarze, et al., "In Vivo Protein Transduction: Delivery of a Biologically Active Protein into the Mouse", Science, vol. 285,pp. 1569-1572, 1999.
Song, et al., "Sustained secretion of human alpha-1 antitrypsin from murine muscle transduced with adeno-associated virus vectors", Proc. Natl. Acad. Sci. USA, vol. 95, pp. 14348-14384, 1998.
Suzuki, et al., "Structure and expression of human thrombomodulin, a thrombin receptor on endothelium acting as a cofactor for protein C activation", EMBO Journal, vol. 6, pp. 1891-1897, 1987.
Wahlfors, et al., "Evaluation of recombinant alphaviruses as vectors in gene therapy", Gene Therapy, vol. 7, pp. 472-480, 2000.
Wang, et al., "A regulatory system for use in gene transfer", Proc. Natl. Acad. Sci. USA, vol. 91, pp. 8180-8184,1994.
Wang, et al., "Ligand-inducible and liver-specific target gene expression in transgenic mice", Nature Biotechnology, vol. 15, pp. 239-243, 1997.
Yamashita, et al., "Electroporation-mediated Interleukin-12 Gene Therapy Hepatocellular Carcinoma in the Mice Model", Cancer Research, vol. 61, pp. 1005-1012,2001.
Ye, et al., "Regulated Delivery of Therapeutic Proteins After in Vivo Somatic Cell Gene Transfer", Science, vol. 283, pp. 88-91, 1999.
Yi, et al., "A Cationic Lipid Emulsion/DNA Complex as a Physically Stable and Serum-Resistant Gene Delivery System", Pharmaceutical Research, vol. 17, No. 3, pp. 314-320, 2000.
Xiao, et al., "Efficient Long-Term Gene Transfer into Muscle Tissue of Immunocompetent Mice by Adeno-Associated Virus Vector", Journal of Virology, vol. 70, No. 11, pp. 8098-8108, 1996.
Xiao, et al., "Adeno-Associated Virus as a Vector for Liver-Directed Gene Therapy", Journal of Virology, vol. 72, No. 12, pp. 10222-10226, 1998.
Zhang, et al., "Long-term expression of human alpha-1 antitrypsin gene in mouse liver achieved by intravenous administration of plasmid DNA using a hydrodynamics-based procedure", Gene Therapy, vol. 7, pp. 1344-1349,2000.
Cui, et al., "Genetic Immunization Using Nanoparticles Engineered from Microemulsion Precursors", Pharmaceutical Research, vol. 19, No. 7, pp. 939-946, 2002.
Kibbe, et al., "Handbook of Pharmaceutical Excipients", 3rd Edition, Pharmaceutical Press London UK, 2000.
Lee, et al., "Crit. Rev. Ther.", Drug Carrier Systems, vol. 14, pp. 173-206, 1997.
Harui, et al., "Vaccination with helper-dependent adenovirus enhances the generation of transgene-specific CTL", Gene Therapy, vol. 11, pp. 1617-1626,2004.
Johansson, et al., "Adenoviral-Mediated Expression of Porphobilinogen Deaminase in Liver Restores the Metabolic Defect in a Mouse Model of Acute Intermittent Porphyria", Molecular Therapy, vol. 10, pp. 337-343, 2004.

Fu, et al., "Overexpression of SR-BI by Adenoviral Vector Reserves the Fibrate-Induced Hypercholesterolemia of Apolipoprotein E-Deficient Mice", Journal of Biological Chemistry, vol. 278, pp. 52559-52563, 2003.

Brevetti, et al., "Overexpression of endothelial nitric oxide synthase increases skeletal muscle blood flow and oxygenation in severe rat hund limb ischemia", The Society for Vascular Sugery, pp. 820-826, 2003.

Li, et al., J. Vase. Surg. 32: 804-813, 2000.

Tohda, et al., Arteriosclerosis, Thrombosis, and Vascular Biology, 18: 1861-1869, 1998.

Kurosawa, et al., J. Biol. Chem., 263(13): 5993-5996, 1988.

Tabuchi, et al., Eur. J. Card. Thor. Surg., 26: 995-1000, 2004.

Miller, et al., FASEB J., 9: 190-199, 1995.

Crystal, Science, 270: 404-410, 1995.

Read, et al., Adv. Gen., 53: 19-46, 2005.

Search Result for SEQ 10 No. 13 in U.S. Appl. No. 11/685,474, 2008.

Marth, et al., Nature Genetics, 23(4): 452-456, 1999.

Wheelan, et al., Genome Research, 11(11): 1952-1957,2001.

Kibbe, et al., "Gene Therapy for Restenosis", Circ. Res., vol. 86, pp. 829-833, 2000.

Shears, et al., "Efficient Inhibition of Intimal Hyperplasia by Adenovirus-Mediated Inducible Nitric Oxide Synthase Gene Transfer to Rats and Pigs in Vivo", J. Am. Coli. Surg., vol. 187, No. 3, pp. 295-306, 1998.

Ross, "The pathogenesis of atherosclerosis: a perspective for the 1990s", Nature, vol. 362, pp. 801-809, 1993.

Sadler, "Thrombomodulin Structure and Function", Tehomb Haemost, vol. 78, pp. 392-395,1997.

Esmon, "Thrombomodulin as a model of molecular mechanisms that modulate protease specificity and function at the vessel surface", Faseb J., vol. 9, pp. 946-955,1995.

Salomaa, et al., "Soluble thrombomodulin as a predictor of incident coronary heart disease and symptomless carotid artery atherosclerosis in the Atherosclerosis Risk in Communities (ARIC) Study: a case-cohort study", Lancet, vol. 353,pp. 1729-1734, 1999.

Palmer, et al., "Nitric oxide release accounts for the biological activity of enothelium-derived relaxing factor", Nature, vol. 88, pp. 4651-4655, 1991.

Kubes, et al., "Nitric oxide: An endogenous modulator of leukocyte adhesion", Proc. Natl. Acad. Sci. USA, vol. 88, pp. 4651-4655,1991.

Steg, et al., "Reduction of Restenosis After Angioplasty in an Atheromatous Rabbit Model by Suicide Gene Therapy", Circulation vol. 96, pp. 401-411, 1997.

Van Belle, et al., "Accelerated Endothelialization by Local Deliery of Recombinant Human Vascular Endothelial Growth Factor Reduces In-Stent Intimal Formation", Biochem. and Biophs. Res. Communications, vol. 235, pp. 311-316, 1997.

Salyapongse, et al., "Gene Therapy and Tissue Engineering", Tissue Engineering, vol. 26, No. 4, pp. 663-676,1999.

Kon, et al., "Bone Morphogenetic Protein-2 Stimulates Differentiation of Cultured Spinal Ligament Cells from Patients with Ossification of the Posterior Longitudinal Ligament", Calcif. Tissue Int., vol. 60, pp. 291-296,1997.

Kibbe, et al., J. Vase. Surg., 34: 156-65,2001.

He, et al., PNAS, 95: 2509-2514,1998.

Marmur, et al., "Strand Separation and Specific Recombination in Deoxyribonucleic Acids: Biological Studies", PNAS USA, vol. 46, pp. 453-461, 1960.

Doty, et al., "Strand Separation and Specific Recombination in Deoxyribonucleic Acids: Physical Chemical Studies", PNAS USA, vol. 46, pp. 461-476, 1960.

Sambrook, et al., "Analysis of Genomic DNA by Southern Hybridization", Molecular Cloning: A Laboratory Manual, vol. II, pp. 9.31-9.62,1989.

Zushi, et al., "Aspartic acid 349 in the forth epidermal growth factor-like structure of human thrombomodulin plays a role in its Ca(2+)-mediated binding to protein C", The Journal of Biological Chemistry, vol. 266, No. 30, pp. 19886-19889, 1991.

Parks, et al., "A helper-dependent adenovirus vector system: Removal of helper virus by Cre-mediated excision of the viral packaging signal", PNAS, vol. 93, pp. 13565-13570, 1996.

Lieber, et al., "Recombinant Adenoviruses with Large Deletions Generated by Cre-Mediated Excision Exhibit Different Biological Properties Compared with First-Generation Vectors in Vitro and in Vivo", J. Virol., vol. 70, pp. 8944-8960, 1996.

Dittman, et al., "Human Thrombomodulin: Complete eDNA Sequence and Chromosome Localization of the Gene", Biochemistry, vol. 26, pp. 4350-4357, 1987.

Beauchamp, et al., "Development of a FLP/frt System for Generating Helper-Dependent Adenoviral Vectors", Molecular Therapy, vol. 3, No. 5, pp. 809-815, 2001.

Nebel, et al., Science, vol. 249, pp. 1285-1288, 1990.

Tsiang, et al., "Functional domains of membrane-bound human thrombomodulin. EGF-like domains four to six and the serine/threonine-rich domain are required for cofactor activity", The Journal of Biological Chemistry, vol. 267, No. 9, pp. 6164-6170, 1992.

Nagashima, et al., "Alanine-scanning mutagenesis of the epidermal growth factor-like domains of human thrombomodulin identifies critical residues for its cofactor activity", The Journal of Biological Chemistry, vol. 268., No. 4,pp. 2888-2892,1993.

Gerlitz, et al., "Identification of the predominant glycosaminoglycan-attachment site in soluble recombinant human thrombomodulin: potential regulation of functionality by glycosyltransferase competition for serine474", The Biochemical Journal, vol. 295, pp. 131-140,1993.

Lin, et al., "Modulation of glycosaminoglycan additional in naturally expressed and recombinant human thrombomodulin", The Journal of Biological Chemistry, vol. 269, No. 40, pp. 25021-25030,1994.

Adler, et al., "The structure of a 19-residue fragment from the C-loop of the fourth epidermal growth factor-like domain of thrombomodulin", The Journal of Biological Chemistry, vol. 270, No. 40, pp. 23366-23372, 1995.

Weiler-Guettler, et al., "A targeted point mutation in thrombomodulin generated viable mice with a prethrombotic state", The Journal of Clinical Investigation, vol. 101, No. 9, pp. 1983-1991, 1998.

* cited by examiner

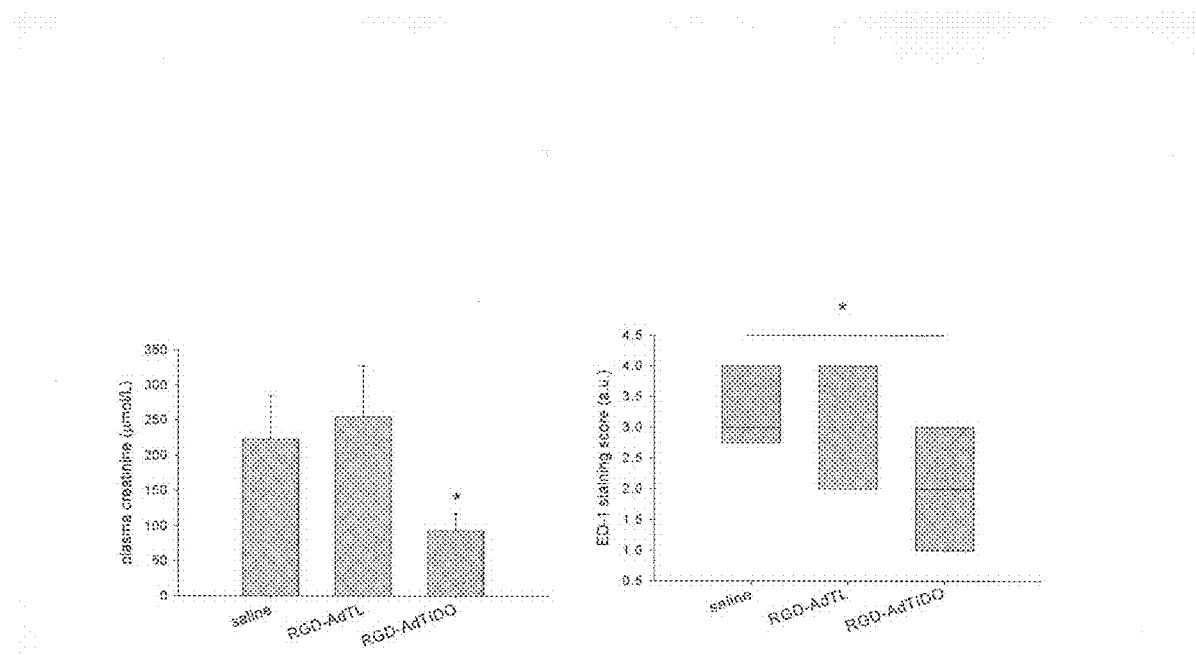
FIG. 16A
FIG. 16B
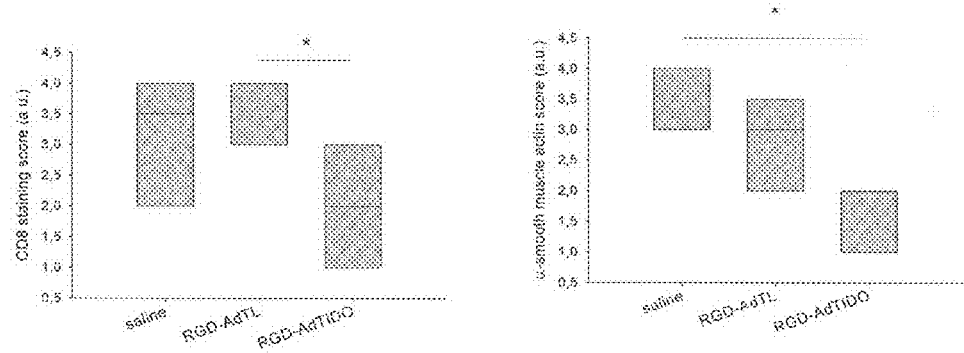
FIG. 16C
FIG. 16D

IN VIVO AND EX VIVO GENE TRANSFER INTO RENAL TISSUE USING GUTLESS ADENOVIRUS VECTORS

This application is a continuation of U.S. patent application Ser. No. 12/320,434, filed Jan. 26, 2009, which is a continuation-in-part of U.S. patent application Ser. No. 11/650,478, now U.S. Pat. No. 7,501,114, filed Jan. 8, 2007, which is a continuation-in-part application of U.S. patent application Ser. No. 10/725,013, now U.S. Pat. No. 7,179,459, filed Dec. 2, 2003, which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the gene transfer into renal tissues and, in particular, is directed to methods and compositions for in vivo or ex vivo gene transfer to renal tissue using gutless adenovirus vector.

BACKGROUND

Kidney-targeted gene transfer has the potential to revolutionize the treatment of renal diseases. Transplanted kidneys also provide an ideal setting for ex vivo gene transfer. Several in vivo gene transfer methods have been attempted to target certain renal structures, for example, the HVJ-liposome method and renal perfusion of adenovirus for glomerular cells, intravenous injection of oligonucleotides (ODNs) for proximal tubule, intra-arterial injection of adenovirus followed by cold incubation with a vasodilator for interstitial vasculature of the outer medulla and adenoviral injection into the renal pelvis for the inner medullary collecting duct. As an ex vivo gene transfer method targeting the glomerulus, the transfusion of genetically-modified mesangial cells has been attempted. Implantation of genetically-modified tubular epithelial cells into the subcapsular region has been employed for ex vivo transfection to the interstitium.

However, although gene therapy theoretically has the distinct potential to treat renal disease at the most fundamental level, its application has been limited by the availability of an adequate system for long term gene delivery to the kidney. There still exists a need for improved gene transfer techniques, especially gene transfer vectors that are capable of mediating effective gene transfer into renal tissues with low toxicity.

SUMMARY

One aspect of the present invention relates to methods for treating a renal disease in a mammal. In one embodiment, the method comprises the step of infusing the kidney with a gutless adenoviral vector comprising a polynucleotide encoding a therapeutic agent and a regulatory element operably linked to the polynucleotide, wherein the gutless adenoviral vector comprises the nucleotide sequence of SEQ ID NO:13 or SEQ ID NO:15. In a related embodiment, the gutless adenovirus vector is infused through the vena renalis. In another related embodiment, the gutless adenovirus vector is infused through the superior mesenteric artery.

In another embodiment, the method comprises the steps of: administering a therapeutically effective amount of a gutless adenovirus vector into a segment of a renal blood vessel in vivo, wherein the gutless adenovirus vector comprises the nucleotide sequence of SEQ ID NO:13 or SEQ ID NO:15, and is capable of expressing a therapeutic agent. In a related embodiment, the gutless adenovirus vector is administered using a stent.

Another aspect of the present invention pertains to a method for improving allograft survival. The method comprises the steps of perfusing a kidney harvested from an organ donor with a gutless adenovirus vector carrying a nucleotide sequence encoding a immune modulator and a regulatory element operably linked to the nucleotide sequence; and transplanting the perfused kidney into a subject. In a related embodiment, the immune modulator is indoleamine dioxygenase.

Another aspect of the present invention pertains to a gutless adenovirus vector comprising a polynucleotide encoding a therapeutic protein, a renal tissue specific regulatory element operably linked to the polynucleotide sequence; and a stuffer comprising the nucleotide sequence of SEQ ID NO:13 or SEQ ID NO:15.

Another aspect of the present invention pertains to a gutless adenovirus vector comprising a polynucleotide encoding an indoleamine dioxygenase, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a renal vascular disease, comprising the gutless adenovirus vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 16 is a composite of graphs showing reduction of plasma creatinin levels (panel A), ED-1 staining (panel B), CD8 staining (panel C) and smooth muscle actin score (panel D) in kidney tissue infected by gutless adenovirus carrying the IDO gene.

DETAILED DESCRIPTION

Figure 1:
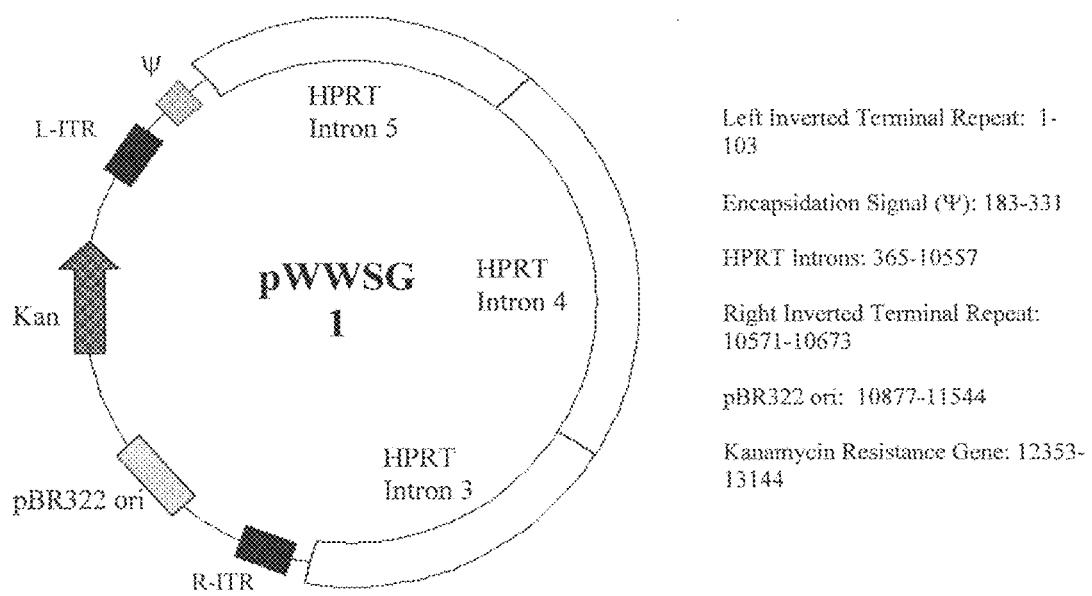
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating renal diseases and improving kidney allograft survival using gene transfer technologies. One aspect of the present invention relates to a method for treating a renal disease by infusing the kidney in vivo with an effective amount of gutless adenovirus vector carrying a DNA sequence encoding a therapeutic agent. The virus-mediated expression of the therapeutic agent in renal tissue ameliorates symptoms of the renal diseases. This local approach eliminates the need to inject a large quantity of virus into a patient and hence significantly reduces the viral-related toxicity.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The Gutless Adenovirus Vector

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The genome of an adenovirus can be manipulated such that it encodes and expresses a gene product of interest but is inactivated in terms of its ability to replicate in a normal lyric viral life cycle (Curie D T, Ann NY Acad Sci 886, 158-171 [1991]). Suitable adenoidal vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells, muscle cells and renal cells Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

The so-called "gutless" adenovirus vectors contain a minimal amount of adenovirus DNA (i.e., the inverted terminal repeats and encapsidation signal) and are incapable of expressing any adenovirus antigens (hence the term "gutless"). The gutless adenovirus vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

The "inverted terminal repeats (ITRs)" of adenovirus are short elements located at the 5' and 3' termini of the linear adenoviral genome, respectively and are required for replication of the viral DNA. The left ITR is located between 1-130 by in the Ad genome (also referred to as 0-0.5 mu). The right ITR is located from about 3,7500 by to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward. The "encapsidation signal" or "packaging sequence" of adenovirus refers to the ψ sequence which comprises five (AI-AV) packaging signals and is required for encapsidation of the mature linear genome; the packaging signals are located from about 194 to 358 by in the Ad genome (about 0.5-1.0 mµ).

In one embodiment, a viral backbone shuttle vector is used for the construction of gutless adenovirus vectors. The viral backbone shuttle vector contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb (SEQ ID NO: 1). In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1. In another embodiment, the viral backbone shuttle vector of the present invention comprises the nucleotide sequence of SEQ ID NO:13 or SEQ ID NO:15.

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may contain coding sequence for a protein, an iRNA agent, or an antisense RNA. The foreign DNA may further contain regulatory elements operably linked to the coding sequence. The term "operably linked," as used herein, refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence. Similarly, intervening untranscribed sequences can be present between an enhancer sequence and the coding sequence and the enhancer sequence can still be considered "operably linked" to the coding sequence.

Examples of regulatory elements include, but are not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human origin.

Renal Specific Expression

In one embodiment, the therapeutic agent is expressed in a tissue-specific manner either using a renal-specific regulatory element or using an inducible regulatory element combined with kidney-specific induction. Examples of renal-specific regulatory element include, but are not limited to, high-capacity (type 2) Na$^+$/glucose cotransporter gene (Sglt2)promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

Examples of inducible regulatory elements include, but are not limited to, regulatory elements that responded to exogenous signals or stresses, such as heat, hormones, hypoxia, cytokines or metal ions, as well as artificial inducible systems such as the tetracycline inducible system; the FK506/rapamycin inducible system, the RU486/mifepristone inducible system, and the ecdysone inducible system. These systems are briefly described below.

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP 16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

In one embodiment, a kidney tissue is infected with a gutless virus containing an inducible regulatory element. The infected tissue is then exposed to an inducing agent, such as tetracycline or rapamycin, or an inducing condition such as local heating or hypoxia, to induce expression of the therapeutic agent. The inducible system thus allows kidney specific expression of the therapeutic agent and minimizes the side effect of the therapeutic agent. In addition, the level and duration of the therapeutic agent expression may also be controlled by the dose of the inducing agent and the frequency of inducing agent administration. In one embodiment, the coding sequence of the therapeutic agent is controlled by the tet-on system and the expression of the therapeutic agent can be induced by an oral dose of tetracycline.

The Renal Diseases

The renal disease can be any disease or disorder that affects the function of the kidneys and for which a therapeutic gene or genes have been identified. Examples of the renal diseases include, but are not limited to, glomerulonephritis, renal vein thrombosis, diabetic nephropathy, ischemia/reperfusion injury (shock kidneys), hypertension, proteinuric kidney diseases (post glomerulonephritis), ischemic nephropathy, obstruction nephropathy, atheroembolic renal disease, chronic nephritis, congenital nephrotic syndrome, interstitial nephritis, lupus nephritis, membranoproliferative glomerulonephritis, membranous nephropathy, minimal change disease, necrotizing glomerulonephritis, nephropathy—IgA, nephrosis (nephrotic syndrome), post-streptococcal GN, reflux nephropathy, renal artery embolism, renal artery stenosis, and renal underperfusion.

The Therapeutic Agents

The therapeutic agent can be any molecule that is, when expressed in a renal tissue or in the proximity of a renal tissue, capable of ameliorating symptoms of a renal disease. The therapeutic agents include, but are not limited to, proteins, iRNA agents and antisense RNA. The term "expression," as used herein, refers to the process of transcription of mRNA from a coding sequence and/or translation of mRNA into a polypeptide.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA.

Protein as a Therapeutic Agent

In one embodiment, the therapeutic agent is a protein or peptide capable of ameliorates symptoms of the renal disease. For example, the therapeutic agent can be thrombomodulin for treating renal vein thrombosis (RVT) or an antibody that binds specifically to a target molecule which is involved in a renal disease (e.g., an inflammatory cytokine which has been found to be associated with the chronic kidney disease (CKD)).

The term "antibody", as used herein, is defined as an immunoglobulin that has specific binding sites to combine with an antigen. The term "antibody" is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, a humanized antibody and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), F(ab')$_2$, Fv fragment, diabody, linear antibody, single-chain antibody molecule, multispecific antibody, and/or other antigen binding sequences of an antibody.

Examples of the therapeutic protein include, but are not limited to, thrombomodulin (TM), cytokines such as IL-1, IL-2, IL-3, IL-4, IL-5, IL-6, IL-7, IL-8, IL-9, IL-10, IL-11, IL-12, IL-13, IL-14, IL-15 and other interleukins; hematopoietic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-α, TGF-β, and VEGF; antiviral cytokines such as interferons, antiviral proteins induced by interferons, TNF-α, and TNF-β; proteins involved in immune responses such as antibodies, CTLA4, hemagglutinin, MHC proteins, VLA-4, and kallikrein-kininogen-kinin system; ligands such as CD4; growth factor receptors including EGFR, PDGFR, FGFR, and NGFR, GTP-binding regulatory proteins, interleukin receptors, ion channel receptors, leukotriene receptor antagonists, lipoprotein receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb, and variants thereof.

A "variants" of a polypeptide is a polypeptide that differs from a native polypeptide in one or more substitutions, deletions, additions and/or insertions, such that the bioactivity of the native polypeptide is not substantially diminished or enhanced. In other words, the bioactivity of a variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

A variant preferably exhibits at least about 70%, more preferably at least about 90% and most preferably at least about 95% sequence homology to the original polypeptide.

The term "variant' also includes a polypeptides that is modified from the original polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In one embodiment, the therapeutic protein is a native TM or a TM variant for the treatment of renal vein thrombosis (RVT). RVT has numerous etiologies, it occurs most commonly in patients with nephrotic syndrome (i.e., >3 g/d protein loss in the urine, hypoalbuminemia, hypercholesterolemia, edema). The syndrome is responsible for a hypercoagulable state. The excessive urinary protein loss is associated with decreased antithrombin III, a relative excess of fibrinogen, and changes in other clotting factors; all lead to a propensity to clot. Numerous studies have demonstrated a direct relationship between nephrotic syndrome and both arterial and venous thromboses. Why the renal vein is susceptible to thrombosis is unclear. The renal vein also may contain thrombus after invasion by renal cell cancer. Other less common causes include renal transplantation, Behçet syndrome, hypercoagulable states, and antiphospholipid antibody syndrome.

Thrombomodulin (TM) is an integral membrane glycoprotein expressed on the surface of endothelial cells (Sadler et al., *Trhomb Haemost.*, 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.*, 9:946-55 [1995]). The latter two proteins are essential for the function of two of the coagulation proteases, namely factors IXa and Xa. TM thus plays an active role in blood clot formation in vivo and can function as a direct or indirect anticoagulant.

TM and several other proteins or enzymes have been shown to reduce the process of intimal hyperplasia, whose evolution is the causes of late graft failure. For instance, Nitric oxide synthase, an enzyme expressed by endothelial cells has been shown in animal models to inhibit intimal hyperplasia, especially the inducible enzyme (iNOS) (Saimaa et al., *Lancet*, 353:1729-34 [1999]; Palmer et al., *Nature*, 327:524-26 [1987]; Kubes et al., *PNAS USA.*, 88:4651-5 [1991]).

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

siRNA as the Therapeutic Agent

In another embodiment, short interfering RNAs (siRNA) are used as a therapeutic agent to inhibit a disease-related gene expression. For example, elevated levels of transforming growth factor-$\beta_1$ (TGF-$\beta_1$) and platelet-derived growth factor (PDGF) have been associated with the development of glomerular injury. Therefore, inhibition of the expression of TGF-$\beta_1$ and/or PDGF in kidney tissues may be used to prevent or reduce glomerular injury.

siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

siRNAs can be expressed in vivo from adenovirus vectors. This approach can be used to stably express siRNAs in kidney tissues. In one embodiment, siRNA expression vectors are engineered to drive siRNA transcription from polymerase III (pal III) transcription units. Pol III transcription units are suitable for hairpin siRNA expression, since they deploy a short AT rich transcription termination site that leads to the addition of 2 by overhangs (UU) to hairpin siRNAs—a feature that is helpful for siRNA function. Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database. Any target sequences with more than 16-17 contiguous base pairs of homology to other coding sequences may be eliminated from consideration in certain cases.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., *Proc. Natl. Acad. Sci. USA* 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., *Nature Biotechnology* 20:500-505, 2002).

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

Route of Administration

The gutless adenovirus may be introduced into the kidney by intravenous, intrarterial, or retrograde infusion. In one embodiment, the virus is infused through the vene renalis. In another embodiment, the virus is infused through the superior mesenteric artery. In yet another embodiment, the virus is infused through a retrograde catheter into the pyelic cavity. Since only a relatively small amount of virus is needed for the kidney infusion, the virus-related toxicity is reduced. In yet another embodiment, the kidney is perfused with the virus, i.e., the virus enters the kidney through the vene renalis or the superior mesenteric artery, and is collected through the superior mesenteric artery or vene renalis. Since the leftover virus does not enter the blood circulation, a large amount of virus may be used for the perfusion. In addition, a close-circuit perfusion allows constant exposure to virus over an extended period of time (e.g., 10-60 minutes) and hence significantly increases the number of infected cells.

In another embodiment, the virus is administered into a segment of a renal blood vessel in vivo. In a related embodiment, the gutless adenovirus vector is administered using a stent. The viral vector is embedded in the stent and is released only at a treatment site. Since the viral infection is restricted at the treatment site and the surrounding area, only a small amount of the virus is needed and the virus-related toxicity is reduced.

Another aspect of the present invention relates to a method for improving allograft survival. The method comprises the steps of perfusing a kidney harvested from an organ donor with a gutless adenovirus vector carrying a nucleotide sequence encoding an immune modulator and a regulatory element operably linked to the nucleotide sequence; and transplanting the perfused kidney into a subject. The term "immune modulator," as used herein, refers to a polypeptide or a polynucleotide capable of modulating an immune response and improving allograft survival.

In one embodiment, the immune modulator is indoleamine dioxygenase (IDO). IDO is an enzyme that is expressed in the placenta and plays an important role in foeto-maternal tolerance. IDO metabolizes the amino acid tryptophan. The function of T cells, the most important cell-type involved in organ transplant rejection, is dependent on tryptophan. In addition, the metabolites of tryptophan (kynurenines) are toxic to T-cells. It has been shown that over-expression of IDO in renal tissues protects against renal transplant damage.

Typically, kidneys must be preserved prior to transplantation to obtain proper pathology assessment of the suitability of the organ for transplantation. Lack of proper preservation leads to degradation of organ function due to thrombosis (blood clotting), ischemia (lack of oxygen), or ischemia followed by reperfusion (the restoration of blood flow upon transplantation). These events bring about inflammation, cell death, and eventually failure of the organ. Kidney preservation is a process in which the renal artery is connected to a kidney perfusion machine in order to simulate the normal process by which nutrients are supplied to the kidney. A solution is continuously perfused through a closed circuit which includes the kidney, which is typically maintained at a low temperature (e.g., 5° C.) to reduce the cell metabolic rate and oxygen consumption. During the perfusion process, the perfusion pressure, flow, and vascular resistance, as well as the organ's chemistries, including base excess, oxygen saturation, calcium, potassium, hematocrit, $pO_2$, pH, and bicarbonate, are monitored closely to prevent tissue damage. The adenovirus vectors can be added to the perfusion solution and infect the kidney tissue during the perfusion period. Kidney perfusion solutions are commercially available. In one embodiment, the kidney perfusion solution is Lactated Ringer's solution.

In one embodiment, the regulatory element is a constitutive promoter, such as CMV or RSV promoter. In another embodiment, the gutless adenovirus contains the nucleotide sequence of SEQ ID NO:25 or SEQ ID NO:26.

In another embodiment, the gutless adenovirus is suspended in the perfusion solution to a final concentration of $10^9$-$10^{12}$ particles/ml and perfused for a period of 10-120 minutes.

Another aspect of the present invention pertains to a gutless adenovirus vector comprising a polynucleotide encoding a therapeutic agent, a renal-specific regulatory element or inducible regulatory element operably linked to the polynucleotide sequence; and a stuffer comprising the nucleotide sequence of SEQ ID NO:13 or SEQ ID NO:15.

In one embodiment, the renal-specific regulatory element is selected from the group consisting of high-capacity (type 2) Na+/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-Related Peptide Receptor Gene.

In another embodiment, the inducible regulatory element is selected from the group consisting of heat inducible regulatory elements, hormone inducible regulatory elements, hypoxia inducible regulatory elements, cytokine inducible regulatory elements, metal ion inducible regulatory elements, and artificial inducible regulatory elements.

Yet another aspect of the present invention pertains to a pharmaceutical composition for treating a renal vascular disease, comprising the gutless adenovirus vector described above and a pharmaceutically acceptable carrier. As used herein, a "pharmaceutically acceptable carrier" is intended to include any and all solvents, solubilizers, stabilizers, absorbents, bases, buffering agents, controlled release vehicles, diluents, emulsifying agents, humectants, dispersion media, antibacterial or antifungal agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition is formulated to be compatible with its intended route of administration. Solutions or suspensions used for parenteral application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

It is especially advantageous to formulate parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention is further illustrated by the following examples which should not be construed as limiting. The contents of all references, patents and published patent applications cited throughout this application, as well as the Figures and Tables are incorporated herein by reference.

Example 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At by 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at by 3667 and there was also an EcoRI site inside the MCS at by 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 by fragment that was cloned into the EcoRI/XbaI digested viral backbone. Then the HPRT source was digested with only XbaI yielding a 2715 by fragment. One of the XbaI sites in this cut is the same XbaI site that was cut from the EcoRI/XbaI double digest in step 1. The viral backbone was cut with only XbaI and the 2715 by fragment was inserted.

Overall, from the HPRT source, the HPRT stuffer sequence is inserted into the viral backbone in reverse orientation, hence intron 5, then 4, then 3. The 2715 by fragment was inserted and checked to follow the original source sequence. The new plasmid is designated as pShuttle-ITR-HPRT (SEQ ID NO:1).

Example 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the Xba1/EcoRV restriction enzyme site locations. The CMV from ps5 was removed using XbaI/EcoRV.

pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]). The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at by 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                        (SEQ ID NO: 8)
5'-gtaacactgg cccaggaggc ctttctggtg acccc-3'

(SEQ ID NO: 9)
3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
Forward:
5'TAGTTCCTTCTGCCTGGAATAC 3'    (SEQ ID NO: 10)

Reverse:
5'CAAGTCACAAGGATGGACTACA 3'    (SEQ ID NO: 11)
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 by was inserted into the BstEII and SfiI sites of pTMadap, resulting in pTMadap-stuffer1.

2(a)-4 Creation of pTMadap-Stuffer1-Short

To reduce the size of the stuffed fragment in pTMadap-stuffer1, pTMadap-stuffer1 was digested with SanDI and BstEII and the resulting DNA ends were modified by a fill-in reaction with Klenow. Re-ligation resulted in the 25207 by vector pTMadap-stuffer1-short. The sequence of stuffer1-short fragment is shown in SEQ ID NO:13.

2(a)-5 Creation of pTMadap-Stuffer1-Short-Stuffer2

The plasmid p2-2 (SEQ ID NO: 14, obtained from GenBank) was cut with NotI and the resulting fragment of approximately 5954 by (stuffer 2, SEQ ID NO: 15) was inserted into the NotI site of pTMadap-stuffer1short, resulting in pTMadap-stuffer1-short-stuffer2.

2(a)-6 Removal of PacI Site from pTMadap-Stuffer1short-Stuffer2

Figure 2:
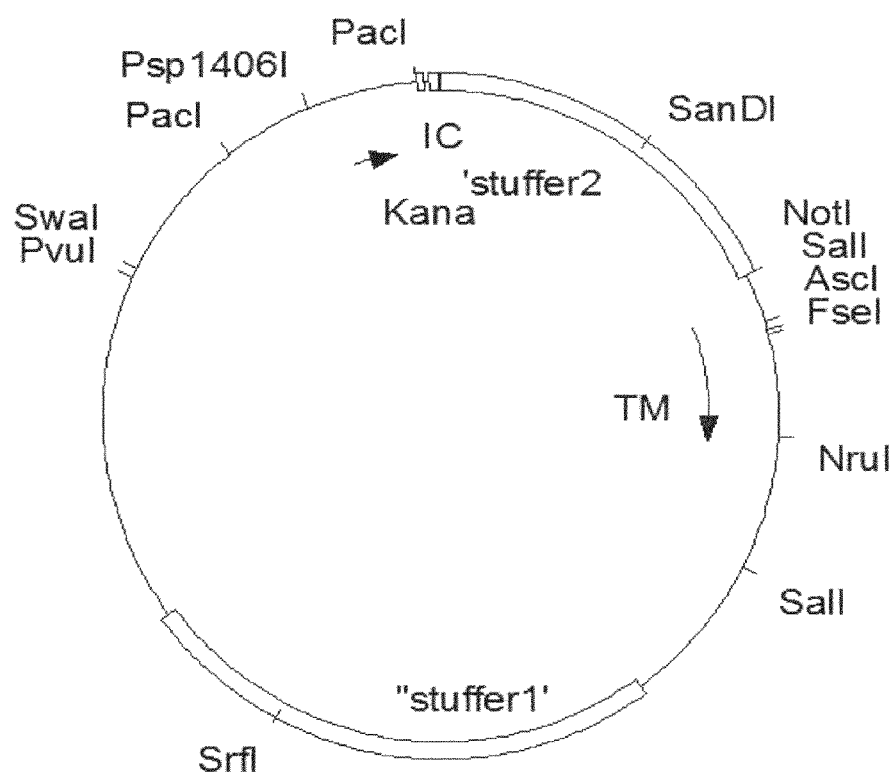
FIG. 2 is a schematic drawing of an embodiment of the full length backbone vector pTM-final.

Plasmid pTMadap-stuffer1-short-stuffer2 was cut with AclI and BsiW1. The resulting 28790 by fragment was isolated from gel. pShuttle-ITR-HPRT (SEQ ID NO:1) was cut with AclI and Acc65I. The resulting 1966 by fragment was ligated into the isolated 28790 by fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette, pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

Example 3

Preparation of Gutless Adenovirus Carrying Human Thrombomodulin Gene (gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 µg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETON. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/mL. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris—pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5, 10, and 15 μg/ml. (BSA is fine). Sample cuvettes were prepared using 1-10 μl of sample, depending on estimate of titer. (Sample OD must be within the linear range of the standard line.) OD was taken at 5957 and formula of the line was calculated from standards. The protein concentration of the samples was calculated using this formula. The following formula was used to convert protein concentration to titer: $[12.956+224.15 (\mu g/ml)] \times 10^8$.

Example 4

Figure 3:
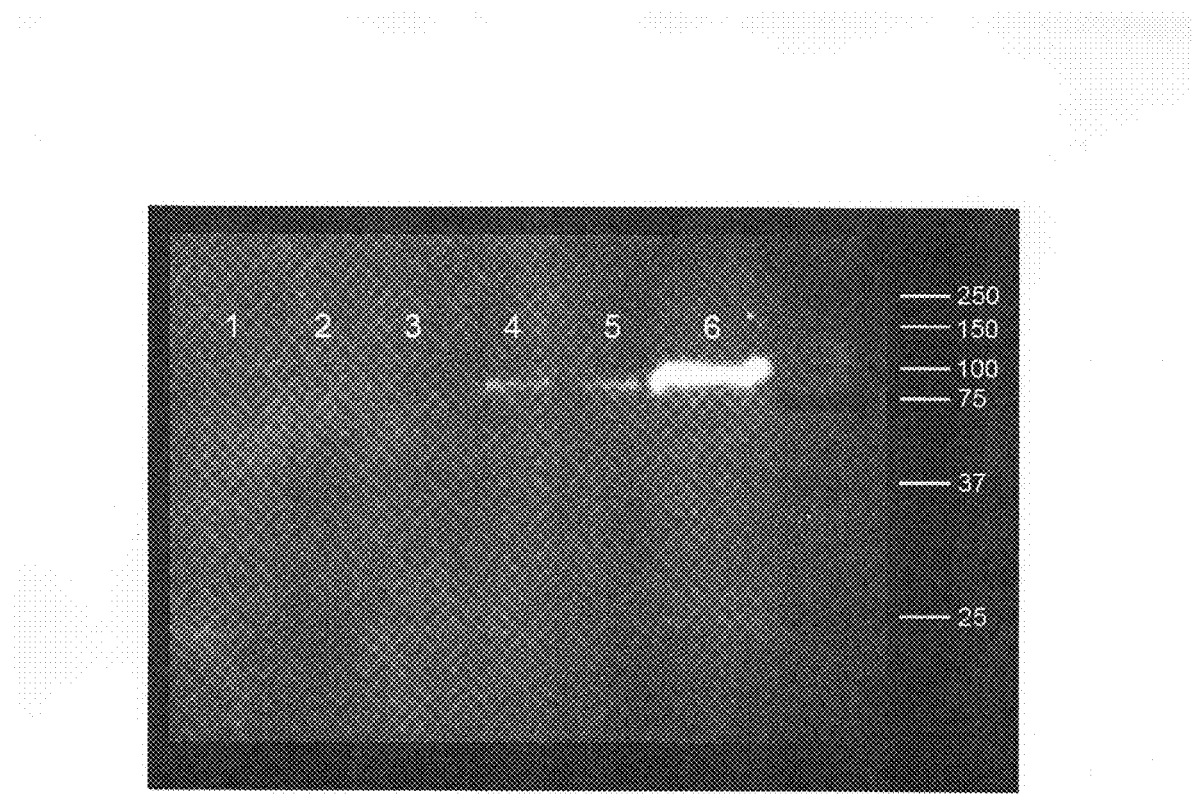
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 μg of pTM-final. After 24 hours, the cells were washed with PBS and lysed in 1250 RIPA buffer with protease inbitors Protein samples (16 μl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 μl Igepal ca-630, 50 mg sodium deoxycholate, 500 μl 20% SDS, 10 mM β-mercapto ethanol, and 1 ml 10×PBS, and add water to a final volume of 10 ml at room temperature. A cocktail of protease inhibitors containing 11.5 μl PMSF (from 34.8 mg/ml in isopropanol, 64 μl Benzamidine (from 15.6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(B) Expression of hTM in P2 Lysate of 293FLP Cells

Figure 4:
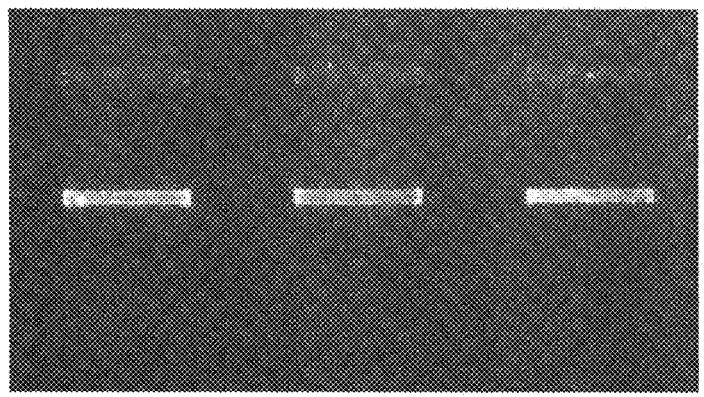
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 μl RIPA buffer. 7 ul of 5× loading buffer was added to 35 μl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 μl PMSF (from 34, 8 mg/ml in isopropanol, 64 μl Benzamidine (from 15, 6 mg/ml stock), 100 μl sodium orthovanadate (100 mM), 5 pepstadine (from 1 mg/ml stock), 1 μl leupeptine (from 5 mg/ml stock), and 1 μl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
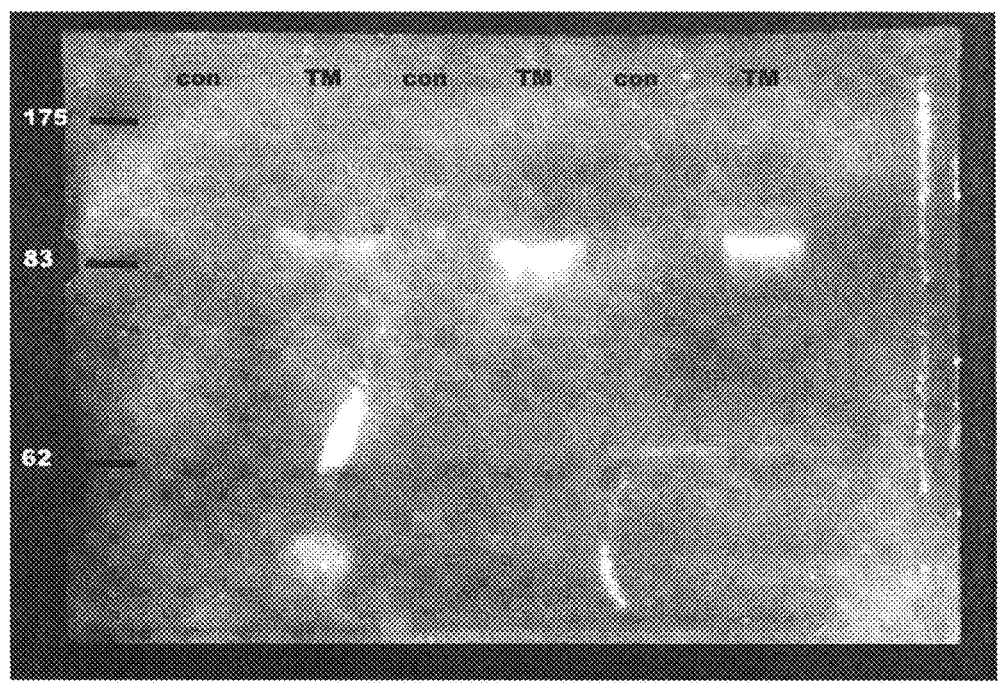
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with Pad, 293CRE cells were cultured in a 60 mm dish at 80% confluency. Cells were transfected with 5 μg of Pad digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P-1. This procedure was repeated until P=6.

Figure 6:
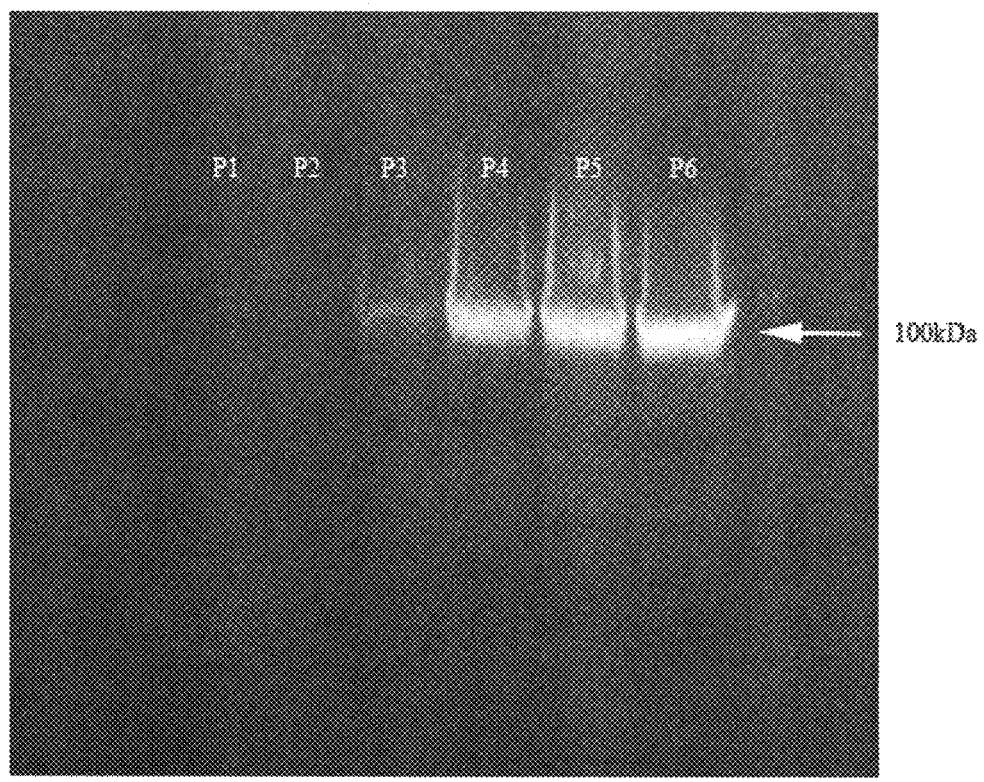
FIG. 6 is a picture of a Western bolt showing TM expression in CRE cells at passage number 1-6 (P1-P6).
Figure 7:
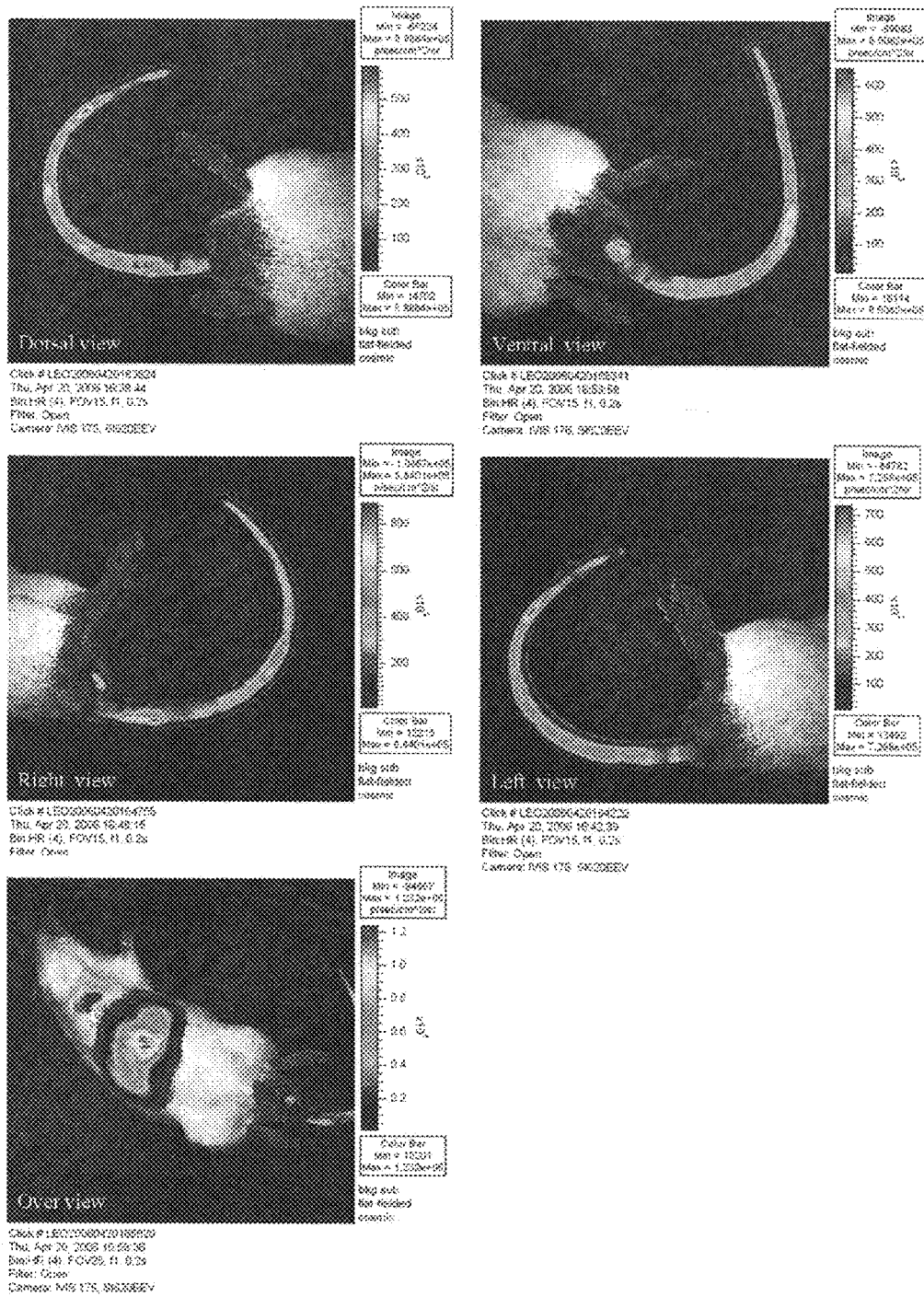
FIG. 7 is a composite of images showing gutless adenovirus-mediated luciferase expression in rat tail vein.

HEK 293 cells were cultured in a 6 well cluster and transfected with 200 µl of TM gutless virus of passage 1-6. After 24 hours, the cells were washed with PBS and lysed in 125 µl RIPA buffer. Protein samples (16 µl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 µl Igepal ca-630, 50 mg sodium deoxycholate, 500 µl 20% SDS, 10 mM β-mercapto ethanol, 1 ml 10× PBS, add water to make up 10 ml. Immediately before use, the following protease inhibitors were added to the RIPA buffer: 115 µl PMSF (from 34.8 mg/ml in isopropanol), 64 µl Benzamidine (from 15.6 mg/ml stock), 100 µl sodium orthovanadate (100 mM), 5 µl pepstatin (from 1 mg/ml stock), 1 µl leupeptin (from 5 mg/ml stock), 1 aprotin (from 5 mg/ml stock).

Example 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

Example 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

Example 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

Example 8

In Vivo Expression of TM by Intravenous Infusion of Viral Vectors

Material and Methods

Infection with gutless TM virus: 3 male Wistar rats weighing approximately 300 grams were intravenously injected in the tail vein with a low dose of gutless TM virus (approximately $2 \times 10^{10}$ viral particles) in a total volume of 500 ul of sucrose buffer. After three weeks, the animals were sacrificed and liver tissue and blood plasma was collected and immediately frozen in liquid nitrogen.

TM expression in the liver was determined by western blotting. Approximately 500 mg of liver tissue was homogenized in 2 ml of RIPA buffer. Liver protein samples (20 µg) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins.

Detection of rat Anti-TM antibodies in the plasma of TM infected rats: HEK 293 cells were cultured in a 6 well cluster. 3 wells were infected with 100 µl of TM gutless virus (approximately $4 \times 10^9$ virus particles) and 3 wells received no virus. After 24 hours, non-infected and TM infected cells were washed with PBS and lysed in 125 µl RIPA buffer. Protein samples (16 µl) were separated on a 7.5% polyacrylamide/SDS gel and transferred to nitrocellulose membrane. Blots containing protein from both TM expressing cells and non-infected cells were incubated with primary antibody TM (c-17) (1:2000, Santa Cruz) or plasma from TM infected rats (1:20, 1:100 and 1:1000 dilution). Detection of primary antibodies was performed using Polyclonal Rabbit Anti-Goat Immunoglobulins/HRP (1:4000, DakoCytomation) and Polyclonal Rabbit Anti-Rat Immunoglobulins/HRP (1:4000, DakoCytomation), respectively. RIPA buffer was prepared as described in Example 4.

Figure 8:
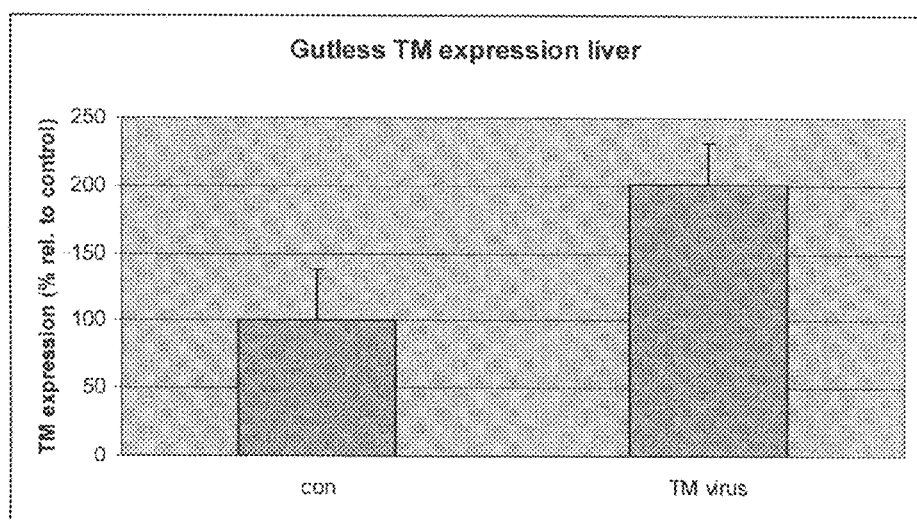
FIG. 8 is a diagram showing TM expression in livers of non-infected rats (con) and TM gutless virus infected rats (TM virus).

TM expression in the liver: No adverse effects of the injection of gutless TM virus could be detected. Animals displayed normal growth characteristics and did not suffer from excessive bleeding. Three weeks after injection, animals were sacrificed and no internal bleeding could be detected. Liver TM expression was evaluated using western-blot. TM expression was elevated two-fold above background levels, indicating modest over-expression of TM gutless virus in the liver three weeks after infection (FIG. 8).

Figure 9:
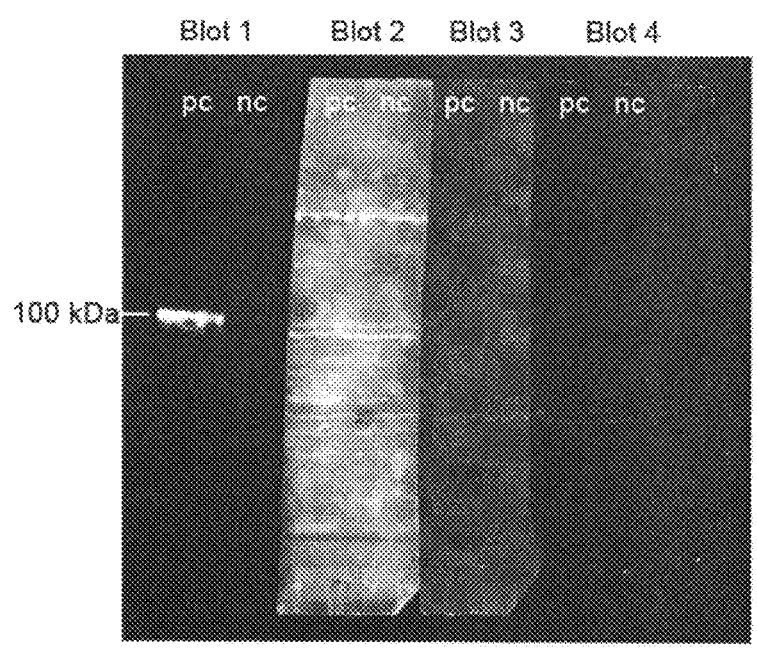
FIG. 9 is a picture of Western blots using a anti-TM antibody (blot 1) and plasma from animals infected with TM virus (blots 2-4).

To detect TM antibodies in the plasma of rats infected with the gutless TM virus, four western blots were made. Each blot contains a protein sample from human cells expressing TM (positive control) and a sample from the same cells that do not produce TM (negative control). Blot 1 was probed with a commercial antibody against TM (FIG. 9, blot 1), indicating the presence of human TM only in the positive control lane. Blots 2, 3 and 4 were probed with plasma from animals infected with TM virus in the dilution 1:20, 1:100 and 1:1000, respectively. Although some immunoreactivity is observed, the plasma of rats did not lead to the specific detection of TM in the positive control lane. Therefore, the plasma of these rats do not contain detectable levels of rat IgG antibodies against human TM.

Conclusion: Intravenous administration of low dose gutless TM virus into rat tail vein resulted in modest expression of TM in the liver of the recipient rats three weeks after injection. The viral injection did not result in the production of IgG antibodies against TM.

Example 9

Adenovirus-Mediated In Vivo Gene Transfer to Vena Cava

Inbred male Brown Norway rats (BN/rijHsd, Harlan, Netherlands) with an age of 11 weeks were used. Animals were housed in a light and temperature controlled environment and fed standard rodent chow and water ad libitum. Rats were anaesthetized with isoflurane (3% in $O_2$). The vene cava with the branches was exposed by a mid-line incision. The vene cava was clamped just below the vene renalis of the left kidney. All accessible sidebranches of the vena cava in the region between the vena renalis and the bifurcation were also clamped. The virus particles were administered through an insulin syringe (29-gauge needle) with a volume of 290 ul containing $2\times10^{11}$ virus particles. After injection of the viral solution, the syringe with needle was not removed from the vena cava but remained in place during the following incubation period of 20 minutes. Subsequently, the clamps on the sidebranches of the vene cava were removed. The transfected segment of vena cava was washed by making a puncture with a needle 25-gauge needle just below the clamp near the vena renalis. The expelled blood containing excess virus was absorbed with a cotton bud. After bleeding a volume of approximately 0.5 ml, the bleeding was stopped by applying a pressure on the puncture site with a cottonswab. Subsequently, the clamp near the vene renalis was released and the abdomen was sutured. For post-operative pain relief, the rats received buprenorphin (Temgesic®) 10 µg/kg subcutaneously. The rats were allowed to recover with access to water and food ad libitum.

Two days after the transfection procedure, rats were anaesthetized with isoflurane (3% in $O_2$). The vene cava was exposed by a mid-line incision and clamped just below the vena renalis of the left kidney. The abdomen was temporarily closed during the incubation time of 2 hours. Subsequently, the abdomen was reopened and blood was collected from the aorta. The vena cava was harvested from the bifurcation till above the clamp. The vene cava was opened longitudinally and the thrombus was removed and placed in saline for size evaluation. The results of the experiment were summarized in Table I.

TABLE I

Vena cava thrombus in the experimental animals

| Group | Thrombus size in individual animals |
|---|---|
| sucrose | 1623.98 |
|  | 1507.23 |
|  | 239.84 |
|  | 398.25 |
|  | 107.97 |
|  | 32.24 |
|  | 85.40 |
| gfp virus | 97.00 |
|  | 107.13 |
|  | 158.93 |
|  | 0.00 |
|  | 89.04 |
|  | 87.63 |
|  | 1281.56 |
|  | 137.13 |
| TM virus | 0.00 |
|  | 280.04 |
|  | 0.00 |
|  | 0.00 |
|  | 140.21 |
|  | 60.65 |
|  | 0.00 |
|  | 108.69 |

Example 10

Adenovirus-Mediated Gene Transfer to Kidney Via Intravenous Infusion

This example describes the procedure for slowly infusing a recombinant adenovirus into the renal circulation. Male Sprague-Dawley rats (100-150 g) were injected intramuscularly with 20,000 units of penicillin, anesthetized with ketamine (70 mg/kg, ip) and xylazine (7 mg/kg, ip) and underwent surgical exposure of the right kidney, the aorta and the right renal blood vessels. The right renal blood flow was interrupted by clamping the aorta above and below the right renal artery and the superior mesenteric artery (SMA). This setting selectively excluded the right kidney without interrupting the blood circulation through the left kidney and allowed infusion of virus into the right kidney through the SMA. A 27-gauge winged infusion needle was inserted into the SMA and fixed in place with a microaneurism clamp. 1.5 ml of recombinant adenovirus in phosphate buffered saline (PBS) containing 5 units of heparin/ml were slowly infused into the right kidney with a Razel A-99 syringe pump at a flow rate of 0.1 ml/min. The right kidney was packed with ice during the infusion to minimize ischemic damage. Renal circulation was reestablished at the end of infusion. The abdominal cavity was closed with sutures. The animal was placed on a warm pad to recover from the anesthesia and was returned to its cage after recovery.

Example 11

Adenovirus-Mediated Gene Transfer to Kidney via Balloon Catheter

In this application, a catheter is inserted in a vein near or in the kidney. Both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

Example 12

In Vivo Treatment with Virus Containing Stent

In this application, a virus-coated stent is placed at a treatment site in or near the kidney. Alternatively, the virus may be embedded in the stent and is releases gradually through a time-releasing mechanism well-known to one skilled in the art.

Example 13

Construction of Gutless Adenovirus Vectors Carrying the IDO Gene

Rat and human IDO cDNA were amplified by RT-PCR using the following set of primers:
Forward Primer (Containing a FseI Restriction Site):

```
                                           (SEQ ID NO: 17)
5'-TATTTATTGGCCGGCCGCGTTAAGATACATTGATGAG-3'
```

Reverse Primer (Containing a SbfI Restriction Site):

```
                                           (SEQ ID NO: 18)
5'-TATTTATTCCTGCAGGTCGTAGGTCAAGGTAGTAGA-3'.
```

The amplified rat IDO cDNA (SEQ ID NO:19) and human IDO cDNA (SEQ ID NO:20) were cloned into expression plasmids pAdTrackCMV-rIDO and pAdTrackCMV-hIDO, respectively.

Expression cassettes comprising a CMV promoter, IDO cDNA and poly-adenylation signal were constructed using PCR. PCR primers were equipped with additional restriction enzyme sites to facilitate cloning into the gutless backbone vector.

Forward Primer (Containing a FseI Restriction Site):

```
                                           (SEQ ID NO: 17)
    tatttattggccggcCGCGTTAAGATACATTGATGAG
```

Reverse Primer (Containing a SbfI Restriction Site):

```
                                           (SEQ ID NO: 18)
    tatttattcctgcaggTCGTAGGTCAAGGTAGTAGA
```

Figure 10:
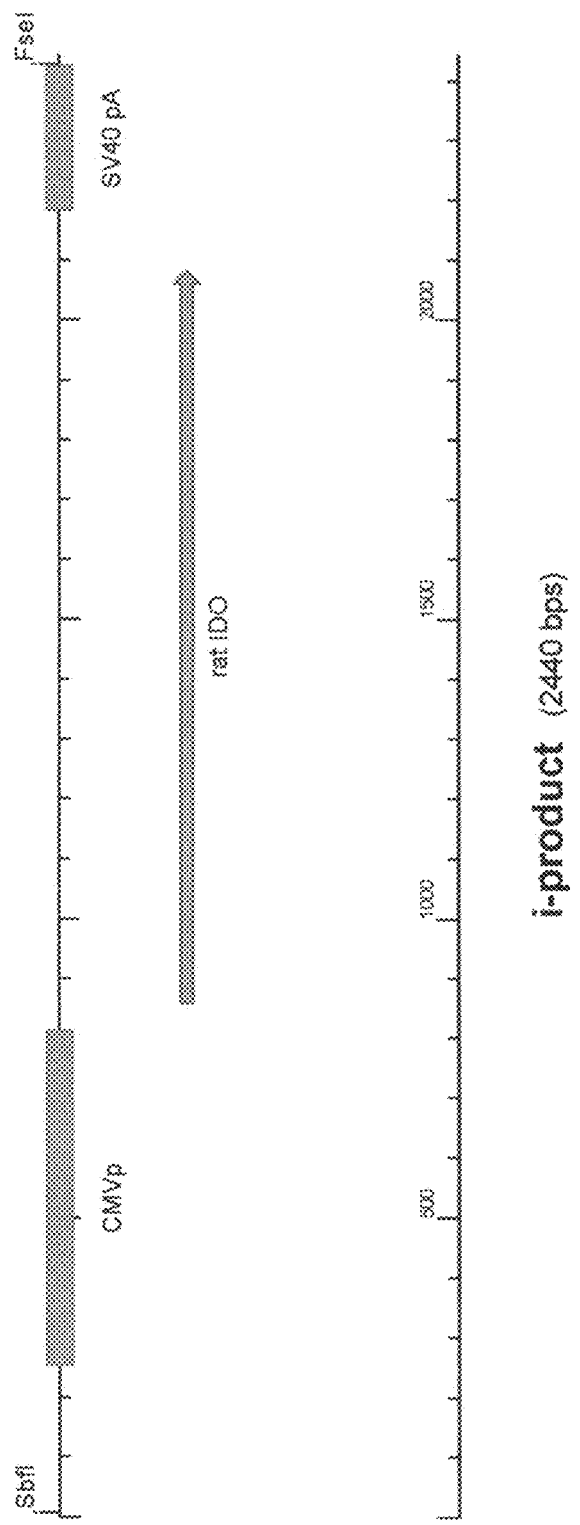
FIG. 10 is a schematic drawing of an embodiment of the rat IDO expression cassette.
Figure 11:
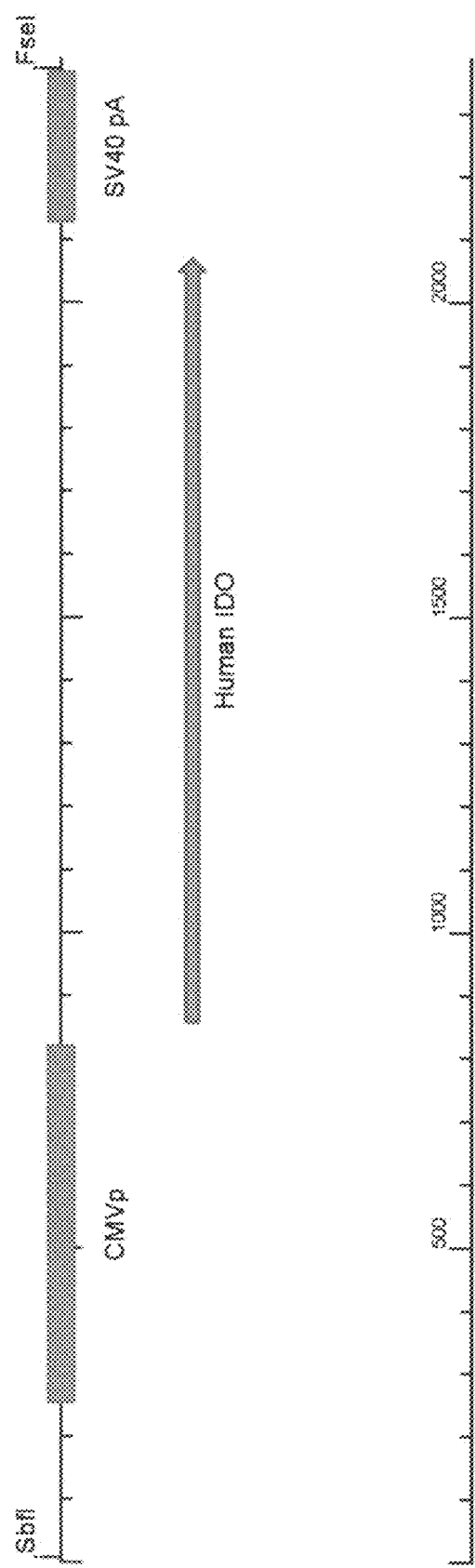
FIG. 11 is a schematic drawing of an embodiment of the human IDO expression cassette.

The resulting PCR fragments were cloned into pGEM-T-EASY for sequencing and cloning. Sequencing confirmed the presence of rat IDO expression cassette (FIG. 10, SEQ ID NO:21) and human IDO expression cassette (FIG. 11, SEQ ID NO:22).

Figure 12:
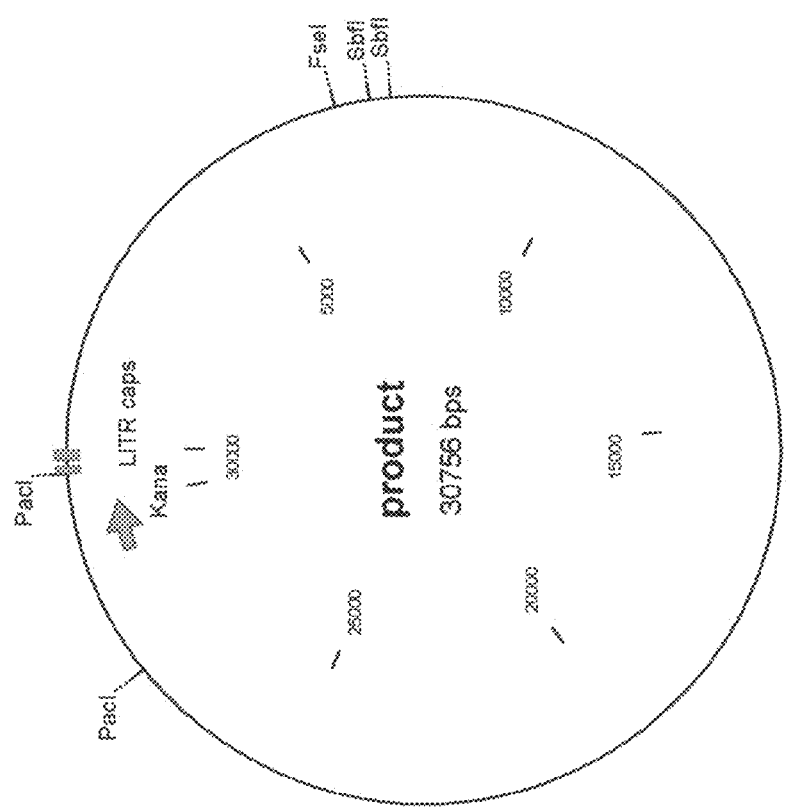
FIG. 12 is a schematic drawing of a gutless backbone vector.
Figure 13:
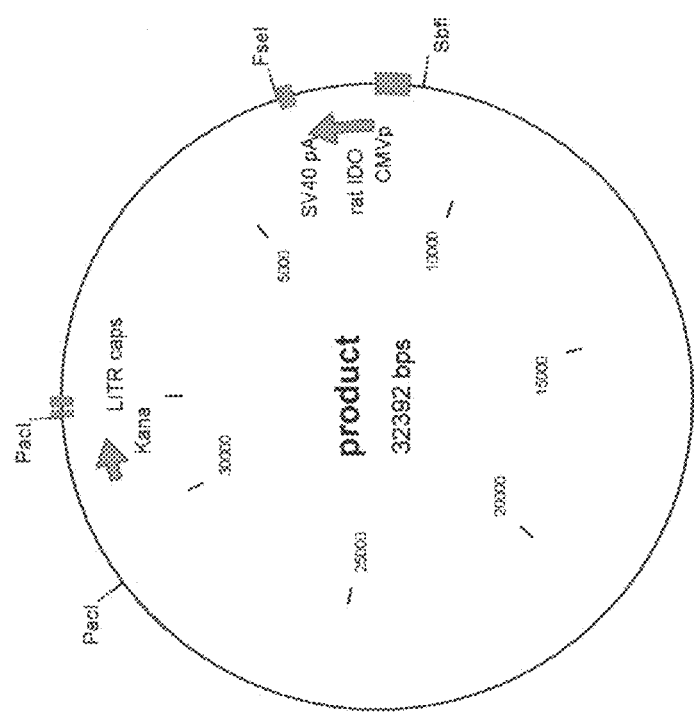
FIG. 13 is a schematic drawing of an embodiment of the rat gutless IDO backbone vector.
Figure 14:
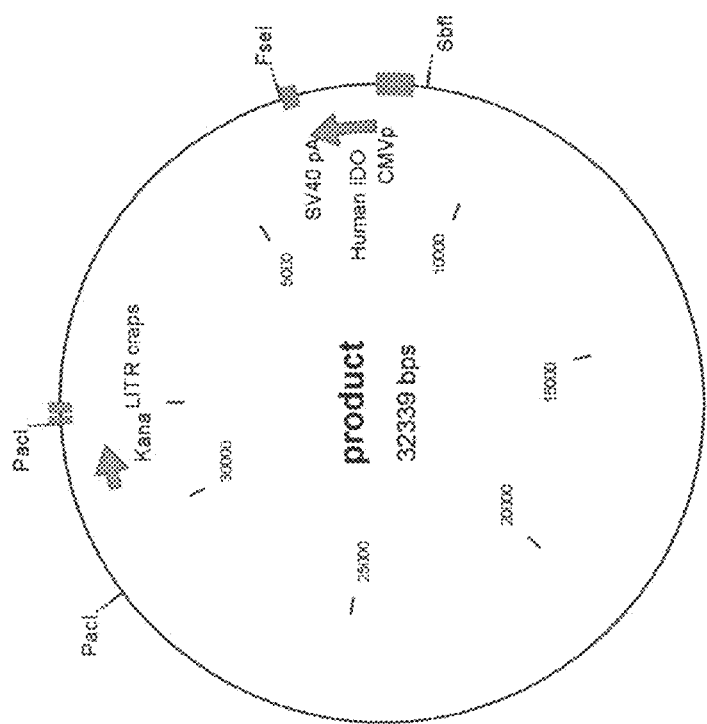
FIG. 14 is a schematic drawing of an embodiment of the human gutless IDO backbone vector.

The gutless backbone (SEQ ID NO:23, FIG. 12) was cut with SbfI and FseI to release the TM expression cassette. The backbone was subsequently dephosphorylated to prevent vector self-ligation. Rat and human IDO expression cassettes were released from pGEM-T-Easy by digestion with FseI and SbfI and ligated into the FseI and SbfI sites of the gutless backbone. The resulting constructs prIDO-final (FIG. 13, SEQ ID NO:24) and phIDO-final (FIG. 14, SEQ ID NO:25) were cloned in E-coli DH5α. DNA midipreps were generated for the production of high quality plasmid DNA. Gutless adenovirus containing rat IDO or human IDO was produced using the procedure described in Example 3.

Example 14

Perfusion of Kidney Transplant with Gutless Adenovirus Vectors Carrying the IDO Gene The experiment was carried out in Fisher-Lewis kidney transplantation model. Gutless adenoviruses carrying the IDO gene (Ad.TIDO) or luciferase gene (Ad.TL) were surface-modified with cyclic arginine-glycine-aspartic acid (RGD) peptides through a bifunctional poly(ethyleneglycol) linker for integrin alpha(v)beta(3) specific delivery. The resulting RGD modified viruses were designated RGD-Ad.TIDO and Ad.TL. The transplanted kidneys were incubated with either RGD-AdTIDO (n=6) or RGD-AdTL (n=5) at 4° C. for 20 min with saline. The transplanted animals were sacrificed at day 7. The transplanted kidneys were isolated and subjected to Western blot and immunohistological examination.

Figure 15:
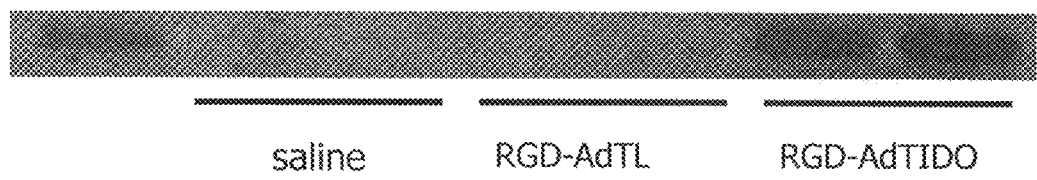
FIG. 15 is a picture of a Western blot showing gutless adenovirus mediated IDO expression in transplanted kidney (lane 1=hIDO control, other lanes as indicated)

As shown in FIG. 15, IDO expression was detected in the kidneys infected with RGD-AdTIDO but not in kidneys infected with RGD-AdTL. FIGS. 16A-16D shows that, comparing to kidneys perfused with saline or control virus (RGD-AdTL), kidneys infected with RGD-AdTIDO showed reduced plasma creatinin levels (FIG. 16A). Kidneys infected with RGD-AdTIDO also showed reduced tissue damage, as evidenced by the reduced ED-1 staining (FIG. 16B), reduced macrophage influx (FIG. 16C, CD-8 staining for T-lymphocytes), and reduced fibrotic response (FIG. 16D, staining for smooth muscle actin).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for modulating an immune response in a kidney allograft recipient, comprising:
   perfusing a kidney harvested from an organ donor with an effective amount of a gutless adenovirus carrying a nucleotide sequence encoding an immune modulator and a regulatory element operably linked to said nucleotide sequence; and
   transplanting the perfused kidney into a subject in need of a kidney transplant,
   wherein said gutless adenovirus expresses said immune modulator in said kidney,
   wherein said immune modulator is indoleamine dioxygenase, and
   wherein the gutless adenovirus is administered in an amount sufficient for reducing plasma creatinin levels, reducing tissue damage, reducing macrophage influx or reducing a fibrotic response in said recipient following transplantation, as compared to the amount observed in a control organ that received only saline.

2. The method of claim 1, wherein said regulatory element comprises a constitutive promoter or a renal-specific regulatory element.

3. The method of claim 2, wherein said renal-specific regulatory element is a renal-specific promoter.

4. The method of claim 3, wherein said renal-specific promoter is selected from the group consisting of high-capacity (type 2) Na+/glucose cotransporter gene (Sglt2)promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

5. The method of claim 1, wherein said gutless adenovirus vector comprises a stuffer comprising the nucleotide sequence of SEQ ID NO:13 or SEQ ID NO:15.

6. The method of claim 1, wherein said kidney is perfused with said gutless virus for a period of 10-120 minutes.

7. The method of claim 1, wherein said gutless adenovirus is suspended at a concentration of $10^9$-$10^{12}$ particles/ml.

8. A method for modulating an immune response in a kidney allograft recipient, comprising:
   perfusing a kidney harvested from an organ donor with an effective amount of a gutless adenovirus carrying a nucleotide sequence encoding an immune modulator and a regulatory element operably linked to said nucleotide sequence; and
   transplanting the perfused kidney into a subject in need of a kidney transplant,
   wherein said gutless adenovirus expresses said immune modulator in said kidney,
   wherein the gutless adenovirus is administered in an amount sufficient for reducing plasma creatinin levels, reducing tissue damage, reducing macrophage influx or reducing a fibrotic response in said recipient following transplantation, as compared to the amount observed in a control organ that received only saline, and
   wherein said gutless adenovirus vector comprises the nucleotide sequence of SEQ ID NO:21 or SEQ ID NO:22.

* * * * *

SEQUENCE LISTING

```
<160> NUMBER OF SEQ ID NOS: 25

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid
```

<400> SEQUENCE: 1

```
catcatcaat aatataccct atttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacgatg tggcaaaagt gacgttttg      180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tactggtacc gcggccgcct    360
cgagtctaga actagtggat cccccgggct gcaggaattc tgatggctct caaaattcct    420
gcctccttta gggataaaag actttaagac tttttaacaa aaaagaaaaa gaaaaaaaaa    480
attcctgcct cctggtgtac acacacgaaa gggttccctc cccttgaatg tgaccaggat    540
ctgtgaaaat aacgggatag ccgctcctgt gattaggtta tgtggtagac tagagcaaga    600
ttctcctgct ggttttgaag aagtcagctg ccatgttgtg agactgtcat gggctagggc    660
atgagccttt aaatatctgg gagcaacccc tggccagcag ccagtgagaa acgggccct     720
cagtcctaca atcacaagga actaaattct gccaacaacc tgaaggaact ttgaagagga    780
tcatgagtcc cttgattcag cttgatgagc ccctgagcag aggatacagc taacttgtac    840
tagggaagta taaaaaacat gcatgggaat gatatatatc aactttaagg ataattgtca    900
tacttctggg aatgaaggga agaaatgggg gctttagttg tattatgatc tttaatttct    960
caaaaaaaat aagatcagaa gcaaatatgg caaaatgtta atacttttgt gggtacgtag   1020
gtattcagca tacccttttt tctgagttca aaatatttta taattaaaat gaaatgcagg   1080
ccaggcacag tggctcatgc ctataatacc agcactttgc gaggccgagg tgggaggatg   1140
gcttgaggcc agaccagcct ggccaacatg gcaaaacccc atctctactt aaaaaaaaaa   1200
aaactatata tatatatatg tgtgtgtgtg tgtatatata tatatgtata tatatttata   1260
tatgtgtgta tatatatata tgtatatata tttatatatg tgtgtgtata tatatatata   1320
cacacacaca catatataca tacatacata cacacacaca cacacacaat tagccaggca   1380
tggtggcgca cacctgtagt cccagctact tgggaggctg agacatgaga attgcttgaa   1440
cctgggaggc agagtagtta gtgagctgag atcataccac tgcactccag cctggtgaca   1500
gagtgagact ctgtcttaaa aaaataaaa attaaaatta aatgcaaaag gtccaagtga   1560
attgaagagg aaaggggtat caaggaaggt tttgtggagg tgacgtttga gctgggtctt   1620
aaatgactta aacatgggat aagaagggag ggaataagga catttcaggt acgagaaata   1680
aggagcaaac agtggaaaca acctaacgtc tgtcaaccag tgaatggata acaaaaatgt   1740
aattcagatg gtatccaact tacgatggtt caacatgaga tttttctgac tttaggatag   1800
atttatcaaa gtagtaaatc cattttcaac ttatgatatt ttcaacttca gatgggttta   1860
tcaggacaca gttgaggaac acctgtctat ccatacaatt tggcaataaa aaggaaatga   1920
gtgcagatat actccacaac atgaatgaac cttgaaaaca ttaagtgaga gaagccagat   1980
acaaaaggcc acatattgta tgattctatt tatacaaaat gtccagaata ggcaaatctt   2040
atagacagca gtaggtaga tgatcagttt gctaggtgct gggggaaggg gaaatgggga    2100
gtgatggcta agggattgg gtttcttgt ggggcaatga aaatgtttta aaattgagcg     2160
tgataatgat tgcacaatgc tgcatatata tataatctat agattatata tatataaaga   2220
gaggctgtta gacagtgata agtgatatat atatatatat acatagagag agagagagag   2280
agagagagag gctgttagtg ataagtgatc aggaaaataa aagtattgag gaggaatacg   2340
```

```
aagttgacgg tgtgaaaaca tgagatttta tataggatgg ccagggaagg ccttaatgag   2400
aaagtgactt atgagtaaaa acaagggatc ctaaaccttta gcatgcatca gaatcactcg   2460
gaaacttgtt aaagcatagc ttgctgggcc tcatcacaga tattttgatt cggtaggttc   2520
ttgtctgata ttaatacttt tggtctaggg aaccacattt tgagaaccac tgagctaaag   2580
gaagtaaagg tttcccttag tttactagct ggtaaccctta ggaaactgct tagcctctcg   2640
gtgctaagat acaaaatact ttagcacata ataacacatg gaaaatagtc tataaattat   2700
aaatattatt ttttatgtac caaatattac ataagacaaa atctaagcaa gatatatata   2760
tatatacata aaatataaga tatatatgta tatattatat atagataaat agagagagag   2820
agttatgttt agaaagaaaa tacttcaaac taaaaaaaga gaggtaggaa gtataccatt   2880
ccattattgg taaaaacaaa ttactaagta gtctttacaa aaaaccaatc tcactccttt   2940
agaacacaag cccaccatta aaactgatgc agaggaattt ctctccctgg cttacctttta   3000 ggatggtgca tactaagtta gaaaagtcat aaatgttata ttaaaagtaa atgtgaactt   3060
acttccacaa tcaagacatt ctagaagaaa aagagaaatg aaaatcagta caatgaataa   3120
aacggtattt ccaattataa gtcaaatcac atcataacaa ccctaaggaa ttatccaaac   3180
tcttgttttt agatgcttta ttatatcaaa ctctccttta aacaagtggc ccatctgctg   3240
ggatttggaa gcctgtaata ctgaaatttt catcataatg gaaattttaa aaacagaatt   3300
tgacccacct gttttttaaaa cactttcatt acttaacaag aggtctaatc ttgggcaagt   3360
cttgaaattt ctctggcctt agtttcccat gtgttaaatg aaacttgaag cagttggtct   3420
cttatagtct cctgactcta acattctaag aattatattt gtacaataac tcaaaaatca   3480
cataatttaa tttaccatat ggactccaaa atatattttc tcattaggct aaacttgatc   3540
tgcattttct ggatgtgtcc atattcttgg actacactaa acatgatac caatgcttcc   3600 tctcaccata aaccctcact tcgctttcta catttaagaa ttttatagct ggaagagtcc   3660
ttaacagaaa ataccatcta ataattaccc ctcaaaatcg agaaagtcct atctgttctt   3720
atgctagtta taagaatgag gcagcatttc acataatggt tataaacact gccacaagaa   3780
gattcatgat gtgttgttta tctgtagctc tcatcatact ctgtcatata actatagcat   3840
taagatttta atgttctata tattcttcta agacagtgtt taccagagta aggcacaaaa   3900
gatccactgg tttgcaagaa agattagaac ttttaaattt tttacctcac cttgtttaat   3960 ctatatttttt gtatgtattt tgtaacatat atattattat taccataaat catatataat   4020
ttaaaatgca tatattaggg gtaaatgctc aggaaacttt ttataaattg ggcatgcaaa   4080
tacaagtttg aagactcact gttctaggta ttaaaagtaa agttataacc aagtaaagct   4140
tccacctttt catgtctcaa agcagtttat tgttggaggt aagatctctt agaagcctaa   4200
acaggtccaa gtacagaatg aagtaaggct agcccataac ttgtggcaag caattcatac   4260
tatttctctc atgctgagct ctcctcagtg aagcagctac tatagacaac tgcagcctat   4320
tggtagccta ttttacaggc aggaaaaaaa ttacttttta ttcaaagtgg aactcaggac   4380
atggggagaa aatgaataca aaaaatagg tcaatccaaa ggcacacagc aaatgagtaa   4440
cacagttatg tttttttccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaaacaaaa gaatgccatt attgagtttt tgaattatat   4620
caagtagtta catctctact taataaatga gaaaacgag gataagaggc catttgataa   4680
aatgaaaata gccaagaagt ggtattagag acttgaatac aggtattcgg gtccaaagtt   4740
```

-continued

```
catctgctca aatactaact ggggaaaaga gggaaaaata tttatataca tatatatctg    4800
cacacaaaaa taccccccaaa agacaaaatg aggccaggca gggtggctca cacccgtaat    4860
cccggtactt tggagggctg aggcaggtgg atacctgaga tcaggagttg agatcagcc    4920 tggtcaacat ggtgaaaccc tgtctctact aaagataaaa aaattagcca ggcatggtgg    4980
cgtgcgcctg taatcccagc tacttgggag tctgaggcag gagaatcact tgaactggga    5040
aggggaggtt gcagtgagcc aagatcgtac tactgcactc cagcctgggc agcagagtga    5100
gactccatca caaaaataaa taaataaata aaatacaatg aaacagaaag ttcaaataat    5160
cccataatct taccaccaag aaataacttt cactcgttat acttattgat ttttccataa    5220
taaatgtact ttactgtgac tatcatgaaa agaaagttat tttagaaaca gagaactgtt    5280
tcagatcaaa tctatgtagt agaacagagc cattaggtgg gaaagacgag atcaaactaa    5340
atctcagaag gcctaaaagg ctaggtccat ccagcacta aaaactgacc agacaagtaa    5400
tggcttcaac agcttctaaa tatggacaaa gcatgctgaa agggaaggac aggtctaaca    5460
gtggtatatg aaatgaacag gaggggcaaa gctcatttct cctctgaagt tttccaaaga    5520
tgctgaggag gacattagtt tgacatgacc ctgatatggg acaagataat ttcacagaag    5580
ttttacatgt taaagttttc ttatagatac tcattcaagt aagcaatgaa cactaaaatc    5640
taaagaaaga aaagagcttt agagtcaggt ctgtattcaa attcaagctc taccacttac    5700
tggttctgtg actttgggca agtcttttaa ccttattaag tcttaatttc ctgatttgta    5760
aaatggggat atcgtctccc tcacaggatt gttgtgaaac ttttatgaga ttaatgcctt    5820
tatatttggc atagtgtaag taaacaataa ctggcagctt caaaaaaaaa aagcagtagc    5880
attccatcat ttattattgg ttactctcaa aaagttttc aatgtactag aagataaata    5940
ttcaaatacc ttaatatctc cattattttc aggtaaacag catgctcctg aacaaccaat    6000
gggtcaacaa ataaattaaa agggaaatct aaaaacatct tgatattaaa ctacatggaa    6060
gcacaatata ccaaaaccaa tggttcacac taggagaatt ttaaggtaca agaaaactct    6120
ttgagatttc ttaaaataat agtatgtctg aatttattga gtgatttacc agaaactgtt    6180
gtaagagctc tacttgcatt atagcactta atcctcttaa ctctatggct gctattatca    6240
acctcaccct aatcacatat gggacacaga gaggttaagt aacttgccca aggtcagagt    6300
taggaagtac taagccatgc tttgaatcag ttgtcaggct ccggaactca cactttcagc    6360
cactacataa tactgctttg ctatcttta ggaaactatg tgagtctacc tcacatagac    6420
tcacataggt ttgtttttt tttttttta aaggctatct tttccccccat caatgttttt    6480 tgaaggatcc caaattagag tcccacagag gcagacagca gtacttgaca atatggacat    6540
ttaaggttaa tgttggattc tactgtcttt ttactacatg acctagggaa cgataattaa    6600
cctagactgc ttccaagggt taaataaccc atttagttat actatgtaaa ttatctctta    6660
gtgattgatt gaaagcacac tgttactaat tgactcggta tgaagtgctt ttttttcttc    6720
cctttcaaga tacataccct tccagttaaa gttgagagat catctccacc aattactttt    6780
atgtcccctg ttgactggtc attctagtta aaaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt gatgttttta agagtcctaa    7080
aaaatgggtt acatccattt ttaagtgggt agtattataa cagccaccca tcttcaatca    7140
```

```
cagtgatttc tgaattgtga gggaagttat tagcatgaca ggtgtctggt tctggccctg    7200
tacgattccc atgagtcaag caaattgtaa gggctggtct atatcacacc caaccccaag    7260
gatatgtccc tcaaaagtct agcccaggcc ccgtcatctt cagcatcatc tgggaaacca    7320
ggtctgatta gtagtccttt aaggaatacc tcttaggctc ccattttact gctatcacag    7380
aatccaataa aacccttaca ggagattcaa tgggaaatgc tcaacaccca ctgtagttgg    7440
tggtgacaat gaccataatt tggctgtgct ggattcagga cagaaatttt gggtgaaaga    7500
gcaggtgaac aaaagagctt cgacttgccc tagcagagag caagccatac cataccacaa    7560
agccacagca attacaacgg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaaataaag ccataagtgg actggaagaa aatagagaat tttttttaac    7860
atccgtagaa agggtaaaaa cccaggcatg acatgaacca aaactgaaga ggttctgtaa    7920
caaatacccc cttttatata ttgggctcca acaataagaa cccataggaa atggagaat     7980 gaacacaaat agacaattta tagaagagaa ggttataagg tgtaaaatta tatctatctg    8040
agaaacaaac actaaacaa tgtgattcta ctgttctccc acccatactg gcaaaactta     8100
agcctgataa tatgctgagg ggaaataagc actcttgttg gtgagagtat taattggcat    8160
agcttctttt gaaatgaca tagcaatacc tgttaaaatt gcaaacatgc atgtcactta     8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tcttttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca ttttattca     8640 acatttaaac aaatttgtaa cagcaattac atgagtagtg acaatggcgt ttatgagact    8700
tttcactttt atgtgcttct attttgtta tgcttctata tatacatcca tttattatgg     8760
agtgttactt tcaaaaatca caatgggcc agtattattt ggtgttgcaa ggtgagcata     8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120 atgggagtcat ggaaaaattg ctgtgatcca aaggctacgg tgataggaca agaaacaaga   9180
gaactccaag cagtaagaca ctgctgttct attagcatcc aaacctccat actcctgttt    9240
gccccaaggc tttttaaaa atagagaca ggatctcact attttgctca ggctggtctt      9300
gaactcctgg actcaagcta tcctcctgcc tcggcctcct aaagtgccga gattacaggc    9360
ttgagtcacc atacctggct atttattttt tcttaactct cttgcctggc ctatagccac    9420 catgaagct aataaagaat attaatttaa gagtaatggt atagttcact acattggaat     9480
acaggtataa gtgcctacat tgtacatgaa tggcatacat ggatcaatta ccccacctgg    9540
```

```
gtggccaaag gaactgcgcg aacctccctc cttggctgtc tggaacaagc ttcccactag   9600
atcccttac tgagtgcctc cctcatcttt aattatggtt aagtctagga taacaggact    9660
ggcaaaggtg aggggaaagc ttcctccaga gttgctctac cctctcctct accgtcctat   9720
ctcctcactc tctcagcca aggagtccaa tctgtcctga actcagagcg tcactgtcaa    9780
ctacataaaa ttgccagaga agctctttgg gactacaaac atatacccctt aatgtcttta  9840
tttctatttt gtctacctct tcagtctagg tgaaaaaata ggaaggataa tagggaagaa   9900
ctttgtttat gcctacttat ccgcccctag gaattttgaa acctctagg tagcaataag    9960
aactgcagca tggtatagaa aagaggagg aaagctgtat agaaatgcat aataaatggg    10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttcttta ggatcctaga atggactttt ttttttatc ggaaaacagt    10260
cattctctca acattcaagc aggcccccaag tctaccacac tcaatcacat tttctcttca  10320
tatcataatc tctcaaccat tctctgtcct tttaactgtt tttctatacc ctgatcaaat   10380
gccaacaaaa gtgagaatgt tagaatcatg tattttaga ggtagactgt atctcagata    10440
aaaaaaaagg gcagatattc cattttccaa aatatgtatg cagaaaaaat aagtatgaaa   10500
ggacatatgc tcaggtaaca agttaatttg tttacttgta ttttatgaat tccctaaaac   10560
ctacgtcacc cgccccgttc ccacgccccg cgccacgtca caaactccac ccctcatta    10620
tcatattggc ttcaatccaa aataaggtat attattgatg atgttaatta acatgcatgg   10680
atccatatgc ggtgtgaaat accgcacaga tgcgtaagga gaaataccg catcaggcgc    10740
tcttccgctt cctcgctcac tgactcgctg cgctcggtcg ttcggctgcg gcgagcggta   10800
tcagctcact caaaggcggt aatacggtta tccacagaat caggggataa cgcaggaaag   10860
aacatgtgag caaaaggcca gcaaaaggcc aggaaccgta aaaaggccgc gttgctggcg   10920
ttttccata ggctccgccc ccctgacgag catcacaaaa atcgacgctc aagtcagagg    10980
tggcgaaacc cgacaggact ataaagatac caggcgtttc cccctggaag ctccctcgtg   11040
cgctctcctg ttccgaccct gccgcttacc ggatacctgt ccgcctttct cccttcggga   11100
agcgtggcgc tttctcatag ctcacgctgt aggtatctca gttcggtgta ggtcgttcgc   11160
tccaagctgg gctgtgtgca cgaaccccc gttcagcccg accgctgcgc cttatccggt    11220
aactatcgtc ttgagtccaa cccggtaaga cacgacttat cgccactggc agcagccact   11280
ggtaacagga ttagcagagc gaggtatgta ggcggtgcta cagagttctt gaagtggtgg   11340
cctaactacg gctacactag aaggacagta tttggtatct gcgctctgct gaagccagtt   11400
accttcggaa aaagagttgg tagctcttga tccggcaaac aaaccaccgc tggtagcggt   11460
ggttttttg tttgcaagca gcagattacg cgcagaaaaa aaggatctca agaagatcct    11520
ttgatctttt ctacggggtc tgacgctcag tggaacgaaa actcacgtta agggattttg   11580
gtcatgagat tatcaaaaag gatcttcacc tagatccttt taaattaaaa atgaagtttt   11640
aaatcaatct aaagtatata tgagtaaact tggtctgaca gttaccaatg cttaatcagt   11700
gaggcaccta tctcagcgat ctgtctattt cgttcatcca tagttgcctg actccccgtc   11760
gtgtagataa ctacgatacg ggagggctta ccatctggcc ccagtgctgc aatgataccg   11820
cgagacccac gctcaccggc tccagattta tcagcaataa accagccagc cggaagggcc   11880
gagcgcagaa gtggtcctgc aactttatcc gcctccatcc agtctattaa ttgttgccgg   11940
```

-continued

```
gaagctagag taagtagttc gccagttaat agtttgcgca acgttgttgc cattgctgca    12000
gccatgagat tatcaaaaag gatcttcacc tagatccttt tcacgtagaa agccagtccg    12060
cagaaacggt gctgaccccg gatgaatgtc agctactggg ctatctggac aagggaaaac    12120
gcaagcgcaa agagaaagca ggtagcttgc agtgggctta catggcgata gctagactgg    12180
gcggttttat ggacagcaag cgaaccggaa ttgccagctg gggcgccctc tggtaaggtt    12240
gggaagccct gcaaagtaaa ctggatggct ttcttgccgc caaggatctg atggcgcagg    12300
ggatcaagct ctgatcaaga gacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480 cttttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
gatccggcta cctgcccatt cgaccaccaa gcgaaacatc gcatcgagcg agcacgtact    12780
cggatggaag ccggtcttgt cgatcaggat gatctggacg aagagcatca ggggctcgcg    12840
ccagccgaac tgttcgccag gctcaaggcg agcatgcccg acggcgagga tctcgtcgtg    12900
acccatggcg atgcctgctt gccgaatatc atggtggaaa atggccgctt ttctggattc    12960
atcgactgtg gccggctggg tgtggcggac cgctatcagg acatagcgtt ggctacccgt    13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccaa taggccgaaa tcggcaaaat    13200
cccttataaa tcaaaagaat agaccgagat agggttgagt gttgttccag tttggaacaa    13260
gagtccacta ttaaagaacg tggactccaa cgtcaaaggg cgaaaaaccg tctatcaggg    13320
cgatggccca ctacgtgaac catcacccta atcaagtttt tggggtcga ggtgccgtaa    13380 agcactaaat cggaacccta agggagcccc cgatttaga gcttgacggg gaaagccggc    13440
gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                       13602
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80
```

-continued

```
Val Gly Arg Arg Arg Leu Trp Ile Gly Leu Gln Leu Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
            130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
            210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
            370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
            450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Ala Val Gly Leu
            500                 505                 510
```

Val His Ser Gly Leu Leu Ile Gly Ile Ser Ile Ala Ser Leu Cys Leu
     515                 520                 525

Val Val Ala Leu Leu Ala Leu Leu Cys His Leu Arg Lys Lys Gln Gly
530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
            565                 570                 575

<210> SEQ ID NO 3
<211> LENGTH: 1725
<212> TYPE: DNA
<213> ORGANISM: Homo sapiens

<400> SEQUENCE: 3

| | |
|---|---:|
| atgcttgggg tcctggtcct tggcgcgctg gccctggccg gcctggggtt ccccgcaccc | 60 |
| gcagagccgc agccgggtgg cagccagtgc gtcgagcacg actgcttcgc gctctacccg | 120 |
| ggccccgcga ccttcctcaa tgccagtcag atctgcgacg gactgcgggg ccacctaatg | 180 |
| acagtgcgct cctcggtggc tgccgatgtc atttccttgc tactgaacgg cgacggcggc | 240 |
| gttggccgcc ggcgcctctg gatcggcctg cagctgccac ccggctgcgg cgaccccaag | 300 |
| cgcctcgggc cctgcgcgg cttccagtgg gttacgggag acaacaacac cagctatagc | 360 |
| aggtgggcac ggctcgacct caatggggct cccctctgcg cccgttgtg cgtcgctgtc | 420 |
| tccgctgctg aggccactgt gcccagcgag ccgatctggg aggagcagca gtgcgaagtg | 480 |
| aaggccgatg cttcctctg cgagttccac ttcccagcca cctgcaggcc actggctgtg | 540 |
| gagcccggcg ccgcggctgc cgccgtctcg atcacctacg caccccgtt cgcggcccgc | 600 |
| ggagcggact tccaggcgct gccggtgggc agctccgccg cggtggctcc cctcggctta | 660 |
| cagctaatgt gcaccgcgcc gcccggagcg gtccaggggc actgggccag ggaggcgccg | 720 |
| ggcgcttggg actgcagcgt ggagaacggc ggctgcgagc acgcgtgcaa tgcgatccct | 780 |
| ggggctcccc gctgccagtg cccagccggc gccgccctgc aggcagacgg cgcgctcctgc | 840 |
| accgcatccg cgacgcagtc ctgcaacgac ctctgcgagc acttctgcgt tcccaacccc | 900 |
| gaccagccgg gctcctactc gtgcatgtgc gagaccggct accggctggc ggccgaccaa | 960 |
| caccggtgcg aggacgtgga tgactgcata ctggagccca gtccgtgtcc gcagcgctgt | 1020 |
| gtcaacacac agggtggctt cgagtgccac tgctacccta actacgacct ggtggacggc | 1080 |
| gagtgtgtgg agcccgtgga cccgtgcttc agagccaact gcgagtacca gtgccagccc | 1140 |
| ctgaaccaaa ctagctacct ctgcgtctgc gccgagggct tcgcgcccat tcccacgag | 1200 |
| ccgcacaggt gccagatgtt ttgcaaccag actgcctgtc cagccgactg cgaccccaac | 1260 |
| acccaggcta gctgtgagtg ccctgaaggc tacatcctgg acgacggttt catctgcacg | 1320 |
| gacatcgacg agtgcgaaaa cggcggcttc tgctccgggg tgtgccacaa cctccccggt | 1380 |
| accttcgagt gcatctgcgg gcccgactcg gcccttgccc gccacattgg caccgactgt | 1440 |
| gactccggca aggtggacgg tggcgacagc ggctctggcg agccccgcc cagcccgacg | 1500 |
| cccggctcca ccttgactcc tccggccgtg gggctcgtgc attcggcgct gctcataggc | 1560 |
| atctccatcg cgagcctgtg cctggtggtg gcgcttttgg cgctcctctg ccacctgcgc | 1620 |
| aagaagcagg gcgccgccag ggccaagatg gagtacaagt gcgcggcccc ttccaaggag | 1680 |
| gtagtgctgc agcacgtgcg gaccgagcgg acgccgcaga gactc | 1725 |

```
<210> SEQ ID NO 4
<211> LENGTH: 649
<212> TYPE: DNA
<213> ORGANISM: Homo sapiens
<220> FEATURE:
<221> NAME/KEY: misc_feature
<222> LOCATION: (1)..(649)
<223> OTHER INFORMATION: n= a, c, g, t, unknown or other

<400> SEQUENCE: 4
tctagacgcg ttgacattga ttattgacta gttattaata gtaatcaatt acgggtcat      60 tagttcatag cccatgatat catatggagt tccgcgttac ataacttacg gtaaatggcc     120
cgcctggctg accgcccaac gacccccgcc cattgacgtc aataatgacg tatgttccca     180
tagtaacgcc aatagggact ttccattgac gtcaatgggt ggagtattta cggtaaactg     240
cccacttggc agtacatcaa gtgtatcata tgccaagtac gccccctat tgacgtcaat      300 gacggtaaat ggcccgcctg gcattatgcc cagtncatga ccttatggga ctttcctact     360
tggcagacat ctacgtatta gtcatcgcta ttaccatggt gatgcggttt tggcagtaca     420
tcaatgggcg tggatagcgg tttgactcac ggggattttc caagtctcca ccccattgac     480
gtcaatggga gtttgttttg gcaccaaaat caacgggact ttccaaaatg tcgtaacaac     540
tccgccccat tgacgcaaat gggcggtagg cgtgtacggt gggaggtcta tataagcaga     600
gctctctggc taactagaga acccctgctt actggcttat cgagatatc                 649

<210> SEQ ID NO 5
<211> LENGTH: 3693
<212> TYPE: DNA
<213> ORGANISM: Homo sapiens

<400> SEQUENCE: 5
ggcagcgcgc agcggcaaga agtgtctggg ctgggacgga caggagaggc tgtcgccatc      60
ggcgtcctgt gcccctctgc tccggcacgg ccctgtcgca gtgcccgcgc tttcccggc      120 gcctgcacgc ggcgcgcctg ggtaacatgc ttggggtcct ggtccttggc gcgctggccc     180
tggccggcct ggggttcccc gcacccgcag agccgcagcc gggtggcagc cagtgcgtcg     240
agcacgactg cttcgcgctc tacccgggcc ccgcgacctt cctcaatgcc agtcagatct     300
gcgacggact gcggggccac ctaatgacag tgcgctcctc ggtggctgcc gatgtcattt     360
ccttgctact gaacggcgac ggcggcgttg gccgccggcg cctctggatc ggcctgcagc     420
tgccacccgg ctgcggcgac cccaagcgcc tcgggcccct gcgcggcttc cagtgggtta     480
cgggagacaa caacaccagc tatagcaggt gggcacggct cgacctcaat ggggctcccc     540
tctgcggccc gttgtgcgtc gctgtctccg ctgctgaggc cactgtgccc agcgagccga     600
tctgggagga gcagcagtgc gaagtgaagg ccgatggctt cctctgcgag ttccacttcc     660
cagccacctg caggccactg gctgtggagc ccggcgccgc ggctgccgcc gtctcgatca     720
cctacggcac cccgttcgcg gcccgcggag cggacttcca ggcgctgccg gtgggcagct     780
ccgccgcggt ggctcccctc ggcttacagc taatgtgcac cgcgccgccc ggagcggtcc     840 agggggcactg ggccagggag gcgccgggcg cttgggactg cagcgtggag aacgcggct      900 gcgagcacgc gtgcaatgcg atccctgggg ctccccgctg ccagtgccca gccggcgccg     960
ccctgcaggc agacgggcgc tcctgcaccg catccgcgac gcagtcctgc aacgacctct    1020
gcgagcactt ctgcgttccc aaccccgacc agccggctc ctactcgtgc atgtgcgaga    1080
ccggctaccg gctggcggcc gaccaacacc ggtgcgagga cgtggatgac tgcatactgg     1140
agcccagtcc gtgtccgcag cgctgtgtca acacacaggg tggcttcgag tgccactgct     1200
```

```
accctaacta cgacctggtg gacggcgagt gtgtggagcc cgtggacccg tgcttcagag    1260
ccaactgcga gtaccagtgc cagccccctga accaaactag ctacctctgc gtctgcgccg   1320
agggcttcgc gcccattccc cacgagccgc acaggtgcca gatgttttgc aaccagactg    1380
cctgtccagc cgactgcgac cccaacaccc aggctagctg tgagtgccct gaaggctaca    1440
tcctggacga cggttttcatc tgcacggaca tcgacgagtg cgaaaacggc ggcttctgct   1500
ccggggtgtg ccacaacctc cccggtacct tcgagtgcat ctgcgggccc gactcggccc    1560
ttgcccgcca cattggcacc gactgtgact ccggcaaggt ggacggtggc gacagcggct    1620
ctggcgagcc cccgcccagc ccgacgcccg gctccacctt gactcctccg gccgtggggc    1680
tcgtgcattc gggcttgctc ataggcatct ccatcgcgag cctgtgcctg gtggtggcgc    1740
ttttggcgct cctctgccac ctgcgcaaga agcagggcgc cgccagggcc aagatggagt    1800
acaagtgcgc ggccccttcc aaggaggtag tgctgcagca cgtgcggacc gagcggacgc    1860
cgcagagact ctgagcggcc tccgtccagg agcctggctc cgtccaggag cctgtgcctc    1920
ctcaccccca gctttgctac caaagcacct tagctggcat tacagctgga gaagaccctc    1980
cccgcacccc ccaagctgtt ttcttctatt ccatggctaa ctggcgaggg ggtgattaga    2040
gggaggagaa tgagcctcgg cctcttccgt gacgtcactg gaccactggg caatgatggc    2100
aattttgtaa cgaagacaca gactgcgatt tgtcccaggt cctcactacc gggcgcagga    2160
gggtgagcgt tattggtcgg cagccttctg ggcagacctt gacctcgtgg gctagggatg    2220
actaaaatat ttatttttt taagtattta ggttttttgtt tgtttccttt gttcttacct    2280
gtatgtctcc agtatccact ttgcacagct ctccggtctc tctctctcta caaactccca    2340
cttgtcatgt gacaggtaaa ctatcttggt gaatttttt ttcctagccc tctcacattt     2400
atgaagcaag ccccacttat tccccattct tcctagtttt ctcctcccag gaactgggcc    2460
aactcacctg agtcacccta cctgtgcctg accctacttc ttttgctctt agctgtctgc    2520
tcagacagaa cccctacatg aaacagaaac aaaaacacta aaataaaaa tggccatttg     2580 cttttttcacc agatttgcta atttatcctg aaatttcaga ttcccagagc aaaataattt   2640
taaacaaagg ttgagatgta aaaggtatta aattgatgtt gctggactgt catagaaatt    2700
acacccaaag aggtatttat ctttacttttt aaacagtgag cctgaatttt gttgctgttt   2760
tgatttgtac tgaaaaatgg taattgttgc taatcttctt atgcaatttc ctttttttgtt  2820 attattactt ttttttgaca gtgttgaaaa tgttcagaag gttgctctag attgagagaa    2880
gagacaaaca cctcccagga gacagttcaa gaaagcttca aactgcatga ttcatgccaa    2940
ttagcaattg actgtcactg ttccttgtca ctggtagacc aaaataaaac cagctctact    3000
ggtcttgtgg aattgggagc ttgggaatgg atcctggagg atgcccaatt agggcctagc    3060
cttaatcagg tcctcagaga atttctacca tttcagagag gccttttgga atgtggcccc    3120
tgaacaagaa ttggaagctg ccctgcccat gggagctggt tagaaatgca gaatcctagg    3180
ctccacccca tccagttcat gagaatctat atttaacaag atctgcaggg ggtgtgtctg    3240
ctcagtaatt tgaggacaac cattccagac tgcttccaat tttctggaat acatgaaata    3300
tagatcagtt ataagtagca ggccaagtca ggcccttatt ttcaagaaac tgaggaattt    3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
tggaaataaa tgtatcatag aaatgtaact tttgtaagac aaaggttttc ctcttctatt    3540
ttgtaaactc aaaatatttg tacatagtta tttatttatt ggagataatc tagaacacag    3600
```

```
gcaaaatcct tgcttatgac atcacttgta caaaataaac aaataacaat gtgaaaaaaa    3660
aaaaaaaaaa aaaaaaaaaa aaaaaaaaaa aaa                                 3693

<210> SEQ ID NO 6
<211> LENGTH: 4457
<212> TYPE: DNA
<213> ORGANISM: Homo sapiens
<220> FEATURE:
<221> NAME/KEY: misc_feature
<222> LOCATION: (1)..(4457)
<223> OTHER INFORMATION: n= a, c, g, t, unknown or other

<400> SEQUENCE: 6
gtttaaacgg gccctctaga cgcgttgaca ttgattattg actagttatt aatagtaatc     60
aattacgggg tcattagttc atagcccatg atatcatatg gagttccgcg ttacataact    120
tacggtaaat ggcccgcctg gctgaccgcc caacgacccc cgcccattga cgtcaataat    180
gacgtatgtt cccatagtaa cgccaatagg gactttccat tgacgtcaat gggtggagta    240
tttacggtaa actgcccact tggcagtaca tcaagtgtat catatgccaa gtacgccccc    300
ctattgacgt caatgacggt aaatggcccg cctggcatta tgcccagtnc atgaccttat    360
gggactttcc tacttggcag acatctacgt attagtcatc gctattacca tggtgatgcg    420
gttttggcag tacatcaatg ggcgtggata gcggtttgac tcacgggat ttccaagtc     480 tccaccccat tgacgtcaat gggagtttgt tttggcacca aaatcaacgg gactttccaa    540
aatgtcgtaa caactccgcc ccattgacgc aaatgggcgg taggcgtgta cggtgggagg    600
tctatataag cagagctctc tggctaacta gagaacccct gcttactggc ttatcgagat    660
atctgcagaa ttcatctgtc gactgctacc ggcagcgcgc agcggcaaga agtgtctggg    720
ctgggacgga caggagaggc tgtcgccatc ggcgtcctgt gcccctctgc tccggcacgg    780
ccctgtcgca gtcccgcgc tttccccggc gcctgcacgc ggcgcgcctg ggtaacatgc    840
ttggggtcct ggtccttggc gcgctggccc tggccggcct ggggttcccc gcacccgcag    900
agccgcagcc gggtggcagc cagtgcgtcg agcacgactg cttcgcgctc tacccgggcc    960
ccgcgacctt cctcaatgcc agtcagatct gcgacggact gcggggccac ctaatgacag   1020
tgcgctcctc ggtggctgcc gatgtcattt ccttgctact gaacggcgac ggcggcgttg   1080
gccgccggcg cctctggatc ggcctgcagc tgccacccgg ctgcggcgac cccaagcgcc   1140 tcggcccct gcgcggcttc cagtgggtta cgggagacaa caacaccagc tatagcaggt   1200
gggcacggct cgacctcaat ggggctcccc tctgcggccc gttgtgcgtc gctgtctccg   1260
ctgctgaggc cactgtgccc agcgagccga tctgggagga gcagcagtgc gaagtgaagg   1320
ccgatggctt cctctgcgag ttccacttcc cagccacctg caggccactg gctgtggagc   1380
ccggcgccgc ggctgccgcc gtctcgatca cctacggcac cccgttcgcg gcccgcggag   1440
cggacttcca ggcgctgccg gtgggcagct ccgccgcggt ggctcccctc ggcttacagc   1500
taatgtgcac cgcgccgccc ggagcggtcc aggggcactg ggccagggag cgccgggcg   1560 cttgggactg cagcgtggag aacggcgcgct gcgagcacgg gtgcaatgcg atccctgggg   1620
ctccccgctg ccagtgccca gccggcgccg ccctgcaggc agacgggcgc tcctgcaccg   1680
catccgcgac gcagtcctgc aacgacctct gcgagcactt ctgcgttccc aaccccgacc   1740
agccgggctc ctactcgtgc atgtgcgaga ccggctaccg gctggcggcc gaccaacacc   1800
ggtgcgagga cgtggatgac tgcatactgg agcccagtcc gtgtccgcag cgctgtgtca   1860
acacacaggg tggcttcgag tgccactgct acccctaacta cgacctggtg gacggcgagt   1920
```

```
gtgtggagcc cgtggacccg tgcttcagag ccaactgcga gtaccagtgc cagcccctga    1980
accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcacccc ccaagctgtt ttcttctatt    2700
ccatggctaa ctggcgaggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttattttttt taagtattta    2940 ggttttgtt tgtttccttt gttcttacct gtatgtctcc agtatccact ttgcacagct    3000
ctccggtctc tctctctcta caaactccca cttgtcatgt gacaggtaaa ctatcttggt    3060
gaattttttt ttcctagccc tctcacattt atgaagcaag ccccacttat tccccattct    3120
tcctagtttt ctcctcccag gaactgggcc aactcacctg agtcaccctc cctgtgcctg    3180
accctacttc ttttgctctt agctgtctgc tcagacagaa cccctacatg aaacagaaac    3240
aaaaacacta aaaataaaaa tggccatttg cttttttcacc agatttgcta atttatcctg    3300
aaatttcaga ttcccagagc aaaataattt taaacaaagg ttgagatgta aaaggtatta    3360
aattgatgtt gctggactgt catagaaatt acacccaaag aggtatttat ctttacttt    3420 aaacagtgag cctgaatttt gttgctgttt tgatttgtac tgaaaaatgg taattgttgc    3480
taatcttctt atgcaatttc ctttttttgtt attattactt attttttgaca gtgttgaaaa    3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
tttcagagag gccttttgga atgtggcccc tgaacaagaa ttggaagctg ccctgcccat    3840
gggagctggt tagaaatgca gaatcctagg ctccacccca tccagttcat gagaatctat    3900
atttaacaag atctgcaggg ggtgtgtctc ctcagtaatt tgaggacaac cattccagac    3960
tgcttccaat tttctggaat acatgaaata tagatcagtt ataagtagca ggccaagtca    4020 gggcccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaaggtttt cctcttctatt ttgtaaactc aaaatatttg tacatagtta    4260
tttatttatt ggagataatc tagaacacag gcaaaatcct tgcttatgac atcacttgta    4320
```

```
caaaataaac aaataacaat gtgaaaaaaa aaaaaaaaaa aaaaaaaaaa aaaaaaaaaa      4380
aaaggtagca gtcgacagat gaattccacc acactggact agtggatccg agctcggtac      4440
caagcttaag tttaaac                                                     4457

<210> SEQ ID NO 7
<211> LENGTH: 17534
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: misc_feature
<222> LOCATION: (1)..(17534)
<223> OTHER INFORMATION: n= a, c, g, t, unknown or other

<400> SEQUENCE: 7
catcatcaat aatatacctt attttggatt gaagccaata tgataatgag ggggtggagt        60
ttgtgacgtg gcgcggggcg tgggaacggg gcgggtgacg tagtagtgtg gcggaagtgt       120
gatgttgcaa gtgtggcgga acacatgtaa gcgacggatg tggcaaaagt gacgttttg        180 gtgtgcgccg gtgtacacag gaagtgacaa ttttcgcgcg gttttaggcg gatgttgtag       240
taaatttggg cgtaaccgag taagatttgg ccattttcgc gggaaaactg aataagagga       300
agtgaaatct gaataatttt gtgttactca tagcgcgtaa tactggtacc gcggccgcct       360
cgagtctaga actagtggat cccccaaacg ggccctctag acgcgttgac attgattatt       420
gactagttat taatagtaat caattacggg gtcattagtt catagcccat gatatcatat       480
ggagttccgc gttacataac ttacggtaaa tggcccgcct ggctgaccgc ccaacgaccc       540
ccgcccattg acgtcaataa tgacgtatgt tcccatagta acgccaatag ggactttcca       600
ttgacgtcaa tgggtggagt atttacggta aactgcccac ttggcagtac atcaagtgta       660
tcatatgcca agtacgcccc cctattgacg tcaatgacgg taaatggccc gcctggcatt       720
atgcccagtn catgacctta tgggactttc ctacttggca gacatctacg tattagtcat       780
cgctattacc atggtgatgc ggttttggca gtacatcaat gggcgtggat agcggtttga       840
ctcacgggga ttttccaagt ctccacccca ttgacgtcaa tgggagtttg ttttggcacc       900
aaaatcaacg ggactttcca aaatgtcgta acaactccgc cccattgacg caaatgggcg       960
gtaggcgtgt acggtgggag gtctatataa gcagagctct ctggctaact agagaacccc      1020
tgcttactgg cttatcgaga tatctgcaga attcatctgt cgactgctac ggcagcgcg       1080 cagcggcaag aagtgtctgg gctgggacgg acaggagagg ctgtcgccat cggcgtcctg      1140 tgccctctg ctccggcacg gccctgtcgc agtgcccgcg cttcccggg cgcctgcacg        1200 cggcgcgcct gggtaacatg cttggggtcc tggtccttgg cgcgctggcc ctggccggcc      1260
tggggttccc cgcacccgca gagccgcagc cgggtggcag ccagtgcgtc gagcacgact      1320
gcttcgcgct ctaccegggc ccgcgacctg tcctcaatgc cagtcagatc tgcgacggac      1380
tgcggggcca cctaatgaca gtgcgctcct cggtggctgc cgatgtcatt tccttgctac      1440
tgaacggcga cggcggcgtt ggccgccggc gcctctggat cggcctgcag ctgccacccg      1500
gctgcggcga ccccaagcgc ctcgggcccc tgcgcggctt ccagtgggtt acggagacaa     1560
acaacaccag ctatagcagg tgggcacggc tcgacctcaa tggggctccc ctctgcggcc     1620
cgttgtgcgt cgctgtctcc gctgctgagg ccactgtgcc cagcgagccg atctgggagg     1680
agcagcagtg cgaagtgaag gccgatggct tcctctgcga gttccacttc ccagccacct     1740
```

```
gcaggccact ggctgtggag cccggcgccg cggctgccgc cgtctcgatc acctacggca   1800
ccccgttcgc ggcccgcgga gcggacttcc aggcgctgcc ggtgggcagc tccgccgcgg   1860
tggctcccct cggcttacag ctaatgtgca ccgcgccgcc cggagcggtc caggggcact   1920
gggccaggga ggcgccgggc gcttgggact gcagcgtgga gaacggcggc tgcgagcacg   1980
cgtgcaatgc gatccctggg gctccccgct gccagtgccc agccggcgcc gccctgcagg   2040
cagacgggcg ctcctgcacc gcatccgcga cgcagtcctg caacgacctc tgcgagcact   2100
tctgcgttcc caaccccgac cagccgggct cctactcgtg catgtgcgag accggctacc   2160
ggctggcggc cgaccaacac cggtgcgagg acgtggatga ctgcatactg gagcccagtc   2220
cgtgtccgca gcgctgtgtc aacacacagg gtggcttcga gtgccactgc taccctaact   2280
acgacctggt ggacggcgag tgtgtggagc ccgtggaccc gtgcttcaga gccaactgcg   2340
agtaccagtg ccagcccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgccc tgaaggctac atcctggacg   2520
acggtttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctgcgagc    2700 ccccgcccag cccgacgccc ggctccacct tgactcctcc ggccgtgggg ctcgtgcatt   2760
cgggcttgct cataggcatc tccatcgcga gcctgtgcct ggtggtggcg cttttggcgc   2820
tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcaccccc   3000
agctttgcta ccaaagcacc ttagctggca ttacagctgg agaagaccct ccccgcaccc   3060
cccaagctgt tttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat ttgtcccagg tcctcactac cgggcgcagg agggtgagcg   3240
ttattggtcg gcagccttct gggcagacct tgacctcgtg ggctagggat gactaaaata   3300
tttatttttt ttaagtattt aggttttgt ttgtttcctt tgttcttacc tgtatgtctc    3360
cagtatccac tttgcacagc tctccggtct ctctctctct acaaactccc acttgtcatg   3420
tgacaggtaa actatcttgg tgaattttt tttcctagcc ctctcacatt tatgaagcaa    3480
gccccactta ttccccattc ttcctagttt tctcctccca ggaactgggc caactcacct   3540
gagtcaccct acctgtgcct gaccctactt cttttgctct tagctgtctg ctcagacaga   3600 accctacat gaaacagaaa caaaaacact aaaaataaaa atggccattt gcttttcac     3660 cagatttgct aatttatcct gaaatttcag attcccagag caaataatt ttaaacaaag    3720 gttgagatgt aaaaggtatt aaattgatgt tgctggactg tcatagaaat tacacccaaa   3780
gaggtattta tctttacttt taaacagtga gcctgaattt tgttgctgtt ttgatttgta   3840
ctgaaaaatg gtaattgttg ctaatcttct tatgcaattt ccttttttgt tattattact   3900 tattttgac agtgttgaaa atgttcagaa ggttgctcta gattgagaga agagacaaac    3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
```

```
gtcctcagag aatttctacc atttcagaga ggccttttgg aatgtggccc ctgaacaaga    4200
attggaagct gccctgccca tgggagctgg ttagaaatgc agaatcctag gctccacccc    4260
atccagttca tgagaatcta tatttaacaa gatctgcagg gggtgtgtct gctcagtaat    4320
ttgaggacaa ccattccaga ctgcttccaa ttttctggaa tacatgaaat atagatcagt    4380
tataagtagc aggccaagtc aggcccttat tttcaagaaa ctgaggaatt ttctttgtgt    4440
agctttgctc tttggtagaa aaggctaggt acacagctct agacactgcc acacagggtc    4500
tgcaaggtct ttggttcagc taagctagga atgaaatcct gcttcagtgt atggaaataa    4560
atgtatcata gaaatgtaac ttttgtaaga caaaggtttt cctcttctat tttgtaaact    4620
caaaatattt gtacatagtt atttatttat tggagataat ctagaacaca ggcaaaatcc    4680
ttgcttatga catcacttgt acaaaataaa caataacaa tgtgaaaaaa aaaaaaaaa    4740 aaaaaaaaa aaaaaaaaa aaaaggtagc agtcgacaga tgaattccac cacactggac    4800
tagtggatcc gagctcggta ccaagcttaa gtttgggctg caggaattct gatggctctc    4860
aaaattcctg cctcctttag ggataaaaga ctttaagact ttttaacaaa aagaaaaag    4920 aaaaaaaaaa ttcctgcctc ctggtgtaca cacacagaag ggttccctcc ccttgaatgt    4980
gaccaggatc tgtgaaaata acgggatagc cgctcctgtg attaggttat gtggtagact    5040
agagcaagat tctcctgctg gttttgaaga agtcagctgc catgttgtga gactgtcatg    5100
ggctagggca tgagccttta aatatctggg agcaacccct ggccagcagc cagtgagaaa    5160
acgggccctc agtcctacaa tcacaaggaa ctaaattctg ccaacaacct gaaggaactt    5220
tgaagaggat catgagtccc ttgattcagc ttgatgagcc cctgagcaga ggatacagct    5280
aacttgtact agggaagtat aaaaaacatg catgggaatg atatatatca actttaagga    5340
taattgtcat acttctggga atgaagggaa agaaatgggg ctttagttgt attatgatct    5400
ttaatttctc aaaaaaaata agatcagaag caaatatggc aaaatgttaa tacttttgtg    5460
ggtacgtagg tattcagcat acccttttt ctgagttcaa aatatttat aattaaaatg    5520 aaatgcaggc caggcacagt ggctcatgcc tataatacca gcactttgcg aggccgaggt    5580
gggaggatgg cttgaggcca gaccagcctg gccaacatgg caaaacccca tctctactta    5640
aaaaaaaaaa aactatatat atatatatgt gtgtgtgtgt gtatatatat atatgtatat    5700
atatttatat atgtgtgtat atatatatat gtatatatat ttatatatgt gtgtgtatat    5760
atatatatac acacacacac atatatacat acatacatac acacacacac acacacaatt    5820
agccaggcat ggtggcgcac acctgtagtc ccagctactt gggaggctga acatgagaa    5880 ttgcttgaac ctgggaggca gagtagttag tgagctgaga tcataccact gcactccagc    5940
ctggtgacag agtgagactc tgtcttaaaa aaaataaaaa ttaaaattaa atgcaaaagg    6000
tccaagtgaa ttgaagagga aaggggtatc aaggaaggtt ttgtggaggt gacgtttgag    6060
ctgggtctta aatgacttaa acatgggata agaaggagg gaataaggac atttcaggta    6120
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccgaaatag    6480
gcaaatctta tagacagcaa gtaggtagat gatcagtttg ctaggtgctg ggggaagggg    6540
```

```
aaatggggag tgatggctaa ggggattggg tttctttgtg gggcaatgaa aatgttttaa      6600
aattgagcgt gataatgatt gcacaatgct gcatatatat ataatctata gattatatat      6660
atataaagag aggctgttag acagtgataa gtgatatata tatatatata catagagaga      6720
gagagagaga gagagagagg ctgttagtga taagtgatca ggaaaataaa agtattgagg      6780
aggaatacga agttgacggt gtgaaaacat gagattttat ataggatggc cagggaaggc      6840
cttaatgaga aagtgactta tgagtaaaaa caagggatcc taaaccttag catgcatcag      6900
aatcactcgg aaacttgtta aagcatagct tgctgggcct catcacagat attttgattc      6960
ggtaggttct tgtctgatat taatactttt ggtctaggga accacatttt gagaaccact      7020
gagctaaagg aagtaaaggt ttcccttagt ttactagctg gtaacactgg cccaggaggc      7080 cttttctggtg acccctaagg aattatccaa actcttgttt ttagatgctt tattatatca      7140
aactctcctt taaacaagtg gcccatctgc tgggatttgg aagcctgtaa tactgaaatt      7200
ttcatcataa tggaaatttt aaaaacagaa tttgacccac ctgttttaa aacactttca       7260 ttacttaaca agaggtctaa tcttgggcaa gtcttgaaat ttctctggcc ttagtttccc      7320
atgtgttaaa tgaaacttga agcagttggt ctcttatagt ctcctgactc taacattcta      7380
agaattatat ttgtacaata actcaaaaat cacataattt aatttaccat atggactcca      7440
aaatatattt tctcattagg ctaaacttga tctgcatttt ctggatgtgt ccatattctt      7500
ggactacact aaaacatgat accaatgctt cctctcacca taaaccctca cttcgctttc      7560
tacatttaag aattttatag ctggaagagt ccttaacaga aaataccatc taataattac      7620
ccctcaaaat cgagaaagtc ctatctgttc ttatgctagt tataagaatg aggcagcatt      7680
tcacataatg gttataaaca ctgccacaag aagattcatg atgtgttgtt tatctgtagc      7740
tctcatcata ctctgtcata taactatagc attaagattt taatgttcta tatattcttc      7800
taagacagtg tttaccagag taaggcacaa aagatccact ggtttgcaag aaagattaga      7860
acttttaaat tttttacctc accttgttta atctatattt ttgtatgtat tttgtaacat      7920
atatattatt attaccataa atcatatata atttaaaatg catatattag gggtaaatgc      7980
tcaggaaact ttttataaat tgggcatgca aatacaagtt tgaagactca ctgttctagg      8040
tattaaaagt aaagttataa ccaagtaaag cttccacctt ttcatgtctc aaagcagttt      8100
attgttggag gtaagatctc ttagaagcct aaacaggtcc aagtacagaa tgaagtaagg      8160
ctagcccata acttgtggca agcaattcat actatttctc tcatgctgag ctctcctcag      8220
tgaagcagct actatagaca actgcagcct attggtagcc tattttacag gcaggaaaaa      8280
aattactttt tattcaaagt ggaactcagg acatgggag aaaatgaata caaaaaatag        8340
ggtcaatcca aaggcacaca gcaaatgagt aacacagtta tgttttttc ccatttgtat       8400 gaggtcccag taaattctaa gtaaactgca aatttaataa tacactaaaa aagccatgca      8460
attgttcaaa tgaatcccag catggtacaa ggagtacaga cactagagtc taaaaaacaa      8520
aagaatgcca ttattgagtt tttgaattat atcaagtagt tacatctcta cttaataaat      8580 gagaaaacg aggataagag gccatttgat aaaatgaaaa tagccaagaa gtggtattag       8640
agacttgaat acaggtattc gggtccaaag ttcatctgct caaatactaa ctggggaaaa      8700
gagggaaaaa tatttatata catatatatc tgcacacaaa aatacccca aaagacaaaa       8760 tgaggccagg cagggtggct cacacccgta atcccggtac tttgggaggc tgaggcaggt      8820
ggatacctga gatcaggagt tggagatcag cctggtcaac atggtgaaac cctgtctcta      8880
ctaaagataa aaaattagc caggcatggt ggcgtgcgcc tgtaatccca gctacttggg       8940
```

```
agtctgaggc aggagaatca cttgaactgg gaaggggagg ttgcagtgag ccaagatcgt    9000
actactgcac tccagcctgg gcagcagagt gagactccat cacaaaaata aataaataaa    9060
taaaatacaa tgaaacagaa agttcaaata atcccataat cttaccacca agaaataact    9120
ttcactcgtt atacttattg attttttccat aataaatgta ctttactgtg actatcatga    9180
aaagaaagtt attttagaaa cagagaactg tttcagatca aatctatgta gtagaacaga    9240
gccattaggt ggggaaagacg agatcaaact aaatctcaga aggcctaaaa ggctaggtcc    9300
attccagcac taaaaactga ccagacaagt aatggcttca acagcttcta aatatggaca    9360
aagcatgctg aaagggaagg acaggtctaa cagtggtata tgaaatgaac aggagggggca    9420 aagctcattt ctcctctgaa gttttccaaa gatgctgagg aggacattag tttgacatga    9480
ccctgatatg ggacaagata atttcacaga agttttacat gttaaagttt cttatagat     9540 actcattcaa gtaagcaatg aacactaaaa tctaagaaa gaaaagagct ttagagtcag     9600
gtctgtattc aaattcaagc tctaccactt actggttctg tgactttggg caagtctttt    9660
aaccttatta agtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaaagcagta gcattccatc atttattatt ggttactctc    9840 aaaaagttttt tcaatgtact agaagataaa tattcaaata ccttaatatc tccattattt    9900
tcaggtaaac agcatgctcc tgaacaacca atgggtcaac aaataaatta aagggaaat     9960 ctaaaaacat cttgatatta aactacatgg aagcacaata taccaaaacc aatggttcac   10020
actaggagaa ttttaaggta caagaaaact ctttgagatt tcttaaaata atagtatgtc   10080
tgaatttatt gagtgattta ccagaaactg ttgtaagagc tctacttgca ttatagcact   10140
taatcctctt aactctatgg ctgctattat caacctcacc ctaatcacat atgggacaca   10200
gagaggttaa gtaacttgcc caaggtcaga gttaggaagt actaagccat gctttgaatc   10260
agttgtcagg ctccggaact cacactttca gccactacta aatactgctt tgctatcttt   10320
taggaaacta tgtgagtcta cctcacatag actcacatag gtttgttttt tttttttttt   10380
taaaggctat ctttttccccc atcaatgttt tttgaaggat cccaaattag agtcccacag   10440
aggcagacag cagtacttga caatatggac atttaaggtt aatgttggat tctactgtct   10500
ttttactaca tgacctaggg aacgataatt aacctagact gcttccaagg gttaaataac   10560
ccatttagtt atactatgta aattatctct tagtgattga ttgaaagcac actgttacta   10620
attgactcgg tatgaagtgc tttttttttct tcccctttcaa gatacatacc tttccagtta   10680
aagttgagag atcatctcca ccaattactt ttatgtcccc tgttgactgg tcattctagt   10740
taaaaaaaaa aaaaactata tatatatata tctacacaca catatgtata tgtatatcct   10800
tatgtacaca cacaaacttc aaattaaatg agaactagaa gatttgagaa gttagctagc   10860
taatatccat agcattatga tattctaaat gatatgaatt ataagaatta ggtttcctga   10920
aatgaatgac tagaaaactt tcaagtagag attagtaaaa attaaaaagt cctaatcggc   10980
cattactgat ttgatgtttt taagagtcct aaaaaatggg ttacatccat ttttaagtgg   11040
gtagtattat aacagccacc catcttcaat cacagtgatt tctgaattgt gagggaagtt   11100
attagcatga caggtgtctg gttctggccc tgtacgattc ccatgagtca agcaaattgt   11160
aagggctggt ctatatcaca cccaaccccca aggatatgtc cctcaaaagt ctagcccagg   11220
ccccgtcatc ttcagcatca tctgggaaac caggtctgat tagtagtcct ttaaggaata   11280
cctcttaggc tcccatttta ctgctatcac agaatccaat aaaacccctta caggagattc   11340
```

```
aatgggaaat gctcaacacc cactgtagtt ggtggtgaca atgaccataa tttggctgtg    11400
ctggattcag gacagaaaat ttgggtgaaa gagcaggtga acaaaagagc ttcgacttgc    11460
cctagcagag agcaagccat accataccac aaagccacag caattacaac ggtgcagtac    11520
cagcacagta aatgaacaaa gtagagccca gaaacagacc cagaactata tgaggattta    11580
gtatacaata aagatggtat ttcgagtcag tagggaaaag atgaattatt caataaatga    11640
tgtttggcca actagtaacc catttgggaa aaaataaaag tatggtccct acctcacagc    11700
atacacaaaa ataaattcca gacggattaa aatctaaatg taaaaaataa agccataagt    11760
ggactggaag aaaatagaga attttttta acatccgtag aaagggtaaa acccaggca    11820 tgacatgaac caaaactgaa gaggttctgt aacaaatacc ccctttata tattgggctc    11880 caacaataag aacccatagg aaaatggaga atgaacacaa atagacaatt tatagaagag    11940
aaggttataa ggtgtaaaat tatatctatc tgagaaacaa acactaaaac aatgtgattc    12000
tactgttctc ccacccatac tggcaaaact taagcctgat aatatgctga ggggaaataa    12060
gcactcttgt tggtgagagt attaattggc atagcttctt ttgaaaatga catagcaata    12120
cctgttaaaa ttgcaaacat gcatgtcact taatccagta atcccacttc tgggaatcaa    12180
tgctacaaaa acactgacaa gtatacaaag atacattcaa gagtgttcac tgggccgggt    12240
gcggtggctt catgcctgta atcccaggga ggcagaggca agacgatcgc ttgaccccag    12300
gagttcaagg ccagcccgag aaacacagca agaccctgtc tctcttttt ttatttaaaa    12360 aataaatgtt cactgtatca gttgttcaca aaaacaaacc aacatgtcca ttaacaggga    12420
accatttaaa ttaatcaagt tcatctacac aatgtaatac catgcaacta ttaaaaagca    12480
cctgataatc caaagcacac tgagacagaa taatgctatt aaaaacacca agtagtggaa    12540
cactgtgttg cctatgacac cattttatt caacattaa acaaatttgt aacagcaatt    12600
acatgagtag tgacaatggc gtttatgaga ctttttcactt ttatgtgctt ctattttgt    12660 tatgcttcta tatatacatc catttattat ggagtgttac tttcaaaaat cacaaatggg    12720
ccagtattat ttggtgttgc aaggtgagca tatgacttct gatatcaacc tttgcatatt    12780
acttctcaat ttagggaaat tacagacatc ccttattcta actaacttaa aacccagcat    12840
ttcaaacata cagaattgat ggggaaaaaa aagaagaag aaagaaagaa aaggcaacaa    12900
gcttcagatg acagtgactc acatcaaatt atttataaaa tctgttaaat agtgccatct    12960
tctggagata cctggtatta cagtccaact ccagttgatg tctttacaga gacaagagga    13020
ataaaggaaa aaatattcaa gaactgaaaa gtatggagtc atgaaaat tgctgtgatc    13080 caaaggctac ggtgatagga caagaaacaa gagaactcca agcagtaaga cactgctgtt    13140
ctattagcat ccaaacctcc atactcctgt ttgccccaag gcttttttaa aaaatagaga    13200
caggatctca ctattttgct caggctggtc ttgaactcct ggactcaagc tatcctcctg    13260
cctcggcctc ctaaagtgcc gagattacag gcttgagtca ccatacctgg ctatttattt    13320
tttcttaact ctcttgcctg gcctatagcc accatggaag ctaataaaga atattaattt    13380
aagagtaatg gtatagttca ctacattgga atacaggtat aagtgcctac attgtacatg    13440
aatggcatac atgatcaat taccccacct gggtggccaa aggaactgcg cgaacctccc    13500
tccttggctg tctggaacaa gcttcccact agatcccttt actgagtgcc tccctcatct    13560
ttaattatgg ttaagtctag gataacagga ctggcaaagg tgaggggaaa gcttcctcca    13620
gagttgctct accctctcct ctaccgtcct atctcctcac tcctctcagc caaggagtcc    13680
aatctgtcct gaactcagag cgtcactgtc aactacataa aattgccaga gaagctcttt    13740
```

```
gggactacaa acacataccc ttaatgtctt tatttctatt ttgtctacct cttcagtcta    13800
ggtgaaaaaa taggaaggat aatagggaag aactttgttt atgcctactt atccgccct     13860 aggaattttg aaaacctcta ggtagcaata agaactgcag catggtatag aaaaagagga    13920
ggaaagctgt atagaaatgc ataataaatg gcaggaaaa gaactgcttg gaacaaacag     13980
ggaggttgaa ctataaggag agaaagcaga gaggctaatc aacaaggctg ggttcccaag    14040
agggcatgat gagactatta ctaaggtagg aattactaag ggctccatgt ccccttagtg    14100
gcttagtact atgtagcttg ctttctgcag tgaacttcag acccttcttt taggatccta    14160
gaatggactt ttttttttta tcggaaaaca gtcattctct caacattcaa gcaggcccca    14220
agtctaccac actcaatcac attttctctt catatcataa tctctcaacc attctctgtc    14280
cttttaactg tttttctata ccctgatcaa atgccaacaa aagtgagaat gttagaatca    14340 tgtatttta gaggtagact gtatctcaga taaaaaaaaa gggcagatat tccattttcc     14400
aaaatatgta tgcagaaaaa ataagtatga aaggacatat gctcaggtaa caagttaatt    14460
tgtttacttg tattttatga attccctaaa acctacgtca cccgcccgt tcccacgccc     14520 cgcgccacgt cacaaactcc acccctcat tatcatattg gcttcaatcc aaaataaggt     14580
atattattga tgatgttaat taacatgcat ggatccatat gcggtgtgaa ataccgcaca    14640
gatgcgtaag gagaaaatac cgcatcaggc gctcttccgc ttcctcgctc actgactcgc    14700
tgcgctcggt cgttcggctg cggcgagcgg tatcagctca ctcaaaggcg gtaatacggt    14760
tatccacaga atcaggggat aacgcaggaa agaacatgtg agcaaaaggc cagcaaaagg    14820
ccaggaaccg taaaaaggcc gcgttgctgg cgttttttcca taggctccgc cccctgacg    14880 agcatcacaa aaatcgacgc tcaagtcaga ggtggcgaaa cccgacagga ctataaagat    14940
accaggcgtt ccccctgga agctccctcg tgcgctctcc tgttccgacc ctgccgctta    15000
ccggatacct gtccgccttt ctcccttcgg gaagcgtggc gctttctcat agctcacgct    15060
gtaggtatct cagttcggtg taggtcgttc gctccaagct gggctgtgtg cacgaacccc    15120
ccgttcagcc cgaccgctgc gccttatccg gtaactatcg tcttgagtcc aacccggtaa    15180
gacacgactt atcgccactg gcagcagcca ctggtaacag gattagcaga gcgaggtatg    15240
taggcggtgc tacagagttc ttgaagtggt ggcctaacta cggctacact agaaggacag    15300
tatttggtat ctgcgctctg ctgaagccag ttaccttcgg aaaaagagtt ggtagctctt    15360
gatccggcaa acaaaccacc gctggtagcg gtggtttttt tgtttgcaag cagcagatta    15420
cgcgcagaaa aaaaggatct caagaagatc ctttgatctt ttctacgggg tctgacgctc    15480
agtggaacga aaactcacgt taagggattt tggtcatgag attatcaaaa aggatcttca    15540
cctagatcct tttaaattaa aaatgaagtt ttaaatcaat ctaaagtata tatgagtaaa    15600
cttggtctga cagttaccaa tgcttaatca gtgaggcacc tatctcagcg atctgtctat    15660
ttcgttcatc catagttgcc tgactccccg tcgtgtagat aactacgata cgggagggct    15720
taccatctgg ccccagtgct gcaatgatac cgcgagaccc acgctcaccg gctccagatt    15780
tatcagcaat aaaccagcca gccggaaggg ccgagcgcag aagtggtcct gcaactttat    15840
ccgcctccat ccagtctatt aattgttgcc gggaagctag agtaagtagt tcgccagtta    15900
atagtttgcg caacgttgtt gccattgctg cagccatgag attatcaaaa aggatcttca    15960
cctagatcct tttcacgtag aaagccagtc cgcagaaacg gtgctgaccc cggatgaatg    16020
tcagctactg ggctatctgg acaagggaaa acgcaagcgc aaagaaaag caggtagctt    16080 gcagtgggct tacatggcga tagctagact gggcggtttt atggacagca agcgaaccgg    16140
```

```
aattgccagc tggggcgccc tctggtaagg ttgggaagcc ctgcaaagta aactggatgg    16200
ctttcttgcc gccaaggatc tgatggcgca ggggatcaag ctctgatcaa gagacaggat    16260
gaggatcgtt tcgcatgatt gaacaagatg gattgcacgc aggttctccg gccgcttggg    16320
tggagaggct attcggctat gactgggcac aacagacaat cggctgctct gatgccgccg    16380
tgttccggct gtcagcgcag gggcgcccgg ttctttttgt caagaccgac ctgtccggtg    16440
ccctgaatga actgcaagac gaggcagcgc ggctatcgtg gctggccacg acgggcgttc    16500
cttgcgcagc tgtgctcgac gttgtcactg aagcgggaag ggactggctg ctattgggcg    16560
aagtgccggg gcaggatctc ctgtcatctc accttgctcc tgccgagaaa gtatccatca    16620
tggctgatgc aatgcggcgg ctgcatacgc ttgatccggc tacctgccca ttcgaccacc    16680
aagcgaaaca tcgcatcgag cgagcacgta ctcggatgga agccggtctt gtcgatcagg    16740
atgatctgga cgaagagcat caggggctcg cgccagccga actgttcgcc aggctcaagg    16800
cgagcatgcc cgacggcgag gatctcgtcg tgacccatgg cgatgcctgc ttgccgaata    16860
tcatggtgga aaatggccgc ttttctggat tcatcgactg tggccggctg ggtgtggcgg    16920
accgctatca ggacatagcg ttggctaccc gtgatattgc tgaagagctt ggcggcgaat    16980
gggctgaccg cttcctcgtg ctttacggta tcgccgctcc cgattcgcag cgcatcgcct    17040
tctatcgcct tcttgacgag ttcttctgaa ttttgttaaa attttgtta aatcagctca    17100 tttttaacc aataggccga atcggcaaa atcccttata aatcaaaga atagaccgag    17160 atagggttga gtgttgttcc agtttggaac aagagtccac tattaaagaa cgtggactcc    17220
aacgtcaaag ggcgaaaaac cgtctatcag ggcgatggcc cactacgtga accatcaccc    17280
taatcaagtt ttttggggtc gaggtgccgt aaagcactaa atcggaaccc taaagggagc    17340
ccccgattta gagcttgacg gggaaagccg gcgaacgtgg cgagaaagga agggaagaaa    17400
gcgaaaggag cgggcgctag ggcgctggca agtgtagcgg tcacgctgcg cgtaaccacc    17460
acacccgccg cgcttaatgc gccgctacag ggcgcgtcca ttcgccattc aggatcgaat    17520
taattcttaa ttaa                                                     17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaacactgg cccaggaggc ctttctggtg acccc                              35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgaccgggtc ctccggaaag accactgggg att                                33

<210> SEQ ID NO 10
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 10
tagttccttc tgcctggaat ac                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagtcacaa ggatggacta ca                                              22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct     60
acttgccctc tggaaccagc tctagggtca ccacatctct gcttctgagt gcctcctcag    120
acacagtctg tatttcctct tccaagctct catcacaaac attgtgctgt attatatgtt    180
tctgtgtggt cttccttcta tgaggaagcc ttggaaagca ggagacttat tttagtcttc    240
tttatgtttc ttttattccc aacacattat gtctgcccca tagaccttttt caataaatga    300 ttattgagtt agtgactcct tttacatgct gacaaatgtg gctcttatta ctccccattt    360
cagtatcaca tatttgtaaa agtgaatcct tcttaatcgt tttactttc tcctagtaaa    420 ttcctcatct atgcctgtct gctgctgttc tctgtgctgc tggcccttcg tttggatggc    480
atcatacagt ggagttactg ggctgtcttt gctccaatat ggctgtggaa gttaatggtc    540
attgttggag cctcagttgg aactggagtc tgggcacgaa atcctcaata tcggtaatac    600
tgctttatac aacccattgg tctctagcat gagggagcaa tatcttgact tttctcactt    660
ttgatgaagt aaggaccatt ttatttttcta cctatctggg gtcttagaac tatagtataa    720
gctaacagat ctcttctgtg ttttttgaaaa tttagtcttt ggtatgtatt ttcttacaaa    780
agcagtgcca tttggggta agttgccagc cagctcacag atgcctatat aatccaaaat    840
gcacccaaaa tacagaactg gtatgccata ctagactaag cagcatgaaa ccaccctgtt    900
tttaggaaaa gacactcata ttatgtttgg tcatgaaaga tctttctcca atacagtttt    960
ggaactgggg ctcccctttgt cccaccctcc tagtcccaga gctttaggac tattagcagt    1020
gtaggggagg tggcttgacc aggagaccat gagtccctga cagcagct ggggaatgag    1080 gaaagtcaaa gattggatgc cgagaaggaa agcagagcct ttgggggcag gggagagggg    1140
taccctttac cgtttccaac tcttgccctc cctgctcttg gatgcctccg ctggcccaaa    1200
ttcctgggag ttgctcacgc cagcatgcaa cctgcttgtt gctgggacct gcgagagtct    1260
ttcccttctc tgccacagag actgtaacta cataaaggga aaaggggga cttaagactg    1320 ggaggctatt atgaacctcc actgggaaaa tgaggagtac aggaattccc agaaggcagc    1380
tgctcatgtg ggaaaagtgt aaagttgaaa ctaccgcacc tttttttttt tttttttttt    1440
tttttttttt ttgagacaga gtttcgctct tgttgcccag gctggagtgc aatggtgtga    1500
tctcggccca ctgcagcctc cacatcccgg gttcaagtga ttctcctgcc tcggcctcct    1560

```
gagtagctgg gattacaggc acctgccacc atgcccagct aattttttgt attttagta    1620
gagatagggt ttcaccatgc caggctagtt ttgaactcct gacatcaggt gatccacccg   1680
ccttggcctc ctgaagtgct gggattacag gtgtgagcca ccacgtccgg ccactacatc   1740
aacttttaa atttttgttt actaaatatg aaaatgattc agattgtgta aattacatat    1800
cacatacatg tctaagaact gtaaaacagt tacacagaga gccttggcag gtgagggaca   1860
ttcatgtata gctgtttcag agttcttaga ttttttttga aagattgatg acctgtgtgg   1920
ctgtatgtgt tttatttttt tatgagatat tttcagatat ctaatattaa ttgcttctca   1980
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
taacaatagt tactactatc ttgaaatata actggcactt gttcatagaa ctagagttat   2580
ttttataata ttgtgtgaag ggtggtttac atggtttctt gaaaaatgag gatcatgaga   2640
cttaaggggt atttgcctgg ttttagcagc agaagcaaat cagcttgaat aatcttggaa   2700
gtaactcttg ttgttgaatt taagatgtg aacagaagtg tttatgtaca ttgtcaggga    2760
aataagaact ggctattact tttgagaata tccttatacg gttaaaacat taaattctgg   2820
tttggttgta atgttcattt tgtattatgt agtagttctt cgatgtttca gagattgcct   2880
accaaagctt aggtttaagt tagctttcta cctgatttcc ctttgctttt gtcaaatttt   2940
caagtaaaat tcaaagtata aatataagtt ggtatttgcc ctgaactgct tgcttatagt   3000
ggagattctg aactgagggt gttttcttct tctctccctt ttttagagca gaaggagaaa   3060
cgtgtgtgga gtttaaagcc atgttgattg cagtgggcat ccacttgctc ttgttgatgt   3120
ttgaagttct ggtctgtgac agaatcgaga gaggaagcca tttctggctc ctggtcttca   3180
tgccgctgtt ctttgtttcc ccggtgtctg ttgcagcttg cgtttggggc tttcgacatg   3240
acaggtcact agaggtgaga tttcatatat ttaagaatgt tttccacttt gggaggtcaa   3300
ggcaggtgga tcacttgagg tcaggagttt gagaccagcc tggccaacat ggtgaaaccc   3360
catctctact aataatacaa aaattagccg ggtgtggtgg catgcgccag taatcccagc   3420
ttctccggag gctgaggcgg agaatctct tgaacccagg aggcggaggt tgcagtgagc     3480
caagattgaa ccattgcact ccagcctggg tgacagaatg aaactccgtc ttaaaaaaaa   3540
aaaaaagaa tgttttcaaa agtaaaatat tttgctcagt tattcagatg tcaatttctt    3600
acccctttgtt aggaagagct tgatcattac caactctaca tcatgagaca acaaggcaac  3660
aaaagatgat ggaaataaca attttttctt cttcacttag aacactagct tttcacccag   3720
gacatcagcc ttctcccagc ttcacatcct gtatcaatca gacagaaaca gaactgatag   3780
gttagataca gatatatgta taaagagagt taaggaactg gctcacatta ctgtgtgggct 3840
ggcaagtctg aaatctccag ggcaggtgaa caggctggag acctaggagg agttgacact   3900
gcagtcctgg cacagaattt tttcctctcc aggaaaccac agttttgct tttaaggcct    3960
```

```
tcacctgatt gcatgaggcc cacccatgct atggagggta gtctccttta ttcaaagtca   4020
gtaccttcac tgcaacagca agcttagtgt ttgattaaat aactgggtac tatagcccag   4080
ccaagttgac actcaaaact gaccatctcc ccacctcaga ccccatgatt tagcacctcc   4140
cctgctgtct ggttagctta tcctgatgtg cccctgtgtt tgtttattca ttcaataaac   4200
atttatcaag tatttactag atgccaagcc cttttccct aagcatagag gatatgcaga   4260
tgaataaaat accaggacta gtaataatag taatgaaagt aattgcagat aacgtttatt   4320
gagcacttac tgtgtgccag gcattgtgcg aggcacatta catgtggtag ttttcttact   4380
aactaactct gtgaggtagg tccagagaag ataagtcatt tgttcatggc cacatgtgaa   4440
ggggcaggac caggattccg tttgagtcag cccgactcta aagcccgggc acataactac   4500
ataactgcat agaagctgag ggcccaaagc tgaatactga tgggttgagg ggagaactag   4560
aggctgtaga tgcctggttt tgagccgtgt ggatgaagag tgaagggaga agactgcagt   4620
tggcttagga agtaaacata gcagctgtag ggtgggtcag gcatataagc ctagacccca   4680
ggtatgggcg tgaggggaag gtatgtagac agagggacgg tgatggagca aggccctgtg   4740
ggactcaggg agaatgggac ctagagcacc aggaagggtt tggccttgaa caaggggagc   4800
tattccctga ttttcatgct ggtggaaagg ccacagcatg ggtatagtgg taggtaggag   4860
tgagccgtgg agggagagta tctgatggtc cactttcacc ctccctacaa ttcccagttt   4920
atatcaggga cttgagcatc catggatttt ggtatccaca gggggtcctg gaaccaatcc   4980
cccacagata ctgagggaca actatacaag gactaggact gcattgggcc tgaattacag   5040
aaagtaagtc tttcatatat tcacactcta ggcattcctg cccttggaag aaacaacata   5100
ccaggagctg agctccctcc tcctgtgatg caagaacagt acctatgttg gtgaggggt   5160 ggtctggagt aggctcatac agagatggga aggaggagtt gagggtctgc caggaagccc   5220
tgtgttggga gggaagggat ggcattttg ggacacattg aagcctagag gcaggaaaca   5280
ctccatcagc tgagtggact gtggcgattc agatccgacg ggagcacaag gtggaaagga   5340
aggaactgtg ggagttgaga agagaggag cctctacaga gggattgggg caaatagggg   5400
ccacgtcctc agcccacaga gcatgtgctg aagtgcccca ggcaccccag tgcactcaca   5460
gggcaccagg ggatagtgga cattttgagg aaaacagtaa tacctgacat tgttgggac   5520 accatacaaa ctactagctt gaaatagttt acaggtttat ttttaggcca cactgcattc   5580
ctttcagtga cgtcgtatct ttaagaagct gggttttcag cagttgctgt gaaaacaaaa   5640
aaggctaatg ctgtgtgaaa atccgggtga agaacaggta acgagtggga gcaccttgtc   5700
tgattccaag gcgtgggaaa tggtgagcta cctgacaggc acacgcatcc cactgggaat   5760
tagttttggt tatttaagaa taatattaac atttttcttt agatttatat gaattatttt   5820
ttctagtggc tacttagaaa tacttactaa gttagatgta attacttaaa tcagtgcaac   5880
tgttggcatt cccagccaca ttagggattt cttttggcct agaggtctat ggaggaatta   5940
ctaaattccc catgtaccta tgtactgaga acttttggga agctctgggc ctggtcccag   6000
atttcaattt tgtgggcaag aatgtacttt accagagtga ggagcagcct gcagggcgtt   6060
tgggctggag gcgggaggtt agtaaggggt tgctgaagtg gtaggcggat ggtgccgaag   6120
aaggcctcac taggcagtca tcatcaggat aggaagtggg cacggattc aggagaaatc   6180 tggactttac agtggacagg atgtggtgac tgaacgtgac agtgtgggaa aaagaatgca   6240
gggtgattcc cggctcatg gcttgagaaa tgagaccact gttgtgcctc caagtgacat   6300
gggaggctat agaaagtgac atgggaggct atagaaagtg acatgggagg ccatagaaag   6360
```

```
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgacatggga ggccatagaa agtgacatgg gaggctatag aaagaggaga    6600
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccagggtg cagcgggtga gtgaaaatat gtgtgtttgt    6840
gtgtctgtct tcctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg ccaggagga ggggagcaaa aaggaaagag tcatccacag     7020
tatcagtagg atgccagttg aagtgttttt gctgcctccc ggttatcggt gactttgatg    7080
aaagctgtct tctggtggtc atgggggtgg aggccagatc acaaggaagc tgggaatggt    7140
agatgagata gtaggggctt gcatattcat tactgtctcg cagagagaaa cctgaggcta    7200 agagggtct tggatcaaag gatggggtgg gtttatctgg tttcggggct tttgttttta     7260
atgagaagga gtcatttctg tgctgctagg agggatcaat ggaataggtg gggttaaaga    7320
tacagtacgg aatctacagt tgatggcttg atgtgacaag gtcctcaagg agcctgaaag    7380
gaaggggtgg ggtccaaggg caaaaccgag gtatgagaag aaggatgcac aaggatggtt    7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc atttttagtt agaaatcctg    7800
tgttctgtca acattctcca gtttatattc attgccttaa gactggacaa gatcatccac    7860
tggccctggc ttgtatgtaa ctttttaaaat ccttaaataa acttcttttt tattataaaa   7920
gtaattcata ttcactgtac aaagcttgga aaagacggac aagcagaagt aatagcctaa    7980
tagtcaccca taatcccacc atggggagat aacatggtta gtgttttat gtctgtgttt     8040 tatacaaaca gtttggatat aactgtgtgc accatttgt atcctgattt ttttgtttta     8100
atgttgtatc ataaacattt tatcatgtta ataaaggtc tttataaaca tgacttctaa     8160
agtttaattg atacaaaata ttcttcaagt gcatgtatca gaccatcctc ttatttctaa    8220
aatatggtat ttccattgtt gccagtgttg aatgatttta aatcatactg cagtatatat    8280
gtttatgcat taaaatttt gcctttttgtt ttttggttgt tttcttagga aatagtccag     8340
aaatagtgtt actgagctag aggttgggaa ctatttgaga ttcctatata cgtatactgc    8400
actgccaact tgcttttcca aaagccatac ctggccaggc gcagtggctt acacttacag    8460
tcccagcact ttgggaggcc gaggtgagct gatcacttga gctcaggagt tcgagaccaa    8520
cctgtgcaat gtagcaagac cctgtctcaa aagaaaaaaa aaaaaagcca tacccattta    8580
cactcttgct ggtggtggca tctatgtcat gcttctaaac tgtgacttca gttactgggc    8640
atttggttga aattaactgt gaataaatgg tagatggat gcagagatag aaagataagt      8700
ggcaaggtag aaattagaga acacagtata gattccacta ttaaatgcat ggaaaaaga     8760
```

```
tggagactaa aggcagaaga gttccattgc cactgggagg taaggtcatg ctagtgtttt    8820
tgttcggttt tattttctct gttgtttgat gtataatttt gcatacaata tattttatgt    8880
attaaatata gctaccctta aaaagtgaaa agtatagtaa agaattggga gcagagaaga    8940
aatgaaggga acctaagtat actccatatt taaagatggg aataatcact tctgcccaaa    9000
gtctttgata aaacattcat aataaaaaat attcagtcac tcatcctaca acttcacagt    9060
gctgtatctg gagaatggtc attgggttca aaactgtttc tgttgtgacg tgaaggaaac    9120
atatctaaac aagaccaaat tttttcgtat aagatactgt cagggaaaaa aaagattagt    9180
aattttgaga gctttccaca aatgagaaga aagattttt ctgcccttca tcctctgtag     9240
atcccagttg atgaagcagt ctgagtacat gtttcccata gtgagcaaga gaaaacaagg    9300
aagcctattg agatctaaca ttccacccat gaagggaact tcagtaaaaa ggagaatctc    9360
atcacagaat ggggaacggg gaagaaaggc tgtgcataga ctctgcagag aaacctacaa    9420
tcaagaactg gtcaggagaa gtaaaattcg tatgccaact caaatcatag atctaaaaga    9480
aaatgtaaaa ctatagatct gttaggaaat aacataggac agaatctttg gggtttgcaa    9540
ttaggcagag agtacttaga aatggcactg ttaatatggt ccatacgaga gagaaatcat    9600
aaatttggac ttcctcaaaa ttaaaatgaa atgaagacag gccacagact gggagaaaat    9660
atttgcaaag cacacatcaa aacactgact tgcacccaga acatacagag aactcttaaa    9720
aactcaaaac tgcaaaaaga aacacctaaa aattggcaaa agagttgaca atttgcgaag    9780
gggatataca catggcgaaa aagcacagga aaagatgctc aacgccatta caggttaggg    9840
aagacaaact acaaccagga tgagggcccg aaacacatgg cttcagaatg gtgaaactca    9900
gcaacactga cgaggccacg tgcctgggag gatgcagagg aactgggaca ctccagtgtt    9960
actgcgggga aggcaggtgg tacgggcact gtagaaaatg gtttggccat ctctgatgca   10020
gttaaaagcg cacttcccgt gggacttggc tgccccactc ctgggtataa gatttacccc   10080
cagagaagtg aaagcgcgca gccttgtaga aacccacaca ccagtgtttg tagcagtctt   10140
gtttgcattt tggatagcgg ccttgttttgg ttttcacaaa ccaccctcag cggacagtca   10200
gataaactgt aggcatccat acaatggaat accactcaga tctgagaggg aacgacctgt   10260
ggatacaggg agggaacaac ttggatgaat ctcattagag acattatgtg gatggcggga   10320
agccagtctc aacaggttac ttgtctcgcg atgccatcta cataaagttc cagcagagac   10380
aaaagtacag tgagagaaca gatcagtgtt tgccggggct aatggtgggg acggtgtgat   10440
agtgaaggga cagcacggag agtttttgcag ggtgacagac ctcttctgca tcctgccaac   10500
ggctgtgtga atctacttgt gtgaagactc agggaactca caccaaagga agacggtcac   10560 tttttcctact gtatgataga taattaataa aaagggagaa cggaggagtg tcgtcccagg   10620
aggcagggca ggagggcgaa gacgtgtcac aggggagcct ggccaagtgg cgccccgga    10680 actcgtcctc tgggcttgtg tgtggatgag acaaggtcta cctggtacga cagggacata   10740
ctgggaatgc gcccttgccg tggaggcggg gacccggcag cgctacgtat ccagcatcaa   10800
cctgtatcca gcatcaaccc gccaagttca ctaacttggt agggggtgagg ttagggatcc   10860 ttaggagccc aggcagccag acttctcggg gagcccattc ccatttgtgt tgccaaagta   10920
cccccagcag gttgtgggaa tgttgcctgt gaagagagtc tgttgggggtg agatcttgtg   10980 tgtgtgcaca gggtgacagt tgtgtcccat ttcccgggaa gctgtgatgg cagcagaacc   11040
tagaggagcc tgagagagtg tgggagagtg ggctctgga agagtagagg ctgcggagcc    11100
aggtgcaggg ctgtctgtca cccaaaggaa gagggactga tgactcactg agcgtgtgtg   11160
```

```
tcccctggtg gcagcaggcc ccatagtgaa cataccatac cttttctgtc ctgagcgatg  11220
ctcccagcag tcctgggaga tggaacggtc cttattcggc tcacaggaag gaccgcctta  11280
actggacaga cacagcaagg tgctaaagat gccttccatc agaggccagg ttggaagctc  11340
taaagagact tctcttgctg ttctctcacc caccccagg ttgtgtgtgt cccgctgtgg   11400
attctcatgt cctttctgtg cctggtggtc ctctactaca ttgtgtggtc cgtcttgttc  11460
ttgcgctcta tggatgtgat tgcggacagc gcaggacaca cataaccatg gcccgagct   11520 ggatgaccat cgtcgtgccc cttcttacat ttgaggtaag cgttccacgg gaagcctctt  11580
cagcccctga agcttgcgct tcccctgaca ggattctgca cccctagaaa ggcagcctct  11640
gtccctcgag ctcacagtga gcccactcca ggagagggga gagaacacag ccatctccga  11700
gagggagctt cggtgaaagg agagcatcct tcctttctct tggggcagc acgtggggct   11760 ggcagggaga agagtgcacc tttttagcca tggtgcctct gtatggctcc agtttccact  11820
ctggggaaag cagagtggga tgtcagattt gtgtattgga gtcacgtgga gaattctaga  11880
atgggagctg ttgactcctt agaacaaaca cccggaggag tttgccataa aactgctggc  11940
actgggaact tttcaagtgg ataggctatt gccgagctct gaagagggac ataaaagctc  12000
atttcgagct ttccccaggg ataggtggtt tcctgccttt ttctggcggt gctgatgttc  12060
cctcttgtgg gagctcacgc gggggtgggg tggtggggag gaactgccta atgaagtctg  12120
gcttccgcct ctgcccattt tcggtgctgg catcaaccgg gactatgtct ctttctttag  12180
attctgctgg ttcacaaact ggatggccac aacgccttct cctgcatccc gatctttgtc  12240
cccctttggc tctcgttgat cacgctgatg gcaaccacat ttggacagaa gggaggaaac  12300
cactgtatgt actcagcatt tcagaagtcc ttggtgtgtg tctgggggg gaccaggggg   12360 tgggggtgg cggatagaag tctaggaagg gatgagtccc cgagggcccc aatttagaag   12420
cttgtgtggg aaagtgaggg ctgaggaaat tctgggacct tctaagggaa gggcatgccg  12480
taactctggt gttctgctgg cctgcaccgg gactttctc gcagtgcacg ctgccatttg    12540
aggtagaacc agacacggca ggcaacctct cagagatccc gttccctcct ctgcaaaatg  12600
gggatcaaga cagattcttc ccaggcccgg gagggtttga tggaaaatcc acatctccca  12660
cccaaacctg ggattcatcc taggtccctg ttggccgctc tgcctccccc atatccttgc  12720
tgccatcacc cgagtcttgc ctgtcttgcc ttgctaacac tctattcccc tccacctgct  12780
tgctgaggca gacacttcca aaacgatctc tgcagagggt gccttcctgg caaggctgtg  12840
ggctccatgg cacggaagcc cagagcattg cccttcggaa agccagtggg tttgggggca  12900
gggcctcact gcagcccagc agcccgggct gtgcttgctg tttgtgcctc tgcccctac   12960 cccgcacccg ggagcaggga gggcttgcac cgagctgaca ctccagtagc ctacagagag  13020
gagtagtggg actgggaaag tggctttaag gtggctccat gagttcaggc cccctcctgg  13080
ccaacccgtg catgactacc gccctcacgg attccagagg gtgacagaaa tcttgttctt  13140
gggtggcact gtcatccatg agtttatcct ggctggagaa gattagcgga agacaccgta  13200
gtctgcgcac cacagatatt ttgagactca ctggagcagt agttctcaaa tttgggcatc  13260
cagcagaatc ccaaaagggc caggaaaagg ggaccgctgg agcccaccct agcccgactc  13320
agtttctgga ggtctgggct ggggcccgag aatggcatcc ctaactaggc cccgtggacg  13380
ctgtccctgc cggtccggga accccactcc aagcaccaca gagctagcat ttgcacttct  13440
tccccatttt gggtactcaa gccctgttca ggctttgtga ctcaggagtc tggataaagt  13500
atgttatgac attgtaggag tgaaacttct tgttacggaa agaaagttaa caggaaggtc  13560
```

```
agttgagcct cgtgtgtgaa ataaaaaatt cttattttc agggtggttt ggtatccgca    13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtaccctct tccccgtcag acccactggg agatggctgc    14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctgggc agtcagtagg aactgtaact atgtctctga    14340
tgcaccacgt gtttagacac agcacagtcc ttttttctgt tcctactgtg gaagtagttt   14400
ctctttgggc atgctgacag cagttttca tagcctcacg gatgagccct ttctacggga    14460
gtgactccat gcttgtatac agagtattta tacaaatgtt ttagcatctt catatgcggt   14520
gttaacccct agttctgtac agcatattct gttcaagtat tttttacaa gcttgtgctg    14580 taggcacatg ccttctgctg cagaagtgga cgcccgtggc acactccccc ccccccccg    14640 tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
tcctgcctga aaacaaatag gtcctttgct gaaaagaggg taaaaaaaga gctttgatct   15060
tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca ggcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
ttgccacact tgttactgct taggaggctt tctggagtgt tccttgggtg ctacgacaat   15600
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg attttcagtc ctgtgggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
```

```
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
cggccgggtt gagcatcagc agtctgtttg cagacccctc actgtcaccc cctgagccag   16140
tgcgccttgg gccctgcggt caggatgtct caagcgtgga ggcatcaccg gttcgtggca   16200
gtctctggaa ggtcactgag ctctgtgccc agaatcgagt cgggggagtc tgtgcagagg   16260
tggccctgtg tgtggggaca gtgtgtgaca cagacactgc tttggatgga cacctctccc   16320
gtgacctcct agcatccaat cccaaaggaa caactgttgc agagatggac cgctggacac   16380
aaacccacgt gcgtttctct ggagacactg gccaaggaaa acaaaacatg ctcgaaggcc   16440
aacagctgca tgccccaccg cgatgtgacc gcagacaccc ggggtgtaga agggtctctg   16500
cctggtgggg ggacacgtgc aggccgagga gaggcaggaa ggaggctgcc tccgactccc   16560
cactggactg catggcgacg gcgtgtggtg gggcagtcag ctaagccatt tgcctaaggg   16620
gctgtcgggc atctgcgtgc tggggaccga cagtgtgggt gtgttaggag gatctgtatg   16680
gagcacattg ctgcctctgg ctaggacagg gtggaaaggg tggcgtggct acagcctgac   16740
ccatgggcac cgtcctaccc tttgttctgt gcttccgagt gtcagtcatg tgctggggtc   16800
tgtgggccca tgactcagac ggtgagctct gaccttcctg agccagggct ttgctgtagt   16860
tgtgcctggc tcaggagctc taggacaagg ggaccgctcc aggtctgcat ctacggtgtg   16920
gcagggcccc tcggcactct tgtgcactag tgtcatcttt cccattgaaa tgactgtgag   16980
gaccagaatg tgcacatgca gatgggcagc tacttgtctg ccttggccct ttattacaca   17040
acttgctggg ggtggagatg ccaccccccg gcagtcagag cccctttatg atgtcatggg   17100
gctggttaca tgactgccaa ggggtgctgc tggccacact gcactagcaa gtttgccaga   17160
tggaggacaa gcgatcattg agtatggctc gctgtgaaga aagaaattcg agaggacagg   17220
atcatggctt ggaaagggtg ccttcccctc cccagttgca gtcagagacc taccttcacc   17280
cagcagatcc ttcccctgcc tgggacgacc cggggtccac tgggagccct aacttgaggc   17340
tgctgacaga agaaatcgct ttccaacctc tggccgagga agcttcgttc agaaggccgc   17400
accctgacgg tgacgtcccg ccccagggag aagataatct cctctccctc cccttttccac   17460 agaaactgtg gagactggtc agcagcaacc agttttcgtc catctggtgg gatgacagtg   17520
gggcttgtag agtgatcaat caaaaactct ttgaaaagga gattctcaaa agggacgtcg   17580
cacacaaagt gtttgccaca acttcgataa agagcttctt ccgccagcta aacttgtatg   17640
gcttccgaaa acgcgtcaa tgcactttca ggaccttcac ccgcattttc tccgcaaaaa   17700
ggctggtctc catcttgaat aaggtaatga acgacaagcc tctggagggg ttaagtcggt   17760
gggctctggg gcctggtcgg gtggaagtcc caggactgcc tcctgggaag tgggcgacct   17820
caggcagggt gtggggccat cgctgtgggc ctgtgtcccc ctctgggtgg aggtgacatg   17880
aactaagagt gaatgtgggg agagggctga ggatggtgcg ggccctctc gagtgtgtaa    17940 aatatcacag gtgccaagta gccgtatctg cgtgtcgtcc tccccggggc cagccatgtc   18000
atctggtggt tgctgtgtcc ccctgactcc acagcacatt ccctgtgag gtgagcaggc    18060 caggggagtc tggtatttgt accactgtca ccctagctgg tgtctggaga ggtgctcaag   18120
tggaagcact gaagggcgcc tggcgcagga ggtgcagatg ctcctgctgc ccttggtagg   18180
tgggcccctg gtgtggaaga gccagtaccc agggcctcca acccagccgg ggtgcattct   18240
gttgccagct gacactgcat gggggaggcc cagaatcttc ttccctcctg gtctgcaact   18300
tcaaagaccc tttccgccgg ccatggacac cctaatctgc cattttgagg cttttttccaa   18360
```

```
gacggaaagg cccgccacaa cttggtaaac cttgacgatg tgaacgcgag tccccagctt   18420
cctttgggga ctgggacctt ttccagaaag gcctcctggg ccagtagagt tctcttgcac   18480
aggggcgtag atggttggta gttgtagtcc atccttgtga cttg                    18524

<210> SEQ ID NO 13
<211> LENGTH: 7695
<212> TYPE: DNA
<213> ORGANISM: Homo sapiens

<400> SEQUENCE: 13
ggcccaggag gcctttctgg aaaaggtccc agtccccaaa ggaagctggg gactcgcgtt     60
cacatcgtca aggtttacca agttgtggcg ggcctttccg tcttggaaaa agcctcaaaa    120
tggcagatta gggtgtccat ggccggcgga aagggtcttt gaagttgcag accaggaggg    180
aagaagattc tgggcctccc ccatgcagtg tcagctggca acagaatgca ccccggctgg    240
gttggaggcc ctgggtactg gctcttccac accaggggcc cacctaccaa gggcagcagg    300
agcatctgca cctcctgcgc caggcgccct tcagtgcttc cacttgagca cctctccaga    360
caccagctag ggtgacagtg gtacaaatac cagactcccc tggcctgctc acctcacagg    420
gtaatgtgct gtggagtcag ggggacacag caaccaccag atgacatggc tggccccggg    480
gaggacgaca cgcagatacg gctacttggc acctgtgata ttttacacac tcgagagggg    540
cccgcaccat cctcagccct ctccccacat tcactcttag ttcatgtcac ctccacccag    600
agggggacac aggcccacag cgatggcccc acccctgcc tgaggtcgcc cacttcccag     660
gaggcagtcc tgggacttcc acccgaccag gcccagagc ccaccgactt aacccctcca     720
gaggcttgtc gttcattacc ttattcaaga tggagaccag cctttttgcg gagaaaatgc    780
gggtgaaggt cctgaaagtg cattgacgcc gttttcggaa gccatacaag tttagctggc    840
ggaagaagct ctttatcgaa gttgtggcaa cactttgtg tgcgacgtcc cttttgagaa      900 tctcctttc aaagagtttt tgattgatca ctctacaagc cccactgtca tcccaccaga     960
tggacgaaaa ctggttgctg ctgaccagtc tccacagttt ctgtggaaag ggagggaga    1020 ggagattatc ttctccctgg ggcgggacgt caccgtcagg gtgcggcctt ctgaacgaag   1080
cttcctcggc cagaggttgg aaagcgattt cttctgtcag cagcctcaag ttagggctcc    1140
cagtggaccc cgggtcgtcc caggcagggg aaggatctgc tgggtgaagg taggtctctg   1200
actgcaactg gggagggaaa ggcacccttt ccaagccatg atcctgtcct ctcgaatttc    1260
tttcttcaca gcgagccata tcaatgatc gcttgtcctc catctggcaa acttgctagt    1320
gcagtgtggc cagcagcacc ccttggcagt catgtaacca gccccatgac atcataaagg    1380
ggctctgact gccgggggt ggcatctcca ccccagcaa gttgtgtaat aaagggccaa     1440
ggcagacaag tagctgccca tctgcatgtg cacattctgg tcctcacagt catttcaatg   1500
ggaaagatga cactagtgca caagagtgcc gaggggccct gccacaccgt agatgcagac   1560
ctggagcggt ccccttgtcc tagagctcct gagccaggca caactacagc aaagccctgg    1620
ctcaggaagg tcagagctca ccgtctgagt catgggccca cagacccag cacatgactg     1680 acactcggaa gcacagaaca aagggtagga cggtgcccat gggtcaggct gtagccacgc   1740 cacccttttcc accctgtcct agccagaggc agcaatgtgc tccatacaga tcctcctaac    1800
acacccacac tgtcggtccc cagcacgcag atgcccgaca gccccttagg caaatggctt    1860
agctgactgc ccaccacac gccgtcgcca tgcagtccag tggggagtcg gaggcagcct    1920
ccttcctgcc tctcctcggc ctgcacgtgt cccccacca ggcagagacc cttctacacc    1980
```

-continued

```
ccgggtgtct gcggtcacat cgcggtgggg catgcagctg ttggccttcg agcatgtttt    2040
gttttccttg gccagtgtct ccagagaaac gcacgtgggt ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca gggggtgaca    2340
gtgaggggtc tgcaaacaga ctgctgatgc tcaacccggc cgctgccgag ctgtgtgact    2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccacctgt ggcctctggt tacaacccac aggactgaaa    2640
atccttccag ccacagcaac tggtgaattt cctggtcaat tgccacaagt catgagctga    2700
accccacttg agtttcagtt caggcagaac tctagagacg actagggcaa gctagacagc    2760
gactgcagag cctttgttg cagcgtgagc agtcctcagc tgttgacatc actggggagc    2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtataccct gggacctgtg    3000
cactgaagga ctcattctaa aggctgtgcc cctgcagccg ccagcctcac tcactggctg    3060
cctgtgccag ctagagattt ctttcctctg aggctggctg agaggaccac tccagttttcc    3120 tggcccatcc agcaaagaag atacacatca tgcacgtgta aaatgaggaa ccggtttatt    3180
gaacagctta aggagagcaa aaatagtggc tttagctaca tttttttacac actgagcagg    3240 aaagtctaaa ccatcccgtt ccctgtacc ccaaagagaa cagggcttgc tggaggccag    3300
tgccaagggc ggagtcgtgc tcgcagcaga cttgaattaa ccccatgtag gccggcgagc    3360
agttgcccgc gtgaaaacac caccctcttc tcctggctga aagatcaaa gctctttttt    3420 taccctcttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttcccacgca    3600
tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtggca gtagcagcta ctacgtacct gcacgagttc    3780
cagggcagaa gtggcaatgt cccatgaagg cgtggcaccc cacgggggg ggggggagt    3840 gtgccacggg cgtccacttc tgcagcagaa ggcatgtgcc tacagcacaa gcttgtaaaa    3900
aaatacttga acagaatatg ctgtacagaa ctagggtta acaccgcata tgaagatgct    3960
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatacttt gattgggatt    4260 tcagcaccgt atagacagat gttccttctg ggggcctggc aagcagccat ctcccagtgg    4320
gtctgacggg gaagaggggt acctggagcc cctcccagac agacggtaat cccaccctg    4380
```

```
ttctcacact cttcctggca tccgcatctg ctggcacaca ccccgtcac ctgccacttc    4440 cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560
gaaggcggag agagtgcgtc ccagtccact taagctctgt ccccggaagt ggcatctaat    4620
ctggcatttc gatatttaat ttgggaggtg ggagcacata cttcccaggg ctctgggtaa    4680
tgaccaccct ggccttcttt cgaaacatgg gtgcgatttt agggggctcc ggaactgggg    4740
tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaattttt atttcacaca cgaggctcaa ctgaccttcc tgttaacttt    4920
ctttccgtaa caagaagttt cactcctaca atgtcataac atactttatc cagactcctg    4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt cccctttcc tggccctttt gggattctgc tggatgccca aatttgagaa    5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtaggggg cagaggcaca    5520
aacagcaagc acagcccggg ctgctgggct gcagtgaggc cctgccccca aacccactgg    5580 cttttccgaag ggcaatgctc tgggcttccg tgccatggag cccacagcct tgccaggaag    5640
gcaccctctg cagagatcgt tttggaagtg tctgcctcag caagcaggtg gaggggaata    5700
gagtgttagc aaggcaagac aggcaagact cgggtgatgg cagcaaggat atggggagg    5760 cagagcggcc aacagggacc taggatgaat cccaggtttg ggtgggagat gtggattttc    5820
catcaaaccc tcccgggcct gggaagaatc tgtcttgatc cccatttgc agaggaggga    5880 acgggatctc tgagaggttg cctgccgtgt ctggttctac ctcaaatggc agcgtgcact    5940
gcgagaaaag tcccggtgca ggccagcaga acaccagagt tacggcatgc ccttccctta    6000
gaaggtccca gaatttcctc agccctcact ttcccacaca agcttctaaa ttggggccct    6060
cggggactca tcccttccta gacttctatc cgccaccccc cacccctgg tccccccca    6120 gacacacacc aaggacttct gaaatgctga gtacatacag tggtttcctc ccttctgtcc    6180
aaatgtggtt gccatcagcg tgatcaacga gagccaaagg gggacaaaga tcggatgca    6240 ggagaaggcg ttgtggccat ccagtttgtg aaccagcaga atctaaagaa agagacatag    6300
tcccggttga tgccagcacc gaaaatgggc agaggcggaa gccagacttc attaggcagt    6360
tcctccccac caccccaccc ccgcgtgagc tcccacaaga gggaacatca gcaccgccag    6420
aaaaaggcag gaaaccacct atccctgggg aaagctcgaa atgagctttt atgtccctct    6480
tcagagctcg gcaatagcct atccacttga aaagttccca gtgccagcag ttttatggca    6540
aactcctccg ggtgtttgtt ctaaggagtc aacagctccc attctagaat tctccacgtg    6600
actccaatac acaaatctga catcccactc tgctttcccc agagtggaaa ctggagccat    6660
acagaggcac catggctaaa aaggtgcact cttctccctg ccagcccac gtgctgcccc    6720 caagagaaag gaaggatgct ctcctttcac cgaagctccc tctcggagat ggctgtgttc    6780
```

```
tctcccctct cctggagtgg gctcactgtg agctcgaggg acagaggctg cctttctagg    6840
ggtgcagaat cctgtcaggg gaagcgcaag cttcaggggc tgaagaggct tcccgtggaa    6900
cgcttacctc aaatgtaaga aggggcacga cgatggtcat ccagctcagg gccatggtta    6960
tgtgtgtcct gcgctgtccg caatcacatc catagagcgc aagaacaaga cggaccacac    7020
aatgtagtag aggaccacca ggcacagaaa ggacatgaga atccacagcg gacacacac    7080 aacctggggg tgggtgagag aacagcaaga gaagtctctt tagagcttcc aacctggcct    7140
ctgatggaag gcatctttag caccttgctg tgtctgtcca gttaaggcgg tccttcctgt    7200
gagccgaata aggaccgttc catctcccag gactgctggg agcatcgctc aggacagaaa    7260
aggtatggta tgttcactat ggggcctgct gccaccaggg gacacacacg ctcagtgagt    7320
catcagtccc tcttcctttg ggtgacagac agccctgcac ctggctccgc agcctctact    7380
cttccagagg cccactctcc cacactctct caggctcctc taggttctgc tgccatcaca    7440
gcttcccggg aaatgggaca caactgtcac cctgtgcaca cacacaagat ctcaccccaa    7500
cagactctct tcacaggcaa cattcccaca acctgctggg ggtactttgg caacacaaat    7560
gggaatgggc tccccagaaa gtctggctgc ctgggctcct aaggatccct aacctcaccc    7620
ctaccaagtt agtgaacttg gcgggttgat gctggataca ggttgatgct ggatacgtag    7680
cgctgccggg tgacc                                                    7695

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14
gggcgaattg ggcccgacgt cgcatgctcc cggccgccat ggcggccgcg ggaattcgat      60
atcactagtg aattcgcggc cggcgattgg gcccgacgtc gcatgctccc ggccgccatg     120
gcggccgcgg gaattcgatt ccttaattaa gtcgactggg acccaaactt tggagtcgtt     180
gacagatgtg acaggtgaag cctgggatga catcgccaaa aatgcaacgt tcactcatt     240 gtcactactc ccagggctca gtcgtcactg gggaaaatct ccagaaggta gcgcgggcca     300
aggtgacagg tgtctgccaa gatctgcccg ccagactccc gggcggcgcg ctccctccct     360
gcaggccttc agcccgtcag catcccttc ctcggggccc tgctcactcc cagcctccat     420 cccctgcca tctcctccgc cggtcgcgtg cggacacaag gatgggggacc tcccagcgag     480 gagcgctctg ggcggggctc cggacgcatg cgcggccctc gtacggaagc ccggaaggag     540 gggcagggg cggtggctca ggtttctccg ggcggcggcg gcggcggcgg cggcgacggc     600
gacggcgacg gcagcgggga cggcagcagt agcgggagca gcagcgtgga cgcggctggc     660
gctggcgcca tgaacccgct gtaaggcgca ggctgtgcag cacggggtgc ggggaggag     720 gaggaggacg ccgcgtgaa gttctccgcc atgaacctga gggcctctt ccaggacttc     780 aacccgaggt gaggcggcgt cgttggcgcc cccgggagtc cgcgctgcgg gctcgggcgc     840
gggctggtgt tcggctccgg ggaggcacgg cgggcgagat gctgcagccc gaggacccgg     900
gcgcctgccc gagcctccct gcgggtgcaa gcggtcccca ggcaaaacag tcggcctcgg     960
cgcccgcccg cttcctcctc ccgtgccgg tgctttcagc ccctgccggg ccacggccgg    1020
aagggcccgg ccgcgagccc cgtcctgccc caagggaacc ccattctttt ctgcttgctg    1080
tccctcattg gtgtcccaac ttcttcgtct cggttccatc ctcttctgcg ccgctgcggg    1140
```

```
cctccattc tccgcgtcag ggccgtctca ctcgacccaa cacccctacc cccaccccag    1200
ctgtttcctc cagttcctcg cagtccttgg ggttttcctt gggtttatgc ccatccctct    1260
cttgtttgct tctttgttga acggatacct gaaacactgt tgaatccttg gagtcagtgt    1320
cggggtatgg caataccttt ataatgcat  ttctgggtga gcctgatcat tttccatact    1380
cattttctca tcagtcttca ctacaagttt atttgcagga agtagatatt gctgtccttc    1440
ttttccagat ggggaacacc cagtggacag tgtggagaaa acactggcta agcactcaag    1500
cgcctgtcct tgcacttgcc cgactgtttt gtaactgttc tttacccag  gctgtgagct    1560 ccctgaagct gagaccatct cctgctcatc tcagtgtccc cagcgcctcc cacccaccgt    1620
atctggcaca tagtaggcac atataaaatg tttgtggaac taaactgagc ccaaagactt    1680
ggattggaga cgaggccata tgtaactggg tgattctctg cccttctttg gcccttctgt    1740
aaaatgagga gttggcctaa ctgatctctt aaatgcacta ctctccgaaa ggagtatccg    1800
tttcccttat ttgccagttg ggaagacgtg ctcagtaaat atttgtgtgc tgtaacctat    1860
gttaggtgct ttagatgctg gcggtctcag catggggtga agaagggctt gtacacttaa    1920
gatgccttac agtactgtgc agtgctgtac tgcggggggcc aactctgggg acctatgcct    1980
tggctgcttg ttgaggatga aaggaagttt taggggagta tttgtatgtt gagggtgcag    2040
tctccctagg gatggtgaca ttttaacttg tgagtcattg tgactttgta tgtgccctta    2100
ttccactttg agttcatgtt ctggttagga gtgccagtgt ctctaacacg gtgcagacat    2160
tatcattgtt ggcttcgaag gcatagagga ggtaacagaa ctaactgcag tcccttcctc    2220
tgctgcatca gggggttaag attggtctgc agggtagtag ggttggtgct gtggctggac    2280
aagccctgta tgtcttctat ttggagatgg tgataagaaa gttaagtaaa aactgaattg    2340
ttttgtgccc ttgggcaact cacttatcta ttgttttatc tgtagaatga gtataatctc    2400
tcagtggggt agggaggcca attaaggatt gattacaaag tgccttacaa atagaaagct    2460
acagtgactt gttttgcaagg tgacagagaa ttcagaagcc tcaagaaact gccttaagtg    2520
atcaaacagg ctaacggagt tgccaaagca aaatagtgct gcactgatac tacctttaac    2580
cgttttttcc tttagcccctt ttccccccaa aaaaattagt atatgaaatt acagtgaaat    2640
acctggtatc taagcagatt tatagtaatt ctcaacatat tcatcaatct cttaattcta    2700
cctgcattaa aatgtatttc tacctgaaaa gtttaaaggt cttttatact gtgccatttt    2760
cctgattcat tgttgccaga ggtagtgagt tccttaattt tacagatatt tcaagaggac    2820
attggccagg tattattggt aaatcagatt tgttttttta gctggtagtg tttcacctct    2880
cctgagcact cctagttttt gacagtgtgc tttagtctcc ttccatgctg aggaaggcct    2940
tctctatagg agaaagaaaa ctgaggggtg tacacaggaa gttaccttat gctggggact    3000
caaaccttga tgctactgct ttgctccctg cctctatttt tgaaccaatt caacatctcc    3060
ctcctacccc aggaccttgt cacacactgt tctctttacc aggaatgttt ccctctcttt    3120
tcctctcctc cagacctagt gaactcctat ttatcctcac ttggcacttg ctaagggaag    3180
cattcctgac ttccctgacc agatttactg ctccctgttt ctacagttcc tgtagtattt    3240
actactcctc catcatagtg catatttgta cccttgtgtc tgtctggatg cttatttgat    3300
taatacctgc ctccccccact aaactttaag ctccatgggg tcaaggccgt gactgtgtca    3360
gtatcgtagc ctgcatactt ggaatagtac ctggctcaat aaatatttgt ggagtaaata    3420
actgaataac tctccagagc ctataagata aatctagagc tgctgctttc aatcactgct    3480
ttcctggtgg tctgtggcct ggttctcttt cttctcacac tcttcccacc ttcagagtgc    3540
```

```
agccattgct ttggagagat gggagagaac atggcactaa ggcagaatat ggctatattt   3600
actttgaaga gcatgtcttt gtcatagaaa tagtcactgt catggtttgg tgggtcccaa   3660
ggcatgggtc atggctccag atccccttc cagccttttg gatcttggta agtctgaacc    3720
cactgctgcg ttggcaaggc tctggaaact atagtgacag agaatgattc acaagtgtca   3780
acactcagat gtacagggct gccagctgac ccactctacc tatttccatc tggcactgaa   3840
ctggttgatc atgaacttct tttcataatt gcttttagt tatgcaggtt aagacatgcc    3900
gaaacagatg taccgaccc acaaacaagt ccttccttga atgcctgagg cttcctaaca    3960
gtgaaagagc cctgttctta gagtaggcaa actgattctg aggcattgta ggtggtaggg   4020
atctggtagt aggtagcatt aggtgggctc ccggcactca ccatggagcc ttgaaatttt   4080
ctgctacttt gggggagttg ctggttcaga gaaggcct ccaccctggt agccatgtgg     4140
cactggaagg ctgtgaaaac tctgctgggc cttcttagtc atctgttgtg agctcctgat   4200
gggagtgtgg tgtatccctc aggtgtgcta gactggaaca aaggctgaga agtgttgctc   4260
tgggggttcc aacttgtggg catggggtac tgatgagatc agtagtgttt ggagacttct   4320
gtatgctcca tcttcagaag acattctgga gtccatataa gttatcttgt ctcttgtttg   4380
aagcaggaaa aaggaatgcg attgctggta atatagttca ctaaagtcag ctacctggcc   4440
tctaacagtt atttgcaaag tatattataa cattgattcc tcaaacatct agattcctat   4500
ctcgtgccaa gtgatgtact aggtgctcta agtacaaaaa taaggaata tagtcctcct    4560 ctcaatgcgt aagcctagtg gaagaagcag aaatgaaagg gaataagaa ttcaatagag    4620 tatgaggcat tacagtgaaa gaaaccaaat gtcttagaag tacaaatggc agagctacta   4680
attctgtctc gagcaggcag ggaagagtct atagtgaaa tgactttga gctagatttt     4740 gaattgagct agtcttttga gccagacttt tgagctagaa ttgtagggtt gtcatcagac   4800
cagagagtag gaagggtacc ttgtgaggaa gagagagaga gatcagattg ttactgtgtc   4860
tatgtagaaa aggaagacat aagaaactcc attttgatct gtactaagaa aaattgtttc   4920
tgctttgaga tgctgttaac ctgtaacttt agtcccaacc ctgtgctcac agaaacctgt   4980
gctgtaatga atcaaggttt aatggattta gggctgtgca ggatgtacct tgttaacaat   5040
atgtttgcag gcagtatgct tggtaaaagt catcgccatt ctccattctc gattaaccag   5100
ggacacagtg cactgcggaa ggccgcaggg acatctgccc aagaaagcct gggtattgtc   5160
caaggtttcc ccccactgag acagcctgag atatggcctt gtgggaaagg aaagacctta   5220 ccaccccca gcccgacacc cgtaaagtgt ctgtgctgag gaggagtagt gaaagagcgg    5280
ggcctctttg cagttgagat aagaggaagg cttctgtctc ctgctcatcc ctgggaatgg   5340
aatgtctctg tgtaaagctg accattccca ttcgttctat tctgagatag gagaaaacca   5400
ccctgtggct ggaggcgaag tatgctggca gcaatactgc tctgttactc tttgctacac   5460
tgagttgttt gggtaaagag aaacataaat ctagcctgcg tgcacatcca ggcacagtac   5520 cttccttga acttattcat gatacagatt cctttgctca cgtttccctg ctgaccttct    5580
ccccacctgt tgccctgcta cactcccctc gctaagatag taaaataat gatcagtaaa    5640 tactgaggta actcagaggc tagcgctggt gcgggtcctc cgtatgctga gtgccggtcc   5700
cctgggccca ctgttctttc tctatacttt gtttctgtgt cttatttctt ttctcagtct   5760
cgtcccacct gacgagaaat acccacaggt gtggagggc tggccccttt cagtatctca    5820
gaagggacaa agtacacaaa ggcatggggt catgatagtg cctggtatgt tcaggtagtg   5880
aagaggtcca tgtggtatga gcactgcaga tgatatgtgt cgtatgaatt aaaaatacat   5940
```

```
agttactgca aatagttttt acaggttatt gtttttaaga aagcagtatc taatgcacga   6000
gtgtactgtc agtactgtca atgaactact taccactcaa gtgactgctt acgcgtcgaa   6060
tcactagtga attcgcggcc gcctgcaggt cgaccatatg ggagagctcc caacgcgttg   6120
gatgcatagc ttgagtattc tatagtgtca cctaaatagc ttggcgtaat catggtcata   6180
gctgtttcct gtgtgaaatt gttatccgct cacaattcca cacaacatac gagccggaag   6240
cataaagtgt aaagcctggg gtgcctaatg agtgagctaa ctcacattaa ttgcgttgcg   6300
ctcactgccc gctttccagt cgggaaacct gtcgtgccag ctgcattaat gaatcggcca   6360
acgcgcgggg agaggcggtt tgcgtattgg gcgctcttcc gcttcctcgc tcactgactc   6420
gctgcgctcg tcgttcggc tgcggcgagc ggtatcagct cactcaaagg cggtaatacg   6480
gttatccaca gaatcagggg ataacgcagg aaagaacatg tgagcaaaag gccagcaaaa   6540
ggccaggaac cgtaaaaagg ccgcgttgct ggcgtttttc cataggctcc gcccccctga   6600
cgagcatcac aaaaatcgac gctcaagtca gaggtggcga aacccgacag gactataaag   6660
ataccaggcg tttccccctg gaagctccct cgtgcgctct cctgttccga cctgccgct   6720 taccggatac ctgtccgcct ttctcccttc gggaagcgtg gcgctttctc atagctcacg   6780
ctgtaggtat ctcagttcgg tgtaggtcgt tcgctccaag ctgggctgtg tgcacgaacc   6840
ccccgttcag cccgaccgct gcgccttatc cggtaactat cgtcttgagt ccaacccggt   6900
aagacacgac ttatcgccac tggcagcagc cactggtaac aggattagca gagcgaggta   6960
tgtaggcggt gctacagagt tcttgaagtg gtggcctaac tacggctaca ctagaagaac   7020
agtatttggt atctgcgctc tgctgaagcc agttaccttc ggaaaaagag ttggtagctc   7080
ttgatccggc aaacaaacca ccgctggtag cggtggtttt tttgtttgca agcagcagat   7140
tacgcgcaga aaaaaggat ctcaagaaga tcctttgatc ttttctacgg ggtctgacgc   7200
tcagtggaac gaaaactcac gttaagggat tttggtcatg agattatcaa aaaggatctt   7260
cacctagatc cttttaaatt aaaaatgaag ttttaaatca atctaaagta tatatgagta   7320
aacttggtct gacagttacc aatgcttaat cagtgaggca cctatctcag cgatctgtct   7380
atttcgttca tccatagttg cctgactccc cgtcgtgtag ataactacga tacgggaggg   7440
cttaccatct ggccccagtg ctgcaatgat accgcgagac ccacgctcac cggctccaga   7500
tttatcagca ataaaccagc cagccggaag ggccgagcgc agaagtggtc ctgcaacttt   7560
atccgcctcc atccagtcta ttaattgttg ccgggaagct agagtaagta gttcgccagt   7620
taatagtttg cgcaacgttg ttgccattgc tacaggcatc gtggtgtcac gctcgtcgtt   7680
tggtatggct tcattcagct ccggttccca acgatcaagg cgagttacat gatcccccat   7740
gttgtgcaaa aaagcggtta gctccttcgg tcctccgatc gttgtcagaa gtaagttggc   7800
cgcagtgtta tcactcatgg ttatggcagc actgcataat tctcttactg tcatgccatc   7860
cgtaagatgc ttttctgtga ctggtgagta ctcaaccaag tcattctgag aatagtgtat   7920
gcggcgaccg agttgctctt gcccggcgtc aatacgggat aataccgcgc cacatagcag   7980
aactttaaaa gtgctcatca ttggaaaacg ttcttcgggg cgaaaactct caaggatctt   8040
accgctgttg agatccagtt cgatgtaacc cactcgtgca cccaactgat cttcagcatc   8100
ttttactttc accagcgttt ctgggtgagc aaaaacagga aggcaaaatg ccgcaaaaaa   8160
gggaataagg gcgacacgga aatgttgaat actcatactc ttcctttttc aatattattg   8220
aagcatttat cagggttatt gtctcatgag cggatacata tttgaatgta tttagaaaaa   8280
taaacaaata ggggttccgc gcacatttcc ccgaaaagtg ccacctgatg cggtgtgaaa   8340
```

```
taccgcacag atgcgtaagg agaaaatacc gcatcaggaa attgtaagcg ttaatatttt      8400
gttaaaattc gcgttaaatt tttgttaaat cagctcattt tttaaccaat aggccgaaat      8460
cggcaaaatc ccttataaat caaaagaata gaccgagata gggttgagtg ttgttccagt      8520
ttggaacaag agtccactat taaagaacgt ggactccaac gtcaagggc gaaaaccgt        8580 ctatcagggc gatggcccac tacgtgaacc atcaccctaa tcaagttttt tggggtcgag      8640
gtgccgtaaa gcactaaatc ggaaccctaa agggagcccc cgatttagag cttgacgggg      8700
aaagccggcg aacgtggcga aaggaagg gaagaaagcg aaaggagcgg gcgctagggc        8760
gctggcaagt gtagcggtca cgctgcgcgt aaccaccaca cccgccgcgc ttaatgcgcc      8820
gctacagggc gcgtccattc gccattcagg ctgcgcaact gttgggaagg gcgatcggtg      8880
cgggcctctt cgctattacg ccagctggcg aaaggggat gtgctgcaag gcgattaagt       8940
tgggtaacgc cagggttttc ccagtcacga cgttgtaaaa cgacggccag tgaattgtaa      9000
tacgactcac tata                                                        9014

<210> SEQ ID NO 15
<211> LENGTH: 5954
<212> TYPE: DNA
<213> ORGANISM: Homo sapiens

<400> SEQUENCE: 15
ggccgcggga attcgattcc ttaattaagt cgactgggac ccaaactttg gagtcgttga        60
cagatgtgac aggtgaagcc tgggatgaca tcgccaaaaa tgcaacgtct cactcattgt       120
cactactccc agggctcagt cgtcactggg gaaaatctcc agaaggtagc gcgggccaag       180
gtgacaggtg tctgccaaga tctgcccgcc agactcccgg gcggcgcgct ccctccctgc       240
aggccttcag cccgtcagca tccccttcct cggggccctg ctcactccca gcctccatcc       300
ccctgccatc tcctccgccg gtcgcgtgcg gacacaagga tggggacctc ccagcgagga       360
gcgctctggg cggggctccg gacgcatgcg cggccctcgt acggaagccc ggaaggaggg       420
gcagggggcg gtggctcagg tttctccggg cggcggcggc ggcggcggcg gcgacggcga       480
cggcgacggc agcggggacg gcagcagtag cgggagcagc agcgtggacg cggctggcgc       540
tggcgccatg aacccgctgt aaggcgcagg ctgtgcagca cggggtgcgg gggaggagga       600
ggaggacgcc gcggtgaagt tctccgccat gaacctgagg ggcctcttcc aggacttcaa       660
cccgaggtga ggcggcgtcg ttggcgcccc cgggagtccg cgctgcgggc tcggcgcgg       720 gctggtgttc ggctccgggg aggcacggcg ggcgagatgc tgcagcccga ggacccgggc       780
gcctgcccga gctccctgc gggtgcaagc ggtccccagg caaaacagtc ggcctcggcg       840
cccgcccgct tcctcctccc gtgcccggtg ctttcagccc ctgcccggcc acggccggaa       900
gggcccggcc gcgagccccg tcctgcccca agggaacccc attctttct gcttgctgtc        960 cctcattggt gtcccaactt cttcgtctcg gttccatcct cttctgcgcc gctgcgggcc      1020
ctccattctc cgcgtcaggg ccgtctcact cgacccaaca cccctacccc caccccagct      1080
gtttcctcca gttcctcgca gtccttgggg ttttccttgg gttatgccc atccctctct       1140 tgtttgcttc tttgttgaac ggatacctga aacactgttg aatccttgga gtcagtgtcg      1200
gggtatggca ataccttata taatgcattt ctgggtgagc ctgatcattt tccatactca      1260
ttttctcatc agtcttcact acaagtttat ttgcaggaag tagatattgc tgtccttctt      1320
ttccagatgg gaacaccca gtggacagtg tggagaaaac actggctaag cactcaagcg       1380
cctgtccttg cacttgcccg actgttttgt aactgttctt taccccaggc tgtgagctcc      1440
```

```
ctgaagctga gaccatctcc tgctcatctc agtgtcccca gcgcctccca cccaccgtat   1500
ctggcacata gtaggcacat ataaaatgtt tgtggaacta aactgagccc aaagacttgg   1560
attggagacg aggccatatg taactgggtg attctctgcc cttcttggc ccttctgtaa    1620 aatgaggagt tggcctaact gatctcttaa atgcactact ctccgaaagg agtatccgtt   1680
tcccttattt gccagttggg aagacgtgct cagtaaatat ttgtgtgctg taacctatgt   1740
taggtgcttt agatgctggc ggtctcagca tggggtgaag aagggcttgt acacttaaga   1800
tgccttacag tactgtgcag tgctgtactg cggggccaa ctctggggac ctatgccttg    1860
gctgcttgtt gaggatgaaa ggaagtttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgcccct gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc cttaagtgat   2400
caaacaggct aacggagttg ccaaagcaaa atagtgctgc actgatacta cctttaaccg   2460
ttttttcctt tagccctttt cccccaaaa aaattagtat atgaaattac agtgaaatac     2520
ctggtatcta agcagattta tagtaattct caacatattc atcaatctct taattctacc   2580
tgcattaaaa tgtatttcta cctgaaaagt ttaaaggtct tttatactgt gccattttcc   2640
tgattcattg ttgccagagg tagtgagttc cttaatttta cagatatttc aagaggacat   2700
tggccaggta ttattggtaa atcagatttg ttttttttagc tggtagtgtt tcacctctcc   2760
tgagcactcc tagtttttga cagtgtgctt tagtctcctt ccatgctgag aaggccttc    2820 tctataggag aaagaaaact gaggggtgta cacaggaagt tacctatgc tgggactca     2880 aaccttgatg ctactgcttt gctccctgcc tctatttttg aaccaattca acatctccct   2940
cctaccccag gaccttgtca cacactgttc tctttaccag gaatgtttcc ctctcttttc   3000
ctctcctcca gacctagtga actcctattt atcctcactt ggcacttgct aagggaagca   3060
ttcctgactt ccctgaccag atttactgct ccctgtttct acagttcctg tagtatttac   3120
tactcctcca tcatagtgca tatttgtacc cttgtgtctg tctggatgct tatttgatta   3180 ataccctgcct ccccactaa actttaagct ccatggggtc aaggccgtga ctgtgtcagt   3240
atcgtagcct gcatacttgg aatagtacct ggctcaataa atatttgtgg agtaaataac   3300
tgaataactc tccagagcct ataagataaa tctagagctg ctgctttcaa tcactgcttt   3360
cctggtggtc tgtggcctgg ttctctttct tctcacactc ttcccacctt cagagtgcag   3420
ccattgcttt ggagagatgg gagagaacat ggcactaagg cagaatatgg ctatatttac   3480
tttgaagagc atgtctttgt catagaaata gtcactgtca tggtttggtg ggtcccaagg   3540
catgggtcat ggctccagat cccctttcca gccttttgga tcttggtaag tctgaaccca   3600
ctgctgcgtt ggcaaggctc tggaaactat agtgacagag aatgattcac aagtgtcaac   3660
actcagatgt acagggctgc cagctgaccc actctaccta tttccatctg gcactgaact   3720
ggttgatcat gaacttcttt tcataattgc ttttagtta tgcaggttaa gacatgccga     3780
aacagatgta ccggacccac aaacaagtcc ttccttgaat gcctgaggct tcctaacagt   3840
```

```
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgttt gaa    4260 gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga ataagaatt caatagagta    4500 tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagacttttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
ctttgagatg ctgttaacct gtaactttag tcccaaccct gtgctcacag aaacctgtgc    4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaggaa agaccttacc    5100 acccccagc ccgacacccg taaagtgtct gtgctgagga ggagtagtga aagagcgggg    5160
cctctttgca gttgagataa gaggaaggct tctgtctcct gctcatccct gggaatggaa    5220
tgtctctgtg taaagctgac cattcccatt cgttctattc tgagatagga gaaaccacc    5280 ctgtggctgg aggcgaagta tgctggcagc aatactgctc tgttactctt tgctacactg    5340
agttgtttgg gtaaagagaa acataaatct agcctgcgtg cacatccagg cacagtacct    5400
ttccttgaac ttattcatga tacagattcc tttgctcacg tttccctgct gaccttctcc    5460
ccacctgttg ccctgctaca ctcccctcgc taagatagta aaataatga tcagtaaata    5520 ctgaggtaac tcagaggcta gcgctggtgc gggtcctccg tatgctgagt gccggtcccc    5580
tgggcccact gttctttctc tatactttgt ttctgtgtct tatttctttt ctcagtctcg    5640
tcccacctga cgagaaatac ccacaggtgt ggaggggctg gccccttttca gtatctcaga    5700 agggacaaag tacacaaagg catggggtca tgatagtgcc tggtatgttc aggtagtgaa    5760
gaggtccatg tggtatgagc actgcagatg atatgtgtcg tatgaattaa aaatacatag    5820
ttactgcaaa tagttttttac aggttattgt ttttaagaaa gcagtatcta atgcacgagt    5880
gtactgtcag tactgtcaat gaactactta ccactcaagt gactgcttac gcgtcgaatc    5940
actagtgaat tcgc                                                      5954
```

<210> SEQ ID NO 16  
<211> LENGTH: 30756  
<212> TYPE: DNA  
<213> ORGANISM: Homo sapiens  
<220> FEATURE:  
<221> NAME/KEY: misc_feature

```
<222> LOCATION: (1)..(30756)
<223> OTHER INFORMATION: n= a, c, g, t, unknown or other

<400> SEQUENCE: 16
gtacggaagc ccggaaggag gggcagggggg cggtggctca ggtttctccg ggcggcggcg      60
gcggcggcgg cggcgacggc gacggcgacg gcagcgggga cggcagcagt agcgggagca     120
gcagcgtgga cgcggctggc gctgcgccaa tgaacccgct gtaaggcgca ggctgtgcag     180
cacggggtgc gggggaggag gaggaggacg ccgcggtgaa gttctccgcc atgaacctga     240
ggggcctctt ccaggacttc aacccgaggt gaggcggcgt cgttggcgcc cccgggagtc     300
cgcgctgcgg gctcgggcgc gggctggtgt tcggctccgg ggaggcacgg cgggcgagat     360
gctgcagccc gaggacccgg gcgcctgccc gagcctccct gcgggtgcaa gcggtcccca     420
ggcaaaacag tcggcctcgg cgcccgcccg cttcctcctc ccgtgcccgg tgctttcagc     480
ccctgcccgg ccacggccgg aagggcccgg ccgcgagccc cgtcctgccc caagggaacc     540
ccattctttt ctgcttgctg tccctcattg gtgtcccaac ttcttcgtct cggttccatc     600
ctcttctgcg ccgctgcggg ccctccattc tccgcgtcag ggccgtctca ctcgacccaa     660 caccccctacc cccaccccag ctgtttcctc cagttcctcg cagtccttgg ggttttcctt    720
gggtttatgc ccatccctct cttgtttgct tctttgttga acggatacct gaaacactgt     780
tgaatccttg gagtcagtgt cggggtatgg caataccttta tataatgcat ttctgggtga    840
gcctgatcat tttccatact cattttctca tcagtcttca ctacaagttt atttgcagga     900
agtagatatt gctgtccttc ttttccagat ggggaacacc cagtggacag tgtggagaaa     960
acactggcta agcactcaag cgcctgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gcccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgccttac agtactgtgc agtgctgtac tgcggggggcc    1440 aactctgggg acctatgcct tggctgcttg ttgaggatga aaggaagttt taggggagta    1500
tttgtatgtt gagggtgcag tctccctagg gatggtgaca tttaacttg tgagtcattg    1560 tgactttgta tgtgcccttta ttccactttg agttcatgtt ctggttagga gtgccagtgt   1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac taccttttaac cgttttttcc tttagcccctt ttccccccaa aaaaattagt   2100
atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220 ctttatact gtgccatttt cctgattcat tgttgccaga ggtagtgagt tccttaattt     2280
```

-continued

| | | | | |
|---|---|---|---|---|
| tacagatatt | tcaagaggac | attggccagg | tattattggt | aaatcagatt tgttttttta | 2340 |
| gctggtagtg | tttcacctct | cctgagcact | cctagttttt | gacagtgtgc tttagtctcc | 2400 |
| ttccatgctg | aggaaggcct | tctctatagg | agaaagaaaa | ctgagggggtg tacacaggaa | 2460 |
| gttaccttat | gctggggact | caaaccttga | tgctactgct | ttgctccctg cctctatttt | 2520 |
| tgaaccaatt | caacatctcc | ctcctacccc | aggaccttgt | cacacactgt tctctttacc | 2580 |
| aggaatgttt | ccctctcttt | tcctctcctc | cagaccctagt | gaactcctat ttatcctcac | 2640 |
| ttggcacttg | ctaagggaag | cattcctgac | ttccctgacc | agattactg ctccctgttt | 2700 |
| ctacagttcc | tgtagtattt | actactcctc | catcatagtg | catatttgta cccttgtgtc | 2760 |
| tgtctggatg | cttatttgat | taatacctgc | ctcccccact | aaactttaag ctccatgggg | 2820 |
| tcaaggccgt | gactgtgtca | gtatcgtagc | ctgcatactt | ggaatagtac ctggctcaat | 2880 |
| aaatatttgt | ggagtaaata | actgaataac | tctccagagc | ctataagata aatctagagc | 2940 |
| tgctgctttc | aatcactgct | ttcctggtgg | tctgtggcct | ggttctcttt cttctcacac | 3000 |
| tcttcccacc | ttcagagtgc | agccattgct | ttggagagat | gggagagaac atggcactaa | 3060 |
| ggcagaatat | ggctatattt | actttgaaga | gcatgtcttt | gtcatagaaa tagtcactgt | 3120 |
| catggtttgg | tgggtcccaa | ggcatgggtc | atggctccag | atccccttc cagccttttg | 3180 |
| gatcttggta | agtctgaacc | cactgctgcg | ttggcaaggc | tctggaaact atagtgacag | 3240 |
| agaatgattc | acaagtgtca | acactcagat | gtacagggct | gccagctgac ccactctacc | 3300 |
| tatttccatc | tggcactgaa | ctggttgatc | atgaacttct | tttcataatt gcttttagt | 3360 |
| tatgcaggtt | aagacatgcc | gaaacagatg | taccggaccc | acaaacaagt ccttccttga | 3420 |
| atgcctgagg | cttcctaaca | gtgaaagagc | cctgttctta | gagtaggcaa actgattctg | 3480 |
| aggcattgta | ggtggtaggg | atctggtagt | aggtagcatt | aggtgggctc ccggcactca | 3540 |
| ccatggagcc | ttgaaatttt | ctgctacttt | ggggagttg | ctggttcaga gaaggccctt | 3600 |
| ccaccctggt | agccatgtgg | cactggaagg | ctgtgaaaac | tctgctgggc cttcttagtc | 3660 |
| atctgttgtg | agctcctgat | gggagtgtgg | tgtatccctc | aggtgtgcta gactggaaca | 3720 |
| aaggctgaga | agtgttgctc | tgggggttcc | aacttgtggg | catggggtac tgatgagatc | 3780 |
| agtagtgttt | ggagacttct | gtatgctcca | tcttcagaag | acattctgga gtccatataa | 3840 |
| gttatcttgt | ctcttgtttg | aagcaggaaa | aaggaatgcg | attgctggta atatagttca | 3900 |
| ctaaagtcag | ctacctggcc | tctaacagtt | atttgcaaag | tatattataa cattgattcc | 3960 |
| tcaaacatct | agattcctat | ctcgtgccaa | gtgatgtact | aggtgctcta agtacaaaaa | 4020 |
| taaaggaata | tagtcctcct | ctcaatgcgt | aagcctagtg | gaagaagcag aaatgaaagg | 4080 |
| gaaataagaa | ttcaatagag | tatgaggcat | tacagtgaaa | gaaaccaaat gtcttagaag | 4140 |
| tacaaatggc | agagctacta | attctgtctc | gagcaggcag | ggaagagtct atagtggaaa | 4200 |
| tgacttttga | gctagatttt | gaattgagct | agtcttttga | gccagacttt tgagctagaa | 4260 |
| ttgtagggtt | gtcatcagac | cagagagtag | gaagggtacc | ttgtgaggaa gagagagaga | 4320 |
| gatcagattg | ttactgtgtc | tatgtagaaa | aggaagacat | aagaaactcc attttgatct | 4380 |
| gtactaagaa | aaattgtttc | tgctttgaga | tgctgttaac | ctgtaacttt agtcccaacc | 4440 |
| ctgtgctcac | agaaacctgt | gctgtaatga | atcaaggttt | aatggattta gggctgtgca | 4500 |
| ggatgtacct | tgttaacaat | atgtttgcag | gcagtatgct | tggtaaaagt catcgccatt | 4560 |
| ctccattctc | gattaaccag | ggacacagtg | cactgcggaa | ggccgcaggg acatctgccc | 4620 |
| aagaaagcct | gggtattgtc | caaggtttcc | ccccactgag | acagcctgag atatggcctt | 4680 |

```
gtgggaaagg aaagacctta ccacccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac cttttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gttttttaaga   5460 aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca acgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880 ccccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg ggatttttcc   6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgcttccc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcgagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgaccccaa   6720
gcgcctcggg ccctgcgcg gcttccagtg ggttacggga gacaacaaca ccagctatag   6780
caggtgggca cggctcgacc tcaatggggc tcccctctgc ggccgttgt gcgtcgctgt   6840 ctccgctgct gaggccactg tgcccagcga ccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcaccccgt tcgcggcccc   7020
cggagcggac ttccaggcgc tgccggtggg cagctccgcc gcggtggctc ccctcggctt   7080
```

```
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgacccccaa  7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagcccccgc ccagcccgac   7920
gcccggctcc accttgactc ctccggccgt ggggctcgtg cattcgggct gctcatagg    7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac ccccagcttt gctaccaaag   8220
caccttagct ggcattacag ctggagaaga ccctccccgc acccccaag ctgttttctt    8280
ctattccatg gctaactggc gaggggggtga ttagagggag gagaatgagc ctcggcctct  8340
tccgtgacgt cactggacca ctgggcaatg atggcaattt tgtaacgaag acacagactg   8400
cgatttgtcc caggtcctca ctaccgggcg caggagggtg agcgttattg gtcggcagcc   8460
ttctgggcag accttgacct cgtgggctag ggatgactaa atatttatt tttttttaagt   8520
atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttttcct agccctctca catttatgaa gcaagcccca cttattcccc   8700
attcttccta gttttctcct cccaggaact gggccaactc acctgagtca ccctacctgt    8760
gcctgaccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gcccctgaac aagaattgga agctgccctg   9420
cccatgggag ctggttagaa atgcagaatc ctaggctcca ccccatccag ttcatgagaa   9480
```

```
tctatattta acaagatctg caggggtgt gtctgctcag taatttgagg acaaccattc    9540
cagactgctt ccaattttct ggaatacatg aaatatagat cagttataag tagcaggcca    9600
agtcaggccc ttattttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgcatcac     9900
ttgtacaaaa taaacaaata acaatgtgaa aaaaaaaaa aaaaaaaaa aaaaaaaaa       9960
aaaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gacttttttaa caaaaagaa aaagaaaaaa aaaattcctg   10140
cctcctggtg tacacacaca gaagggttcc ctccccttga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag ggcatgagcc   10320
tttaaatatc tgggagcaac ccctggccag cagccagtga gaaaacgggc cctcagtcct   10380
acaatcacaa ggaactaaat tctgccaaca acctgaagga actttgaaga ggatcatgag   10440
tcccttgatt cagcttgatg agcccctgag cagaggatac agctaacttg tactagggaa   10500
gtataaaaaa catgcatggg aatgatatat atcaacttta aggataattg tcatacttct   10560
gggaatgaag ggaaagaaat ggggctttag ttgtattatg atctttaatt tctcaaaaaa   10620
aataagatca gaagcaaata tggcaaaatg ttaatacttt tgtgggtacg taggtattca   10680
gcatacccctt ttttctgagt tcaaaatatt ttataattaa aatgaaatgc aggccaggca   10740
cagtggctca tgcctataat accagcactt tgcgaggccg aggtgggagg atggcttgag   10800
gccagaccag cctggccaac atggcaaaac cccatctcta cttaaaaaaa aaaaaactat   10860
atatatatat atgtgtgtgt gtgtgtatat atatatatgt atatatattt atatatgtgt   10920
gtatatatat atatgtatat atatttatat atgtgtgtgt atatatatat atacacacac   10980
acacatatat acatcatac atacacacac acacacacac aattagccag gcatggtggc   11040
gcacacctgt agtcccagct acttgggagg ctgagacatg agaattgctt gaacctggga   11100
ggcagagtag ttagtgagct gagatcatac cactgcactc cagcctggtg acagagtgag   11160
actctgtctt aaaaaaaata aaaattaaaa ttaaatgcaa aaggtccaag tgaattgaag   11220
aggaaagggg tatcaaggaa ggttttgtgg aggtgacgtt tgagctgggt cttaaatgac   11280
ttaaacatgg gataagaagg gagggaataa ggacatttca ggtacgagaa ataaggagca   11340
aacagtggaa acaacctaac gtctgtcaac cagtgaatgg ataacaaaaa tgtaattcag   11400
atggtatcca acttacgatg gttcaacatg agatttttct gactttagga tagatttatc   11460
aaagtagtaa atccattttc aacttatgat attttcaact tcagatgggt ttatcaggac   11520
acagttgagg aacacctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctgggggaa ggggaaatgg ggagtgatgg   11760
ctaagggat tgggttcttt tgtggggcaa tgaaaatgtt ttaaaattga gcgtgataat   11820
gattgcacaa tgctgcatat atatataatc tatagattat atatatataa agagaggctg   11880
```

```
ttagacagtg ataagtgata tatatatata tatacataga gagagagaga gagagagaga    11940
gaggctgtta gtgataagtg atcaggaaaa taaaagtatt gaggaggaat acgaagttga    12000
cggtgtgaaa acatgagatt ttatatagga tggccaggga aggccttaat gagaaagtga    12060
cttatgagta aaaacaaggg atcctaaacc ttagcatgca tcagaatcac tcggaaactt    12120
gttaaagcat agcttgctgg gcctcatcac agatattttg attcggtagg ttcttgtctg    12180
atattaatac ttttggtcta gggaaccaca ttttgagaac cactgagcta aaggaagtaa    12240
aggtttccct tagttactta gctggtaaca ctggcccagg aggcctttct ggaaaaggtc    12300
ccagtcccca aaggaagctg ggactcgcg ttcacatcgt caaggtttac caagttgtgg     12360
cgggcctttc cgtcttggaa aaagcctcaa aatggcagat tagggtgtcc atggccggcg    12420
gaaagggtct ttgaagttgc agaccaggag ggaagaagat tctgggcctc ccccatgcag    12480
tgtcagctgg caacagaatg caccccggct gggttggagg ccctgggtac tggctcttcc    12540
acaccagggg cccacctacc aagggcagca ggagcatctg cacctcctgc gccaggcgcc    12600
cttcagtgct tccacttgag cacctctcca gacaccagct agggtgacag tggtacaaat    12660
accagactcc cctggcctgc tcacctcaca gggtaatgtg ctgtggagtc aggggacac    12720 agcaaccacc agatgacatg gctggccccg gggaggacga cacgcagata cggctacttg    12780
gcacctgtga tattttacac actcgagagg ggcccgcacc atcctcagcc ctctccccac    12840
attcactctt agttcatgtc acctccaccc agaggggac acaggcccac agcgatggcc    12900
ccacaccctg cctgaggtcg cccacttccc aggaggcagt cctgggactt ccacccgacc    12960
aggccccaga gcccaccgac ttaacccctc cagaggcttg tcgttcatta ccttattcaa    13020
gatggagacc agccttttg cggagaaaat gcgggtgaag gtcctgaaag tgcattgacg    13080
ccgttttcgg aagccataca agtttagctg gcggaagaag ctctttatcg aagttgtggc    13140
aaacactttg tgtgcgacgt ccctttgag aatctccttt tcaaagagtt tttgattgat     13200
cactctacaa gccccactgt catcccacca gatggacgaa aactggttgc tgctgaccag    13260
tctccacagt ttctgtggaa aggggaggga gaggagatta tcttctccct ggggcgggac    13320
gtcaccgtca gggtgcggcc ttctgaacga agcttcctcg gccagaggtt ggaaagcgat    13380
ttcttctgtc agcagcctca agttagggct cccagtggac cccgggtcgt cccaggcagg    13440
ggaaggatct gctgggtgaa ggtaggtctc tgactgcaac tggggaggga aaggcaccct    13500
ttccaagcca tgatcctgtc ctctcgaatt tctttcttca cagcgagcca tactcaatga    13560
tcgcttgtcc tccatctggc aaacttgcta gtgcagtgtg gccagcagca ccccttggca    13620
gtcatgtaac cagccccatg acatcataaa ggggctctga ctgccggggg gtggcatctc    13680
cacccccagc aagttgtgta ataaagggcc aaggcagaca agtagctgcc catctgcatg    13740
tgcacattct ggtcctcaca gtcatttcaa tgggaaagat gacactagtg cacaagagtg    13800
ccgaggggcc ctgccacacc gtagatgcag acctggagcg gtcccttgt cctagagctc     13860 ctgagccagg cacaactaca gcaaagccct ggctcaggaa ggtcagagct caccgtctga    13920
gtcatgggcc cacagacccc agcacatgac tgacactcgg aagcacagaa caaagggtag    13980
gacggtgccc atgggtcagg ctgtagccac gccaccctt ccaccctgtc ctagccagag     14040
gcagcaatgt gctccataca gatcctccta acacaccac actgtcggtc cccagcacgc     14100
agatgcccga cagcccctta ggcaaatggc ttagctgact gccccaccac acgccgtcgc    14160
catgcagtcc agtggggagt cggaggcagc ctccttcctg cctctcctcg gcctgcacgt    14220
gtccccccac caggcagaga cccttctaca ccccgggtgt ctgcggtcac atcgcggtgg    14280
```

```
ggcatgcagc tgttggcctt cgagcatgtt ttgttttcct tggccagtgt ctccagagaa    14340
acgcacgtgg gtttgtgtcc agcggtccat ctctgcaaca gttgttcctt tgggattgga    14400
tgctaggagg tcacgggaga ggtgtccatc caaagcagtg tctgtgtcac acactgtccc    14460
cacacacagg gccacctctg cacagactcc cccgactcga ttctgggcac agagctcagt    14520
gaccttccag agactgccac gaaccggtga tgcctccacg cttgagacat cctgaccgca    14580
gggcccaagg cgcactggct cagggggtga cagtgagggg tctgcaaaca gactgctgat    14640
gctcaacccg gccgctgccg agctgtgtga cttgggcacg tcacttaacc tctctcggcc    14700
tctgtctcct cccggggata agagtagtag cacctgcttc ccggggctgt gaggatccag    14760
tgggacgtat aggaactagc gaggcaccgg cagttgggtc agagctactg ttgtcacttc    14820
acaaggcatt ttcttcaaca gcaagtcgga aatctcatga gcctaaggca gaatccacct    14880
gtggcctctg gttacaaccc acaggactga aaatccttcc agccacagca actggtgaat    14940
ttcctggtca attgccacaa gtcatgagct gaacccccact tgagtttcag ttcaggcaga    15000
actctagaga cgactagggc aagctagaca gcgactgcag agccttttgt tgcagcgtga    15060
gcagtcctca gctgttgaca tcactgggga gcaaacgagg accaggagcg gtgaaaggac    15120
agtgtctgct gcagattgtc gtagcaccca aggaacactc cagaaagcct cctaagcagt    15180
aacaagtgtg gcaaggtgta gcccagccaa cagtggcatc tgcgaggcgt ccctccttc    15240 ctcccactac cccgtatacc ctgggacctg tgcactgaag gactcattct aaaggctgtg    15300
cccctgcagc cgccagcctc actcactggc tgcctgtgcc agctagagat ttctttcctc    15360
tgaggctggc tgagaggacc actccagttt cctggcccat ccagcaaaga agatacacat    15420
catgcacgtg taaaatgagg aaccggttta ttgaacagct taaggagagc aaaaatagtg    15480
gctttagcta cattttttac acactgagca ggaaagtcta aaccatcccg ttcccctgta    15540
ccccaaagag aacagggctt gctggaggcc agtgccaagg gcggagtcgt gctcgcagca    15600
gacttgaatt aaccccatgt aggccggcga gcagttgccc gcgtgaaaac accaccctct    15660
tctcctggct gagaagatca aagctctttt tttaccctct tttcagcaaa ggacctattt    15720
gttttcaggc aggaggatgt taaacttgca gcctctgaca cacggtggaa cctgcagtgc    15780
ttggagaaac ggcacgcaca cgtgaaaaca tcatgcctac tccaaagcct tcttgttgct    15840
ggcaggaggg aagcttgaga ctttcccacg catagtcgtg acccgcgtgg ccgtttctgc    15900
tctcagcaac attctctagt gttccggctt caagcagcgc ttgtcaggtt tgaagctagc    15960
cactattctg agaacgtcag aaaagcatgg accatctctt gcttggtgtt gccgttgtgg    16020
cagtagcagc tactacgtac ctgcacgagt tccagggcag aagtggcaat gtcccatgaa    16080
ggcgtggcac cccacggggg ggggggggga gtgtgccacg ggcgtccact tctgcagcag    16140
aaggcatgtg cctacagcac aagcttgtaa aaaaatactt gaacagaata tgctgtacag    16200 aactagggt taacaccgca tatgaagatg ctaaaacatt tgtataaata ctctgtatac    16260
aagcatggag tcactcccgt agaaagggct catccgtgag gctatgaaaa actgctgtca    16320
gcatgcccaa agagaaacta cttccacagt aggaacagaa aaaaggactg tgctgtgtct    16380
aaacacgtgg tgcatcagag acatagttac agttcctact gactgcccca gccacgacct    16440
gggagtgctg aggacctggg agtgctcagc gagctgcagg aggtcagccc tgtggagaaa    16500
tacatttcta aacaatactt ttgattggga tttcagcacc gtatagacag atgttccttc    16560
tgggggcctg gcaagcagcc atctcccagt gggtctgacg gggaagaggg gtacctggag    16620
cccctcccag acagacggta atcccacccc tgttctcaca ctcttcctgg catccgcatc    16680
```

```
tgctggcaca cacccccgtc acctgccact tccgcgtccc gtcgtggtga gtggctgata   16740
ggcgctggat gcaaacaagg catgagatgg acgtacctgg agacccagct ccagtactgg   16800
ttctggtctg cggggtgaac gagggggcag aggaaggcgg agagagtgcg tcccagtcca   16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttaggggget ccggaactgg ggtctcttcg gtttcttcat tatcttcgtg   17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctaggtg ggctccagcg gtccccttt cctggccctt   17460
ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcacccte tgcagagatc gttttggaag   17940
tgtctgcctc agcaagcagg tggaggggaa tagagtgtta gcaaggcaag acaggcaaga   18000
ctcgggtgat ggcagcaagg atatggggga ggcagagcgg ccaacaggga cctaggatga   18060
atcccaggtt tgggtgggag atgtggattt ccatcaaaac cctcccgggc ctgggaagaa   18120
tctgtcttga tccccatttt gcagaggagg gaacgggatc tctgagaggt tgcctgccgt   18180
gtctggttct acctcaaatg gcagcgtgca ctgcagaaaa agtcccggtg caggccagca   18240
gaacaccaga gttacggcat gcccttccct tagaaggtcc cagaatttcc tcagccctca   18300
ctttcccaca caagcttcta aattgggggcc ctcggggact catcccttcc tagacttcta   18360
tccgccaccc cccacccccct ggtcccccccc cagacacaca ccaaggactt ctgaaatgct   18420
gagtacatac agtggttttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaagagacat agtcccggtt gatgccagca ccgaaaatgg   18600
gcagaggcgg aagccagact tcattaggca gttcctcccc accacccac ccccgcgtga   18660
gctcccacaa gagggaacat cagcaccgcc agaaaaggc aggaaccac ctatccctgg   18720
ggaaagctcg aaatgagctt ttatgtccct cttcagagct cggcaatagc ctatccactt   18780
gaaaagttcc cagtgccagc agttttatgg caaactcctc cgggtgtttg ttctaaggag   18840
tcaacagctc ccattctaga attctccacg tgactccaat acacaaatct gacatcccac   18900
tctgcttttcc ccagagtgga aactggagcc atacagaggc accatggcta aaaaggtgca   18960
ctcttctccc tgccagcccc acgtgctgcc cccaagagaa aggaaggatg ctctcctttc   19020
accgaagctc cctctcggag atggctgtgt tctctcccct ctcctggagt gggctcactg   19080
```

```
tgagctcgag ggacagaggc tgcctttcta ggggtgcaga atcctgtcag gggaagcgca    19140
agcttcaggg gctgaagagg cttcccgtgg aacgcttacc tcaaatgtaa aagggggcac    19200
gacgatggtc atccagctca gggccatggt tatgtgtgtc ctgcgctgtc cgcaatcaca    19260
tccatagagc gcaagaacaa gacggaccac acaatgtagt agaggaccac caggcacaga    19320
aaggacatga gaatccacag cgggacacac acaacctggg ggtgggtgag agaacagcaa    19380
gagaagtctc tttagagctt ccaacctggc ctctgatgga aggcatcttt agcaccttgc    19440
tgtgtctgtc cagttaaggc ggtccttcct gtgagccgaa taaggaccgt tccatctccc    19500
aggactgctg ggagcatcgc tcaggacaga aaaggtatgg tatgttcact atggggcctg    19560
ctgccaccag gggacacaca cgctcagtga gtcatcagtc cctcttcctt tgggtgacag    19620
acagccctgc acctggctcc gcagcctcta ctcttccaga ggcccactct cccacactct    19680
ctcaggctcc tctaggttct gctgccatca cagcttcccg ggaaatggga cacaactgtc    19740
accctgtgca cacacacaag atctcacccc aacagactct cttcacaggc aacattccca    19800
caacctgctg ggggtacttt ggcaacacaa atgggaatgg gctccccaga aagtctggct    19860
gcctgggctc ctaaggatcc ctaacctcac ccctaccaag ttagtgaact tggcgggttg    19920
atgctggata caggttgatg ctggatacgt agcgctgccg ggtcgtgacc cctaaggaat    19980
tatccaaact cttgttttta gatgctttat tatatcaaac tctccttaa acaagtggcc    20040 catctgctgg gatttggaag cctgtaatac tgaaattttc atcataatgg aaattttaaa    20100
aacagaattt gacccacctg tttttaaaac actttcatta cttaacaaga ggtctaatct    20160
tgggcaagtc ttgaaatttc tctggcctta gtttcccatg tgttaaatga aacttgaagc    20220
agttggtctc ttatagtctc ctgactctaa cattctaaga attatatttg tacaataact    20280
caaaaatcac ataatttaat ttaccatatg gactccaaaa tatattttct cattaggcta    20340
aacttgatct gcattttctg gatgtgtcca tattcttgga ctacactaaa acatgatacc    20400
aatgcttcct ctcaccataa accctcactt cgctttctac atttaagaat tttatagctg    20460
gaagagtcct taacagaaaa taccatctaa taattacccc tcaaaatcga gaaagtccta    20520
tctgttctta tgctagttat aagaatgagg cagcatttca cataatggtt ataaacactg    20580
ccacaagaag attcatgatg tgttgtttat ctgtagctct catcatactc tgtcatataa    20640
ctatagcatt aagattttaa tgttctatat attcttctaa gacagtgttt accagagtaa    20700
ggcacaaaag atccactggt ttgcaagaaa gattagaact tttaaatttt ttacctcacc    20760
ttgtttaatc tatatttttg tatgtatttt gtaacatata tattattatt accataaatc    20820
atatataatt taaatgcat atattagggg taaatgctca ggaaactttt tataaattgg    20880
gcatgcaaat acaagtttga agactcactg ttctaggtat taaaagtaaa gttataacca    20940
agtaaagctt ccacctttc atgtctcaaa gcagtttatt gttggaggta agatctctta    21000
gaagcctaaa caggtccaag tacagaatga agtaaggcta gcccataact tgtggcaagc    21060
aattcatact atttctctca tgctgagctc tcctcagtga agcagctact atagacaact    21120 gcagccttatt ggtagcctat tttacaggca ggaaaaaaat tacttttat tcaaagtgga    21180 actcaggaca tggggagaaa atgaatacaa aaaatagggt caatccaaag gcacacagca    21240
aatgagtaac acagttatgt tttttttccca tttgtatgag gtcccagtaa attctaagta    21300
aactgcaaat ttaataatac actaaaaaag ccatgcaatt gttcaaatga atcccagcat    21360
ggtacaagga gtacagacac tagagtctaa aaaacaaaag aatgccatta ttgagttttt    21420
gaattatatc aagtagttac atctctactt aataaatgag aaaaacgagg ataagaggcc    21480
```

```
atttgataaa atgaaaatag ccaagaagtg gtattagaga cttgaataca ggtattcggg    21540
tccaaagttc atctgctcaa atactaactg gggaaaagag ggaaaaatat ttatatacat    21600
atatatctgc acacaaaaat accccaaaa  gacaaaatga ggccaggcag ggtggctcac    21660
acccgtaatc ccggtacttt gggaggctga ggcaggtgga tacctgagat caggagttgg    21720
agatcagcct ggtcaacatg gtgaaaccct gtctctacta agataaaaa  aattagccag    21780 gcatggtggc gtgcgcctgt aatcccagct acttgggagt ctgaggcagg agaatcactt    21840
gaactgggaa gggaggttg  cagtgagcca agatcgtact actgcactcc agcctgggca    21900
gcagagtgag actccatcac aaaaataaat aaataaataa aatacaatga aacagaaagt    21960
tcaaataatc ccataatctt accaccaaga ataactttc  actcgttata cttattgatt    22020
tttccataat aaatgtactt tactgtgact atcatgaaaa gaaagttatt ttagaaacag    22080
agaactgttt cagatcaaat ctatgtagta gaacagagcc attaggtggg aaagacgaga    22140
tcaaactaaa tctcagaagg cctaaaaggc taggtccatt ccagcactaa aaactgacca    22200
gacaagtaat ggcttcaaca gcttctaaat atggacaaag catgctgaaa gggaaggaca    22260
ggtctaacag tggtatatga aatgaacagg aggggcaaag ctcatttctc ctctgaagtt    22320
ttccaaagat gctgaggagg acattagttt gacatgaccc tgatatggga caagataatt    22380
tcacagaagt tttacatgtt aaagttttct tatagatact cattcaagta agcaatgaac    22440
actaaaatct aaagaaagaa aagagcttta gagtcaggtc tgtattcaaa ttcaagctct    22500
accacttact ggttctgtga ctttgggcaa gtcttttaac cttattaagt cttaatttcc    22560
tgatttgtaa aatggggata tcgtctccct cacaggattg ttgtgaaact tttatgagat    22620
taatgccttt atatttggca tagtgtaagt aaacaataac tggcagcttc aaaaaaaaaa    22680
agcagtagca ttccatcatt tattattggt tactctcaaa aagttttca  atgtactaga    22740 agataaatat tcaaatacct taatatctcc attattttca ggtaaacagc atgctcctga    22800
acaaccaatg ggtcaacaaa taaattaaaa gggaaatcta aaaacatctt gatattaaac    22860
tacatggaag cacaatatac caaaaccaat ggttcacact aggagaattt taaggtacaa    22920
gaaaactctt tgagatttct taaaataata gtatgtctga atttattgag tgatttacca    22980
gaaactgttg taagagctct acttgcatta tagcacttaa tcctcttaac tctatggctg    23040
ctattatcaa cctcacccta atcacatatg ggacacagag aggttaagta acttgcccaa    23100
ggtcagagtt aggaagtact aagccatgct ttgaatcagt tgtcaggctc cggaactcac    23160
actttcagcc actacataat actgctttgc tatcttttag gaaactatgt gagtctacct    23220
cacatagact cacataggtt tgtttttttt ttttttttaa aggctatctt ttcccccatc    23280 aatgttttt  gaaggatccc aaattagagt cccacagagg cagacagcag tacttgacaa    23340
tatggacatt taaggttaat gttggattct actgtctttt tactacatga cctagggaac    23400
gataattaac ctagactgct tccaagggtt aaataaccca tttagttata ctatgtaaat    23460
tatctcttag tgattgattg aaagcacact gttactaatt gactcggtat gaagtgcttt    23520
tttttcttcc ctttcaagat acataccttt ccagttaaag ttgagagatc atctccacca    23580 attacttta  tgtccctgt  tgactggtca ttctagttaa aaaaaaaaa  aactatatat    23640 atatatatct acacacacat atgtatatgt atatccttat gtacacacac aaacttcaaa    23700
ttaaatgaga actagaagat ttgagaagtt agctagctaa tatccatagc attatgatat    23760
tctaaatgat atgaattata agaattaggt ttcctgaaat gaatgactag aaaacttcca    23820
agtagagatt agtaaaaatt aaaaagtcct aatcggccat tactgatttg atgttttaa    23880
```

```
gagtcctaaa aaatgggtta catccatttt taagtgggta gtattataac agccacccat   23940
cttcaatcac agtgatttct gaattgtgag ggaagttatt agcatgacag gtgtctggtt   24000
ctggccctgt acgattccca tgagtcaagc aaattgtaag ggctggtcta tatcacaccc   24060
aaccccaagg atatgtccct caaaagtcta gcccaggccc cgtcatcttc agcatcatct   24120
gggaaaccag gtctgattag tagtccttta aggaatacct cttaggctcc cattttactg   24180
ctatcacaga atccaataaa acccttacag gagattcaat gggaaatgct caacacccac   24240
tgtagttggt ggtgacaatg accataattt ggctgtgctg gattcaggac agaaaatttg   24300
ggtgaaagag caggtgaaca aaagagcttc gacttgccct agcagagagc aagccatacc   24360
ataccacaaa gccacagcaa ttacaacggt gcagtaccag cacagtaaat gaacaaagta   24420
gagcccagaa acagacccag aactatatga ggatttagta tacaataaag atggtatttc   24480
gagtcagtag ggaaaagatg aattattcaa taaatgatgt ttggccaact agtaacccat   24540
ttgggaaaaa ataaaagtat ggtccctacc tcacagcata cacaaaaata aattccagac   24600
ggattaaaat ctaaatgtaa aaaataaagc cataagtgga ctggaagaaa atagagaatt   24660
ttttttaaca tccgtagaaa gggtaaaaac ccaggcatga catgaaccaa aactgaagag   24720
gttctgtaac aaatacccccc ttttatatat tgggctccaa caataagaac ccataggaaa   24780
atggagaatg aacacaaata gacaatttat agaagagaag gttataaggt gtaaaattat   24840
atctatctga gaaacaaaca ctaaacaat gtgattctac tgttctccca cccatactgg   24900
caaaacttaa gcctgataat atgctgaggg gaaataagca ctcttgttgg tgagagtatt   24960
aattggcata gcttcttttg aaaatgacat agcaatacct gttaaaattg caaacatgca   25020
tgtcacttaa tccagtaatc ccacttctgg gaatcaatgc tacaaaaaca ctgacaagta   25080
tacaaagata cattcaagag tgttcactgg gccgggtgcg gtggcttcat gcctgtaatc   25140
ccagggaggc agaggcaaga cgatcgcttg accccaggag ttcaaggcca gcccgagaaa   25200
cacagcaaga ccctgtctct cttttttta tttaaaaaat aaatgttcac tgtatcagtt   25260
gttcacaaaa acaaaccaac atgtccatta acagggaacc atttaaatta atcaagttca   25320
tctacacaat gtaataccat gcaactatta aaaagcacct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcactttta tgtgcttcta tttttgttat gcttctatat atacatccat   25560
ttattatgga gtgttacttt caaaaatcac aaatgggcca gtattatttg gtgttgcaag   25620
gtgagcatat gacttctgat atcaaccttt gcatattact tctcaattta gggaaattac   25680
agacatccct tattctaact aacttaaaac ccagcatttc aaacatacag aattgatggg   25740
gaaaaaaaag aaagaagaaa gaaagaaaag gcaacaagct tcagatgaca gtgactcaca   25800
tcaaattatt tataaaatct gttaaatagt gccatcttct ggagatacct ggtattacag   25860
tccaactcca gttgatgtct ttacagagac aagaggaata aaggaaaaaa tattcaagaa   25920
ctgaaaagta tggagtcatg gaaaaattgc tgtgatccaa aggctacggt gataggacaa   25980
gaaacaagag aactccaagc agtaagacac tgctgttcta ttagcatcca aacctccata   26040
ctcctgtttg ccccaaggct tttttaaaaa atagagacag gatctcacta ttttgctcag   26100
gctggtcttg aactcctgga ctcaagctat cctcctgcct cggcctccta aagtgccgag   26160
attacaggct tgagtcacca tacctggcta tttatttttt cttaactctc ttgcctggcc   26220
tatagccacc atggaagcta ataaagaata ttaatttaag agtaatggta tagttcacta   26280
```

```
cattggaata caggtataag tgcctacatt gtacatgaat ggcatacatg gatcaattac  26340
cccacctggg tggccaaagg aactgcgcga acctccctcc ttggctgtct ggaacaagct  26400
tcccactaga tccctttact gagtgcctcc ctcatcttta attatggtta agtctaggat  26460
aacaggactg gcaaaggtga ggggaaagct tcctccagag ttgctctacc ctctcctcta  26520
ccgtcctatc tcctcactcc tctcagccaa ggagtccaat ctgtcctgaa ctcagagcgt  26580
cactgtcaac tacataaaat tgccagagaa gctctttggg actacaaaca catacccta  26640 atgtctttat ttctattttg tctacctctt cagtctaggt gaaaaaatag gaaggataat  26700
agggaagaac tttgtttatg cctacttatc cgcccctagg aattttgaaa acctctaggt  26760
agcaataaga actgcagcat ggtatagaaa aagaggagga aagctgtata gaaatgcata  26820
ataaatgggc aggaaaagaa ctgcttggaa caaacaggga ggttgaacta taaggagaga  26880
aagcagagag gctaatcaac aaggctgggt tcccaagagg gcatgatgag actattacta  26940
aggtaggaat tactaagggc tccatgtccc cttagtggct tagtactatg tagcttgctt  27000
tctgcagtga acttcagacc cttcttttag gatcctagaa tggactttt ttttttatcg  27060 gaaaacagtc attctctcaa cattcaagca ggccccaagt ctaccacact caatcacatt  27120
ttctcttcat atcataatct ctcaaccatt ctctgtcctt ttaactgttt ttctataccc  27180
tgatcaaatg ccaacaaaag tgagaatgtt agaatcatgt atttttagag gtagactgta  27240
tctcagataa aaaaaagggg cagatattcc atttttccaaa atatgtatgc agaaaaaata  27300
agtatgaaag gacatatgct caggtaacaa gttaatttgt ttacttgtat tttatgaatt  27360
ccctaaaacc tacgtcaccc gccccgttcc cacgccccgc gccacgtcac aaactccacc  27420
ccctcattat catattggct tcaatccaaa ataaggtata ttattgatga tgttaattaa  27480
catgcatgga tccatatgcg gtgtgaaata ccgcacagat gcgtaaggag aaaataccgc  27540
atcaggcgct cttccgcttc ctcgctcact gactcgctgc gctcggtcgt tcggctgcgg  27600
cgagcggtat cagctcactc aaaggcggta atacggttat ccacagaatc agggggataac  27660 gcaggaaaga acatgtgagc aaaaggccag caaaaggcca ggaaccgtaa aaaggccgcg  27720
ttgctggcgt ttttccatag gctccgcccc cctgacgagc atcacaaaaa tcgacgctca  27780
agtcagaggt ggcgaaaccc gacaggacta taaagatacc aggcgtttcc ccctggaagc  27840
tccctcgtgc gctctcctgt tccgaccctg ccgcttaccg gatacctgtc cgcctttctc  27900
ccttcgggaa gcgtggcgct ttctcatagc tcacgctgta ggtatctcag ttcggtgtag  27960
gtcgttcgct ccaagctggg ctgtgtgcac gaaccccccg ttcagcccga ccgctgcgcc  28020
ttatccggta actatcgtct tgagtccaac ccggtaagac acgacttatc gccactggca  28080
gcagccactg gtaacaggat tagcagagcg aggtatgtag gcggtgctac agagttcttg  28140
aagtggtggc ctaactacgg ctacactaga aggacagtat ttggtatctg cgctctgctg  28200
aagccagtta ccttcggaaa aagagttggt agctcttgat ccggcaaaca aaccaccgct  28260
ggtagcggtg ttttttgt ttgcaagcag cagattacgc gcagaaaaaa aggatctcaa  28320
gaagatcctt tgatcttttc tacggggtct gacgctcagt ggaacgaaaa ctcacgttaa  28380
gggattttgg tcatgagatt atcaaaaagg atcttcacct agatcctttt aaattaaaaa  28440
tgaagtttta aatcaatcta agtatatat gagtaaactt ggtctgacag ttaccaatgc  28500
ttaatcagtg aggcacctat ctcagcgatc tgtctatttc gttcatccat agttgcctga  28560
ctccccgtcg tgtagataac tacgatacgg gagggcttac catctggccc cagtgctgca  28620
atgataccgc gagacccacg ctcaccggct ccagatttat cagcaataaa ccagccagcc  28680
```

```
ggaagggccg agcgcagaag tggtcctgca actttatccg cctccatcca gtctattaat    28740
tgttgccggg aagctagagt aagtagttcg ccagttaata gtttgcgcaa cgttgttgcc    28800
attgctgcag ccatgagatt atcaaaaagg atcttcacct agatcctttt cacgtagaaa    28860
gccagtccgc agaaacggtg ctgaccccgg atgaatgtca gctactgggc tatctggaca    28920
agggaaaacg caagcgcaaa gagaaagcag gtagcttgca gtgggcttac atggcgatag    28980
ctagactggg cggttttatg gacagcaagc gaaccggaat tgccagctgg ggcgccctct    29040
ggtaaggttg ggaagccctg caaagtaaac tggatggctt tcttgccgcc aaggatctga    29100
tggcgcaggg gatcaagctc tgatcaagag acaggatgag gatcgtttcg catgattgaa    29160
caagatggat tgcacgcagg ttctccggcc gcttgggtgg agaggctatt cggctatgac    29220
tgggcacaac agacaatcgg ctgctctgat gccgccgtgt tccggctgtc agcgcagggg    29280
cgcccggttc tttttgtcaa gaccgacctg tccggtgccc tgaatgaact gcaagacgag    29340
gcagcgcggc tatcgtggct ggccacgacg ggcgttcctt gcgcagctgt gctcgacgtt    29400
gtcactgaag cgggaaggga ctggctgcta ttgggcgaag tgccggggca ggatctcctg    29460
tcatctcacc ttgctcctgc cgagaaagta tccatcatgg ctgatgcaat gcggcggctg    29520
catacgcttg atccggctac ctgcccattc gaccaccaag cgaaacatcg catcgagcga    29580
gcacgtactc ggatggaagc cggtcttgtc gatcaggatg atctggacga agagcatcag    29640
gggctcgcgc cagccgaact gttcgccagg ctcaaggcga gcatgcccga cggcgaggat    29700
ctcgtcgtga cccatggcga tgcctgcttg ccgaatatca tggtggaaaa tggccgcttt    29760
tctggattca tcgactgtgg ccggctgggt gtggcggacc gctatcagga catagcgttg    29820
gctacccgtg atattgctga agagcttggc ggcgaatggg ctgaccgctt cctcgtgctt    29880
tacggtatcg ccgctcccga ttcgcagcgc atcgccttct atcgccttct tgacgagttc    29940
ttctgaattt tgttaaaatt tttgttaaat cagctcattt tttaaccaat aggccgaaat    30000
cggcaaaatc ccttataaat caaaagaata gaccgagata gggttgagtg ttgttccagt    30060
ttggaacaag agtccactat taagaacgtg gactccaac gtcaaagggc gaaaaaccgt    30120
ctatcagggc gatggcccac tacgtgaacc atcaccctaa tcaagttttt tggggtcgag    30180
gtgccgtaaa gcactaaatc ggaaccctaa agggagcccc cgatttagag cttgacgggg    30240
aaagccggcg aacgtggcga gaaaggaagg gaagaaagcg aaaggagcgg gcgctagggc    30300
gctggcaagt gtagcggtca cgctgcgcgt aaccaccaca cccgccgcgc ttaatgcgcc    30360
gctacagggc gcgtccattc gccattcagg atcgaattaa ttcttaatta acatcatcaa    30420
taatatacct tattttggat tgaagccaat atgataatga gggggtggag tttgtgacgt    30480 ggcgcgggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                              30756
```

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      Foward PCR primer (containing a Fse I restriction site)

```
<400> SEQUENCE: 17
tatttattgg ccggccgcgt taagatacat tgatgag                                37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      Reverse PCR primer (containing a Sbf I restriction site)

<400> SEQUENCE: 18
tatttattcc tgcaggtcgt aggtcaaggt agtaga                                 36

<210> SEQ ID NO 19
<211> LENGTH: 1224
<212> TYPE: DNA
<213> ORGANISM: Rattus norvegicus

<400> SEQUENCE: 19
atgcctcaca gtcaaatatc tcctgcagaa ggctctagaa ggatccttga agaataccac       60
atagatgaag atgtgggctt tgctctacca catccactgg aggagctgcc tgatacgtac      120
agaccttgga tccttgtggc tagaaatctg cctaagctga ttgagaatgg gaagctccga      180
gaagaagtcg agaagctgcc cacactgcgc accgaagaac tgaggggaca caggttacag      240
cgcctggcac atttggccct ggggtacatc accatggcgt atgtgtggaa ccgaggggat      300
gatgatattc gaaggtgctg ccccgcaat cttgccgttc cctactgcga gctctcggag       360
aagctggggc tgcctcccat tctgtcttac gcagactgcg tcctggcaaa ctggaagaaa      420
aaggacccca tgggcccat gacatacgag aacatggaca ttctgttctc gtttcctggt       480
ggggactgcg ataaaggctt cttcctggtc tctctaatgg tggaaatcgc agcttctcct      540
gcaatcaaag caattcctac tgtatccagt gcagtagagc atcaagaccc gaaagcactg      600
gagaaggcac tgtgtagtat agctgccagt ctggagaaag ccaaggaaat ttttaagagg      660
atgcgtgact tcgtggatcc agacaccttt ttccacgttc ttcgcatata tttgtctggt      720
tggaagggca accctaagct gccggagggt ctgctgtacg agggcgtctg ggacaccccc      780
aaaaaatttt caggggggcag tgcaggccag agcagcatct ttcagagtct tgatgtcctt      840
ctgggaataa agcatgacgt tggtgaagga tctgctgcag aattcctcca ggaaatgaga      900
gagtacatgc ctccagccca ccggaacttc ctctcctcct tagagtcagc cccccagtc      960 cgtgagtttg tcattttaag acgcaatgaa gacttgaagg aggcttataa tgagtgtgtg     1020
aatggcctgg tctccctcag aatgttccac ctctcgatag tagatactta cattgtgaag     1080
ccttcgaagc agaagcccat gggtggccac aagtcagaag agccctcaaa cacggaaaac     1140
agagggactg ggggtactga cgtcatgaat ttcctgagga gtgtgaaaga tacaaccaag     1200
aaagcccttc tgagttggcc ttag                                            1224

<210> SEQ ID NO 20
<211> LENGTH: 1212
<212> TYPE: DNA
<213> ORGANISM: Homo sapiens

<400> SEQUENCE: 20
atggcacacg ctatggaaaa ctcctggaca atcagtaaag agtaccatat tgatgaagaa       60
gtgggctttg ctctgccaaa tccacaggaa aatctacctg atttttataa tgactggatg      120
ttcattgcta acatctgcc tgatctcata gagtctggcc agcttcgaga aagagttgag       180
```

-continued

```
aagttaaaca tgctcagcat tgatcatctc acagaccaca agtcacagcg ccttgcacgt    240
ctagttctgg gatgcatcac catggcatat gtgtggggca aaggtcatgg agatgtccgt    300
aaggtcttgc caagaaatat tgctgttcct tactgccaac tctccaagaa actggaactg    360
cctcctattt tggtttatgc agactgtgtc ttggcaaact ggaagaaaaa ggatcctaat    420
aagcccctga cttatgagaa catggacgtt tgttctcat ttcgtgatgg agactgcagt     480
aaaggattct tcctggtctc tctattggtg gaaatagcag ctgcttctgc aatcaaagta    540
attcctactg tattcaaggc aatgcaaatg caagaacggg acactttgct aaaggcgctg    600
ttggaaatag cttcttgctt ggagaaagcc cttcaagtgt ttcaccaaat ccacgatcat    660
gtgaacccaa aagcattttt cagtgttctt cgcatatatt tgtctggctg gaaaggcaac    720
ccccagctat cagacggtct ggtgtatgaa gggtctggg aagacccaaa ggagtttgca     780
gggggcagtg caggccaaag cagcgtcttt cagtgctttg acgtcctgct gggcatccag    840
cagactgctg gtggaggaca tgctgctcag ttcctccagg acatgagaag atatatgcca    900
ccagctcaca ggaacttcct gtgctcatta gagtcaaatc cctcagtccg tgagtttgtc    960
ctttcaaaag gtgatgctgg cctgcgggaa gcttatgacg cctgtgtgaa agctctggtc    1020
tccctgagga gctaccatct gcaaatcgtg actaagtaca tcctgattcc tgcaagccag    1080
cagccaaagg agaataagac ctctgaagac ccttcaaaac tggaagccaa aggaactgga    1140
ggcactgatt taatgaattt cctgaagact gtaagaagta caactgagaa atccctttg     1200 aaggaaggtt aa                                                        1212
```

<210> SEQ ID NO 21  
<211> LENGTH: 2440  
<212> TYPE: DNA  
<213> ORGANISM: Artificial Sequence  
<220> FEATURE:  
<223> OTHER INFORMATION: Description of Artificial Sequence: Rat IDO expression cassette  
<220> FEATURE:  
<221> NAME/KEY: misc_feature  
<222> LOCATION: (1)..(2440)  
<223> OTHER INFORMATION: n= a, c, g, t, unknown or other

<400> SEQUENCE: 21

```
tatttattcc tgcaggtcgt aggtcaaggt agtagagttt gcgggcagga cggggcgacc     60
atcaatgctg gagcccatca cattctgacg caccccggcc catgggggca tgcgcgttgt    120
caaatatgag ctcacaatgc ttccatcaaa cgagttggtg ctcatggcgg cggcggctgc    180
tgcaaaacag atacaaaact acataagacc cccaccttat atattctttc ccacccttan    240
nntaatagta atcaattacg gggtcattag ttcatagccc atatatggag ttccgcgttg    300
gtaaatggcc cgcctggctg accgcccaac gaccccccgcc cattgacgtc aataatgacg    360
tatgttccca tagtaacgcc aatagggact ttccattgac gtcaatgggt ggagtattta    420
cggtaaactg cccacttggc agtacatcaa gtgtatcata tgccaagtac gccccctatt    480
gacgtcaatg acggtaaatg gcccgcctgg cattatgccc agtacatgac cttatgggac    540
tttcctactt ggcagtacat ctacgtatta gtcatcgcta ttaccatggt gatgcggttt    600
tggcagtaca tcaatgggcg tggatagcgg tttgactcac ggggatttcc aagtctccac    660
cccattgacg tcaatgggag tttgttttgg caccaaaatc aacgggactt tccaaaatgt    720
cgtaacaact ccgccccatt gacgcaaatg ggcggtaggc gtgtacggtg ggaggtctat    780
ataagcagag ctggtttagt gaaccgtcag atccgctaga gatctggtac cgtcgacgcg    840
```

```
gccgcgggaa ttcgattatg cctcacagtc aaatatctcc tgcagaaggc tctagaagga      900
tccttgaaga ataccacata gatgaagatg tgggctttgc tctaccacat ccactggagg      960
agctgcctga tacgtacaga ccttggatcc ttgtggctag aaatctgcct aagctgattg     1020
agaatgggaa gctccgagaa gaagtcgaga agctgcccac actgcgcacc gaagaactga     1080
ggggacacag gttacagcgc ctggcacatt tggccctggg gtacatcacc atggcgtatg     1140
tgtggaaccg aggggatgat gatattcgaa aggtgctgcc ccgcaatctt gccgttccct     1200
actgcgagct ctcggagaag ctggggctgc ctcccattct gtcttacgca gactgcgtcc     1260
tggcaaactg gaagaaaaag gaccccaatg ggcccatgac atacgagaac atggacattc     1320
tgttctcgtt tcctggtggg gactgcgata aggcttctt cctggtctct ctaatggtgg      1380
aaatcgcagc ttctcctgca atcaaagcaa ttcctactgt atccagtgca gtagagcatc     1440
aagacccgaa agcactggag aaggcactgt gtagtatagc tgccagtctg gagaaagcca     1500
aggaaatttt taagaggatg cgtgacttcg tggatccaga caccttttc cacgttcttc      1560 gcatatattt gtctggttgg aagggcaacc ctaagctgcc ggagggtctg ctgtacgagg     1620
gcgtctggga cacccccaaa aaattttcag ggggcagtgc aggccagagc agcatctttc     1680
agagtcttga tgtccttctg ggaataaagc atgacgttgg tgaaggatct gctgcagaat     1740
tcctccagga aatgagagag tacatgcctc cagcccaccg gaacttcctc tcctccttag     1800
agtcagctcc cccagtccgt gagtttgtca ttttaagacg caatgaagac ttgaaggagg     1860
cttataatga gtgtgtgaat ggcctggtct ccctcagaat gttccacctc tcgatagtag     1920
atacttacat tgtgaagcct tcgaagcaga agcccatggg tggccacaag tcagaagagc     1980
cctcaaacac ggaaaacaga gggactgggg gtactgacgt catgaatttc ctgaggagtg     2040
tgaaagatac aaccaagaaa gcccttctga gttggcctta gaatcactag ataagatatc     2100
cgatcnntgg agttcgtgac cgccgccggg atcactctcg gcatggacga gctgtacaag     2160
tccggactca gatccaccgg atctagntaa ctgatcataa tcagccatac cacatttgta     2220
gaggttttac ttgctttaaa aaacctccca cacctccccc tgaacctgaa acataaaatg     2280
aatgcaattg ttgttgttaa cttgtttatt gcagcttata atggttacaa ataaagcaat     2340
agcatcacaa atttcacaaa taaagcattt ttttcactgc attctagttg tggtttgtcc     2400
aaactcatca atgtatctta acgcggccgg ccaataaata                            2440
```

<210> SEQ ID NO 22
<211> LENGTH: 2387
<212> TYPE: DNA
<213> ORGANISM: Artificial Sequence
<220> FEATURE:
<223> OTHER INFORMATION: Description of Artificial Sequence: Human IDO
      expression cassette
<220> FEATURE:
<221> NAME/KEY: misc_feature
<222> LOCATION: (1)..(2387)
<223> OTHER INFORMATION: n= a, c, g, t, unknown or other

<400> SEQUENCE: 22

```
tatttattcc tgcaggtcgt aggtcaaggt agtagagttt gcgggcagga cggggcgacc       60
atcaatgctg gagcccatca cattctgacg caccccggcc catgggggca tgcgcgttgt      120
caaatatgag ctcacaatgc ttccatcaaa cgagttggtg ctcatggcgg cggcggctgc      180
tgcaaaacag atacaaaact acataagacc cccaccttat atattctttc ccaccccttan     240 nntaatagta atcaattacg gggtcattag ttcatagccc atatatggag ttccgcgtta     300
cataacttac ggtaaatggc ccgcctggct gaccgcccaa cgacccccgc ccattgacgt     360
```

```
caataatgac gtatgttccc atagtaacgc caatagggac tttccattga cgtcaatggg    420
tggagtattt acggtaaact gcccacttgg cagtacatca agtgtatcat atgccaagta    480 cgcccctat tgacgtcaat gacggtaaat ggcccgcctg gcattatgcc cagtacatga    540
ccttatggga ctttcctact tggcagtaca tctacgtatt agtcatcgct attaccatgg    600
tgatgcggtt ttggcagtac atcaatgggc gtggatagcg gtttgactca cggggatttc    660
caagtctcca ccccattgac gtcaatggga gtttgttttg gcaccaaaat caacgggact    720
ttccaaaatg tcgtaacaac tccgccccat tgacgcaaat gggcggtagg cgtgtacggt    780
gggaggtcta tataagcaga gctggtttag tgaaccgtca gatccgctag agatctccag    840
aggagcagac tacaagaatg gcacacgcta tggaaaactc ctggacaatc agtaaagagt    900
accatattga tgaagaagtg ggctttgctc tgccaaatcc acaggaaaat ctacctgatt    960
tttataatga ctggatgttc attgctaaac atctgcctga tctcatagag tctggccagc   1020
ttcgagaaag agttgagaag ttaaacatgc tcagcattga tcatctcaca gaccacaagt   1080
cacagcgcct tgcacgtcta gttctgggat gcatcaccat ggcatatgtg tggggcaaag   1140
gtcatggaga tgtccgtaag gtcttgccaa gaaatattgc tgttccttac tgccaactct   1200
ccaagaaact ggaactgcct cctatttttgg tttatgcaga ctgtgtcttg gcaaactgga   1260 agaaaagga tcctaataag cccctgactt atgagaacat ggacgttttg ttctcatttc   1320
gtgatggaga ctgcagtaaa ggattcttcc tggtctctct attggtggaa atagcagctg   1380
cttctgcaat caaagtaatt cctactgtat tcaaggcaat gcaaatgcaa gaacgggaca   1440
ctttgctaaa ggcgctgttg gaaatagctt cttgcttgga gaaagcccctt caagtgtttc   1500 accaaatcca cgatcatgtg aacccaaaag cattttttcag tgttcttcgc atatatttgt   1560
ctggctggaa aggcaacccc cagctatcag acggtctggt gtatgaaggg ttctgggaag   1620
acccaaagga gtttgcaggg ggcagtgcag gccaaagcag cgtctttcag tgctttgacg   1680
tcctgctggg catccagcag actgctggtg gaggacatgc tgctcagttc ctccaggaca   1740
tgagaagata tatgccacca gctcacagga acttcctgtg ctcattagag tcaaatccct   1800
cagtccgtga gtttgtcctt tcaaaaggtg atgctggcct gcgggaagct tatgacgcct   1860
gtgtgaaagc tctggtctcc ctgaggagct accatctgca aatcgtgact aagtacatcc   1920
tgattcctgc aagccagcag ccaaaggaga ataagacctc tgaagaccct tcaaaactgg   1980
aagccaaagg aactggaggc actgatttaa tgaatttcct gaagactgta agaagtacaa   2040
ctgagaaatc ccttttgaag gaaggttaat gtaacccaac aagagcactc gagcctaagc   2100
ttctagataa gatatccgat ccaccggatc tagataactg atcataatca gccataccac   2160
atttgtagag gttttacttg ctttaaaaaa cctcccacac ctccccctga acctgaaaca   2220
taaaatgaat gcaattgttg ttgttaactt gtttattgca gcttataatg gttacaaata   2280
aagcaatagc atcacaaatt tcacaaataa agcatttttt tcactgcatt ctagttgtgg   2340
tttgtccaaa ctcatcaatg tatcttaacg cggccggcca ataaata              2387
```

<210> SEQ ID NO 23
<211> LENGTH: 30756
<212> TYPE: DNA
<213> ORGANISM: Artificial Sequence
<220> FEATURE:
<223> OTHER INFORMATION: Description of Artificial Sequence: Synthetic gutless backbone
<220> FEATURE:
<221> NAME/KEY: misc_feature
<222> LOCATION: (1)..(30756)

<223> OTHER INFORMATION: n=a, c, g, t, unknown or other

<400> SEQUENCE: 23

```
gtacggaagc ccggaaggag gggcaggggg cggtggctca ggtttctccg ggcggcggcg      60
gcggcggcgg cggcgacggc gacgcgacg gcagcgggga cggcagcagt agcgggagca     120
gcagcgtgga cgcggctggc gctggcgcca tgaacccgct gtaaggcgca ggctgtgcag    180
cacggggtgc gggggaggag gaggaggacg ccgcggtgaa gttctccgcc atgaacctga    240
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660
caccccctacc cccaccccag ctgtttcctc cagttcctcg cagtccttgg ggttttcctt   720
gggtttatgc ccatccctct cttgtttgct tctttgttga acggatacct gaaacactgt    780
tgaatccttg gagtcagtgt cggggtatgg caataccta tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgcctgtcct tgcacttgcc cgactgtttt gtaactgttc   1020
tttaccccag gctgtgagct ccctgaagct gagaccatct cctgctcatc tcagtgtccc   1080
cagcgcctcc cacccaccgt atctggcaca tagtaggcac atataaaatg tttgtggaac   1140
taaactgagc ccaaagactt ggattggaga cgaggccata tgtaactggg tgattctctg   1200
cccttctttg gcccttctgt aaaatgagga gttgcctaa ctgatctctt aaatgcacta    1260
ctctccgaaa ggagtatccg tttcccttat ttgccagttg ggaagacgtg ctcagtaaat   1320
atttgtgtgc tgtaacctat gttaggtgct ttagatgctg gcggtctcag catggggtga   1380
agaagggctt gtacacttaa gatgccttac agtactgtgc agtgctgtac tgcgggggcc   1440
aactctgggg acctatgcct tggctgcttg ttgaggatga aaggaagttt tagggagta    1500
tttgtatgtt gagggtgcag tctccctagg gatggtgaca ttttaacttg tgagtcattg   1560
tgactttgta tgtgcccta ttccactttg agttcatgtt ctggttagga gtgccagtgt    1620
ctctaacacg gtgcagacat tatcattgtt ggcttcgaag gcatagagga ggtaacagaa   1680
ctaactgcag tccctttcctc tgctgcatca ggggggtaag attggtctgc agggtagtag   1740
ggttggtgct gtggctggac aagccctgta tgtcttctat ttggagatgg tgataagaaa   1800
gttaagtaaa aactgaattg ttttgtgccc ttgggcaact cacttatcta ttgttttatc   1860
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagccctt ttccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
ctttttatact gtgccatttt cctgattcat tgttgccaga ggtagtgagt tccttaattt   2280
```

```
tacagatatt tcaagaggac attggccagg tattattggt aaatcagatt tgtttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagacctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atcccctttc cagccttttg    3180
gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttagt    3360
tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt ggggagttg ctggttcaga gaaggccctt     3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catggggtac tgatgagatc    3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggttttcc ccccactgag acagcctgag atatggcctt    4680
```

```
gtgggaaagg aaagacctta ccaccccca gcccgacacc cgtaaagtgt ctgtgctgag      4740
gaggagtagt gaaagagcgg ggcctctttg cagttgagat aagaggaagg cttctgtctc      4800
ctgctcatcc ctgggaatgg aatgtctctg tgtaaagctg accattccca ttcgttctat      4860
tctgagatag gagaaaacca ccctgtggct ggaggcgaag tatgctggca gcaatactgc      4920
tctgttactc tttgctacac tgagttgttt gggtaaagag aaacataaat ctagcctgcg      4980
tgcacatcca ggcacagtac ctttccttga acttattcat gatacagatt cctttgctca      5040
cgtttccctg ctgaccttct ccccacctgt tgccctgcta cactcccctc gctaagatag      5100
taaaaataat gatcagtaaa tactgaggta actcagaggc tagcgctggt gcgggtcctc      5160
cgtatgctga gtgccggtcc cctgggccca ctgttctttc tctatacttt gtttctgtgt      5220
cttatttctt ttctcagtct cgtcccacct gacgagaaat acccacaggt gtggaggggc      5280
tggccccttt cagtatctca gaagggacaa agtacacaaa ggcatggggt catgatagtg      5340
cctggtatgt tcaggtagtg aagaggtcca tgtggtatga gcactgcaga tgatatgtgt      5400
cgtatgaatt aaaaatacat agttactgca aatagttttt acaggttatt gttttaaga       5460 aagcagtatc taatgcacga gtgtactgtc agtactgtca atgaactact taccactcaa      5520
gtgactgctt acgcgtcgaa tcactagtga attcgcggcc gcctcgagtc tagaactagt      5580
ggatccccca acgggccct ctagacgcgt tgacattgat tattgactag ttattaatag       5640
taatcaatta cggggtcatt agttcatagc ccatgatatc atatggagtt ccgcgttaca      5700
taacttacgg taaatggccc gcctggctga ccgcccaacg acccccgccc attgacgtca      5760
ataatgacgt atgttcccat agtaacgcca atagggactt tccattgacg tcaatgggtg      5820
gagtatttac ggtaaactgc ccacttggca gtacatcaag tgtatcatat gccaagtacg      5880 ccccctatt gacgtcaatg acggtaaatg gcccgcctgg cattatgccc agtncatgac       5940
cttatgggac tttcctactt ggcagacatc tacgtattag tcatcgctat taccatggtg      6000
atgcggtttt ggcagtacat caatgggcgt ggatagcggt ttgactcacg gggatttccc      6060
aagtctccac cccattgacg tcaatgggag tttgttttgg caccaaaatc aacgggactt      6120
tccaaaatgt cgtaacaact ccgccccatt gacgcaaatg ggcggtaggc gtgtacggtg      6180
ggaggtctat ataagcagag ctctctggct aactagagaa cccctgctta ctggcttatc      6240
gagatatctg cagaattcat ctgtcgactc taccggcag cgcgcagcgg caagaagtgt       6300
ctgggctggg acggacagga gaggctgtcg ccatcggcgt cctgtgcccc tctgctccgg      6360
cacgcccctg tcgcagtgcc cgcgctttcc ccggcgcctg cacgcggcgc gcctgggtaa      6420
catgcttggg gtcctggtcc ttggcgcgct ggccctggcc ggcctggggt tcccgcacc       6480 cgcagagccg cagccgggtg gcagccagtg cgtcgagcac gactgcttcg cgctctaccc      6540
gggccccgcg accttcctca atgccagtca gatctgcgac ggactgcggg gccacctaat      6600
gacagtgcgc tcctcggtgg ctgccgatgt catttccttg ctactgaacg gcgacggcgg      6660
cgttggccgc cggcgcctct ggatcggcct gcagctgcca cccggctgcg gcgaccccaa      6720
gcgcctcggg cccctgcgcg gcttccagtg ggttacggga gacaacaaca ccagctatag      6780
caggtgggca cggctcgacc tcaatggggc tcccctctgc ggcccgttgt gcgtcgctgt      6840
ctccgctgct gaggccactg tgcccagcga gccgatctgg gaggagcagc agtgcgaagt      6900
gaaggccgat ggcttcctct gcgagttcca cttcccagcc acctgcaggc cactggctgt      6960
ggagcccggc gccgcggctg ccgccgtctc gatcacctac ggcaccccgt tcgcggcccg      7020
cggagcggac ttccaggcgc tgccggtggg cagctccgcc gcggtggctc ccctcggctt      7080
```

```
acagctaatg tgcaccgcgc cgcccggagc ggtccagggg cactgggcca gggaggcgcc    7140
gggcgcttgg gactgcagcg tggagaacgg cggctgcgag cacgcgtgca atgcgatccc    7200
tggggctccc cgctgccagt gcccagccgg cgccgccctg caggcagacg ggcgctcctg    7260
caccgcatcc gcgacgcagt cctgcaacga cctctgcgag cacttctgcg ttcccaaccc    7320
cgaccagccg ggctcctact cgtgcatgtg cgagaccggc taccggctgg cggccgacca    7380
acaccggtgc gaggacgtgg atgactgcat actggagccc agtccgtgtc cgcagcgctg    7440
tgtcaacaca cagggtggct tcgagtgcca ctgctaccct aactacgacc tggtggacgg    7500
cgagtgtgtg gagcccgtgg acccgtgctt cagagccaac tgcgagtacc agtgccagcc    7560
cctgaaccaa actagctacc tctgcgtctg cgccgagggc ttcgcgccca ttccccacga    7620
gccgcacagg tgccagatgt tttgcaacca gactgcctgt ccagccgact gcgaccccaa    7680
cacccaggct agctgtgagt gccctgaagg ctacatcctg gacgacggtt tcatctgcac    7740
ggacatcgac gagtgcgaaa acggcggctt ctgctccggg gtgtgccaca acctcccgg    7800 taccttcgag tgcatctgcg ggcccgactc ggcccttgcc cgccacattg gcaccgactg    7860
tgactccggc aaggtggacg gtggcgacag cggctctggc gagcccccgc ccagcccgac    7920
gcccggctcc accttgactc ctccggccgt ggggctcgtg cattcgggct tgctcatagg    7980
catctccatc gcgagcctgt gcctggtggt ggcgcttttg gcgctcctct gccacctgcg    8040
caagaagcag ggcgccgcca gggccaagat ggagtacaag tgcgcggccc cttccaagga    8100
ggtagtgctg cagcacgtgc ggaccgagcg gacgccgcag agactctgag cggcctccgt    8160
ccaggagcct ggctccgtcc aggagcctgt gcctcctcac ccccagcttt gctaccaaag    8220
caccttagct ggcattacag ctggagaaga ccctccccgc acccccaag ctgttttctt    8280 ctattccatg gctaactggc gagggggtga ttagagggag gagaatgagc ctcggcctct    8340
tccgtgacgt cactggacca ctgggcaatg atggcaattt tgtaacgaag acacagactg    8400
cgatttgtcc caggtcctca ctaccgggcg caggaggtg agcgttattg gtcggcagcc    8460
ttctgggcag accttgacct cgtgggctag ggatgactaa aatatttatt ttttttaagt    8520
atttaggttt ttgtttgttt cctttgttct tacctgtatg tctccagtat ccactttgca    8580
cagctctccg gtctctctct ctctacaaac tcccacttgt catgtgacag gtaaactatc    8640
ttggtgaatt ttttttttcct agccctctca catttatgaa gcaagcccca cttattcccc    8700
attcttccta gttttctcct cccaggaact gggccaactc acctgagtca ccctacctgt    8760
gcctgaccct acttcttttg ctcttagctg tctgctcaga cagaacccct acatgaaaca    8820
gaaacaaaaa cactaaaaat aaaaatggcc atttgctttt tcaccagatt tgctaattta    8880
tcctgaaatt tcagattccc agagcaaaat aattttaaac aaaggttgag atgtaaaagg    8940
tattaaattg atgttgctgg actgtcatag aaattacacc caaagaggta tttatcttta    9000
cttttaaaca gtgagcctga attttgttgc tgttttgatt tgtactgaaa atggtaatt    9060 gttgctaatc ttcttatgca atttccttt ttgttattat tacttatttt tgacagtgtt    9120
gaaaatgttc agaaggttgc tctagattga gagaagagac aaacacctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg cccctgaac aagaattgga agctgccctg    9420
cccatgggag ctggttagaa atgcagaatc ctaggctcca ccccatccag ttcatgagaa    9480
```

```
tctatattta acaagatctg caggggggtgt gtctgctcag taatttgagg acaaccattc    9540
cagactgctt ccaattttct ggaatacatg aaatatagat cagttataag tagcaggcca    9600
agtcaggccc ttattttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaaa aaaaaaaaaa aaaaaaaaaa    9960
aaaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gacttttttaa caaaaaagaa aaagaaaaaa aaaattcctg   10140
cctcctggtg tacacacaca gaagggttcc ctccccttga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag ggcatgagcc   10320
tttaaatatc tgggagcaac ccctggccag cagccagtga gaaaacgggc cctcagtcct   10380
acaatcacaa ggaactaaat tctgccaaca acctgaagga actttgaaga ggatcatgag   10440
tcccttgatt cagcttgatg agcccctgag cagaggatac agctaacttg tactagggaa   10500
gtataaaaaa catgcatggg aatgatatat atcaacttta aggataattg tcatacttct   10560
gggaatgaag ggaaagaaat ggggctttag ttgtattatg atctttaatt tctcaaaaaa   10620
aataagatca gaagcaaata tggcaaaatg ttaatacttt tgtgggtacg taggtattca   10680
gcatacccctt ttttctgagt tcaaaatatt ttataattaa aatgaaatgc aggccaggca   10740
cagtggctca tgcctataat accagcactt tgcgaggccg aggtgggagg atggcttgag   10800
gccagaccag cctggccaac atggcaaaac cccatctcta cttaaaaaaa aaaaaactat   10860
atatatatat atgtgtgtgt gtgtgtatat atatatatgt atatatattt atatatgtgt   10920
gtatatatat atatgtatat atatttatat atgtgtgtgt atatatatat atacacacac   10980
acacatatat acatacatac atacacacac acacacacac aattagccag gcatggtggc   11040
gcacacctgt agtcccagct acttgggagg ctgagacatg agaattgctt gaacctggga   11100
ggcagagtag ttagtgagct gagatcatac cactgcactc cagcctggtg acagagtgag   11160
actctgtctt aaaaaaaata aaattaaaa ttaaatgcaa aaggtccaag tgaattgaag   11220
aggaaagggg tatcaaggaa ggttttgtgg aggtgacgtt tgagctgggt cttaaatgac   11280
ttaaacatgg gataagaagg gagggaataa ggacatttca ggtacgagaa ataaggagca   11340
aacagtggaa acaacctaac gtctgtcaac cagtgaatgg ataacaaaaa tgtaattcag   11400
atggtatcca acttacgatg gttcaacatg agatttttct gactttagga tagatttatc   11460
aaagtagtaa atccattttc aacttatgat attttcaact tcagatgggt ttatcaggac   11520
acagttgagg aacaccctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctgggggaa ggggaaatgg ggagtgatgg   11760
ctaagggggat tgggtttctt tgtggggcaa tgaaaatgtt ttaaaattga gcgtgataat   11820
gattgcacaa tgctgcatat atatataatc tatagattat atatatataa agagaggctg   11880
```

```
ttagacagtg ataagtgata tatatatata tatacataga gagagagaga gagagagaga   11940
gaggctgtta gtgataagtg atcaggaaaa taaaagtatt gaggaggaat acgaagttga   12000
cggtgtgaaa acatgagatt ttatatagga tggccaggga aggccttaat gagaaagtga   12060
cttatgagta aaaacaaggg atcctaaacc ttagcatgca tcagaatcac tcggaaactt   12120
gttaaagcat agcttgctgg gcctcatcac agatattttg attcggtagg ttcttgtctg   12180
atattaatac ttttggtcta gggaaccaca ttttgagaac cactgagcta aaggaagtaa   12240
aggtttccct tagtttacta gctggtaaca ctggcccagg aggcctttct ggaaaaggtc   12300
ccagtcccca aaggaagctg gggactcgcg ttcacatcgt caaggtttac caagttgtgg   12360
cgggcctttc cgtcttggaa aaagcctcaa aatggcagat tagggtgtcc atggccggcg   12420
gaaagggtct ttgaagttgc agaccaggag ggaagaagat tctgggcctc ccccatgcag   12480
tgtcagctgg caacagaatg caccccggct gggttggagg ccctgggtac tggctcttcc   12540
acaccagggg cccacctacc aagggcagca ggagcatctg cacctcctgc gccaggcgcc   12600
cttcagtgct tccacttgag cacctctcca gacaccagct agggtgacag tggtacaaat   12660
accagactcc cctggcctgc tcacctcaca gggtaatgtg ctgtggagtc aggggggacac   12720
agcaaccacc agatgacatg gctggccccg gggaggacga cacgcagata cggctacttg   12780
gcacctgtga tattttacac actcgagagg ggcccgcacc atcctcagcc ctctccccac   12840
attcactctt agttcatgtc acctccaccc agaggggac acaggcccac agcgatggcc   12900
ccacaccctg cctgaggtcg cccacttccc aggaggcagt cctgggactt ccacccgacc   12960
aggccccaga gcccaccgac ttaacccctc cagaggcttg tcgttcatta ccttattcaa   13020
gatggagacc agccttttg cggagaaaat gcgggtgaag gtcctgaaag tgcattgacg   13080
ccgttttcgg aagccataca agtttagctg gcggaagaag ctctttatcg aagttgtggc   13140
aaacactttg tgtgcgacgt cccttttgag aatctccttt tcaaagagtt tttgattgat   13200
cactctacaa gccccactgt catcccacca gatggacgaa aactggttgc tgctgaccag   13260
tctccacagt ttctgtggaa aggggaggga gaggagatta tcttctcct ggggcgggac   13320
gtcaccgtca gggtgcggcc ttctgaacga agcttcctcg gccagaggtt ggaaagcgat   13380
ttcttctgtc agcagcctca agttagggct cccagtggac cccgggtcgt cccaggcagg   13440
ggaaggatct gctgggtgaa ggtaggtctc tgactgcaac tggggaggga aaggcaccct   13500
ttccaagcca tgatcctgtc ctctcgaatt tctttcttca cagcgagcca tactcaatga   13560
tcgcttgtcc tccatctggc aaacttgcta gtgcagtgtg gccagcagca ccccttggca   13620
gtcatgtaac cagccccatg acatcataaa ggggctctga ctgccggggg gtggcatctc   13680
caccccagc aagttgtgta ataaagggcc aaggcagaca agtagctgcc catctgcatg   13740
tgcacattct ggtcctcaca gtcatttcaa tgggaaagat gacactagtg cacaagagtg   13800
ccgagggggc ctgccacacc gtagatgcag acctggagcg gtccccttgt cctagagctc   13860
ctgagccagg cacaactaca gcaaagccct ggctcaggaa ggtcagagct caccgtctga   13920
gtcatgggcc cacagacccc agcacatgac tgacactcgg aagcacagaa caaagggtag   13980
gacggtgccc atgggtcagg ctgtagccac gccacccttt ccaccctgtc ctagccagag   14040
gcagcaatgt gctccataca gatcctccta acacacccac actgtcggtc cccagcacgc   14100
agatgcccga cagcccctta ggcaaatggc ttagctgact gccccaccac acgccgtcgc   14160
catgcagtcc agtggggagt cggaggcagc ctccttcctg cctctcctcg gcctgcacgt   14220
gtccccccac caggcagaga cccttctaca ccccgggtgt ctgcggtcac atcgcggtgg   14280
```

-continued

```
ggcatgcagc tgttggcctt cgagcatgtt ttgttttcct tggccagtgt ctccagagaa    14340
acgcacgtgg gtttgtgtcc agcggtccat ctctgcaaca gttgttcctt ggggattgga    14400
tgctaggagg tcacgggaga ggtgtccatc caaagcagtg tctgtgtcac acactgtccc    14460
cacacacagg gccacctctg cacagactcc cccgactcga ttctgggcac agagctcagt    14520
gaccttccag agactgccac gaaccggtga tgcctccacg cttgagacat cctgaccgca    14580
gggcccaagg cgcactggct caggggggtga cagtgagggg tctgcaaaca gactgctgat    14640
gctcaacccg gccgctgccg agctgtgtga cttgggcacg tcacttaacc tctctcggcc    14700
tctgtctcct cccggggata agagtagtag cacctgcttc ccggggctgt gaggatccag    14760
tgggacgtat aggaactagc gaggcaccgg cagttgggtc agagctactg ttgtcacttc    14820
acaaggcatt ttcttcaaca gcaagtcgga aatctcatga gcctaaggca gaatccacct    14880
gtggcctctg gttacaaccc acaggactga aaatccttcc agccacagca actggtgaat    14940
ttcctggtca attgccacaa gtcatgagct gaaccccact tgagtttcag ttcaggcaga    15000
actctagaga cgactagggc aagctagaca gcgactgcag agccttttgt tgcagcgtga    15060
gcagtcctca gctgttgaca tcactgggga gcaaacgagg accaggagcg gtgaaaggac    15120
agtgtctgct gcagattgtc gtagcaccca aggaacactc cagaaagcct cctaagcagt    15180
aacaagtgtg gcaaggtgta gcccagccaa cagtggcatc tgcgaggcgt cccctccttc    15240
ctcccactac cccgtatacc ctgggacctg tgcactgaag gactcattct aaaggctgtg    15300
cccctgcagc cgccagcctc actcactggc tgcctgtgcc agctagagat ttcttcctc     15360
tgaggctggc tgagaggacc actccagttt cctggcccat ccagcaaaga agatacacat    15420
catgcacgtg taaaatgagg aaccggttta ttgaacagct taaggagagc aaaaatagtg    15480
gctttagcta cattttttac acactgagca ggaaagtcta aaccatcccg ttcccctgta    15540
ccccaaagag aacagggctt gctggaggcc agtgccaagg gcggagtcgt gctcgcagca    15600
gacttgaatt aaccccatgt aggccggcga gcagttgccc gcgtgaaaac accacctct     15660
tctcctggct gagaagatca aagctctttt tttaccctct tttcagcaaa ggacctattt    15720
gttttcaggc aggaggatgt taaacttgca gcctctgaca cacggtggaa cctgcagtgc    15780
ttggagaaac ggcacgcaca cgtgaaaaca tcatgcctac tccaaagcct tcttgttgct    15840
ggcaggaggg aagcttgaga ctttcccacg catagtcgtg acccgcgtgg ccgtttctgc    15900
tctcagcaac attctctagt gttccggctt caagcagcgc ttgtcaggtt tgaagctagc    15960
cactattctg agaacgtcag aaaagcatgg accatctctt gcttggtgtt gccgttgtgg    16020
cagtagcagc tactacgtac ctgcacgagt tccagggcag aagtggcaat gtcccatgaa    16080
ggcgtggcac cccacggggg ggggggggga gtgtgccacg ggcgtccact tctgcagcag    16140
aaggcatgtg cctacagcac aagcttgtaa aaaaatactt gaacagaata tgctgtacag    16200
aactaggggt taacaccgca tatgaagatg ctaaaacatt tgtataaata ctctgtatac    16260
aagcatggag tcactcccgt agaaagggct catccgtgag gctatgaaaa actgctgtca    16320
gcatgcccaa agagaaacta cttccacagt aggaacagaa aaaggactg tgctgtgtct      16380
aaacacgtgg tgcatcagag acatagttac agttcctact gactgcccca gccacgacct    16440
gggagtgctg aggacctggg agtgctcagc gagctgcagg aggtcagccc tgtggagaaa    16500
tacatttcta acaatactt ttgattggga tttcagcacc gtatagacag atgttccttc      16560
tgggggcctg gcaagcagcc atctcccagt gggtctgacg gggaagaggg gtacctggag    16620
cccctcccag acagacggta atcccacccc tgttctcaca ctcttcctgg catccgcatc    16680
```

```
tgctggcaca caccccgtc  acctgccact tccgcgtccc gtcgtggtga gtggctgata  16740
ggcgctggat gcaaacaagg catgagatgg acgtacctgg agacccagct ccagtactgg  16800
ttctggtctg cggggtgaac gaggggggcag aggaaggcgg agagagtgcg tcccagtcca  16860
cttaagctct gtccccggaa gtggcatcta atctggcatt tcgatattta atttgggagg  16920
tgggagcaca tacttcccag ggctctgggt aatgaccacc ctggccttct ttcgaaacat  16980
gggtgcgatt ttagggggct ccggaactgg ggtctcttcg gtttcttcat tatcttcgtg  17040
atggagatca taggaaatgt tccatattc tcgtagaaat gggaagattt caagcagaaa  17100
ctgacagaaa tctttgcgga taccaaacca ccctgaaaaa taagaatttt ttatttcaca  17160
cacgaggctc aactgacctt cctgttaact ttctttccgt aacaagaagt ttcactccta  17220
caatgtcata acatacttta tccagactcc tgagtcacaa agcctgaaca gggcttgagt  17280
acccaaaatg gggaagaagt gcaaatgcta gctctgtggt gcttggagtg gggttcccgg  17340
accggcaggg acagcgtcca cggggcctag ttagggatgc cattctcggg ccccagccca  17400
gacctccaga aactgagtcg ggctagggtg ggctccagcg gtccctttt  cctggccctt  17460
ttgggattct gctggatgcc caaatttgag aactactgct ccagtgagtc tcaaaatatc  17520
tgtggtgcgc agactacggt gtcttccgct aatcttctcc agccaggata aactcatgga  17580
tgacagtgcc acccaagaac aagatttctg tcaccctctg gaatccgtga gggcggtagt  17640
catgcacggg ttggccagga gggggcctga actcatggag ccaccttaaa gccactttcc  17700
cagtcccact actcctctct gtaggctact ggagtgtcag ctcggtgcaa gccctccctg  17760
ctcccgggtg cggggtaggg ggcagaggca caaacagcaa gcacagcccg ggctgctggg  17820
ctgcagtgag gccctgcccc caaacccact ggctttccga agggcaatgc tctgggcttc  17880
cgtgccatgg agcccacagc cttgccagga aggcaccctc tgcagagatc gtttggaag  17940
tgtctgcctc agcaagcagg tggaggggaa tagagtgtta gcaaggcaag acaggcaaga  18000
ctcgggtgat ggcagcaagg atatggggga ggcagagcgg ccaacaggga cctaggatga  18060
atcccaggtt tgggtgggag atgtggattt tccatcaaac cctcccgggc tgggaagaa   18120
tctgtcttga tccccatttt gcagaggagg gaacgggatc tctgagaggt tgcctgccgt  18180
gtctggttct acctcaaatg gcagcgtgca ctgcgagaaa agtcccggtg caggccagca  18240
gaacaccaga gttacggcat gcccttccct tagaaggtcc cagaatttcc tcagccctca  18300
ctttcccaca caagcttcta aattggggcc ctcggggact catcccttcc tagacttcta  18360
tccgccaccc cccacccct  ggtccccccc cagacacaca ccaaggactt ctgaaatgct  18420
gagtacatac agtggtttcc tcccttctgt ccaaatgtgg ttgccatcag cgtgatcaac  18480
gagagccaaa gggggacaaa gatcgggatg caggagaagg cgttgtggcc atccagtttg  18540
tgaaccagca gaatctaaag aaagagacat agtcccggtt gatgccagca ccgaaaatgg  18600
gcagaggcgg aagccagact tcattaggca gttcctcccc accacccac  cccgcgtga   18660
gctcccacaa gagggaacat cagcaccgcc agaaaaaggc aggaaaccac ctatccctgg  18720
ggaaagctcg aaatgagctt ttatgtccct cttcagagct cggcaatagc ctatccactt  18780
gaaaagttcc cagtgccagc agttttatgg caaactcctc cgggtgtttg ttctaaggag  18840
tcaacagctc ccattctaga attctccacg tgactccaat acacaaatct gacatcccac  18900
tctgctttcc ccagagtgga aactggagcc atacagaggc accatggcta aaaaggtgca  18960
ctcttctccc tgccagcccc acgtgctgcc cccaagagaa aggaaggatg ctctcctttc  19020
accgaagctc cctctcggag atggctgtgt tctctcccct ctcctggagt gggctcactg  19080
```

```
tgagctcgag ggacagaggc tgcctttcta ggggtgcaga atcctgtcag gggaagcgca   19140
agcttcaggg gctgaagagg cttcccgtgg aacgcttacc tcaaatgtaa aaggggcac    19200 gacgatggtc atccagctca gggccatggt tatgtgtgtc ctgcgctgtc cgcaatcaca   19260
tccatagagc gcaagaacaa gacggaccac acaatgtagt agaggaccac caggcacaga   19320
aaggacatga gaatccacag cgggacacac acaacctggg ggtgggtgag agaacagcaa   19380
gagaagtctc tttagagctt ccaacctggc ctctgatgga aggcatcttt agcaccttgc   19440
tgtgtctgtc cagttaaggc ggtccttcct gtgagccgaa taaggaccgt tccatctccc   19500
aggactgctg ggagcatcgc tcaggacaga aaaggtatgg tatgttcact atggggcctg   19560
ctgccaccag gggacacaca cgctcagtga gtcatcagtc cctcttcctt tgggtgacag   19620
acagccctgc acctggctcc gcagcctcta ctcttccaga ggcccactct cccacactct   19680
ctcaggctcc tctaggttct gctgccatca cagcttcccg ggaaatggga cacaactgtc   19740
accctgtgca cacacacaag atctcacccc aacagactct cttcacaggc aacattccca   19800
caacctgctg ggggtacttt ggcaacacaa atgggaatgg gctccccaga aagtctggct   19860
gcctgggctc ctaaggatcc ctaacctcac ccctaccaag ttagtgaact tggcgggttg   19920
atgctggata caggttgatg ctggatacgt agcgctgccg ggtcgtgacc cctaaggaat   19980
tatccaaact cttgttttta gatgctttat tatatcaaac tctcctttaa acaagtggcc   20040
catctgctgg gatttggaag cctgtaatac tgaaattttc atcataatgg aaattttaaa   20100
aacagaattt gacccacctg ttttaaaac actttcatta cttaacaaga ggtctaatct   20160
tgggcaagtc ttgaaatttc tctggcctta gtttcccatg tgttaaatga aacttgaagc   20220
agttggtctc ttatagtctc ctgactctaa cattctaaga attatatttg tacaataact   20280
caaaaatcac ataatttaat ttaccatatg gactccaaaa tatattttct cattaggcta   20340
aacttgatct gcattttctg gatgtgtcca tattcttgga ctacactaaa acatgatacc   20400
aatgcttcct ctcaccataa accctcactt cgctttctac atttaagaat tttatagctg   20460
gaagagtcct taacagaaaa taccatctaa taattacccc tcaaaatcga gaaagtccta   20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagattttaa tgttctatat attcttctaa gacagtgttt accagagtaa   20700
ggcacaaaag atccactggt ttgcaagaaa gattagaact tttaaatttt ttacctcacc   20760
ttgtttaatc tatattttg tatgtatttt gtaacatata tattattatt accataaatc   20820
atatataatt taaatgcat atattagggg taaatgctca ggaaactttt tataaattgg   20880
gcatgcaaat acaagtttga agactcactg ttctaggtat taaaagtaaa gttataacca   20940
agtaaagctt ccaccttttc atgtctcaaa gcagtttatt gttggaggta agatctctta   21000
gaagcctaaa caggtccaag tacagaatga agtaaggcta gcccataact tgtggcaagc   21060
aattcatact atttctctca tgctgagctc tcctcagtga agcagctact atagacaact   21120 gcagccatt ggtagcctat tttacaggca ggaaaaaaat tacttttat tcaaagtgga   21180 actcaggaca tggggagaaa atgaatacaa aaaataggt caatccaaag gcacacagca   21240
aatgagtaac acagttatgt ttttttccca tttgtatgag gtcccagtaa attctaagta   21300
aactgcaaat ttaataatac actaaaaaag ccatgcaatt gttcaaatga atcccagcat   21360
ggtacaagga gtacagacac tagagtctaa aaaacaaaag aatgccatta ttgagttttt   21420
gaattatatc aagtagttac atctctactt aataaatgag aaaaacgagg ataagaggcc   21480
```

```
atttgataaa atgaaaatag ccaagaagtg gtattagaga cttgaataca ggtattcggg    21540
tccaaagttc atctgctcaa atactaactg gggaaaagag ggaaaaatat ttatatacat    21600
atatatctgc acacaaaaat accccaaaa  gacaaaatga ggccaggcag ggtggctcac    21660
acccgtaatc ccgtactttt gggaggctga ggcaggtgga tacctgagat caggagttgg    21720
agatcagcct ggtcaacatg gtgaaaccct gtctctacta aagataaaaa aattagccag    21780
gcatggtggc gtgcgcctgt aatcccagct acttgggagt ctgaggcagg agaatcactt    21840
gaactgggaa ggggaggttg cagtgagcca agatcgtact actgcactcc agcctgggca    21900
gcagagtgag actccatcac aaaaataaat aaataaataa aatacaatga aacagaaagt    21960
tcaaataatc ccataatctt accaccaaga aataactttc actcgttata cttattgatt    22020
tttccataat aaatgtactt tactgtgact atcatgaaaa gaaagttatt ttagaaacag    22080
agaactgttt cagatcaaat ctatgtagta gaacagagcc attaggtggg aaagacgaga    22140
tcaaactaaa tctcagaagg cctaaaaggc taggtccatt ccagcactaa aaactgacca    22200
gacaagtaat ggcttcaaca gcttctaaat atggacaaag catgctgaaa gggaaggaca    22260
ggtctaacag tggtatatga aatgaacagg aggggcaaag ctcatttctc ctctgaagtt    22320
ttccaaagat gctgaggagg acattagttt gacatgaccc tgatatggga caagataatt    22380
tcacagaagt tttacatgtt aaagttttct tatagatact cattcaagta agcaatgaac    22440
actaaaatct aaagaaagaa aagagcttta gagtcaggtc tgtattcaaa ttcaagctct    22500
accacttact ggttctgtga ctttgggcaa gtcttttaac cttattaagt cttaatttcc    22560
tgatttgtaa aatggggata tcgtctccct cacaggattg ttgtgaaact tttatgagat    22620
taatgccttt atatttggca tagtgtaagt aaacaataac tggcagcttc aaaaaaaaaa    22680
agcagtagca ttccatcatt tattattggt tactctcaaa aagttttttca atgtactaga    22740
agataaaatat tcaaataccct taatatctcc attattttca ggtaaacagc atgctcctga    22800
acaaccaatg ggtcaacaaa taattaaaa  gggaaatcta aaaacatctt gatattaaac    22860
tacatggaag cacaatatac caaaaccaat ggttcacact aggagaattt taaggtacaa    22920
gaaaactctt tgagatttct taaaataata gtatgtctga atttattgag tgatttacca    22980
gaaactgttg taagagctct acttgcatta tagcacttaa tcctcttaac tctatggctg    23040
ctattatcaa cctcacccta atcacatatg ggacacagag aggttaagta acttgcccaa    23100
ggtcagagtt aggaagtact aagccatgct ttgaatcagt tgtcaggctc cggaactcac    23160
actttcagcc actacataat actgctttgc tatcttttag gaaactatgt gagtctacct    23220
cacatagact cacataggtt tgttttttttt ttttttttaa aggctatctt ttcccccatc    23280
aatgttttt  gaaggatccc aaattagagt cccacagagg cagacagcag tacttgacaa    23340
tatggacatt taaggttaat gttggattct actgtctttt tactacatga cctagggaac    23400
gataattaac ctagactgct tccaagggtt aaataaccca tttagttata ctatgtaaat    23460
tatctcttag tgattgattg aaagcacact gttactaatt gactcggtat gaagtgcttt    23520
tttttcttcc ctttcaagat acatacctt  ccagttaaag ttgagagatc atctccacca    23580
attactttta tgtcccctgt tgactggtca ttctagttaa aaaaaaaaaa aactatatat    23640
atatatatct acacacacat atgtatatgt atatccttat gtacacacac aaacttcaaa    23700
ttaaatgaga actagaagat ttgagaagtt agctagctaa tatccatagc attatgatat    23760
tctaaatgat atgaattata agaattaggt ttcctgaaat gaatgactag aaaactttca    23820
agtagagatt agtaaaaatt aaaaagtcct aatcggccat tactgatttg atgttttaa    23880
```

```
gagtcctaaa aaatgggtta catccatttt taagtgggta gtattataac agccacccat    23940
cttcaatcac agtgatttct gaattgtgag ggaagttatt agcatgacag gtgtctggtt    24000
ctggccctgt acgattccca tgagtcaagc aaattgtaag ggctggtcta tatcacaccc    24060
aaccccaagg atatgtccct caaaagtcta gcccaggccc cgtcatcttc agcatcatct    24120
gggaaaccag gtctgattag tagtccttta aggaataccT cttaggctcc cattttactg    24180
ctatcacaga atccaataaa acccttacag gagattcaat gggaaatgct caacaccac     24240 tgtagttggt ggtgacaatg accataattt ggctgtgctg gattcaggac agaaaatttg    24300
ggtgaaagag caggtgaaca aaagagcttc gacttgccct agcagagagc aagccatacc    24360
ataccacaaa gccacagcaa ttacaacggt gcagtaccag cacagtaaat gaacaaagta    24420
gagcccagaa acagacccag aactatatga ggatttagta tacaataaag atggtatttc    24480
gagtcagtag ggaaaagatg aattattcaa taaatgatgt ttggccaact agtaacccat    24540
ttgggaaaaa ataaaagtat ggtccctacc tcacagcata cacaaaaata aattccagac    24600
ggattaaaat ctaaatgtaa aaaataaagc cataagtgga ctggaagaaa atagagaatt    24660 tttttttaaca tccgtagaaa gggtaaaaac ccaggcatga catgaaccaa aactgaagag    24720
gttctgtaac aaatacccccc ttttatatat tgggctccaa caataagaac ccataggaaa    24780
atggagaatg aacacaaata gacaatttat agaagagaag gttataaggt gtaaaattat    24840
atctatctga gaaacaaaca ctaaaacaat gtgattctac tgttctccca cccatactgg    24900
caaaacttaa gcctgataat atgctgaggg gaaataagca ctcttgttgg tgagagtatt    24960
aattggcata gcttcttttg aaaatgacat agcaatacct gttaaaattg caaacatgca    25020
tgtcacttaa tccagtaatc ccacttctgg gaatcaatgc tacaaaaaca ctgacaagta    25080
tacaaagata cattcaagag tgttcactgg gccgggtgcg gtggcttcat gcctgtaatc    25140
ccagggaggc agaggcaaga cgatcgcttg accccaggag ttcaaggcca gcccgagaaa    25200
cacagcaaga ccctgtctct ctttttttta tttaaaaaat aaatgttcac tgtatcagtt    25260
gttcacaaaa acaaaccaac atgtccatta acagggaacc atttaaatta atcaagttca    25320
tctacacaat gtaataccat gcaactatta aaaagcacct gataatccaa agcacactga    25380
gacagaataa tgctattaaa aacaccaagt agtggaacac tgtgttgcct atgacaccat    25440
ttttattcaa catttaaaca aatttgtaac agcaattaca tgagtagtga caatggcgtt    25500
tatgagactt ttcactttta tgtgcttcta tttttgttat gcttctatat atacatccat    25560
ttattatgga gtgttacttt caaaaatcac aaatgggcca gtattatttg gtgttgcaag    25620
gtgagcatat gacttctgat atcaacccttt gcatattact tctcaattta gggaaattac    25680
agacatccct tattctaact aacttaaaac ccagcatttc aaacatacag aattgatggg    25740
gaaaaaaaag aaagaagaaa gaaagaaaag gcaacaagct tcagatgaca gtgactcaca    25800
tcaaattatt tataaaatct gttaaatagt gccatcttct ggagatacct ggtattacag    25860
tccaactcca gttgatgtct ttacagagac aagaggaata aaggaaaaaa tattcaagaa    25920
ctgaaaagta tggagtcatg gaaaaattgc tgtgatccaa aggctacggt gataggacaa    25980
gaaacaagag aactccaagc agtaagacac tgctgttcta ttagcatcca aacctccata    26040
ctcctgtttg ccccaaggct ttttaaaaa atagagacag gatctcacta ttttgctcag    26100
gctggtcttg aactcctgga ctcaagctat cctcctgcct cggcctccta aagtgccgag    26160
attacaggct tgagtcacca tacctggcta tttattttt cttaactctc ttgcctggcc    26220
tatagccacc atggaagcta ataaagaata ttaatttaag agtaatggta tagttcacta    26280
```

```
cattggaata caggtataag tgcctacatt gtacatgaat ggcatacatg gatcaattac    26340
cccacctggg tggccaaagg aactgcgcga acctccctcc ttggctgtct ggaacaagct    26400
tcccactaga tccctttact gagtgcctcc ctcatcttta attatggtta agtctaggat    26460
aacaggactg gcaaaggtga ggggaaagct tcctccagag ttgctctacc ctctcctcta    26520
ccgtcctatc tcctcactcc tctcagccaa ggagtccaat ctgtcctgaa ctcagagcgt    26580
cactgtcaac tacataaaat tgccagagaa gctctttggg actacaaaca catcccttta    26640
atgtctttat ttctattttg tctacctctt cagtctaggt gaaaaaatag gaaggataat    26700
agggaagaac tttgtttatg cctacttatc cgccccctagg aattttgaaa acctctaggt    26760
agcaataaga actgcagcat ggtatagaaa aagaggagga aagctgtata gaaatgcata    26820
ataaatgggc aggaaaagaa ctgcttggaa caaacaggga ggttgaacta aaggagaga    26880 aagcagagag gctaatcaac aaggctgggt tcccaagagg gcatgatgag actattacta    26940
aggtaggaat tactaagggc tccatgtccc cttagtggct tagtactatg tagcttgctt    27000
tctgcagtga acttcagacc cttctttag gatcctagaa tggacttttt ttttttatcg    27060
gaaaacagtc attctctcaa cattcaagca ggccccaagt ctaccacact caatcacatt    27120
ttctcttcat atcataatct ctcaaccatt ctctgtcctt ttaactgttt ttctataccc    27180
tgatcaaatg ccaacaaaag tgagaatgtt agaatcatgt attttagag gtagactgta    27240 tctcagataa aaaaaaggg cagatattcc attttccaaa atatgtatgc agaaaaaata    27300
agtatgaaag gacatatgct caggtaacaa gttaatttgt ttacttgtat tttatgaatt    27360
ccctaaaacc tacgtcaccc gccccgttcc cacgccccgc gccacgtcac aaactccacc    27420
ccctcattat catattggct tcaatccaaa ataaggtata ttattgatga tgttaattaa    27480
catgcatgga tccatatgcg gtgtgaaata ccgcacagat gcgtaaggag aaaataccgc    27540
atcaggcgct cttccgcttc ctcgctcact gactcgctgc gctcggtcgt tcggctgcgg    27600
cgagcggtat cagctcactc aaaggcggta atacggttat ccacagaatc aggggataac    27660
gcaggaaaga acatgtgagc aaaaggccag caaaaggcca ggaaccgtaa aaaggccgcg    27720
ttgctggcgt ttttccatag gctccgcccc cctgacgagc atcacaaaaa tcgacgctca    27780
agtcagaggt ggcgaaaccc gacaggacta taaagatacc aggcgtttcc ccctggaagc    27840
tccctcgtgc gctctcctgt tccgaccctg ccgcttaccg gatacctgtc cgcctttctc    27900
ccttcgggaa gcgtggcgct ttctcatagc tcacgctgta ggtatctcag ttcggtgtag    27960
gtcgttcgct ccaagctggg ctgtgtgcac gaaccccccg ttcagcccga ccgctgcgcc    28020
ttatccggta actatcgtct tgagtccaac ccggtaagac acgacttatc gccactggca    28080
gcagccactg gtaacaggat tagcagagcg aggtatgtag gcggtgctac agagttcttg    28140
aagtggtggc ctaactacgg ctacactaga aggacagtat ttggtatctg cgctctgctg    28200
aagccagtta ccttcggaaa aagagttggt agctcttgat ccggcaaaca aaccaccgct    28260
ggtagcggtg gttttttttgt ttgcaagcag cagattacgc gcagaaaaaa aggatctcaa    28320
gaagatcctt tgatcttttc tacggggtct gacgctcagt ggaacgaaaa ctcacgttaa    28380
gggattttgg tcatgagatt atcaaaaagg atcttcacct agatcctttt aaattaaaaa    28440
tgaagtttta aatcaatcta agtatatat gagtaaactt ggtctgacag ttaccaatgc    28500
ttaatcagtg aggcacctat ctcagcgatc tgtctatttc gttcatccat agttgcctga    28560
ctccccgtcg tgtagataac tacgatacgg gagggcttac catctggccc cagtgctgca    28620
atgataccgc gagacccacg ctcaccggct ccagatttat cagcaataaa ccagccagcc    28680
```

```
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgaccccgg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg ggaagccctg caaagtaaac tggatggctt tcttgccgcc aaggatctga   29100
tggcgcaggg gatcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc tttttgtcaa gaccgacctg tccggtgccc tgaatgaact gcaagacgag   29340
gcagcgcggc tatcgtggct ggccacgacg ggcgttcctt gcgcagctgt gctcgacgtt   29400
gtcactgaag cgggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata gaccgagata gggttgagtg ttgttccagt   30060
ttggaacaag agtccactat taaagaacgt ggactccaac gtcaaagggc gaaaaaccgt   30120
ctatcagggc gatggcccac tacgtgaacc atcaccctaa tcaagttttt tggggtcgag   30180
gtgccgtaaa gcactaaatc ggaaccctaa agggagcccc cgatttagag cttgacgggg   30240
aaagccggcg aacgtggcga gaaaggaagg gaagaaagcg aaaggagcgg cgctagggc   30300
gctggcaagt gtagcggtca cgctgcgcgt aaccaccaca cccgccgcgc ttaatgcgcc   30360
gctacagggc gcgtccattc gccattcagg atcgaattaa ttcttaatta acatcatcaa   30420
taatatacct tattttggat tgaagccaat atgataatga gggggtggag tttgtgacgt   30480
ggcgcggggc gtgggaacgg ggcgggtgac gtagtagtgt ggcggaagtg tgatgttgca   30540
agtgtggcgg aacacatgta agcgacggat gtggcaaaag tgacgttttt ggtgtgcgcc   30600
ggtgtacaca ggaagtgaca attttcgcgc ggttttaggc ggatgttgta gtaaatttgg   30660
gcgtaaccga gtaagatttg gccattttcg cgggaaaact gaataagagg aagtgaaatc   30720
tgaataattt tgtgttactc atagcgcgta atactg                             30756
```

<210> SEQ ID NO 24
<211> LENGTH: 32392
<212> TYPE: DNA
<213> ORGANISM: Artificial Sequence
<220> FEATURE:
<223> OTHER INFORMATION: Description of Artificial Sequence: Synthetic
      PrIDO-final
<220> FEATURE:
<221> NAME/KEY: misc_feature
<222> LOCATION: (1)..(32392)
<223> OTHER INFORMATION: n= a, c, g, t , unknown or other

<400> SEQUENCE: 24

```
gtacggaagc ccggaaggag gggcaggggg cggtggctca ggtttctccg ggcggcggcg      60
gcggcggcgg cggcgacggc gacggcgacg gcagcggggga cggcagcagt agcgggagca    120
gcagcgtgga cgcggctggc gctggcgcca tgaacccgct gtaaggcgca ggctgtgcag    180
cacggggtgc gggggaggag gaggaggacg ccgcggtgaa gttctccgcc atgaacctga    240
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660
cacccctacc cccaccccag ctgtttcctc cagttcctcg cagtccttgg ggttttcctt    720
gggtttatgc ccatccctct cttgtttgct tctttgttga acggataccct gaaacactgt    780
tgaatccttg gagtcagtgt cggggtatgg caataccta tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgcctgtcct tgcacttgcc cgactgtttt gtaactgttc   1020
tttaccccag gctgtgagct ccctgaagct gagaccatct cctgctcatc tcagtgtccc   1080
cagcgcctcc cacccaccgt atctggcaca tagtaggcac atataaaatg tttgtggaac   1140
taaactgagc ccaaagactt ggattggaga cgaggccata tgtaactggg tgattctctg   1200
cccttctttg gcccttctgt aaaatgagga gttggcctaa ctgatctctt aaatgcacta   1260
ctctccgaaa ggagtatccg tttcccttat ttgccagttg ggaagacgtg ctcagtaaat   1320
atttgtgtgc tgtaacctat gttaggtgct ttagatgctg gcggtctcag catggggtga   1380
agaagggctt gtacacttaa gatgcctttac agtactgtgc agtgctgtac tgcgggggcc   1440
aactctgggg acctatgcct tggctgcttg ttgaggatga aggaagttt taggggagta   1500
tttgtatgtt gagggtgcag tctccctagg gatggtgaca tttttaacttg tgagtcattg   1560
tgactttgta tgtgccctta ttccactttg agttcatgtt ctggttagga gtgccagtgt   1620
ctctaacacg gtgcagacat tatcattgtt ggcttcgaag gcatagagga ggtaacagaa   1680
ctaactgcag tcccttcctc tgctgcatca gggggttaag attggtctgc agggtagtag   1740
ggttggtgct gtggctggac aagccctgta tgtcttctat ttggagatgg tgataagaaa   1800
gttaagtaaa aactgaattg ttttgtgccc ttgggcaact cacttatcta ttgttttatc   1860
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac taccttaaac cgttttttcc tttagcccctt ttcccccccaa aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
```

```
tacagatatt tcaagaggac attggccagg tattattggt aaatcagatt tgttttttta      2340
gctggtagtg tttcacctct cctgagcact cctagttttt gacagtgtgc tttagtctcc      2400
ttccatgctg aggaaggcct tctctatagg agaaagaaaa ctgaggggtg tacacaggaa      2460
gttaccttat gctggggact caaaccttga tgctactgct ttgctccctg cctctatttt      2520
tgaaccaatt caacatctcc ctcctacccc aggaccttgt cacacactgt tctctttacc      2580
aggaatgttt ccctctcttt tcctctcctc cagaccuagt gaactcctat ttatcctcac      2640
ttggcacttg ctaagggaag cattcctgac ttccctgacc agattactg ctccctgttt       2700 ctacagttcc tgtagtattt actactcctc catcatagtg catatttgta cccttgtgtc      2760
tgtctggatg cttatttgat taatacctgc ctcccccact aaactttaag ctccatgggg      2820
tcaaggccgt gactgtgtca gtatcgtagc ctgcatactt ggaatagtac ctggctcaat      2880
aaatatttgt ggagtaaata actgaataac tctccagagc ctataagata aatctagagc      2940
tgctgctttc aatcactgct ttcctggtgg tctgtggcct ggttctcttt cttctcacac      3000
tcttcccacc ttcagagtgc agccattgct ttggagagat gggagagaac atggcactaa      3060
ggcagaatat ggctatattt actttgaaga gcatgtcttt gtcatagaaa tagtcactgt      3120
catggtttgg tgggtcccaa ggcatgggtc atggctccag atccccttc cagccttttg       3180 gatcttggta agtctgaacc cactgctgcg ttggcaaggc tctggaaact atagtgacag      3240
agaatgattc acaagtgtca acactcagat gtacagggct gccagctgac ccactctacc      3300
tatttccatc tggcactgaa ctggttgatc atgaacttct tttcataatt gcttttagt       3360 tatgcaggtt aagacatgcc gaaacagatg taccggaccc acaaacaagt ccttccttga      3420
atgcctgagg cttcctaaca gtgaaagagc cctgttctta gagtaggcaa actgattctg      3480
aggcattgta ggtggtaggg atctggtagt aggtagcatt aggtgggctc ccggcactca      3540
ccatggagcc ttgaaatttt ctgctacttt ggggagttg ctggttcaga gaaggccctt       3600
ccaccctggt agccatgtgg cactggaagg ctgtgaaaac tctgctgggc cttcttagtc      3660
atctgttgtg agctcctgat gggagtgtgg tgtatccctc aggtgtgcta gactggaaca      3720
aaggctgaga agtgttgctc tgggggttcc aacttgtggg catgggtac tgatgagatc       3780 agtagtgttt ggagacttct gtatgctcca tcttcagaag acattctgga gtccatataa      3840
gttatcttgt ctcttgtttg aagcaggaaa aaggaatgcg attgctggta atatagttca      3900
ctaaagtcag ctacctggcc tctaacagtt atttgcaaag tatattataa cattgattcc      3960
tcaaacatct agattcctat ctcgtgccaa gtgatgtact aggtgctcta agtacaaaaa      4020
taaaggaata tagtcctcct ctcaatgcgt aagcctagtg gaagaagcag aaatgaaagg      4080
gaaataagaa ttcaatagag tatgaggcat tacagtgaaa gaaaccaaat gtcttagaag      4140
tacaaatggc agagctacta attcgtctc gagcaggcag ggaagagtct atagtggaaa       4200
tgacttttga gctagatttt gaattgagct agtcttttga gccagacttt tgagctagaa      4260
ttgtagggtt gtcatcagac cagagagtag aagggtacc ttgtgaggaa gagagagaga       4320
gatcagattg ttactgtgtc tatgtagaaa aggaagacat aagaaactcc attttgatct      4380
gtactaagaa aaattgtttc tgctttgaga tgctgttaac ctgtaacttt agtcccaacc      4440
ctgtgctcac agaaacctgt gctgtaatga atcaaggttt aatggattta gggctgtgca      4500
ggatgtacct tgttaacaat atgtttgcag gcagtatgct tggtaaaagt catcgccatt      4560
ctccattctc gattaaccag ggacacagtg cactgcggaa ggccgcaggg acatctgccc      4620
aagaaagcct gggtattgtc caaggtttcc ccccactgag acagcctgag atatggcctt      4680
```

```
gtgggaaagg aaagacctta ccaccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac ctttccttga acttattcat gatacagatt cctttgctca   5040
cgtttccctg ctgaccttct ccccaccgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggagggc    5280 tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gttttttaaga  5460 aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca acgggccct ctagacgcgt tgacattgat tattgactag ttattaatag    5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880 ccccctatt gacgtcaatg acggtaaatg gcccgcctgg cattatgccc agtncatgac    5940
cttatgggac tttcctactt ggcagacatc tacgtattag tcatcgctat taccatggtg   6000
atgcggtttt ggcagtacat caatgggcgt ggatagcggt ttgactcacg ggatttttcc   6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgctttcc ccggcgcctg cacgcggcgc gcctgggtaa   6420
catgcttggg gtcctggtcc ttggcgcgct ggcctggcc ggccgcgtta agatacattg    6480
atgagtttgg acaaaccaca actagaatgc agtgaaaaaa atgctttatt tgtgaaattt   6540
gtgatgctat tgctttattt gtaaccatta taagctgcaa taacaagtt aacaacaaca    6600 attgcattca ttttatgttt caggttcagg gggaggtgtg ggaggttttt taaagcaagt   6660
aaaacctcta caaatgtggt atggctgatt atgatcagtt anctagatcc ggtggatctg   6720
agtccggact tgtacagctc gtccatgccg agagtgatcc cggcggcggt cacgaactcc   6780
anngatcgga tatcttatct agtgattcta aggccaactc agaagggctt tcttggttgt   6840
atctttcaca ctcctcagga aattcatgac gtcagtaccc ccagtccctc tgttttccgt   6900
gtttgagggc tcttctgact tgtggccacc catgggcttc tgcttcgaag gcttcacaat   6960
gtaagtatct actatcgaga ggtggaacat tctgagggag accaggccat tcacacactc   7020
attataagcc tccttcaagt cttcattgcg tcttaaaatg acaaactcac ggactggggg   7080
```

```
agctgactct aaggaggaga ggaagttccg gtgggctgga ggcatgtact ctctcatttc    7140
ctggaggaat tctgcagcag atccttcacc aacgtcatgc tttattccca gaaggacatc    7200
aagactctga aagatgctgc tctggcctgc actgccccct gaaaattttt tgggggtgtc    7260
ccagacgccc tcgtacagca gaccctccgg cagcttaggg ttgcccttcc aaccagacaa    7320
atatatgcga agaacgtgga aaaaggtgtc tggatccacg aagtcacgca tcctcttaaa    7380
aatttccttg gctttctcca gactggcagc tatactacac agtgccttct ccagtgcttt    7440
cgggtcttga tgctctactg cactggatac agtaggaatt gctttgattg caggagaagc    7500
tgcgatttcc accattagag agaccaggaa gaagccttta tcgcagtccc caccaggaaa    7560
cgagaacaga atgtccatgt tctcgtatgt catgggccca ttggggtcct ttttcttcca    7620
gtttgccagg acgcagtctg cgtaagacag aatgggaggc agcccagct tctccgagag     7680 ctcgcagtag ggaacggcaa gattgcgggg cagcaccttt cgaatatcat catccctcg     7740 gttccacaca tacgccatgg tgatgtaccc cagggccaaa tgtgccaggc gctgtaacct    7800
gtgtcccctc agttcttcgg tgcgcagtgt gggcagcttc tcgacttctt ctcggagctt    7860
cccattctca atcagcttag gcagatttct agccacaagg atccaaggtc tgtacgtatc    7920
aggcagctcc tccagtggat gtggtagagc aaagcccaca tcttcatcta tgtggtattc    7980
ttcaaggatc cttctagagc cttctgcagg agatatttga ctgtgaggca taatcgaatt    8040
cccgcggccg cgtcgacggt accagatctc tagcggatct gacggttcac taaaccagct    8100
ctgcttatat agacctccca ccgtacacgc ctaccgccca tttgcgtcaa tggggcggag    8160
ttgttacgac attttggaaa gtcccgttga ttttggtgcc aaaacaaact cccattgacg    8220
tcaatggggt ggagacttgg aaatcccgt gagtcaaacc gctatccacg cccattgatg     8280
tactgccaaa accgcatcac catggtaata gcgatgacta atacgtagat gtactgccaa    8340
gtaggaaagt cccataaggt catgtactgg gcataatgcc aggcgggcca tttaccgtca    8400
ttgacgtcaa tagggggcgt acttggcata tgatacactt gatgtactgc caagtgggca    8460
gtttaccgta aatactccac ccattgacgt caatggaaag tccctattgg cgttactatg    8520
ggaacatacg tcattattga cgtcaatggg cggggtcgt tgggcggtca gccaggcggg     8580
ccatttacca acgcggaact ccatatatgg gctatgaact aatgaccccg taattgatta    8640
ctattannnt aagggtggga aagaatatat aaggtggggg tcttatgtag ttttgtatct    8700
gttttgcagc agccgccgcc gccatgagca ccaactcgtt tgatggaagc attgtgagct    8760
catatttgac aacgcgcatg ccccatggg ccggggtgcg tcagaatgtg atgggctcca    8820
gcattgatgg tcgccccgtc ctgcccgcaa actctactac cttgacctac gacctgcagg    8880
cagacgggcg ctcctgcacc gcatccgcga cgcagtcctg caacgacctc tgcgagcact    8940
tctgcgttcc caaccccgac cagccggct cctactcgtg catgtgcgag accggctacc     9000
ggctggcggc cgaccaacac cggtgcgagg acgtggatga ctgcatactg gagcccagtc    9060
cgtgtccgca gcgctgtgtc aacacacagg gtggcttcga gtgccactgc taccctaact    9120
acgacctggt ggacggcgag tgtgtggagc ccgtggaccc gtgcttcaga gccaactgcg    9180
agtaccagtg ccagcccctg aaccaaacta gctacctctg cgtctgcgcc gagggcttcg    9240
cgcccattcc ccacgagccg cacaggtgcc agatgttttg caaccagact gcctgtccag    9300
ccgactgcga ccccaacacc caggctagct gtgagtgccc tgaaggctac atcctggacg    9360
acggtttcat ctgcacggac atcgacgagt gcgaaaacgg cggcttctgc tccggggtgt    9420
gccacaacct ccccggtacc ttcgagtgca tctgcgggcc cgactcggcc cttgcccgcc    9480
```

```
acattggcac cgactgtgac tccggcaagg tggacggtgg cgacagcggc tctggcgagc    9540
ccccgcccag cccgacgccc ggctccacct tgactcctcc ggccgtgggg ctcgtgcatt    9600
cgggcttgct cataggcatc tccatcgcga gcctgtgcct ggtggtggcg cttttggcgc    9660
tcctctgcca cctgcgcaag aagcagggcg ccgccagggc caagatggag tacaagtgcg    9720
cggccccttc caaggaggta gtgctgcagc acgtgcggac cgagcggacg ccgcagagac    9780
tctgagcggc ctccgtccag gagcctggct ccgtccagga gcctgtgcct cctcacccc     9840
agctttgcta ccaaagcacc ttagctggca ttacagctgg agaagaccct ccccgcaccc    9900
cccaagctgt tttcttctat tccatggcta actggcgagg gggtgattag agggaggaga    9960
atgagcctcg gcctcttccg tgacgtcact ggaccactgg gcaatgatgg caattttgta   10020
acgaagacac agactgcgat tgtcccagg tcctcactac cgggcgcagg agggtgagcg    10080
ttattggtcg gcagccttct gggcagacct tgacctcgtg ggctagggat gactaaaata   10140
tttatttttt ttaagtattt aggttttgt ttgtttcctt tgttcttacc tgtatgtctc    10200
cagtatccac tttgcacagc tctccggtct ctctctctct acaaactccc acttgtcatg   10260
tgacaggtaa actatcttgg tgaattttt tttcctagcc ctctcacatt tatgaagcaa    10320
gccccactta ttccccattc ttcctagttt tctcctccca ggaactgggc caactcacct   10380
gagtcaccct acctgtgcct gaccctactt cttttgctct tagctgtctg ctcagacaga   10440
accctacat gaaacagaaa caaaaacact aaaaataaaa atggccattt gcttttcac     10500
cagatttgct aatttatcct gaaatttcag attcccagag caaaataatt ttaaacaaag   10560
gttgagatgt aaaaggtatt aaattgatgt tgctggactg tcatagaaat tacacccaaa   10620
gaggtattta tctttacttt taaacagtga gcctgaattt tgttgctgtt ttgatttgta   10680
ctgaaaaatg gtaattgttg ctaatcttct tatgcaattt ccttttttgt tattattact   10740
tatttttgac agtgttgaaa atgttcagaa ggttgctcta gattgagaga agagacaaac   10800
acctcccagg agacagttca agaaagcttc aaactgcatg attcatgcca attagcaatt   10860
gactgtcact gttccttgtc actggtagac caaaataaaa ccagctctac tggtcttgtg   10920
gaattgggag cttgggaatg atcctggag gatgcccaat tagggcctag ccttaatcag    10980
gtcctcagaa aatttctacc atttcagaga ggcttttgg aatgtggccc ctgaacaaga    11040
attggaagct gccctgccca tgggagctgg ttagaaatgc agaatcctag gctccacccc   11100
atccagttca tgagaatcta tatttaacaa gatctgcagg gggtgtgtct gctcagtaat   11160
ttgaggacaa ccattccaga ctgcttccaa ttttctggaa tacatgaaat atagatcagt   11220
tataagtagc aggccaagtc aggcccttat tttcaagaaa ctgaggaatt tctttgtgt    11280
agctttgctc tttggtagaa aaggctaggt acacagctct agacactgcc acacagggtc   11340
tgcaaggtct ttggttcagc taagctagga atgaaatcct gcttcagtgt atggaaataa   11400
atgtatcata gaaatgtaac ttttgtaaga caaaggtttt cctcttctat tttgtaaact   11460
caaaatattt gtacatagtt atttatttat tgggataat ctagaacaca ggcaaaatcc    11520
ttgcttatga catcacttgt acaaaataaa caaataacaa tgtgaaaaaa aaaaaaaaa    11580
aaaaaaaaaa aaaaaaaaa aaaaggtagc agtcgacaga tgaattccac cacactggac   11640
tagtggatcc gagctcggta ccaagcttaa gtttgggctg caggaattct gatggctctc   11700
aaaattcctg cctcctttag ggataaaaga ctttaagact ttttaacaaa aagaaaaag    11760
aaaaaaaaaa ttcctgcctc ctggtgtaca cacacagaag ggttccctcc ccttgaatgt   11820
gaccaggatc tgtgaaaata acgggatagc cgctcctgtg attaggttat gtggtagact   11880
```

```
agagcaagat tctcctgctg gttttgaaga agtcagctgc catgttgtga gactgtcatg    11940
ggctagggca tgagccttta aatatctggg agcaacccct ggccagcagc cagtgagaaa    12000
acgggccctc agtcctacaa tcacaaggaa ctaaattctg ccaacaacct gaaggaactt    12060
tgaagaggat catgagtccc ttgattcagc ttgatgagcc cctgagcaga ggatacagct    12120
aacttgtact agggaagtat aaaaaacatg catgggaatg atatatatca actttaagga    12180
taattgtcat acttctggga atgaagggaa agaaatgggg ctttagttgt attatgatct    12240
ttaatttctc aaaaaaaata agatcagaag caaatatggc aaaatgttaa tacttttgtg    12300
ggtacgtagg tattcagcat acccttttt ctgagttcaa aatatttat aattaaaatg    12360 aaatgcaggc caggcacagt ggctcatgcc tataatacca gcactttgcg aggccgaggt    12420
gggaggatgg cttgaggcca gaccagcctg gccaacatgg caaaacccca tctctactta    12480 aaaaaaaaa aactatatat atatatatgt gtgtgtgt gtatatatat atatgtatat    12540
atatttatat atgtgtgtat atatatatat gtatatatat ttatatatgt gtgtgtatat    12600
atatatatac acacacacac atatatacat acatacatac acacacacac acacacaatt    12660
agccaggcat ggtggcgcac acctgtagtc ccagctactt gggaggctga gacatgagaa    12720
ttgcttgaac ctgggaggca gagtagttag tgagctgaga tcataccact gcactccagc    12780
ctggtgacag agtgagactc tgtcttaaaa aaaataaaaa ttaaaattaa atgcaaaagg    12840
tccaagtgaa ttgaagagga aagggtatc aaggaaggtt ttgtggaggt gacgtttgag    12900
ctgggtctta aatgacttaa acatgggata agaagggagg aataaggac atttcaggta    12960 cgagaaataa ggagcaaaca gtggaaacaa cctaacgtct gtcaaccagt gaatggataa    13020
caaaaatgta attcagatgg tatccaactt acgatggttc aacatgagat ttttctgact    13080
ttaggataga tttatcaaag tagtaaatcc attttcaact tatgatattt tcaacttcag    13140
atgggtttat caggacacag ttgaggaaca cctgtctatc catacaattt ggcaataaaa    13200
aggaaatgag tgcagatata ctccacaaca tgaatgaacc ttgaaaacat taagtgagag    13260
aagccagata caaaggcca catattgtat gattctattt atacaaaatg tccagaatag    13320
gcaaatctta tagacagcaa gtaggtagat gatcagtttg ctaggtgctg ggggaagggg    13380
aaatggggag tgatggctaa ggggattggg tttcttgtg gggcaatgaa atgtttaa    13440 aattgagcgt gataatgatt gcacaatgct gcatatatat ataatctata gattatatat    13500
atataaagag aggctgttag acagtgataa gtgatatata tatatatata catagagaga    13560
gagagagaga gagagagagg ctgttagtga taagtgatca ggaaaataaa agtattgagg    13620
aggaatacga agttgacggt gtgaaaacat gagatttat ataggatggc cagggaaggc    13680
cttaatgaga aagtgactta tgagtaaaaa caagggatcc taaaccttag catgcatcag    13740
aatcactcgg aaacttgtta aagcatagct tgctgggcct catcacagat attttgattc    13800
ggtaggttct tgtctgatat taatactttt ggtctaggga accacatttt gagaaccact    13860
gagctaaagg aagtaaaggt ttcccttagt ttactagctg gtaacactgg cccaggaggc    13920 cttttctggaa aaggtcccag tccccaaagg aagctgggga ctcgcgttca catcgtcaag    13980
gtttaccaag ttgtggcggg cctttccgtc ttggaaaaag cctcaaaatg gcagattagg    14040
gtgtccatgg ccggcggaaa gggtcttga agttgcagac caggagggaa gaagattctg    14100
ggcctccccc atgcagtgtc agctggcaac agaatgcacc ccggctgggt tggaggccct    14160
gggtactggc tcttccacac cagggggccca cctaccaagg gcagcaggag catctgcacc    14220
tcctgcgcca ggcgcccttc agtgcttcca cttgagcacc tctccagaca ccagctaggg    14280
```

```
tgacagtggt acaaatacca gactcccctg gcctgctcac ctcacagggt aatgtgctgt   14340
ggagtcaggg ggacacagca accaccagat gacatggctg gccccgggga ggacgacacg   14400
cagatacggc tacttggcac ctgtgatatt ttacacactc gagaggggcc cgcaccatcc   14460
tcagccctct ccccacattc actcttagtt catgtcacct ccacccagag ggggacacag   14520
gcccacagcg atggcccac accctgcctg aggtcgccca cttccaggga ggcagtcctg   14580
ggacttccac ccgaccaggc cccagagccc accgacttaa cccctccaga ggcttgtcgt   14640
tcattacctt attcaagatg gagaccagcc tttttgcgga gaaaatgcgg gtgaaggtcc   14700
tgaaagtgca ttgacgccgt tttcggaagc catacaagtt tagctggcgg aagaagctct   14760
ttatcgaagt tgtggcaaac actttgtgtg cgacgtccct tttgagaatc tccttttcaa   14820 agagttttg attgatcact ctacaagccc cactgtcatc ccaccagatg gacgaaaact   14880
ggttgctgct gaccagtctc cacagtttct gtggaaaggg gagggagagg agattatctt   14940
ctccctgggg cgggacgtca ccgtcagggt gcggccttct gaacgaagct tcctcggcca   15000
gaggttggaa agcgatttct tctgtcagca gcctcaagtt agggctccca gtggaccccg   15060
ggtcgtccca ggcaggggaa ggatctgctg ggtgaaggta ggtctctgac tgcaactggg   15120
gagggaaagg caccctttcc aagccatgat cctgtcctct cgaatttctt tcttcacagc   15180
gagccatact caatgatcgc ttgtcctcca tctggcaaac ttgctagtgc agtgtggcca   15240
gcagcacccc ttggcagtca tgtaaccagc ccatgacat cataaagggg ctctgactgc   15300 cgggggtgg catctccacc cccagcaagt tgtgtaataa agggcaagg cagacaagta   15360 gctgcccatc tgcatgtgca cattctggtc ctcacagtca tttcaatggg aaagatgaca   15420
ctagtgcaca agagtgccga ggggccctgc cacaccgtag atgcagacct ggagcggtcc   15480
ccttgtccta gagctcctga gccaggcaca actacagcaa agccctggct caggaaggtc   15540
agagctcacc gtctgagtca tgggcccaca gaccccagca catgactgac actcggaagc   15600
acagaacaaa gggtaggacg gtgcccatgg gtcaggctgt agccacgcca cccttccac   15660 cctgtcctag ccagaggcag caatgtgctc catacagatc ctcctaacac acccacactg   15720
tcggtcccca gcacgcagat gcccgacagc cccttaggca aatggcttag ctgactgccc   15780
caccacacgc cgtcgccatg cagtccagtg gggagtcgga ggcagcctcc ttcctgcctc   15840
tcctcggcct gcacgtgtcc ccccaccagg cagagaccct tctacacccc gggtgtctgc   15900
ggtcacatcg cggtggggca tgcagctgtt ggccttcgag catgttttgt tttccttggc   15960
cagtgtctcc agagaaacgc acgtgggttt gtgtccagcg gtccatctct gcaacagttg   16020
ttcctttggg attggatgct aggaggtcac gggagaggtg tccatccaaa gcagtgtctg   16080
tgtcacacac tgtccccaca cacagggcca cctctgcaca gactcccccg actcgattct   16140
gggcacagag ctcagtgacc ttccagagac tgccacgaac cggtgatgcc tccacgcttg   16200
agacatcctg accgcagggc ccaaggcgca ctggctcagg gggtgacagt gaggggtctg   16260
caaacagact gctgatgctc aacccggccg ctgccgagct gtgtgacttg gcacgtcac   16320 ttaacctctc tcggcctctg tctcctcccg gggataagag tagtagcacc tgcttcccgg   16380
ggctgtgagg atccagtggg acgtatagga actagcgagg caccggcagt tgggtcagag   16440
ctactgttgt cacttcacaa ggcatttct tcaacagcaa gtcggaaatc tcatgagcct   16500
aaggcagaat ccacctgtgg cctctggtta caacccacag gactgaaaat ccttccagcc   16560
acagcaactg tgaatttcc tggtcaattg ccacaagtca tgagctgaac cccacttgag   16620
tttcagttca ggcagaactc tagagacgac tagggcaagc tagacagcga ctgcagagcc   16680
```

```
ttttgttgca gcgtgagcag tcctcagctg ttgacatcac tggggagcaa acgaggacca   16740
ggagcggtga aaggacagtg tctgctgcag attgtcgtag cacccaagga acactccaga   16800
aagcctccta agcagtaaca agtgtggcaa ggtgtagccc agccaacagt ggcatctgcg   16860
aggcgtcccc tccttcctcc cactacccg tatacccctgg gacctgtgca ctgaaggact   16920
cattctaaag gctgtgcccc tgcagccgcc agcctcactc actggctgcc tgtgccagct   16980
agagatttct ttcctctgag gctggctgag aggaccactc cagtttcctg gcccatccag   17040
caaagaagat acacatcatg cacgtgtaaa atgaggaacc ggtttattga acagcttaag   17100
gagagcaaaa atagtggctt tagctacatt ttttacacac tgagcaggaa agtctaaacc   17160
atcccgttcc cctgtacccc aaagagaaca gggcttgctg gaggccagtg ccaagggcgg   17220
agtcgtgctc gcagcagact tgaattaacc ccatgtaggc cggcgagcag ttgcccgcgt   17280
gaaaacacca ccctcttctc ctggctgaga agatcaaagc tcttttttta ccctcttttc   17340
agcaaaggac ctatttgttt tcaggcagga ggatgttaaa cttgcagcct ctgacacacg   17400
gtggaacctg cagtgcttgg agaaacggca cgcacacgtg aaaacatcat gcctactcca   17460
aagccttctt gttgctggca ggaggaagc ttgagacttt cccacgcata gtcgtgaccc   17520
gcgtggccgt ttctgctctc agcaacattc tctagtgttc cggcttcaag cagcgcttgt   17580
caggtttgaa gctagccact attctgagaa cgtcagaaaa gcatggacca tctcttgctt   17640
ggtgttgccg ttgtggcagt agcagctact acgtacctgc acgagttcca gggcagaagt   17700
ggcaatgtcc catgaaggcg tggcacccca cgggggggggg ggggagtgt gccacgggcg   17760 tccacttctg cagcagaagg catgtgccta cagcacaagc ttgtaaaaaa atacttgaac   17820
agaatatgct gtacagaact aggggttaac accgcatatg aagatgctaa acatttgta   17880 taaatactct gtatacaagc atggagtcac tcccgtagaa agggctcatc cgtgaggcta   17940
tgaaaaactg ctgtcagcat gcccaaagag aaactacttc cacagtagga acagaaaaaa   18000
ggactgtgct gtgtctaaac acgtggtgca tcagagacat agttacagtt cctactgact   18060
gccccagcca cgacctggga gtgctgagga cctgggagtg ctcagcgagc tgcaggaggt   18120
cagccctgtg gagaaataca tttctaaaca atactttgga ttgggatttc agcaccgtat   18180
agacagatgt tccttctggg ggcctggcaa gcagccatct cccagtgggt ctgacgggga   18240
agaggggtac ctggagcccc tcccagacag acggtaatcc caccctgtt ctcacactct   18300 tcctggcatc cgcatctgct ggcacacacc cccgtcacct gccacttccg cgtcccgtcg   18360
tggtgagtgg ctgataggcg ctggatgcaa acaaggcatg agatggacgt acctggagac   18420
ccagctccag tactggttct ggtctgcggg gtgaacgagg gggcagagga aggcggagag   18480
agtgcgtccc agtccactta agctctgtcc ccggaagtgg catctaatct ggcatttcga   18540
tatttaattt gggaggtggg agcacatact tcccagggct ctgggtaatg accaccctgg   18600
ccttctttcg aaacatgggt gcgattttag ggggctccgg aactgggtc tcttcggttt   18660 cttcattatc ttcgtgatgg agatcatagg aaatgtttcc atattctcgt agaaatggga   18720
agatttcaag cagaaactga cagaaatctt tgcggatacc aaaccaccct gaaaaataag   18780
aattttttat ttcacacacg aggctcaact gaccttcctg ttaactttct ttccgtaaca   18840
agaagtttca ctcctacaat gtcataacat actttatcca gactcctgag tcacaaagcc   18900
tgaacagggc ttgagtaccc aaaatgggga agaagtgcaa atgctagctc tgtggtgctt   18960 ggagtgggt tccggaccg gcagggacag cgtccacggg gcctagttag ggatgccatt   19020
ctcgggcccc agcccagacc tccagaaact gagtcgggct agggtgggct ccagcggtcc   19080
```

```
ccttttcctg gcccttttgg gattctgctg gatgcccaaa tttgagaact actgctccag   19140
tgagtctcaa aatatctgtg gtgcgcagac tacggtgtct tccgctaatc ttctccagcc   19200
aggataaact catggatgac agtgccaccc aagaacaaga tttctgtcac cctctggaat   19260
ccgtgagggc ggtagtcatg cacgggttgg ccaggagggg gcctgaactc atggagccac   19320
cttaaagcca ctttcccagt cccactactc ctctctgtag gctactggag tgtcagctcg   19380
gtgcaagccc tccctgctcc cgggtgcggg gtaggggggca gaggcacaaa cagcaagcac   19440
agcccgggct gctgggctgc agtgaggccc tgcccccaaa cccactggct ttccgaaggg   19500
caatgctctg ggcttccgtg ccatggagcc cacagccttg ccaggaaggc accctctgca   19560
gagatcgttt tggaagtgtc tgcctcagca agcaggtgga ggggaataga gtgttagcaa   19620
ggcaagacag gcaagactcg ggtgatggca gcaaggatat gggggaggca gagcggccaa   19680
cagggaccta ggatgaatcc caggtttggg tgggagatgt ggattttcca tcaaaccctc   19740
ccgggcctgg gaagaatctg tcttgatccc cattttgcag aggagggaac gggatctctg   19800
agaggttgcc tgccgtgtct ggttctacct caaatggcag cgtgcactgc gagaaaagtc   19860
ccggtgcagg ccagcagaac accagagtta cggcatgccc ttcccttaga aggtcccaga   19920
atttcctcag ccctcacttt cccacacaag cttctaaatt ggggcccctcg gggactcatc   19980 ccttcctaga cttctatccg ccacccccca cccccctggtc ccccccccaga cacacaccaa   20040 ggacttctga aatgctgagt acatacagtg gtttcctccc ttctgtccaa atgtggttgc   20100
catcagcgtg atcaacgaga gccaaagggg gacaaagatc gggatgcagg agaaggcgtt   20160
gtggccatcc agtttgtgaa ccagcagaat ctaaagaaag agacatagtc ccggttgatg   20220
ccagcaccga aaatgggcag aggcggaagc cagacttcat taggcagttc ctcccccacca   20280 ccccaccccc gcgtgagctc ccacaagagg gaacatcagc accgccagaa aaaggcagga   20340
aaccacctat ccctggggaa agctcgaaat gagcttttat gtccctcttc agagctcggc   20400
aatagcctat ccacttgaaa agttcccagt gccagcagtt ttatggcaaa ctcctccggg   20460
tgtttgttct aaggagtcaa cagctcccat tctagaattc tccacgtgac tccaatacac   20520
aaatctgaca tcccactctg cttttcccag agtggaaact ggagccatac agaggcacca   20580
tggctaaaaa ggtgcactct tctccctgcc agccccacgt gctgccccca agagaaagga   20640
aggatgctct cctttcaccg aagctccctc tcggagatgg ctgtgttctc tccctctcc   20700 tggagtgggc tcactgtgag ctcgagggac agaggctgcc tttctagggg tgcagaatcc   20760
tgtcagggga agcgcaagct tcaggggctg aagaggcttc ccgtggaacg cttacctcaa   20820
atgtaagaag gggcacgacg atggtcatcc agctcagggc catggttatg tgtgtcctgc   20880
gctgtccgca atcacatcca tagagcgcaa gaacaagacg gaccacacaa tgtagtagag   20940
gaccaccagg cacagaaagg acatgagaat ccacagcggg acacacacaa cctgggggtg   21000
ggtgagagaa cagcaagaga agtctctttta gagcttccaa cctggcctct gatggaaggc   21060
atctttagca ccttgctgtg tctgtccagt taaggcggtc cttcctgtga gccgaataag   21120
gaccgttcca tctcccagga ctgctgggag catcgctcag gacagaaaag gtatggtatg   21180
ttcactatgg ggcctgctgc caccagggga cacacacgct cagtgagtca tcagtccctc   21240
ttcctttggg tgacagacag ccctgcacct ggctccgcag cctctactct tccagaggcc   21300
cactctccca cactctctca ggctcctcta ggttctgctg ccatcacagc ttcccgggaa   21360
atgggacaca actgtcaccc tgtgcacaca cacaagatct caccccaaca gactctcttc   21420
acaggcaaca ttcccacaac ctgctggggg tactttggca acacaaatgg gaatgggctc   21480
```

```
cccagaaagt ctggctgcct gggctcctaa ggatccctaa cctcacccct accaagttag   21540
tgaacttggc gggttgatgc tggatacagg ttgatgctgg atacgtagcg ctgccgggtc   21600
gtgaccccta aggaattatc caaactcttg tttttagatg ctttattata tcaaactctc   21660 cttttaaacaa gtggcccatc tgctgggatt tggaagcctg taatactgaa attttcatca   21720
taatggaaat tttaaaaaca gaatttgacc cacctgtttt taaaacactt tcattactta   21780
acaagaggtc taatcttggg caagtcttga aatttctctg gccttagttt cccatgtgtt   21840
aaatgaaact tgaagcagtt ggtctcttat agtctcctga ctctaacatt ctaagaatta   21900
tatttgtaca ataactcaaa atcacataa tttaatttac catatggact ccaaaatata    21960
ttttctcatt aggctaaact tgatctgcat tttctggatg tgtccatatt cttggactac   22020
actaaaacat gataccaatg cttcctctca ccataaaccc tcacttcgct ttctacattt   22080
aagaatttta tagctggaag agtccttaac agaaaatacc atctaataat taccccctcaa  22140 aatcgagaaa gtcctatctg ttcttatgct agttataaga atgaggcagc atttcacata   22200
atggttataa acactgccac aagaagattc atgatgtgtt gtttatctgt agctctcatc   22260
atactctgtc atataactat agcattaaga ttttaatgtt ctatatattc ttctaagaca   22320
gtgtttacca gagtaaggca caaaagatcc actggtttgc aagaaagatt agaactttta   22380 aatttttac ctcaccttgt ttaatctata tttttgtatg tattttgtaa catatatatt    22440
attattacca taaatcatat ataatttaaa atgcatatat tagggtaaa tgctcaggaa    22500 acttttata aattgggcat gcaaatacaa gtttgaagac tcactgttct aggtattaaa    22560
agtaaagtta taaccaagta aagcttccac cttttcatgt ctcaaagcag tttattgttg   22620
gaggtaagat ctcttagaag cctaaacagg tccaagtaca gaatgaagta aggctagccc   22680
ataacttgtg gcaagcaatt catactattt ctctcatgct gagctctcct cagtgaagca   22740
gctactatag acaactgcag cctattggta gcctatttta caggcaggaa aaaaattact   22800
ttttattcaa agtggaactc aggacatggg gagaaaatga atacaaaaaa tagggtcaat   22860
ccaaaggcac acagcaaatg agtaacacag ttatgttttt ttcccatttg tatgaggtcc   22920
cagtaaattc taagtaaact gcaaatttaa taatacacta aaaaagccat gcaattgttc   22980
aaatgaatcc cagcatggta caaggagtac agacactaga gtctaaaaaa caaagaatg    23040 ccattattga gttttgaat tatatcaagt agttacatct ctacttaata aatgagaaaa    23100
acgaggataa gaggccattt gataaaatga aaatagccaa gaagtggtat tagagacttg   23160
aatacaggta ttcgggtcca aagttcatct gctcaaatac taactgggga aaagagggaa   23220
aaatatttat atacatatat atctgcacac aaaaatacccc ccaaaagaca aaatgaggcc   23280
aggcagggtg gctcacaccc gtaatcccgg tactttggga ggctgaggca ggtggatacc   23340
tgagatcagg agttggagat cagcctggtc aacatggtga aaccctgtct ctactaaaga   23400
taaaaaaatt agccaggcat ggtggcgtgc gcctgtaatc ccagctactt gggagtctga   23460
ggcaggagaa tcacttgaac tgggaagggg aggttgcagt gagccaagat cgtactactg   23520
cactccagcc tgggcagcag agtgagactc catcacaaaa ataataaat aaataaaata    23580 caatgaaaca gaaagttcaa ataatcccat aatcttacca ccaagaaata actttcactc   23640
gttatactta ttgatttttc cataataaat gtactttact gtgactatca tgaaaagaaa   23700 gttatttag aaacagagaa ctgtttcaga tcaaatctat gtagtagaac agagccatta    23760
ggtgggaaag acgagatcaa actaaatctc agaaggccta aaaggctagg tccattccag   23820
cactaaaaac tgaccagaca agtaatggct tcaacagctt ctaaatatgg acaaagcatg   23880
```

```
ctgaaaggga aggacaggtc taacagtggt atatgaaatg aacaggaggg gcaaagctca  23940
tttctcctct gaagttttcc aaagatgctg aggaggacat tagtttgaca tgaccctgat  24000
atgggacaag ataatttcac agaagtttta catgttaaag ttttcttata gatactcatt  24060
caagtaagca atgaacacta aaatctaaag aaagaaaaga gctttagagt caggtctgta  24120
ttcaaattca agctctacca cttactggtt ctgtgacttt gggcaagtct tttaaccttta  24180
ttaagtctta atttcctgat tgtaaaatg gggatatcgt ctccctcaca ggattgttgt  24240
gaaactttta tgagattaat gcctttatat ttggcatagt gtaagtaaac aataactggc  24300
agcttcaaaa aaaaaagca gtagcattcc atcatttatt attggttact ctcaaaaagt  24360
ttttcaatgt actagaagat aaatattcaa ataccttaat atctccatta ttttcaggta  24420
aacagcatgc tcctgaacaa ccaatgggtc aacaaataaa ttaaaaggga aatctaaaaa  24480
catcttgata ttaaactaca tggaagcaca ataccaaa accatggtt cacactagga    24540
gaattttaag gtacaagaaa actctttgag atttcttaaa ataatagtat gtctgaattt  24600
attgagtgat ttaccagaaa ctgttgtaag agctctactt gcattatagc acttaatcct  24660
cttaactcta tggctgctat tatcaacctc accctaatca catatgggac acagagaggt  24720
taagtaactt gcccaaggtc agagttagga agtactaagc catgctttga atcagttgtc  24780
aggctccgga actcacactt tcagccacta cataatactg ctttgctatc ttttaggaaa  24840
ctatgtgagt ctacctcaca tagactcaca taggtttgtt ttttttttt ttttaaggc   24900
tatcttttcc cccatcaatg ttttttgaag gatcccaaat tagagtccca cagaggcaga  24960
cagcagtact tgacaatatg gacatttaag gttaatgttg gattctactg tcttttact   25020
acatgaccta gggaacgata attaacctag actgcttcca agggttaaat aacccattta  25080
gttatactat gtaaattatc tcttagtgat tgattgaaag cacactgtta ctaattgact  25140
cggtatgaag tgcttttttt tcttcccttt caagatacat acctttccag ttaaagttga  25200
gagatcatct ccaccaatta ctttttatgtc ccctgttgac tggtcattct agttaaaaaa  25260
aaaaaaaact atatatatat atatctacac acacatatgt atatgtatat ccttatgtac  25320
acacacaaac ttcaaattaa atgagaacta gaagatttga gaagttagct agctaatatc  25380
catagcatta tgatattcta aatgatatga attataagaa ttaggtttcc tgaaatgaat  25440
gactagaaaa ctttcaagta gagattagta aaaattaaaa agtcctaatc ggccattact  25500
gatttgatgt ttttaagagt cctaaaaaat gggttacatc cattttttaag tgggtagtat  25560
tataacagcc acccatcttc aatcacagtg atttctgaat tgtgagggaa gttattagca  25620
tgacaggtgt ctggttctgg ccctgtacga ttcccatgag tcaagcaaat tgtaagggct  25680
ggtctatatc acacccaacc ccaaggatat gtccctcaaa agtctagccc aggcccgtc   25740
atcttcagca tcatctggga aaccaggtct gattagtagt cctttaagga atacctctta  25800
ggctcccatt ttactgctat cacagaatcc aataaaaccc ttacaggaga ttcaatggga  25860
aatgctcaac acccactgta gttggtggtg acaatgacca taatttggct gtgctggatt  25920
caggacagaa aatttgggtg aaagagcagg tgaacaaaag agcttcgact tgcccctagca  25980
gagagcaagc cataccatac cacaaagcca cagcaattac aacggtgcag taccagcaca  26040
gtaaatgaac aaagtagagc ccagaaacag acccagaact atatgaggat ttagtataca  26100
ataaagatgg tatttcgagt cagtagggaa aagatgaatt attcaataaa tgatgtttgg  26160
ccaactagta acccatttgg gaaaaaataa agtatggtc cctacctcac agcatacaca   26220
aaaataaatt ccagacggat taaaatctaa atgtaaaaaa taaagccata agtggactgg  26280
```

```
aagaaaatag agaattttttt ttaacatccg tagaaagggt aaaaacccag gcatgacatg   26340
aaccaaaact gaagaggttc tgtaacaaat acccccttttt atatattggg ctccaacaat   26400
aagaacccat aggaaaatgg agaatgaaca caaatagaca atttatagaa gagaaggtta   26460
taaggtgtaa aattatatct atctgagaaa caaacactaa aacaatgtga ttctactgtt   26520
ctcccaccca tactggcaaa acttaagcct gataatatgc tgaggggaaa taagcactct   26580
tgttggtgag agtattaatt ggcatagctt cttttgaaaa tgacatagca atacctgtta   26640
aaattgcaaa catgcatgtc acttaatcca gtaatcccac ttctgggaat caatgctaca   26700
aaaacactga caagtataca aagatacatt caagagtgtt cactgggccg ggtgcggtgg   26760
cttcatgcct gtaatcccag ggaggcagag gcaagacgat cgcttgaccc caggagttca   26820
aggccagccc gagaaacaca gcaagaccct gtctctcttt tttttattta aaaaataaat   26880
gttcactgta tcagttgttc acaaaaacaa accaacatgt ccattaacag gaaccatttt   26940
aaattaatca agttcatcta cacaatgtaa taccatgcaa ctattaaaaa gcacctgata   27000
atccaaagca cactgagaca gaataatgct attaaaaaca ccaagtagtg aacactgtg    27060 ttgcctatga caccattttt attcaacatt taaacaaatt tgtaacagca attacatgag   27120
tagtgacaat ggcgtttatg agacttttca cttttatgtg cttctatttt tgttatgctt   27180
ctatatatac atccatttat tatggagtgt tactttcaaa aatcacaaat gggccagtat   27240
tatttggtgt tgcaaggtga gcatatgact tctgatatca acctttgcat attacttctc   27300
aatttaggga aattacagac atcccttatt ctaactaact taaaacccag catttcaaac   27360
atacagaatt gatggggaaa aaaagaaag aagaagaaa gaaaaggcaa caagcttcag    27420
atgacagtga ctcacatcaa attatttata aaatctgtta aatagtgcca tcttctggag   27480
atacctggta ttacagtcca actccagttg atgtctttac agagacaaga ggaataaagg   27540
aaaaaatatt caagaactga aaagtatgga gtcatggaaa aattgctgtg atccaaaggc   27600
tacggtgata ggacaagaaa caagagaact ccaagcagta agacactgct gttctattag   27660
catccaaacc tccatactcc tgtttgcccc aaggctttt taaaaaatag agacaggatc    27720
tcactatttt gctcaggctg gtcttgaact cctggactca agctatcctc ctgcctcggc   27780
ctcctaaagt gccgagatta caggcttgag tcaccatacc tggctattta ttttttctta   27840
actctcttgc ctggcctata gccaccatgg aagctaataa agaatattaa tttaagagta   27900
atggtatagt tcactacatt ggaatacagg tataagtgcc tacattgtac atgaatggca   27960
tacatggatc aattaccccca cctgggtggc caaaggaact gcgcgaacct ccctccttgg   28020
ctgtctggaa caagcttccc actagatccc tttactgagt gcctccctca tctttaatta   28080
tggttaagtc taggataaca ggactggcaa aggtgagggg aaagcttcct ccagagttgc   28140
tctaccctct cctctaccgt cctatctcct cactcctctc agccaaggag tccaatctgt   28200
cctgaactca gagcgtcact gtcaactaca taaaattgcc agagaagctc tttgggacta   28260
caaacacata cccttaatgt ctttatttct attttgtcta cctcttcagt ctaggtgaaa   28320
aaataggaag gataataggg aagaactttg tttatgccta cttatccgcc cctaggaatt   28380
ttgaaaacct ctaggtagca ataagaactg cagcatggta tagaaaaaga ggaggaaagc   28440
tgtatagaaa tgcataataa atgggcagga aaagaactgc ttggaacaaa cagggaggtt   28500
gaactataag gagagaaagc agagaggcta atcaacaagg ctgggttccc aagagggcat   28560
gatgagacta ttactaaggt aggaattact aagggctcca tgtcccctta gtggcttagt   28620
actatgtagc ttgctttctg cagtgaactt cagacccttc ttttaggatc ctagaatgga   28680
```

```
cttttttttt ttatcggaaa acagtcattc tctcaacatt caagcaggcc ccaagtctac    28740
cacactcaat cacattttct cttcatatca taatctctca accattctct gtccttttaa    28800
ctgtttttct atacccgat caaatgccaa caaaagtgag aatgttagaa tcatgtattt     28860
ttagaggtag actgtatctc agataaaaaa aaagggcaga tattccattt tccaaaatat    28920
gtatgcagaa aaaataagta tgaaaggaca tatgctcagg taacaagtta atttgtttac    28980
ttgtatttta tgaattccct aaaacctacg tcacccgccc cgttcccacg ccccgcgcca    29040
cgtcacaaac tccacccccct cattatcata ttggcttcaa tccaaaataa ggtatattat   29100
tgatgatgtt aattaacatg catggatcca tatgcggtgt gaaataccgc acagatgcgt    29160
aaggagaaaa taccgcatca ggcgctcttc cgcttcctcg ctcactgact cgctgcgctc    29220
ggtcgttcgg ctgcggcgag cggtatcagc tcactcaaag gcggtaatac ggttatccac    29280
agaatcaggg gataacgcag gaaagaacat gtgagcaaaa ggccagcaaa aggccaggaa    29340
ccgtaaaaag gccgcgttgc tggcgttttt ccataggctc cgcccccctg acgagcatca    29400
caaaaatcga cgctcaagtc agaggtggcg aaacccgaca ggactataaa gataccaggc    29460
gtttccccct ggaagctccc tcgtgcgctc tcctgttccg accctgccgc ttaccggata    29520
cctgtccgcc tttctccctt cgggaagcgt ggcgctttct catagctcac gctgtaggta    29580
tctcagttcg gtgtaggtcg ttcgctccaa gctgggctgt gtgcacgaac cccccgttca    29640
gcccgaccgc tgcgccttat ccggtaacta tcgtcttgag tccaacccgg taagacacga    29700
cttatcgcca ctggcagcag ccactggtaa caggattagc agagcgaggt atgtaggcgg    29760
tgctacagag ttcttgaagt ggtggcctaa ctacggctac actagaagga cagtatttgg    29820
tatctgcgct ctgctgaagc cagttacctt cggaaaaaga gttggtagct cttgatccgg    29880
caaacaaacc accgctggta gcggtggttt ttttgtttgc aagcagcaga ttacgcgcag    29940
aaaaaaagga tctcaagaag atcctttgat cttttctacg gggtctgacg ctcagtggaa    30000
cgaaaactca cgttaaggga ttttggtcat gagattatca aaaaggatct tcacctagat    30060
ccttttaaat taaaaatgaa gttttaaatc aatctaaagt atatatgagt aaacttggtc    30120
tgacagttac caatgcttaa tcagtgaggc acctatctca gcgatctgtc tatttcgttc    30180
atccatagtt gcctgactcc ccgtcgtgta gataactacg atacgggagg gcttaccatc    30240
tggccccagt gctgcaatga taccgcgaga cccacgctca ccggctccag atttatcagc    30300
aataaaccag ccagccggaa gggccgagcg cagaagtggt cctgcaactt tatccgcctc    30360
catccagtct attaattgtt gccgggaagc tagagtaagt agttcgccag ttaatagttt    30420
gcgcaacgtt gttgccattg ctgcagccat gagattatca aaaaggatct tcacctagat    30480
ccttttcacg tagaaagcca gtccgcagaa acggtgctga ccccggatga atgtcagcta    30540
ctgggctatc tggacaaggg aaaacgcaag cgcaaagaga aagcaggtag cttgcagtgg    30600
gcttacatgg cgatagctag actgggcggt tttatggaca gcaagcgaac cggaattgcc    30660
agctggggcg ccctctggta aggttgggaa gccctgcaaa gtaaactgga tggctttctt    30720
gccgccaagg atctgatggc gcaggggatc aagctctgat caagagacag gatgaggatc    30780
gtttcgcatg attgaacaag atggattgca cgcaggttct ccggccgctt ggtggagag    30840 gctattcggc tatgactggg cacaacagac aatcggctgc tctgatgccg ccgtgttccg    30900
gctgtcagcg caggggcgcc cggttctttt tgtcaagacc gacctgtccg gtgccctgaa    30960
tgaactgcaa gacgaggcag cgcggctatc gtggctggcc acgacgggcg ttccttgcgc    31020
agctgtgctc gacgttgtca ctgaagcggg aagggactgg ctgctattgg gcgaagtgcc    31080
```

```
ggggcaggat ctcctgtcat ctcaccttgc tcctgccgag aaagtatcca tcatggctga    31140
tgcaatgcgg cggctgcata cgcttgatcc ggctacctgc ccattcgacc accaagcgaa    31200
acatcgcatc gagcgagcac gtactcggat ggaagccggt cttgtcgatc aggatgatct    31260
ggacgaagag catcaggggc tcgcgccagc cgaactgttc gccaggctca aggcgagcat    31320
gcccgacggc gaggatctcg tcgtgaccca tggcgatgcc tgcttgccga atatcatggt    31380
ggaaaatggc cgcttttctg gattcatcga ctgtggccgg ctgggtgtgg cggaccgcta    31440
tcaggacata gcgttggcta cccgtgatat tgctgaagag cttggcggcg aatgggctga    31500
ccgcttcctc gtgctttacg gtatcgccgc tcccgattcg cagcgcatcg ccttctatcg    31560
ccttcttgac gagttcttct gaattttgtt aaaattttg ttaaatcagc tcattttta    31620 accaataggc cgaaatcggc aaaatccctt ataaatcaaa agaatagacc gagatagggt    31680
tgagtgttgt tccagtttgg aacaagagtc cactattaaa gaacgtggac tccaacgtca    31740
aagggcgaaa aaccgtctat cagggcgatg gcccactacg tgaaccatca ccctaatcaa    31800
gttttttggg gtcgaggtgc cgtaaagcac taaatcggaa ccctaaaggg agcccccgat    31860
ttagagcttg acggggaaag ccggcgaacg tggcgagaaa ggaagggaag aaagcgaaag    31920
gagcgggcgc tagggcgctg gcaagtgtag cggtcacgct gcgcgtaacc accacaccg    31980 ccgcgcttaa tgcgccgcta cagggcgcgt ccattcgcca ttcaggatcg aattaattct    32040
taattaacat catcaataat atacctatt ttggattgaa gccaatatga taatgagggg    32100
gtggagtttg tgacgtggcg cggggcgtgg aacggggcg ggtgacgtag tagtgtggcg    32160
gaagtgtgat gttgcaagtg tggcggaaca catgtaagcg acggatgtgg caaaagtgac    32220
gtttttggtg tgcgccggtg tacacaggaa gtgacaattt tcgcgcggtt ttaggcggat    32280
gttgtagtaa atttgggcgt aaccgagtaa gatttggcca ttttcgcggg aaaactgaat    32340
aagaggaagt gaaatctgaa taattttgtg ttactcatag cgcgtaatac tg          32392
```

<210> SEQ ID NO 25
<211> LENGTH: 32339
<212> TYPE: DNA
<213> ORGANISM: Artificial Sequence
<220> FEATURE:
<223> OTHER INFORMATION: Description of Artificial Sequence: Synthetic
      PhIDO-final
<220> FEATURE:
<221> NAME/KEY: misc_feature
<222> LOCATION: (1)..(32339)
<223> OTHER INFORMATION: n= a, c, g, t, unknown or other

<400> SEQUENCE: 25

```
gtacggaagc ccggaaggag gggcaggggg cggtggctca ggtttctccg ggcggcggcg      60
gcggcggcgg cggcgacggc gacggcgacg gcagcgggga cggcagcagt agcgggagca     120
gcagcgtgga cgcggctggc gctggcgcca tgaacccgct gtaaggcgca ggctgtgcag     180
cacggggtgc gggggaggag gaggaggacg ccgcggtgaa gttctccgcc atgaacctga     240
ggggcctctt ccaggacttc aacccgaggt gaggcggcgt cgttggcgcc cccgggagtc     300
cgcgctgcgg gctcgggcgc gggctggtgt tcggctccgg ggaggcacgg cgggcgagat     360
gctgcagccc gaggacccgg gcgcctgccc gagcctccct gcgggtgcaa gcggtccca     420 ggcaaaacag tcggcctcgg cgcccgcccg cttcctcctc ccgtgccgg tgctttcagc     480 ccctgcccgg ccacggccgg aagggccggg ccgcgagccc cgtcctgccc caagggaacc     540
ccattctttt ctgcttgctg tccctcattg gtgtcccaac ttcttcgtct cggttccatc     600
```

```
ctcttctgcg ccgctgcggg ccctccattc tccgcgtcag ggccgtctca ctcgacccaa    660
cacccctacc cccacccag ctgtttcctc cagttcctcg cagtccttgg ggttttcctt    720
gggtttatgc ccatccctct cttgtttgct tctttgttga acggataacct gaaacactgt   780 tgaatccttg gagtcagtgt cggggtatgg caataaccta tataatgcat ttctgggtga   840
gcctgatcat tttccatact cattttctca tcagtcttca ctacaagttt atttgcagga   900
agtagatatt gctgtccttc ttttccagat ggggaacacc cagtggacag tgtggagaaa   960
acactggcta agcactcaag cgcctgtcct tgcacttgcc cgactgtttt gtaactgttc  1020
tttaccccag gctgtgagct ccctgaagct gagaccatct cctgctcatc tcagtgtccc  1080
cagcgcctcc cacccaccgt atctggcaca tagtaggcac atataaaatg tttgtggaac  1140
taaactgagc ccaaagactt ggattggaga cgaggccata tgtaactggg tgattctctg  1200
cccttctttg gcccttctgt aaaatgagga gttggcctaa ctgatctctt aaatgcacta  1260
ctctccgaaa ggagtatccg tttcccttat ttgccagttg ggaagacgtg ctcagtaaat  1320
atttgtgtgc tgtaacctat gttaggtgct ttagatgctg gcggtctcag catggggtga  1380
agaagggctt gtacacttaa gatgcctaac agtactgtgc agtgctgtac tgcgggggcc  1440
aactctgggg acctatgcct tggctgcttg ttgaggatga aggaagtttt taggggagta  1500
tttgtatgtt gagggtgcag tctccctagg gatggtgaca ttttaacttg tgagtcattg  1560
tgactttgta tgtgcccttta ttccactttg agttcatgtt ctggttagga gtgccagtgt  1620
ctctaacacg gtgcagacat tatcattgtt ggcttcgaag gcatagagga ggtaacagaa  1680
ctaactgcag tcccttcctc tgctgcatca gggggttaag attggtctgc agggtagtag  1740
ggttggtgct gtggctggac aagccctgta tgtcttctat ttggagatgg tgataagaaa  1800
gttaagtaaa aactgaattg ttttgtgccc ttgggcaact cacttatcta ttgttttatc  1860
tgtagaatga gtataatctc tcagtggggt agggaggcca attaaggatt gattacaaag  1920
tgccttacaa atagaaagct acagtgactt gtttgcaagg tgacagagaa ttcagaagcc  1980
tcaagaaact gccttaagtg atcaaacagg ctaacggagt tgccaaagca aaatagtgct  2040
gcactgatac tacctttaac cgttttttcc tttagcccctt ttccccccaa aaaaattagt  2100
atatgaaatt acagtgaaat acctggtatc taagcagatt tatagtaatt ctcaacatat  2160
tcatcaatct cttaattcta cctgcattaa aatgtatttc tacctgaaaa gtttaaaggt  2220 ctttttatact gtgccatttt cctgattcat tgttgccaga ggtagtgagt tccttaattt  2280
tacagatatt tcaagaggac attggccagg tattattggt aaatcagatt tgttttttta  2340
gctggtagtg tttcacctct cctgagcact cctagttttt gacagtgtgc tttagtctcc  2400
ttccatgctg aggaaggcct tctctatagg agaaagaaaa ctgaggggtg tacacaggaa  2460
gttaccttat gctggggact caaaccttga tgctactgct ttgctccctg cctctatttt  2520
tgaaccaatt caacatctcc ctcctacccc aggaccttgt cacacactgt tctcttacc  2580 aggaatgttt ccctctcttt tcctctcctc cagacctagt gaactcctat ttatcctcac  2640
ttggcacttg ctaagggaag cattcctgac ttccctgacc agatttactg ctccctgttt  2700
ctacagttcc tgtagtattt actactcctc catcatagtg catatttgta cccttgtgtc  2760
tgtctggatg cttatttgat taatacctgc ctcccccact aaactttaag ctccatgggg  2820
tcaaggccgt gactgtgtca gtatcgtagc ctgcatactt ggaatagtac ctggctcaat  2880
aaatatttgt ggagtaaata actgaataac tctccagagc ctataagata aatctagagc  2940
tgctgctttc aatcactgct ttcctggtgg tctgtggcct ggttctcttt cttctcacac  3000
```

```
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atccccttc cagccttttg     3180
gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttagt     3360
tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt ggggagttg ctggttcaga aaggcccctt     3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catgggtac tgatgagatc      3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgcttttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggttttcc ccccactgag acagcctgag atatggcctt    4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttttccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggagggc     5280
tggcccttt cagtatctca gaagggacaa agtacacaaa ggcatggggt catgatagtg      5340
cctggtatgt tcaggtagtg aagaggtcca tgtggtatga gcactgcaga tgatatgtgt    5400
```

-continued

```
cgtatgaatt aaaaatacat agttactgca aatagttttt acaggttatt gttttttaaga    5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg accccgccc attgacgtca    5760 ataatgacgt atgttcccat agtaacgcca atagggactt tccattgacg tcaatgggtg    5820
gagtatttac ggtaaactgc ccacttggca gtacatcaag tgtatcatat gccaagtacg    5880 ccccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa cccctgctta ctggcttatc    6240
gagatatctg cagaattcat ctgtcgactg ctaccggcag cgcgcagcgg caagaagtgt    6300
ctgggctggg acgacagga gaggctgtcg ccatcggcgt cctgtgcccc tctgctccgg    6360
cacggccctg tcgcagtgcc cgcgctttcc ccggcgcctg cacgcggcgc gcctgggtaa    6420
catgcttggg gtcctggtcc ttggcgcgct ggcctggcc ggccgcgtta agatacattg    6480
atgagtttgg acaaaccaca actagaatgc agtgaaaaaa atgctttatt tgtgaaattt    6540
gtgatgctat tgctttattt gtaaccatta taagctgcaa taaacaagtt aacaacaaca    6600
attgcattca ttttatgttt caggttcagg gggaggtgtg ggaggttttt taaagcaagt    6660
aaaacctcta caaatgtggt atggctgatt atgatcagtt atctagatcc ggtggatcgg    6720
atatcttatc tagaagctta ggctcgagtg ctcttgttgg gttacattaa ccttccttca    6780
aaagggattt ctcagttgta cttcttacag tcttcaggaa attcattaaa tcagtgcctc    6840
cagttccttt ggcttccagt tttgaagggt cttcagaggt cttattctcc tttggctgct    6900
ggcttgcagg aatcaggatg tacttagtca cgatttgcag atggtagctc ctcagggaga    6960
ccagagcttt cacacaggcg tcataagctt cccgcaggcc agcatcacct tttgaaagga    7020
caaactcacg gactgaggga tttgactcta atgagcacag gaagttcctg tgagctggtg    7080
gcatatatct tctcatgtcc tggaggaact gagcagcatg tcctccacca gcagtctgct    7140
ggatgcccag caggacgtca aagcactgaa agacgctgct ttggcctgca ctgccccctg    7200
caaactcctt tgggtcttcc cagaacccett catacaccag accgtctgat agctgggggt    7260
tgcctttcca gccagacaaa tatatgcgaa gaacactgaa aaatgctttt gggttcacat    7320
gatcgtggat ttggtgaaac acttgaaggg ctttctccaa gcaagaagct atttccaaca    7380
gcgcctttag caaagtgtcc cgttcttgca tttgcattgc cttgaataca gtaggaatta    7440
ctttgattgc agaagcagct gctatttcca ccaatagaga gaccaggaag aatcctttac    7500
tgcagtctcc atcacgaaat gagaacaaaa cgtccatgtt ctcataagtc aggggcttat    7560
taggatcctt tttcttccag tttgccaaga cacagtctgc ataaaccaaa ataggaggca    7620
gttccagttt cttggagagt tggcagtaag gaacagcaat atttcttggc aagaccttac    7680
ggacatctcc atgacctttg ccccacacat atgccatggt gatgcatccc agaactagac    7740
gtgcaaggcg ctgtgacttg tggtctgtga gatgatcaat gctgagcatg tttaacttct    7800
```

```
caactctttc tcgaagctgg ccagactcta tgagatcagg cagatgttta gcaatgaaca    7860
tccagtcatt ataaaaatca ggtagatttt cctgtggatt tggcagagca aagcccactt    7920
cttcatcaat atggtactct ttactgattg tccaggagtt ttccatagcg tgtgccattc    7980
ttgtagtctg ctcctctgga gatctctagc ggatctgacg gttcactaaa ccagctctgc    8040
ttatatagac ctcccaccgt acacgcctac cgcccatttg cgtcaatggg gcggagttgt    8100
tacgacattt tggaaagtcc cgttgatttt ggtgccaaaa caaactccca ttgacgtcaa    8160
tggggtggag acttggaaat ccccgtgagt caaaccgcta ccacgcccca ttgatgtact    8220
gccaaaaccg catcaccatg gtaatagcga tgactaatac gtagatgtac tgccaagtag    8280
gaaagtccca taaggtcatg tactgggcat aatgccaggc gggccattta ccgtcattga    8340
cgtcaatagg gggcgtactt ggcatatgat acacttgatg tactgccaag tgggcagttt    8400
accgtaaata ctccacccat tgacgtcaat ggaaagtccc tattggcgtt actatgggaa    8460
catacgtcat tattgacgtc aatgggcggg ggtcgttggg cggtcagcca ggcgggccat    8520
ttaccgtaag ttatgtaacg cggaactcca tatatgggct atgaactaat gaccccgtaa    8580
ttgattacta ttannntaag ggtgggaaag aatatataag gtgggggtct tatgtagttt    8640
tgtatctgtt ttgcagcagc cgccgccgcc atgagcacca actcgtttga tggaagcatt    8700
gtgagctcat atttgacaac gcgcatgccc ccatgggccg gggtgcgtca gaatgtgatg    8760
ggctccagca ttgatggtcg ccccgtcctg cccgcaaact ctactacctt gacctacgac    8820
ctgcaggcag acgggcgctc ctgcaccgca tccgcgacgc agtcctgcaa cgacctctgc    8880
gagcacttct gcgttcccaa ccccgaccag ccgggctcct actcgtgcat gtgcgagacc    8940
ggctaccggc tggcggccga ccaacaccgg tgcgaggacg tggatgactg catactggag    9000
cccagtccgt gtccgcagcg ctgtgtcaac acacagggtg gcttcgagtg ccactgctac    9060
cctaactacg acctggtgga cggcgagtgt gtggagcccg tggacccgtg cttcagagcc    9120
aactgcgagt accagtgcca gccctgaac caaactagct acctctgcgt ctgcgccgag    9180
ggcttcgcgc ccattcccca cgagccgcac aggtgccaga tgttttgcaa ccagactgcc    9240
tgtccagccg actgcgaccc caacacccag gctagctgtg agtgccctga aggctacatc    9300
ctggacgacg gtttcatctg cacggacatc gacgagtgcg aaaacggcgg cttctgctcc    9360
ggggtgtgcc acaacctccc cggtaccttc gagtgcatct gcgggcccga ctcggccctt    9420
gcccgccaca ttggcaccga ctgtgactcc ggcaaggtgg acggtggcga cagcggctct    9480
ggcgagcccc cgcccagccc gacgcccggc tccaccttga ctcctccggc cgtgggctc    9540 gtgcattcgg gcttgctcat aggcatctcc atcgcgagcc tgtgcctggt ggtggcgctt    9600
ttggcgctcc tctgccacct gcgcaagaag cagggcgccg ccaggccaa gatggagtac    9660 aagtgcgcgg cccccttccaa ggaggtagtg ctgcagcacg tgcggaccga gcggacgccg    9720
cagagactct gagcggcctc cgtccaggag cctggctccg tccaggagcc tgtgcctcct    9780
cacccccagc tttgctacca aagcacctta gctggcatta cagctggaga agaccctccc    9840 cgcaccccc aagctgtttt cttctattcc atggctaact ggcgaggggg tgattagagg    9900
gaggagaatg agcctcggcc tcttccgtga cgtcactgga ccactgggca atgatggcaa    9960
ttttgtaacg aagacacaga ctgcgatttg tcccaggtcc tcactaccgg gcgcaggagg    10020
gtgagcgtta ttggtcggca gccttctggg cagaccttga cctcgtgggc tagggatgac    10080
taaaatattt attttttttta agtatttagg ttttgtttg tttcctttgt tcttacctgt    10140
atgtctccag tatccacttt gcacagctct ccggtctctc tctctctaca aactcccact    10200
```

```
tgtcatgtga caggtaaact atcttggtga attttttttt cctagccctc tcacatttat    10260
gaagcaagcc ccacttattc cccattcttc ctagttttct cctcccagga actgggccaa    10320
ctcacctgag tcaccctacc tgtgcctgac cctacttctt ttgctcttag ctgtctgctc    10380
agacagaacc cctacatgaa acagaaacaa aaacactaaa aataaaaatg gccatttgct    10440
ttttcaccag atttgctaat ttatcctgaa atttcagatt cccagagcaa ataaatttta    10500
aacaaaggtt gagatgtaaa aggtattaaa ttgatgttgc tggactgtca tagaaattac    10560
acccaaagag gtatttatct ttacttttaa acagtgagcc tgaattttgt tgctgttttg    10620
atttgtactg aaaaatggta attgttgcta atcttcttat gcaatttcct ttttgttat     10680 tattacttat ttttgacagt gttgaaaatg ttcagaaggt tgctctagat tgagagaaga    10740
gacaaacacc tcccaggaga cagttcaaga aagcttcaaa ctgcatgatt catgccaatt    10800
agcaattgac tgtcactgtt ccttgtcact ggtagaccaa aataaaacca gctctactgg    10860
tcttgtggaa ttgggagctt gggaatggat cctggaggat gcccaattag ggcctagcct    10920
taatcaggtc ctcagagaat tctaccatt tcagagaggc cttttggaat gtggcccctg      10980
aacaagaatt ggaagctgcc ctgcccatgg gagctggtta gaaatgcaga atcctaggct    11040
ccaccccatc cagttcatga gaatctatat ttaacaagat ctgcaggggg tgtgtctgct    11100
cagtaatttg aggacaacca ttccagactg cttccaattt tctggaatac atgaaatata    11160
gatcagttat aagtagcagg ccaagtcagg cccttatttt caagaaactg aggaattttc    11220
tttgtgtagc tttgctcttt ggtagaaaag gctaggtaca cagctctaga cactgccaca    11280
cagggtctgc aaggtctttg gttcagctaa gctaggaatg aaatcctgct tcagtgtatg    11340
gaaataaatg tatcatagaa atgtaacttt tgtaagacaa aggttttcct cttctatttt    11400
gtaaactcaa aatatttgta catagttatt tatttattgg agataatcta gaacacaggc    11460
aaaatccttg cttatgacat cacttgtaca aaataaacaa ataacaatgt gaaaaaaaaa    11520
aaaaaaaaaa aaaaaaaaa aaaaaaaaaa aggtagcagt cgacagatga attccaccac    11580
actggactag tggatccgag ctcggtacca agcttaagtt tgggctgcag gaattctgat    11640
ggctctcaaa attcctgcct cctttaggga taaaagactt taagactttt taacaaaaaa    11700 gaaaagaaa aaaaaaattc ctgcctcctg gtgtacacac acagaagggt tccctcccct    11760
tgaatgtgac caggatctgt gaaaataacg ggatagccgc tcctgtgatt aggttatgtg    11820
gtagactaga gcaagattct cctgctggtt ttgaagaagt cagctgccat gttgtgagac    11880
tgtcatgggc tagggcatga gccttttaaat atctgggagc aacccctggc cagcagccag    11940
tgagaaaacg ggccctcagt cctacaatca aaggaacta aattctgcca acaacctgaa     12000
ggaactttga agaggatcat gagtcccttg attcagcttg atgagcccct gagcagagga    12060
tacagctaac ttgtactagg gaagtataaa aaacatgcat gggaatgata tatatcaact    12120
ttaaggataa ttgtcatact tctgggaatg aagggaaaga aatgggggctt tagttgtatt    12180 atgatcttta atttctcaaa aaaaataaga tcagaagcaa atatggcaaa atgttaatac    12240
ttttgtgggt acgtaggtat tcagcatacc ctttttctg agttcaaaat attttataat     12300
taaaatgaaa tgcaggccag gcacagtggc tcatgcctat aataccagca ctttgcgagg    12360
ccgaggtggg aggatggctt gaggccagac cagcctggcc aacatggcaa accccatct     12420 ctacttaaaa aaaaaaaaac tatatatata tatatgtgtg tgtgtgtgta tatatata      12480 tgtatatata tttatatatg tgtgtatata tatatgta tatatattta tatatgtgtg     12540
tgtatatata tatatacaca cacacacata tatacataca tacatacaca cacacacaca    12600
```

```
cacaattagc caggcatggt ggcgcacacc tgtagtccca gctacttggg aggctgagac   12660
atgagaattg cttgaacctg ggaggcagag tagttagtga gctgagatca taccactgca   12720
ctccagcctg gtgacagagt gagactctgt cttaaaaaaa ataaaaatta aaattaaatg   12780
caaaaggtcc aagtgaattg aagaggaaag gggtatcaag gaaggttttg tggaggtgac   12840
gtttgagctg ggtcttaaat gacttaaaca tgggataaga agggagggaa taaggacatt   12900
tcaggtacga gaaataagga gcaaacagtg gaaacaacct aacgtctgtc aaccagtgaa   12960
tggataacaa aaatgtaatt cagatggtat ccaacttacg atggttcaac atgagatttt   13020
tctgacttta ggatagattt atcaaagtag taaatccatt ttcaacttat gatattttca   13080
acttcagatg ggtttatcag gacacagttg aggaacacct gtctatccat acaatttggc   13140
aataaaaagg aaatgagtgc agatatactc cacaacatga atgaacctkg aaaacattaa   13200
gtgagagaag ccagatacaa aaggccacat attgtatgat tctatttata caaaatgtcc   13260
agaataggca atcttatag acagcaagta ggtagatgat cagtttgcta ggtgctgggg   13320
gaaggggaaa tggggagtga tggctaaggg gattgggttt ctttgtgggg caatgaaaat   13380
gttttaaaat tgagcgtgat aatgattgca caatgctgca tatatatata atctatagat   13440
tatatatata taagagagg ctgttagaca gtgataagtg atatatatat atatatacat   13500
agagagagag agagagagag agagaggctg ttagtgataa gtgatcagga aaataaaagt   13560
attgaggagg aatacgaagt tgacggtgtg aaaacatgag attttatata ggatggccag   13620
ggaaggcctt aatgagaaag tgacttatga gtaaaaacaa gggatcctaa accttagcat   13680
gcatcagaat cactcggaaa cttgttaaag catagcttgc tgggcctcat cacagatatt   13740
ttgattcggt aggttcttgt ctgatattaa tacttttggt ctaggaacc acattttgag   13800 aaccactgag ctaaaggaag taaaggtttc ccttagttta ctagctggta acactggccc   13860
aggaggcctt tctggaaaag gtcccagtcc ccaaaggaag ctgggggactc gcgttcacat   13920 cgtcaaggtt taccaagttg tggcgggcct ttccgtcttg gaaaaagcct caaaatggca   13980
gattagggtg tccatggccg gcggaaaggg tcttggaagt tgcagaccag gagggaagaa   14040
gattctgggc ctcccccatg cagtgtcagc tggcaacaga atgcacccg gctgggttgg   14100 aggccctggg tactggctct tccacaccag ggccccacct accaagggca gcaggagcat   14160
ctgcacctcc tgcgccaggc gcccttcagt gcttccactt gagcacctct ccagacacca   14220
gctagggtga cagtggtaca aataccagac tcccctggcc tgctcacctc acagggtaat   14280
gtgctgtgga gtcaggggga cacagcaacc accagatgac atggctggcc ccggggagga   14340
cgacacgcag atacggctac ttggcacctg tgatatttta cacactcgag aggggcccgc   14400
accatcctca gccctctccc cacattcact cttagttcat gtcacctcca cccagagggg   14460
gacacaggcc cacagcgatg gccccacacc ctgcctgagg tcgcccactt cccaggaggc   14520
agtcctggga cttccacccg accaggcccc agagcccacc gacttaaccc ctccagaggc   14580
ttgtcgttca ttaccttatt caagatggag accagccttt ttgcggagaa aatgcgggtg   14640
aaggtcctga aagtgcattg acgccgtttt cggaagccat acaagtttag ctggcggaag   14700
aagctcttta tcgaagttgt ggcaaacact ttgtgtgcga cgtccctttt gagaatctcc   14760 tttcaaaga gttttgatt gatcactcta caagccccac tgtcatccca ccagatggac   14820 gaaactggt tgctgctgac cagtctccac agtttctgtg gaaaggggag ggagaggaga   14880
ttatcttctc cctggggcgg gacgtcaccg tcagggtgcg gccttctgaa cgaagcttcc   14940
tcggccagag gttggaaagc gatttcttct gtcagcagcc tcaagttagg gctcccagtg   15000
```

-continued

```
gaccccgggt cgtcccaggc aggggaagga tctgctgggt gaaggtaggt ctctgactgc    15060
aactggggag ggaaaggcac cctttccaag ccatgatcct gtcctctcga atttcttttct   15120 tcacagcgag ccatactcaa tgatcgcttg tcctccatct ggcaaacttg ctagtgcagt    15180
gtggccagca gcacccttg gcagtcatgt aaccagcccc atgacatcat aaagggctc     15240 tgactgccgg ggggtggcat ctccaccccc agcaagttgt gtaataaagg gccaaggcag    15300
acaagtagct gcccatctgc atgtgcacat tctggtcctc acagtcattt caatgggaaa    15360
gatgacacta gtgcacaaga gtgccgaggg gccctgccac accgtagatg cagacctgga    15420
gcggtcccct tgtcctagag ctcctgagcc aggcacaact acagcaaagc cctggctcag    15480
gaaggtcaga gctcaccgtc tgagtcatgg gcccacagac cccagcacat gactgacact    15540
cggaagcaca gaacaaaggg taggacggtg cccatgggtc aggctgtagc cacgccaccc    15600
tttccaccct gtcctagcca gaggcagcaa tgtgctccat acagatcctc ctaacacacc    15660
cacactgtcg gtccccagca cgcagatgcc cgacagcccc ttaggcaaat ggcttagctg    15720
actgccccac cacacgccgt cgccatgcag tccagtgggg agtcggaggc agcctccttc    15780
ctgcctctcc tcggcctgca cgtgtccccc caccaggcag agaccttct acaccccggg     15840 tgtctgcggt cacatcgcgg tggggcatgc agctgttggc cttcgagcat gttttgtttt    15900
ccttggccag tgtctccaga gaaacgcacg tgggtttgtg tccagcggtc catctctgca    15960
acagttgttc ctttgggatt ggatgctagg aggtcacggg agaggtgtcc atccaaagca    16020
gtgtctgtgt cacacactgt ccccacacac agggccacct ctgcacagac tcccccgact    16080
cgattctggg cacagagctc agtgaccttc cagagactgc cacgaaccgg tgatgcctcc    16140
acgcttgaga catcctgacc gcagggccca aggcgcactg gctcagggg tgacagtgag     16200 gggtctgcaa acagactgct gatgctcaac ccggccgctg ccgagctgtg tgacttgggc    16260
acgtcactta acctctctcg gcctctgtct cctcccgggg ataagagtag tagcacctgc    16320
ttcccggggc tgtgaggatc cagtgggacg tataggaact agcgaggcac cggcagttgg    16380
gtcagagcta ctgttgtcac ttcacaaggc attttcttca acagcaagtc ggaaatctca    16440
tgagcctaag gcagaatcca cctgtggcct ctggttacaa cccacaggac tgaaaatcct    16500
tccagccaca gcaactggtg aatttcctgg tcaattgcca caagtcatga gctgaacccc    16560
acttgagttt cagttcaggc agaactctag agacgactag ggcaagctag acagcgactg    16620
cagagccttt tgttgcagcg tgagcagtcc tcagctgttg acatcactgg ggagcaaacg    16680
aggaccagga gcggtgaaag gacagtgtct gctgcagatt gtcgtagcac caaggaaca    16740 ctccagaaag cctcctaagc agtaacaagt gtggcaaggt gtagcccagc caacagtggc    16800
atctgcgagg cgtcccctcc ttcctcccac taccccgtat accctgggac ctgtgcactg    16860
aaggactcat tctaaaggct gtgcccctgc agccgccagc ctcactcact ggctgcctgt    16920
gccagctaga gatttctttc ctctgaggct ggctgagagg accactccag tttcctggcc    16980
catccagcaa agaagataca catcatgcac gtgtaaaatg aggaaccggt ttattgaaca    17040
gcttaaggag agcaaaaata gtggctttag ctacattttt tacacactga gcaggaaagt    17100
ctaaaccatc ccgttcccct gtaccccaaa gagaacaggg cttgctggag gccagtgcca    17160
agggcggagt cgtgctcgca gcagacttga attaacccca tgtaggccgg cgagcagttg    17220
cccgcgtgaa acaccaccc tcttctcctg gctgagaaga tcaaagctct ttttttaccc     17280
tcttttcagc aaaggaccta tttgttttca ggcaggagga tgttaaactt gcagcctctg    17340
acacacggtg gaacctgcag tgcttggaga aacggcacgc acacgtgaaa acatcatgcc    17400
```

```
tactccaaag ccttcttgtt gctggcagga gggaagcttg agactttccc acgcatagtc   17460
gtgacccgcg tggccgtttc tgctctcagc aacattctct agtgttccgg cttcaagcag   17520
cgcttgtcag gtttgaagct agccactatt ctgagaacgt cagaaaagca tggaccatct   17580
cttgcttggt gttgccgttg tggcagtagc agctactacg tacctgcacg agttccaggg   17640
cagaagtggc aatgtcccat gaaggcgtgg caccccacgg gggggggggg ggagtgtgcc   17700
acgggcgtcc acttctgcag cagaaggcat gtgcctacag cacaagcttg taaaaaata   17760 cttgaacaga atatgctgta cagaactagg ggttaacacc gcatatgaag atgctaaaac   17820
atttgtataa atactctgta tacaagcatg gagtcactcc cgtagaaagg gctcatccgt   17880
gaggctatga aaaactgctg tcagcatgcc caaagagaaa ctacttccac agtaggaaca   17940
gaaaaaagga ctgtgctgtg tctaaacacg tggtgcatca gagacatagt tacagttcct   18000
actgactgcc ccagccacga cctgggagtg ctgaggacct gggagtgctc agcgagctgc   18060
aggaggtcag ccctgtggag aaatacattt ctaaacaata cttttgattg ggatttcagc   18120
accgtataga cagatgttcc ttctgggggc ctggcaagca gccatctccc agtgggtctg   18180
acggggaaga ggggtacctg gagccctcc cagacagacg gtaatcccac ccctgttctc   18240
acactcttcc tggcatccgc atctgctggc acacaccccc gtcacctgcc acttccgcgt   18300
cccgtcgtgg tgagtggctg ataggcgctg gatgcaaaca aggcatgaga tggacgtacc   18360
tggagaccca gctccagtac tggttctggt ctgcggggtg aacgagggg cagaggaagg   18420 cggagagagt gcgtccccagt ccacttaagc tctgtccccg gaagtggcat ctaatctggc   18480
atttcgatat ttaatttggg aggtgggagc acatacttcc cagggctctg ggtaatgacc   18540
accctggcct tctttcgaaa catggggtgcg atttttagggg gctccggaac tggggtctct   18600
tcggtttctt cattatcttc gtgatggaga tcataggaaa tgtttcccata ttctcgtaga   18660 aatgggaaga tttcaagcag aaactgacag aaatctttgc ggataccaaa ccaccctgaa   18720
aaataagaat tttttatttc acacacgagg ctcaactgac cttcctgtta actttctttc   18780
cgtaacaaga agtttcactc ctacaatgtc ataacatact ttatccagac tcctgagtca   18840
caaagcctga acagggcttg agtacccaaa atggggaaga agtgcaaatg ctagctctgt   18900
ggtgcttgga gtggggttcc cggaccggca gggacagcgt ccacggggcc tagttaggga   18960
tgccattctc gggccccagc ccagacctcc agaaactgag tcgggctagg gtgggctcca   19020
gcggtcccct tttcctggcc cttttgggat tctgctggat gcccaaattt gagaactact   19080
gctccagtga gtctcaaaat atctgtggtg cgcagactac ggtgtcttcc gctaatcttc   19140
tccagccagg ataaactcat ggatgacagt gccacccaag aacaagattt ctgtcaccct   19200
ctggaatccg tgagggcggt agtcatgcac gggttggcca ggaggggggcc tgaactcatg   19260 gagccacctt aaagccactt tcccagtccc actactcctc tctgtaggct actggagtgt   19320
cagctcggtg caagccctcc ctgctcccgg gtgcggggta ggggcagag gcacaaacag   19380 caagcacagc ccgggctgct gggctgcagt gaggccctgc ccccaaaccc actggctttc   19440
cgaagggcaa tgctctgggc ttccgtgcca tggagcccac agccttgcca ggaaggcacc   19500
ctctgcagag atcgttttgg aagtgtctgc ctcagcaagc aggtggaggg gaatagagtg   19560
ttagcaaggc aagacaggca agactcgggt gatggcagca aggatatggg ggaggcagag   19620
cggccaacag ggacctagga tgaatcccag gtttgggtgg gagatgtgga ttttccatca   19680
aaccctcccg ggcctgggaa gaatctgtct tgatccccat tttgcagagg agggaacggg   19740
atctctgaga ggttgcctgc cgtgtctggt tctacctcaa atggcagcgt gcactgcgag   19800
```

```
aaaagtcccg gtgcaggcca gcagaacacc agagttacgg catgcccttc ccttagaagg   19860
tcccagaatt tcctcagccc tcactttccc acacaagctt ctaaattggg ccctcgggg    19920 actcatccct tcctagactt ctatccgcca cccccaccc cctggtcccc ccccagacac    19980
acaccaagga cttctgaaat gctgagtaca tacagtggtt tcctccttc tgtccaaatg    20040 tggttgccat cagcgtgatc aacgagagcc aaggggac aaagatcggg atgcaggaga    20100
aggcgttgtg gccatccagt ttgtgaacca gcagaatcta aagaaagaga catagtcccg   20160
gttgatgcca gcaccgaaaa tgggcagagg cggaagccag acttcattag gcagttcctc   20220
cccaccaccc caccccgcg tgagctccca caagagggaa catcagcacc gccagaaaaa    20280
ggcaggaaac cacctatccc tggggaaagc tcgaaatgag cttttatgtc cctcttcaga   20340
gctcggcaat agcctatcca cttgaaaagt tcccagtgcc agcagtttta tggcaaactc   20400
ctccgggtgt ttgttctaag gagtcaacag ctcccattct agaattctcc acgtgactcc   20460
aatacacaaa tctgacatcc cactctgctt tccccagagt ggaaactgga gccatacaga   20520
ggcaccatgg ctaaaaaggt gcactcttct ccctgccagc ccacgtgct gcccccaaga    20580 gaaaggaagg atgctctcct ttcaccgaag ctccctctcg gagatggctg tgttctctcc   20640
cctctcctgg agtgggctca ctgtgagctc gaggacaga ggctgccttt ctaggggtgc    20700
agaatcctgt caggggaagc gcaagcttca ggggctgaag aggcttcccg tggaacgctt   20760
acctcaaatg taagaagggg cacgacgatg gtcatccagc tcagggccat ggttatgtgt   20820
gtcctgcgct gtccgcaatc acatccatag agcgcaagaa caagacggac cacacaatgt   20880
agtagaggac caccaggcac agaaaggaca tgagaatcca cagcgggaca cacacaacct   20940
gggggtgggt gagagaacag caagagaagt ctctttagag cttccaacct ggcctctgat   21000
ggaaggcatc tttagcacct tgctgtgtct gtccagttaa ggcggtcctt cctgtgagcc   21060
gaataaggac cgttccatct cccaggactg ctgggagcat cgctcaggac agaaaaggta   21120
tggtatgttc actatggggc ctgctgccac caggggacac acacgctcag tgagtcatca   21180
gtccctcttc ctttgggtga cagacagccc tgcacctggc tccgcagcct ctactcttcc   21240
agaggcccac tctcccacac tctctcaggc tcctctaggt tctgctgcca tcacagcttc   21300
ccgggaaatg ggacacaact gtcaccctgt gcacacacac aagatctcac cccaacagac   21360
tctcttcaca ggcaacattc ccacaacctg ctgggggtac tttggcaaca caaatggaa    21420 tgggctcccc agaaagtctg gctgcctggg ctcctaagga tccctaacct caccccctacc  21480 aagttagtga acttggcggg ttgatgctgg atacaggttg atgctggata cgtagcgctg   21540
ccgggtcgtg acccctaagg aattatccaa actcttgttt ttagatgctt tattatatca   21600
aactctcctt taaacaagtg gcccatctgc tgggatttgg aagcctgtaa tactgaaatt   21660
ttcatcataa tggaaatttt aaaaacagaa tttgacccac ctgttttta aacactttca    21720 ttacttaaca agaggtctaa tcttgggcaa gtcttgaaat ttctctggcc ttagtttccc   21780
atgtgttaaa tgaaacttga agcagttggt ctcttatagt ctcctgactc taacattcta   21840
agaattatat ttgtacaata actcaaaaat cacataattt aatttaccat atggactcca   21900
aaatatattt tctcattagg ctaaacttga tctgcatttt ctggatgtgt ccatattctt   21960
ggactacact aaaacatgat accaatgctt cctctcacca taaaccctca cttcgctttc   22020
tacatttaag aatttatag ctggaagagt ccttaacaga aaataccatc taataattac    22080
ccctcaaaat cgagaaagtc ctatctgttc ttatgctagt tataagaatg aggcagcatt   22140
tcacataatg gttataaaca ctgccacaag aagattcatg atgtgttgtt tatctgtagc   22200
```

```
tctcatcata ctctgtcata taactatagc attaagattt taatgttcta tatattcttc   22260
taagacagtg tttaccagag taaggcacaa aagatccact ggtttgcaag aaagattaga   22320
acttttaaat ttttttacctc accttgttta atctatattt ttgtatgtat tttgtaacat   22380
atatattatt attaccataa atcatatata atttaaaatg catatattag gggtaaatgc   22440
tcaggaaact ttttataaat tgggcatgca aatacaagtt tgaagactca ctgttctagg   22500
tattaaaagt aaagtttataa ccaagtaaag cttccacctt ttcatgtctc aaagcagttt   22560
attgttggag gtaagatctc ttagaagcct aaacaggtcc aagtacagaa tgaagtaagg   22620
ctagcccata acttgtggca agcaattcat actatttctc tcatgctgag ctctcctcag   22680
tgaagcagct actatagaca actgcagcct attggtagcc tattttacag gcaggaaaaa   22740
aattactttt tattcaaagt ggaactcagg acatggggag aaaatgaata caaaaaatag   22800
ggtcaatcca aaggcacaca gcaaatgagt aacacagtta tgttttttc ccatttgtat   22860 gaggtcccag taaattctaa gtaaactgca aatttaataa tacactaaaa aagccatgca   22920
attgttcaaa tgaatcccag catggtacaa ggagtacaga cactagagtc taaaaaacaa   22980
aagaatgcca ttattgagtt tttgaattat atcaagtagt tacatctcta cttaataaat   23040
gagaaaaacg aggataagag gccatttgat aaaatgaaaa tagccaagaa gtggtattag   23100
agacttgaat acaggtattc gggtccaaag ttcatctgct caaatactaa ctggggaaaa   23160
gagggaaaaa tatttatata catatatatc tgcacacaaa aatacccca aaagacaaaa   23220 tgaggccagg cagggtggct cacacccgta atcccggtac tttgggaggc tgaggcaggt   23280
ggatacctga gatcaggagt tggagatcag cctggtcaac atggtgaaac cctgtctcta   23340
ctaaagataa aaaaattagc caggcatggt ggcgtgcgcc tgtaatccca gctacttggg   23400
agtctgaggc aggagaatca cttgaactgg gaaggggagg ttgcagtgag ccaagatcgt   23460
actactgcac tccagcctgg gcagcagagt gagactccat cacaaaaata aataaataaa   23520
taaaatacaa tgaaacagaa agttcaaata atcccataat cttaccacca agaaataact   23580
ttcactcgtt atacttattg attttttccat aataaatgta ctttactgtg actatcatga   23640
aaagaaagtt attttagaaa cagagaactg tttcagatca aatctatgta gtagaacaga   23700
gccattaggt gggaaagacg agatcaaact aaatctcaga aggcctaaaa ggctaggtcc   23760
attccagcac taaaaactga ccagacaagt aatggcttca acagcttcta aatatggaca   23820
aagcatgctg aaagggaagg acaggtctaa cagtggtata tgaaatgaac aggaggggca   23880
aagctcattt ctcctctgaa gttttccaaa gatgctgagg aggacattag tttgacatga   23940
ccctgatatg ggacaagata atttcacaga agttttacat gttaaagttt tcttatagat   24000
actcattcaa gtaagcaatg aacactaaaa tctaaagaaa gaaagagct ttagagtcag   24060 gtctgtattc aaattcaagc tctaccactt actggttctg tgactttggg caagtctttt   24120
aaccttatta agtcttaatt tcctgatttg taaaatgggg atatcgtctc cctcacagga   24180
ttgttgtgaa acttttatga gattaatgcc tttatatttg gcatagtgta agtaaacaat   24240
aactggcagc ttcaaaaaaa aaaagcagta gcattccatc attttattatt ggttactctc   24300 aaaaagtttt tcaatgtact agaagataaa tattcaaata ccttaatatc tccattattt   24360
tcaggtaaac agcatgctcc tgaacaacca atgggtcaac aaataaatta aagggaaat   24420 ctaaaaacat cttgatatta aactacatgg aagcacaata taccaaaacc aatggttcac   24480
actaggagaa ttttaaggta caagaaaact ctttgagatt tcttaaaata atagtatgtc   24540
tgaatttatt gagtgattta ccagaaactg ttgtaagagc tctacttgca ttatagcact   24600
```

```
taatcctctt aactctatgg ctgctattat caacctcacc ctaatcacat atgggacaca   24660
gagaggttaa gtaacttgcc caaggtcaga gttaggaagt actaagccat gctttgaatc   24720
agttgtcagg ctccggaact cacactttca gccactacat aatactgctt tgctatcttt   24780
taggaaacta tgtgagtcta cctcacatag actcacatag gtttgttttt ttttttttt    24840 taaaggctat cttttccccc atcaatgttt tttgaaggat cccaaattag agtcccacag   24900
aggcagacag cagtacttga caatatggac atttaaggtt aatgttggat tctactgtct   24960
ttttactaca tgacctaggg aacgataatt aacctagact gcttccaagg gttaaataac   25020
ccatttagtt atactatgta aattatctct tagtgattga ttgaaagcac actgttacta   25080
attgactcgg tatgaagtgc ttttttttct tcccttttcaa gatacatacc tttccagtta   25140
aagttgagag atcatctcca ccaattactt ttatgtcccc tgttgactgg tcattctagt   25200
taaaaaaaaa aaaactata tatatatata tctacacaca catatgtata tgtatatcct   25260
tatgtacaca cacaaacttc aaattaaatg agaactagaa gatttgagaa gttagctagc   25320
taatatccat agcattatga tattctaaat gatatgaatt ataagaatta ggtttcctga   25380
aatgaatgac tagaaaactt tcaagtagag attagtaaaa attaaaaagt cctaatcggc   25440
cattactgat ttgatgtttt taagagtcct aaaaaatggg ttacatccat ttttaagtgg   25500
gtagtattat aacagccacc catcttcaat cacagtgatt tctgaattgt gagggaagtt   25560
attagcatga caggtgtctg gttctggccc tgtacgattc ccatgagtca agcaaattgt   25620
aagggctggt ctatatcaca cccaacccca aggatatgtc cctcaaaagt ctagcccagg   25680
ccccgtcatc ttcagcatca tctgggaaac caggtctgat tagtagtcct ttaaggaata   25740
cctcttaggc tcccatttta ctgctatcac agaatccaat aaaaccctta caggagattc   25800
aatgggaaat gctcaacacc cactgtagtt ggtggtgaca atgaccataa tttggctgtg   25860
ctggattcag gacagaaaat ttgggtgaaa gagcaggtga acaaagagc ttcgacttgc    25920 cctagcagag agcaagccat accataccac aaagccacag caattacaac ggtgcagtac   25980
cagcacagta aatgaacaaa gtagagccca gaaacagacc cagaactata tgaggattta   26040
gtatacaata aagatggtat ttcgagtcag tagggaaaag atgaattatt caataaatga   26100
tgtttggcca actagtaacc catttgggaa aaaataaaag tatggtccct acctcacagc   26160
atacacaaaa ataaattcca gacggattaa aatctaaatg taaaaaataa agccataagt   26220
ggactggaag aaaatagaga attttttta acatccgtag aaagggtaaa aacccaggca   26280
tgacatgaac caaaactgaa gaggttctgt aacaaatacc ccctttttata tattgggctc   26340 caacaataag aacccatagg aaaatggaga atgaacacaa atagacaatt tatagaagag   26400
aaggttataa ggtgtaaaat tatatctatc tgagaaacaa acactaaaac aatgtgattc   26460
tactgttctc ccacccatac tggcaaaact taagcctgat aatatgctga ggggaaataa   26520
gcactcttgt tggtgagagt attaattggc atagcttctt ttgaaaatga catagcaata   26580
cctgttaaaa ttgcaaacat gcatgtcact taatccagta atcccacttc tgggaatcaa   26640
tgctacaaaa acactgacaa gtatacaaag atacattcaa gagtgttcac tgggccgggt   26700
gcggtggctt catgcctgta atcccaggga ggcagaggca agacgatcgc ttgaccccag   26760
gagttcaagg ccagcccgag aaacacagca agaccctgtc tctcttttt ttatttaaaa    26820 aataaatgtt cactgtatca gttgttcaca aaaacaaacc aacatgtcca ttaacaggga   26880
accatttaaa ttaatcaagt tcatctcacac aatgtaatac catgcaacta ttaaaaagca   26940
cctgataatc caaagcacac tgagacagaa taatgctatt aaaaacacca agtagtggaa   27000
```

```
cactgtgttg cctatgacac catttttatt caacatttaa acaaatttgt aacagcaatt    27060
acatgagtag tgacaatggc gtttatgaga cttttcactt ttatgtgctt ctattttgt    27120 tatgcttcta tatatacatc catttattat ggagtgttac tttcaaaaat cacaaatggg    27180
ccagtattat ttggtgttgc aaggtgagca tatgacttct gatatcaacc tttgcatatt    27240
acttctcaat ttagggaaat tacagacatc ccttattcta actaacttaa aacccagcat    27300
ttcaaacata cagaattgat ggggaaaaaa agaaagaag aaagaaagaa aaggcaacaa    27360
gcttcagatg acagtgactc acatcaaatt atttataaaa tctgttaaat agtgccatct    27420
tctggagata cctggtatta cagtccaact ccagttgatg tctttacaga dacaagagga    27480
ataaaggaaa aaatattcaa gaactgaaaa gtatggagtc atggaaaaat tgctgtgatc    27540
caaaggctac ggtgatagga caagaaacaa gagaactcca agcagtaaga cactgctgtt    27600
ctattagcat ccaaacctcc atactcctgt ttgccccaag gctttttaa aaaatagaga    27660 caggatctca ctattttgct caggctggtc ttgaactcct ggactcaagc tatcctcctg    27720
cctcggcctc ctaaagtgcc gagattacag gcttgagtca ccatacctgg ctatttattt    27780
tttcttaact ctcttgcctg cctatagcc accatggaag ctaataaaga atattaattt    27840
aagagtaatg gtatagttca ctacattgga atacaggtat aagtgcctac attgtacatg    27900
aatggcatac atggatcaat taccccacct gggtggccaa aggaactgcg cgaacctccc    27960
tccttggctg tctgaacaa gctcccact agatcccttt actgagtgcc tccctcatct    28020
ttaattatgg ttaagtctag gataacagga ctggcaaagg tgaggggaaa gcttcctcca    28080
gagttgctct accctctcct ctaccgtcct atctcctcac tcctctcagc caaggagtcc    28140
aatctgtcct gaactcagag cgtcactgtc aactacataa aattgccaga gaagctcttt    28200
gggactacaa acacatacc ttaatgtctt tatttctatt ttgtctacct cttcagtcta    28260
ggtgaaaaaa taggaaggat aatagggaag aactttgttt atgcctactt atccgcccct    28320
aggaattttg aaaacctcta ggtagcaata agaactgcag catggtatag aaaaagagga    28380
ggaaagctgt atagaaatgc ataataaatg ggcaggaaaa gaactgcttg gaacaaacag    28440
ggaggttgaa ctataaggag agaaagcaga gaggctaatc aacaaggctg ggttcccaag    28500
agggcatgat gagactatta ctaaggtagg aattactaag ggctccatgt cccccttagtg    28560 gcttagtact atgtagcttg cttctctgcag tgaacttcag acccttcttt taggatccta    28620
gaatggactt tttttttta tcggaaaaca gtcattctct caacattcaa gcaggcccca    28680
agtctaccac actcaatcac attttctctt catatcataa tctctcaacc attctctgtc    28740
cttttaactg tttttctata ccctgatcaa atgccaacaa aagtgagaat gttagaatca    28800 tgtatttta gaggtagact gtatctcaga taaaaaaaaa gggcagatat tccattttcc    28860
aaaatatgta tgcagaaaaa ataagtatga aggacatat gctcaggtaa caagttaatt    28920
tgtttacttg tattttatga attccctaaa acctacgtca cccgcccgt tcccacgccc    28980 cgcgccacgt cacaaactcc accccctcat tatcatattg gcttcaatcc aaaataaggt    29040
atattattga tgatgttaat taacatgcat ggatccatat gcggtgtgaa ataccgcaca    29100
gatgcgtaag gagaaaatac cgcatcaggc gctcttccgc ttcctcgctc actgactcgc    29160
tgcgctcggt cgttcggctg cggcgagcgg tatcagctca ctcaaaggcg gtaatacggt    29220
tatccacaga atcaggggat aacgcaggaa agaacatgtg agcaaaaggc cagcaaaagg    29280
ccaggaaccg taaaaaggcc gcgttgctgg cgttttccca taggctccgc cccctgacg    29340 agcatcacaa aaatcgacgc tcaagtcaga ggtggcgaaa cccgacagga ctataaagat    29400
```

```
accaggcgtt tccccctgga agctccctcg tgcgctctcc tgttccgacc ctgccgctta   29460
ccggataccct gtccgccttt ctcccttcgg gaagcgtggc gctttctcat agctcacgct   29520
gtaggtatct cagttcggtg taggtcgttc gctccaagct gggctgtgtg cacgaacccc   29580
ccgttcagcc cgaccgctgc gccttatccg gtaactatcg tcttgagtcc aacccggtaa   29640
gacacgactt atcgccactg gcagcagcca ctggtaacag gattagcaga gcgaggtatg   29700
taggcggtgc tacagagttc ttgaagtggt ggcctaacta cggctacact agaaggacag   29760
tatttggtat ctgcgctctg ctgaagccag ttaccttcgg aaaaagagtt ggtagctctt   29820
gatccggcaa acaaaccacc gctggtagcg gtggtttttt tgtttgcaag cagcagatta   29880
cgcgcagaaa aaaggatct caagaagatc ctttgatctt ttctacgggg tctgacgctc   29940
agtggaacga aaactcacgt taagggattt tggtcatgag attatcaaaa aggatcttca   30000
cctagatcct tttaaattaa aaatgaagtt ttaaatcaat ctaaagtata tatgagtaaa   30060
cttggtctga cagttaccaa tgcttaatca gtgaggcacc tatctcagcg atctgtctat   30120
ttcgttcatc catagttgcc tgactccccg tcgtgtagat aactacgata cgggagggct   30180
taccatctgg ccccagtgct gcaatgatac cgcgagaccc acgctcaccg gctccagatt   30240
tatcagcaat aaaccagcca gccggaaggg ccgagcgcag aagtggtcct gcaactttat   30300
ccgcctccat ccagtctatt aattgttgcc gggaagctag agtaagtagt tcgccagtta   30360
atagtttgcg caacgttgtt gccattgctg cagccatgag attatcaaaa aggatcttca   30420
cctagatcct tttcacgtag aaagccagtc cgcagaaacg gtgctgaccc cggatgaatg   30480
tcagctactg ggctatctgg acaagggaaa acgcaagcgc aaagagaaag caggtagctt   30540
gcagtgggct tacatggcga tagctagact gggcggtttt atggacagca agcgaaccgg   30600
aattgccagc tggggcgccc tctggtaagg ttgggaagcc ctgcaaagta aactggatgg   30660
ctttcttgcc gccaaggatc tgatggcgca ggggatcaag ctctgatcaa gagacaggat   30720
gaggatcgtt tcgcatgatt gaacaagatg gattgcacgc aggttctccg gccgcttggg   30780
tggagaggct attcggctat gactgggcac aacagacaat cggctgctct gatgccgccg   30840
tgttccggct gtcagcgcag gggcgcccgg ttcttttttgt caagaccgac ctgtccggtg   30900
ccctgaatga actgcaagac gaggcagcgc ggctatcgtg gctggccacg acgggcgttc   30960
cttgcgcagc tgtgctcgac gttgtcactg aagcgggaag ggactggctg ctattgggcg   31020
aagtgccggg gcaggatctc ctgtcatctc accttgctcc tgccgagaaa gtatccatca   31080
tggctgatgc aatgcggcgg ctgcatacgc ttgatccggc tacctgccca ttcgaccacc   31140
aagcgaaaca tcgcatcgag cgagcacgta ctcggatgga agccggtctt gtcgatcagg   31200
atgatctgga cgaagagcat caggggctcg cgccagccga actgttcgcc aggctcaagg   31260
cgagcatgcc cgacggcgag gatctcgtcg tgacccatgg cgatgcctgc ttgccgaata   31320
tcatggtgga aaatggccgc ttttctggat tcatcgactg tggccggctg ggtgtggcgg   31380
accgctatca ggacatagcg ttggctaccc gtgatattgc tgaagagctt ggcggcgaat   31440
gggctgaccg cttcctcgtg ctttacggta tcgccgctcc cgattcgcag cgcatcgcct   31500
tctatcgcct tcttgacgag ttcttctgaa ttttgttaaa attttttgtta aatcagctca   31560
ttttttaacc aataggccga atcggcaaa atccctttata aatcaaaaga ataggaccgag   31620
atagggttga gtgttgttcc agtttggaac aagagtccac tattaaagaa cgtggactcc   31680
aacgtcaaag ggcgaaaaac cgtctatcag ggcgatggcc cactacgtga accatcaccc   31740
taatcaagtt ttttggggtc gaggtgccgt aaagcactaa atcggaaccc taaagggagc   31800
```

```
ccccgattta gagcttgacg gggaaagccg gcgaacgtgg cgagaaagga agggaagaaa   31860
gcgaaaggag cgggcgctag ggcgctggca agtgtagcgg tcacgctgcg cgtaaccacc   31920
acacccgccg cgcttaatgc gccgctacag ggcgcgtcca ttcgccattc aggatcgaat   31980
taattcttaa ttaacatcat caataatata ccttattttg gattgaagcc aatatgataa   32040
tgagggggtg gagtttgtga cgtggcgcgg ggcgtgggaa cggggcgggt gacgtagtag   32100
tgtggcggaa gtgtgatgtt gcaagtgtgg cggaacacat gtaagcgacg gatgtggcaa   32160
aagtgacgtt tttggtgtgc gccggtgtac acaggaagtg acaattttcg cgcggtttta   32220
ggcggatgtt gtagtaaatt tgggcgtaac cgagtaagat ttggccattt tcgcgggaaa   32280
actgaataag aggaagtgaa atctgaataa ttttgtgtta ctcatagcgc gtaatactg    32339
```